United States Patent
Koga et al.

(10) Patent No.: US 9,447,090 B2
(45) Date of Patent: Sep. 20, 2016

(54) IMIDAZOPYRIDINE COMPOUNDS

(71) Applicant: Astellas Pharma Inc., Chuo-ku, Tokyo (JP)

(72) Inventors: Yuji Koga, Tokyo (JP); Kyoichi Maeno, Tokyo (JP); Ippei Sato, Tokyo (JP); Yoshimasa Imamura, Tokyo (JP); Takeshi Hanazawa, Tokyo (JP); Maiko Iida, Tokyo (JP); Kazuhiko Ohne, Tokyo (JP); Kenichiro Imamura, Tokyo (JP); Tsubasa Watanabe, Tokyo (JP); Eisuke Nozawa, Tokyo (JP); Hiroshi Shibata, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 295 days.

(21) Appl. No.: 14/090,074

(22) Filed: Nov. 26, 2013

(65) Prior Publication Data

US 2014/0088080 A1   Mar. 27, 2014

Related U.S. Application Data

(63) Continuation-in-part of application No. PCT/JP2012/063695, filed on May 29, 2012.

(30) Foreign Application Priority Data

May 30, 2011  (JP) ................................ 2011-119826
Dec. 28, 2011  (JP) ................................ 2011-287682

(51) Int. Cl.
*C07D 471/04* (2006.01)
*C07D 453/02* (2006.01)
*C07D 519/00* (2006.01)

(52) U.S. Cl.
CPC ........... *C07D 471/04* (2013.01); *C07D 453/02* (2013.01); *C07D 519/00* (2013.01)

(58) Field of Classification Search
None
See application file for complete search history.

(56) References Cited

U.S. PATENT DOCUMENTS 8,865,734 B2 * 10/2014 No ................................ 514/300
2010/0029653 A1   2/2010 Schirok

FOREIGN PATENT DOCUMENTS

| JP | 7242666 A | 9/1995 |
|---|---|---|
| WO | 98/37080 A1 | 8/1998 |
| WO | 99/63940 A2 | 12/1999 |
| WO | 00/27394 A1 | 5/2000 |
| WO | 01/32604 A1 | 5/2001 |
| WO | 01/96335 A1 | 12/2001 |
| WO | 03/076408 A2 | 9/2003 |
| WO | 2008/031513 A1 | 3/2008 |
| WO | 2011/113606 A1 | 9/2011 |

OTHER PUBLICATIONS

Stasch et al., Soluble Guanylate Cyclase as an Emerging Therapeutic Target in Cardiopulmonary Disease. Circulation, 2011, 123, 2263-2273.*
CAPLUS printout of foreign patent application publication No. JP07242666.*
Ito et al., A medium-term rat liver bioassay for rapid in vivo detection of carcinogenic potential of chemicals. Cancer Science, 2003, 94, 3-8.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Abstract of JP 7242666 A—English language.
Kaminski, James J. et al., (1985) J. Med. Chem. vol. 28 pp. 876-892.
Ko, Feng-Nien et al. (Dec. 15, 1994) Blood vol. 84 No. 12 pp. 4226-4233.
Priviero, Fernanda B.M. and Webb R. Clinton (Sep. 2010) J Cardiovasc Pharmacol vol. 56, No. 3, pp. 229-233.
Office Action issued on Sep. 16, 2014 in Eurasian Patent Application No. 201391769/28 and English translation thereof.

* cited by examiner

*Primary Examiner* — Rebecca Anderson
*Assistant Examiner* — Po-Chih Chen
(74) *Attorney, Agent, or Firm* — Amy H. Fix

(57) ABSTRACT

An excellent drug for treating or preventing cardiovascular diseases, based on cGMP production enhancing action due to soluble guanylate cyclase activating action, is provided. It was found that imidazopyridine compounds having a carbamoyl group at the 3-position and a substituent bonded at the 8-position via an oxygen atom in an imidazo[1,2-a]pyridine skeleton exhibits a cGMP production enhancing action by a potent soluble guanylate cyclase activating action, and is useful as a drug for treating or preventing various soluble guanylate cyclase-related cardiovascular diseases, thereby completing the present invention.

15 Claims, No Drawings

IMIDAZOPYRIDINE COMPOUNDS

TECHNICAL FIELD

The present invention relates to imidazopyridine compounds useful as active ingredients of pharmaceutical compositions, for example, pharmaceutical compositions for treating or preventing various cardiovascular diseases, which have soluble guanylate cyclase (sGC) activation based on improvement of cGMP signals.

BACKGROUND ART cGMP (cyclic guanosine monophosphate) is an important intracellular messenger and is involved in the regulation of various physiological phenomena such as relaxation and proliferation of smooth muscle cells, aggregation and adhesion of platelets, and signaling of nerve cells, through the control of a cGMP-dependent protein kinase, a phosphodiesterase, and ion channels. The cGMP is catalytically produced from guanosine triphosphate (GTP) by a guanylate cyclase in the response to various extracellular and intracellular stimulation. There have been reported two groups of guanylate cyclases to date, that is, particulate guanylate cyclases stimulated by peptidic messengers (for example, atrial natriuretic peptides, brain natriuretic peptides, and the like) and soluble guanylate cyclase stimulated by nitric oxide (NO).

The sGC is one of the most important target molecules of NO that is a messenger which plays a very important role in maintaining homeostasis of the body, and forms an NO/sGC/cGMP pathway. It has been reported that this enzyme is constituted with two subunits, each of the heterodimer contains one heme, and the heme plays a central role in an activation mechanism. It is believed that when NO binds to the iron in the heme, the enzyme is changed to an active conformation. Therefore, there is no stimulation by NO with enzyme preparations containing no heme. Although carbon monoxide (CO) may also bind to the iron in the heme, but the stimulation by CO is significantly lower than that by NO.

The sGC is constituted with $\alpha$ and $\beta$ subunits. Analysis of cGC from tissue-specific distributions and in different growth steps demonstrated multiple isotypes with different subunit compositions. The distribution of the respective subunits have been studied with mammals including a human, and it has been widely recognized that al and $\beta 1$ subunits are expressed in many tissues and the $\alpha 1\beta 1$ forms have a pattern of a heterodimer that works functionally. $\alpha 2$ subunits have been also recognized, which exist fewer organs as compared to the $\alpha 1$, and it has been reported that the $\alpha 2$ subunits are expressed more frequently than $\alpha 1$ in the brain, the lung, the colon, the heart, the spleen, the uterus, and the placenta. Subunits called $\alpha 3$ and $\beta 3$ were isolated from the human brain, but are homologous to $\alpha 1$ and $\beta 1$. In addition, according to recent studies, $\alpha 2i$ subunits which contain an insert in the catalytic domain have identified. All of the subunits exhibit high homology in catalytic domain regions.

Under pathophysiological conditions, it has been reported that there is inhibition of the production of or promotion of the degradation of sGC activating factors such as NO for the reasons of increased generation of free radicals, and the like. With a decrease in the sGC activating factors, NO/sGC/cGMP signals are attenuated, which results in, for example, increased blood pressure, platelet activation, or increased cell proliferation and cell adhesion. As a result, a variety of cardiovascular diseases, specifically, hypertension (including pulmonary hypertension), atherosclerosis, peripheral arterial diseases, lumbar spinal canal stenosis, intermittent claudication, critical limb ischemia, stable or unstable angina pectoris, heart failure, thrombosis, stroke, and sexual dysfunction occur. Therefore, a new drug having a mechanism of selectively activating sGC is believed to have the potential of normalizing cGMP production, and thus or prevent such diseases can be treated or prevented.

As the sGC activator, there have been known, for example, "heme-dependent stimulants" which activate sGC depending on heme groups, such as NO donors as described later and the like, and "heme-independent activators" which are independent on the heme groups (Non-Patent Document 2).

For the activation of sGC, a group of compounds called NO donors such as organic nitrates have been widely used so far. These compounds are heme-dependent stimulants which activate sGC by being metabolized in vivo to produce NO, which then binds to a central iron atom of a heme. However, the NO donors have critical disadvantages such as expression of a resistance, a decrease in the effects and the like is expressed in addition to side-effects, and therefore, there is a demand for a novel sGC activator that does not have these disadvantages.

For example, compounds of the following formulae (a) to (c) have been reported as compounds having sGC activating action (Patent Document 1).

[Chem. 1]

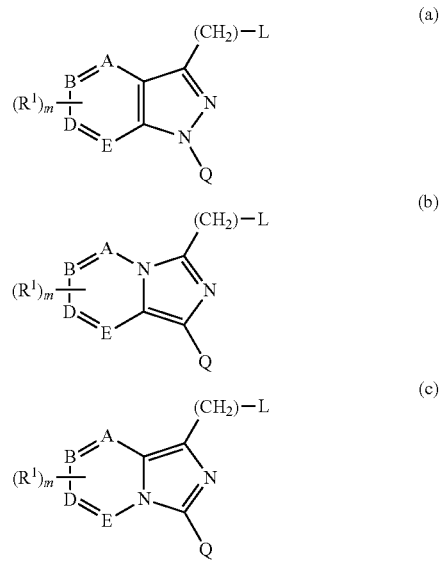

(Compounds of the formula (a) are pyrazolo[3,4]fused bicyclic compounds, and compounds of formulae (b) and (c) are imidazo[1,5]fused bicyclic compounds. Further, Q means substituted heterocycle in any one of the formulae (a) to (c). For details, refer to the document.)

In this document, there is no disclosure or suggestion of compounds having an imidazo[1,2-a]pyridine skeleton.

In addition, pyrazole derivatives or pyrazolo[3,4-b]pyridine derivatives are disclosed as the sGC activating compounds in International Publications WO 2000/06569, WO 2000/21954, WO 2001/83490, WO 2003/004503, WO 2003/095451, WO 2003/086407, WO 2003/097063, WO 2007/124854, WO 2007/128454, WO 2008/031513, WO 2008/061657, WO 2010/078900, and WO 2010/079120. However, in any of these documents, there is no disclosure or suggestion of compounds having an imidazo[1,2-a]pyridine skeleton.

Furthermore, compounds of the following formula (d) have been reported as sGC activators (Patent Document 2).

[Chem. 2]

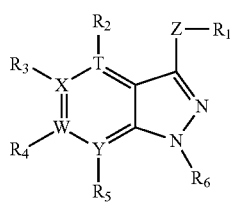

(d)

(wherein Z is O, S, or N($R_7$), $R_7$ is H or alkyl, and $R_6$ is aryl, arylalkenyl, heterocycle, -(alkenyl)-(heterocycle), or heterocycloalkyl).

However, this document does not disclose or suggest compounds having an imidazo[1,2-a]pyridine skeleton.

As other sGC activators, 1H-pyrazole-5-carboxylic acid derivatives (Patent Document 3), biaryl derivatives (Patent Document 4), and benzylindazole derivatives (Non-Patent Document 1) have been reported.

Furthermore, compounds having an imidazopyridine skeleton, for example, compounds of the following formula (e) useful for the treatment of gastrointestinal ulcer as an H+/K+-ATPase enzyme inhibitors have been reported (Non-Patent Document 3).

[Chem. 3]

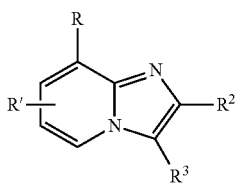

(e)

(wherein R means substituted alkoxy group, R' means H or phenethyl, $R^2$ means H or lower alkyl, and $R^3$ means substituted alkyl or the like. For details, refer to the document).

This document does not disclose or suggest sGC activators, and compound of formula (I) of the present invention as described later has a different structure from that of the compound of the formula (e) in that the compound of formula (I) has an aminocarbonyl group at the 3-position.

Moreover, compounds of the formula (f) useful for the treatment of allergy, inflammation, pain, or the like as bradykinin antagonists have been reported (Patent Document 5).

[Chem. 4]

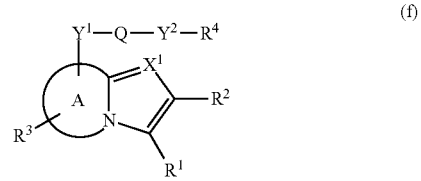

(f)

(wherein $R^1$ to $R^3$ each mean hydrogen, lower alkyl, or the like, $R^4$ means an aryl group which may have a suitable substituent, or the like, Q means O, NH, or the like, $X^1$ means N or C—$R^5$, $Y^1$ and $Y^2$ each mean a single bond or a lower alkylene group, and Ring A means 6-membered nitrogen-containing heterocycle. For details, refer to the document).

This document does not disclose or suggest sGC activators, and the compound of formula (I) of the present invention as described later has a different structure from that of the compound of formula (f) in that the compound of formula (I) has an aminocarbonyl group at the 3-position.

Furthermore, compounds of formula (g) with H+/K+-ATPase enzyme inhibitory activities and useful for the inhibition of gastric acid secretion have been reported (Patent Document 6).

[Chem. 5]

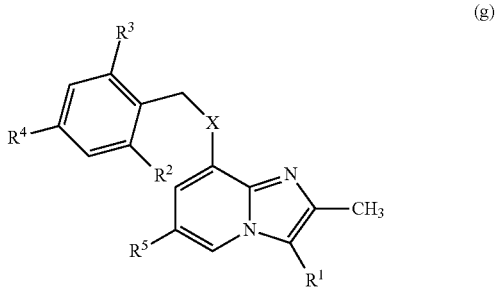

(g)

(wherein $R^1$ is $CH_3$ or $CH_2OH$, $R^2$ and $R^3$ are each lower alkyl, $R^4$ is H or halogen, $R^5$ is H, halogen, or lower alkyl, and X is NH or O. For details, refer to the document).

This document does not disclose or suggest sGC activators, and the compound of formula (I) of the present invention as described later have different structure from that of the compound of formula (g) in that the compound of formula (I) has an aminocarbonyl group at the 3-position.

Moreover, compounds of formula (h) have been reported as cardiac ion channel modulators and as antiarrhythmic agents (Patent Document 7).

[Chem. 6]

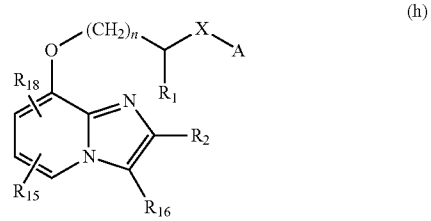

(h)

(wherein $R_2$, $R_{15}$, $R_{16}$, and $R_{18}$ are each Br, Cl, F, carboxy, H, —OH, hydroxymethyl, or the like, and $R_1$ is H, $C_{1-6}$ alkyl, aryl, benzyl, or the like. For details, refer to the document).

This document does not disclose or suggest sGC activators, and the compound of formula (I) of the present invention as described later have different structure from that of the compound of formula (h) in that the compound of formula (I) has an aminocarbonyl group at the 3-position.

In addition, compound of formula (i) useful as a drug for treating bacterial infection, particularly tuberculosis, have been reported (Patent Document 8).

[Chem. 7]

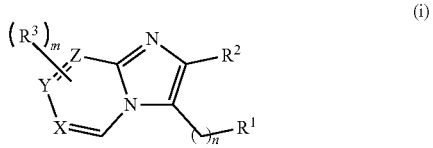

(i)

(wherein X, Y, and Z are each CH or the like, n is 0 or the like, m is 1 or the like, $R^1$ is —C(O)N($R^4$)$_2$ or the like, $R^2$ is $C_{1-10}$ alkyl or the like, $R^3$ is —$OR^6$ or the like, and $R^6$ is $C_{1-10}$ alkyl optionally substituted, or the like. For details, refer to the document).

This document specifically discloses a compound, in which X, Y, and Z are each CH, n is 0, $R^1$ is —C(O)N($R^4$)$_2$, $R^2$ is $C_{1-10}$ alkyl, m is 1, $R^3$ is —$OR^6$, and $R^6$ is H, methyl, or difluoromethyl. However, this document does not disclose or suggest sGC activators, and the compound of formula (I) of the present invention as described later has a different structure from that of the compounds disclosed in this document in that the substituent $A^1$ is lower alkyl.

RELATED ART

Patent Document

[Patent Document 1] Pamphlet of International Publication WO 2008/031513
[Patent Document 2] Pamphlet of International Publication WO 2003/076408
[Patent Document 3] Pamphlet of International Publication WO 2000/027394
[Patent Document 4] Pamphlet of International Publication WO 2001/032604
[Patent Document 5] JP-A-H7-242666
[Patent Document 6] Pamphlet of International Publication WO 1998/37080
[Patent Document 7] Pamphlet of International Publication WO 2001/096335
[Patent Document 8] Pamphlet of International Publication WO 2011/113606
[Non-Patent Document 1] Blood (1994), Vol. 84, p. 4226
[Non-Patent Document 2] Journal of Cardiovascular Pharmacology (2010), Vol. 56, p. 229
[Non-Patent Document 3] Journal of Medicinal Chemistry (1985), Vol. 28, p. 876

DISCLOSURE OF INVENTION

Technical Problem

Problems to Be Solved by the Invention

Imidazopyridine compounds, useful as active ingredients of pharmaceutical compositions, for example, pharmaceutical compositions for treating or preventing various cardiovascular diseases, which have soluble guanylate cyclase (sGC) activities based on improvement of cGMP signals, are provided.

Means for Solving the Problems

The present inventors have made extensive studies on compounds having sGC activation, and as a result, they have found that compounds of formula (I) which are imidazo[1,2-a]pyridine compounds having a carbamoyl group at the 3-position and a substituent bonded at the 8-position via an oxygen atom, and a salt thereof have sGC activation, and are useful as active ingredients of pharmaceutical compositions for treating or preventing various sGC-related cardiovascular diseases, in particular, peripheral arterial diseases, intermittent claudication, critical limb ischemia, and hypertension (including pulmonary hypertension), thereby completing the present invention.

That is, the present invention relates to a compound of formula (I) or a salt thereof, and pharmaceutical compositions comprising the compound of formula (I) or a salt thereof and a pharmaceutically acceptable excipient.

[Chem. 8]

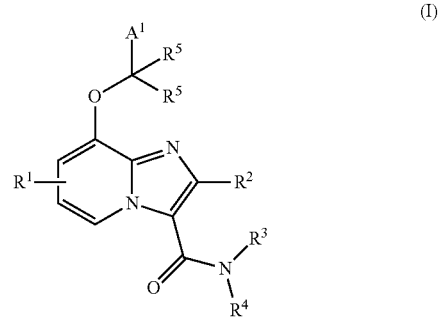

(I)

[the symbols in the formula have the following meanings:
$A^1$: $R^0$, —$R^{00}$-(aryl), halogeno-lower alkyl, optionally substituted cycloalkyl, optionally substituted heterocycloalkyl, optionally substituted aryl, or optionally substituted heteroaryl,
$R^0$: the same as or different from each other, and each representing lower alkyl,
$R^{00}$: the same as or different from each other, and each representing lower alkylene,
$R^1$: H, $R^0$, halogen, —CN, —$CO_2H$, —$CO_2R^0$, or —$R^{00}$—OH,
$R^2$: H, $R^0$, $C_{3-6}$ cycloalkyl, or halogeno-lower alkyl,
$R^3$: H, $R^0$, —$R^{00}$—$CO_2H$, or —$R^{00}$—$CO_2R^0$,
$R^4$: —Y-$A^2$ or $A^3$, or $R^3$ and $R^4$, together with N atom to which they are both bonded, may form a nitrogen-containing saturated heterocycle optionally substituted with at least one group selected from the group consisting of —OH, —$R^{00}$—OH, —$CO_2H$, —$CO_2R^0$, and phenyl,
Y: $C_{1-10}$ alkylene optionally substituted with at least one group selected from Group $G^2$, $C_{2-10}$ alkenylene optionally substituted with at least one group selected from Group $G^2$, or —$SO_2$-(lower alkylene optionally substituted with at least one group selected from Group $G^2$)-,
Group $G^2$: —$CO_2H$, —$CO_2R^0$, —OH, —$OR^0$, —O—CO—$R^0$, —$OSi(R^0)_3$, —$NH_2$, —$NHR^0$, —$N(R^0)_2$, —NH—CO—$R^0$, —$SR^0$, —CO—NH—$SO_2$—$R^0$, optionally substituted aryl, and optionally substituted heteroaryl, $A^2$: H, —OH, —O-(aryl), —CO—$R^0$, —CO—$R^{00}$—OH, —$CO_2$—$R^{00}$-(aryl), —CO—$NH_2$, —CO—$NHR^0$, —CO—$N(R^0)_2$, optionally substituted cycloalkyl, optionally substituted heterocycloalkyl, optionally substituted aryl, or optionally substituted heteroaryl, $A^3$: H, cycloalkyl optionally substituted with at least one group selected from Group $G^1$, heterocycloalkyl optionally substituted with at least one group selected from Group $G^1$, aryl optionally substituted with at least one group selected from Group $G^1$, or heteroaryl optionally substituted with at least one group selected from Group $G^1$, Group $G^1$: $R^0$, halogen-lower alkyl, —$R^{00}$—OH, halogen, oxo, —$NO_2$, —OH, —$OR^0$, —O—$R^{00}$—$N(R^0)_2$, —$NH_2$, —CO—$R^0$, —CO—$R^{00}$—OH, —$CO_2H$, —$CO_2R^0$, —CO—$NH_2$, —CO—$NHR^0$, —CO—$N(R^0)_2$, —$CO_2$—$R^{00}$-(phenyl), —$SO_2$—$R^0$, —$SO_2$—$NH_2$, —$SO_2$—$NHR^0$, —$SO_2$—$N(R^0)_2$, —$SO_2$—$R^{00}$—$CO_2H$, —$SO_2$—$R^{00}$—$CO_2R^0$, —$SO_2$-(phenyl), —$SO_2$—$R^{00}$-(phenyl), —$R^{00}$—$CO_2H$, —$R^{00}$—$CO_2R^0$, —$R^{00}$—CO—$NH_2$, —$R^{00}$—CO—$NHR^0$, —$R^{00}$—CO—$N(R^0)_2$, —$R^{00}$—$NH_2$, —$R^{00}$—$NHR^0$, —$R^{00}$—$N(R^0)_2$, —$R^{00}$-(phenyl), —$R^{00}$-(phenylene)-$R^0$, —$R^{00}$-(cycloalkyl), —$R^{00}$-(heterocycloalkyl), —$R^{00}$-(monocyclic nitrogen-containing heteroaryl), cycloalkyl, phenyl, -(phenylene)-$R^0$, -(phenylene)-$CO_2H$, -(phenylene)-$CO_2R^0$, -(pyridinediyl)-$CO_2H$, -(pyridinediyl)-$CO_2R^0$, -(piperidinediyl)-$R^0$, -(phenylene)-$R^{00}$—$CO_2H$, —$R^{00}$-(phenylene)-$CO_2H$, —$R^{00}$-(phenylene)-$CO_2R^0$, monocyclic nitrogen-containing heteroaryl, and heterocycloalkyl, and $R^5$: the same as or different from each other, and each representing H or $R^0$, provided that the compound of the formula (I) is neither 8-(benzyloxy)-2-methylimidazo[1,2-a]pyridine-3-carboxamide nor 8-(benzyloxy)-2-methylimidazo[1,2-a]pyridin-3-yl](piperazin-1-yl)methanone)].

Furthermore, unless specifically described otherwise, when symbols in one formula in the present specification are also used in other formulae, same symbols denote same meanings.

Moreover, the present invention relates to pharmaceutical compositions for treating sGC-related cardiovascular diseases, which include compound of formula (I) or a salt thereof. Further, said pharmaceutical compositions include agents for treating sGC-related cardiovascular diseases, which includes compounds of the formula (I) or a salt thereof.

The present invention further relates to use of compound of formula (I) or a salt thereof for preparation of pharmaceutical compositions for treating or preventing sGC-related cardiovascular diseases, use of compound of formula (I) or a salt thereof for treating or preventing sGC-related cardiovascular diseases, compound of the formula (I) or a salt thereof for treating or preventing sGC-related cardiovascular diseases, and methods for treating or preventing sGC-related cardiovascular diseases, comprising administering to a subject an effective amount of compound of formula (I) or a salt thereof. In this regard, the "subjects" refer to humans or other animals in need of the prevention or treatment, and in a certain embodiment, humans in need of the prevention or treatment.

Effects of the Invention

Compound of formula (I) has an sGC activation and can be used as active ingredients of pharmaceutical compositions for treating or preventing sGC-related cardiovascular diseases, for example, hypertension, atherosclerosis, lumbar spinal canal stenosis, peripheral arterial diseases, intermittent claudication, critical limb ischemia, stable or unstable angina pectoris, heart failure, thrombosis, stroke, sexual dysfunction, pulmonary hypertension, or the like.

EMBODIMENTS FOR CARRYING OUT THE INVENTION

Hereinbelow, the present invention will be described in detail.

In the present specification, the "cardiovascular disease" refers to a disease based on the abnormal symptoms of circulatory organs such as heart, blood vessels, and the like. Among these, the "sGC-related cardiovascular disease" is known to be involved in an NO/sGC/cGMP system, and is a cardiovascular disease that can be treated or prevented by sGC activation. Examples thereof include hypertension (including pulmonary hypertension), atherosclerosis, lumbar spinal canal stenosis, peripheral arterial disease, intermittent claudication, critical limb ischemia, stable or unstable angina pectoris, heart failure, thrombosis, stroke, sexual dysfunction, and the like. In another embodiment, the "sGC-related cardiovascular disease" is intermittent claudication and critical limb ischemia caused by peripheral arterial diseases. In another embodiment, it is intermittent claudication caused by peripheral arterial diseases, and in another embodiment, critical limb ischemia caused by peripheral arterial diseases.

Here, examples of the peripheral arterial diseases include occlusive thrombotic vasculitis, peripheral arterial occlusive disease, Raynaud's disease, and Raynaud's syndrome.

The "peripheral arterial disease" is a disorder in which stenosis and occlusions caused by atherosclerosis, thrombosis and other impairments produce deficient blood flow, especially in the lower limbs. The symptoms are cold leg or feet, intermittent claudication, lower limb pain and critical limb ischemia (lower limb ulcers and necrosis). Diagnosis and treatment guidelines for peripheral arterial disease can be found in the following reference.

Eur. J. Vasc. Endovasc. Surg, 2007, 33(1), S1

"Intermittent claudication" means in one embodiment, intermittent claudication caused by peripheral arterial diseases, and in another embodiment intermittent claudication caused by peripheral arterial occlusive disease.

"Critical limb ischemia" means in one embodiment, critical limb ischemia caused by peripheral arterial diseases, and in another embodiment critical limb ischemia caused by peripheral arterial occlusive disease.

Further, the "sGC-related cardiovascular disease" means in one embodiment, hypertension or pulmonary hypertension.

The "hypertension" means, in a one embodiment, essential hypertension, abnormal circadian blood pressure variability, renal parenchymal hypertension, renovascular hypertension, primary aldosteronism, Cushing's syndrome, hibernoma, or hypertension associated with endocrine diseases. The "pulmonary hypertension" is, in a certain embodiment, pulmonary arterial pulmonary hypertension, pulmonary hypertension associated with heart diseases, pulmonary hypertension associated with lung diseases such as chronic obstructive pulmonary diseases or interstitial lung diseases, or pulmonary hypertension associated with chronic thrombotic or obstructive diseases.

The "lower alkyl" is a monovalent group formed by the removal of any one hydrogen atom from a linear or branched saturated hydrocarbon having 1 to 6 carbon atoms (hereinafter simply referred to as $C_{1-6}$), and it is specifically methyl, ethyl, n-propyl, isopropyl, n-butyl, isobutyl, sec-butyl, tert-butyl, n-pentyl, n-hexyl, or the like, in another embodiment, $C_{1-4}$ alkyl, and in a still another embodiment, methyl, ethyl, n-propyl, or isopropyl.

The "$C_{1-10}$ alkylene" is a divalent group formed by the removal of any two hydrogen atoms from a linear or branched saturated hydrocarbon having 1 to 10 carbon atoms, and it is, for example, methylene, ethylene, trimethylene, tetramethylene, pentamethylene, hexamethylene, propylene, methylmethylene, ethylethylene, 1,2-dimethylethylene, 1,1,2,2-tetramethylethylene, or the like, in another embodiment, methylene or ethylene, and in still another embodiment, methylene.

The "lower alkylene" means "$C_{1-6}$ alkylene" among the "$C_{1-10}$ alkylene" above, and it is, in a certain embodiment, methylene, ethylene, trimethylene, or the like, and in another embodiment, methylene or ethylene.

The "$C_{2-10}$ alkenylene" is a divalent group formed by the removal of any two hydrogen atoms from a linear or branched hydrocarbon having a double bond and 2 to 10 carbon atoms. It is, in a certain embodiment, ethylidene, propenylene, or butenylene, in another embodiment, ethylidene, and in still another embodiment, trans-1,2-ethylidene.

The "cycloalkyl" is a $C_{3-10}$ saturated hydrocarbon ring group, which may have a bridge, may be combined with another cycloalkyl to form a spiro ring, may partly have unsaturated bond and may be fused with a ring selected from a benzene ring, a furan ring, a thiophene ring, and a pyrrole ring. Examples of the "cycloalkyl" include cyclopropyl, cyclobutyl, cyclopentyl, cyclohexyl, cycloheptyl, cyclooctyl, adamantyl, indanyl, tetrahydronaphthyl, indanyl, indenyl, cyclohexenyl, spiro[3.5]nonyl, dihydrocyclopentathienyl, dihydrocyclopentafuranyl, dihydrocyclopentapyrrolyl, or the like. In a certain embodiment, "cycloalkyl" is a monocyclic $C_{3-8}$ cycloalkyl, in another embodiment, cyclohexyl, and in still another embodiment, indanyl. Here, when fused with a pyrrole ring, the cycloalkyl is fused to a carbon-carbon bond of the pyrrole ring.

The "halogen" is F, Cl, Br, or I, and in a certain embodiment, F or Cl.

The "halogeno-lower alkyl" is $C_{1-6}$ alkyl substituted with one or more halogen atoms, in a certain embodiment, $C_{1-6}$ alkyl substituted with 1 to 5 halogen atoms, and in another embodiment, difluoromethyl or trifluoromethyl.

The "aryl" is a $C_{6-14}$ monocyclic to tricyclic aromatic hydrocarbon ring group, in a certain embodiment, phenyl or naphthyl, and in another embodiment, phenyl.

The "heteroaryl" means a 5- to 14-membered, monocyclic to tricyclic aromatic heterocyclic group containing 1 to 6 hetero atoms selected from N, O, and S as a ring-constituting atom. The "heteroaryl" is, in a certain embodiment, monocyclic heteroaryl, for example, pyridyl, pyrimidinyl, triazinyl, furyl, thienyl, pyrrolyl, imidazolyl, pyrazolyl, tetrazolyl, oxazolyl, thiazolyl, isoxazolyl, or the like, in another embodiment, bicyclic heteroaryl, for example, indolyl, quinolyl, quinoxalinyl, or the like, and in still another embodiment, pyridyl, thienyl, or indolyl.

The "nitrogen-containing saturated heterocycle" is a 5- to 8-membered saturated heterocycle that contains one nitrogen atom as a ring-constituting atom and may further contain one or two hetero atoms selected from N, O, and S, and it may be fused with a benzene ring. Examples of the nitrogen-containing saturated heterocyclic group include azetidinyl, pyrrolidinyl, piperidyl, piperazinyl, azepanyl, diazepanyl, azocanyl, morpholinyl, thiomorpholinyl, tetrahydropyridinyl, and groups formed by fusion of any one of these ring groups with a benzene ring. The nitrogen-containing saturated heterocyclic group is, in another embodiment, pyrrolidinyl, piperidyl, piperazinyl, or indolin-1-yl, and in still another embodiment, pyrrolidinyl or indolin-1-yl.

The "monocyclic nitrogen-containing heteroaryl" means a monocycle containing a nitrogen atom as a ring-constituting atom among the "heteroaryl" above, and it is, in a certain embodiment, pyridyl, pyrimidinyl, thiazolyl, pyrazolyl, or oxadiazolyl, and in another embodiment, pyridyl.

The "heterocycloalkyl" is a 3- to 14-membered, saturated or partially unsaturated heterocyclic group that contains 1 to 6 hetero atoms selected from N, O, and S as a ring-constituting atom, and it may be bridged or fused. The "heterocycloalkyl" is, in a certain embodiment, azetidinyl, pyrrolidinyl, imidazolidinyl, piperidyl, pyrazolyl, piperazinyl, morpholinyl, thiomorpholyl, oxazolidinyl, tetrahydrofuranyl, tetrahydropyranyl, 1,3-dioxanyl, 1,4-dioxanyl, indolinyl, dihydrobenzofuranyl, or quinuclidinyl, and in another embodiment, pyrrolidinyl, piperidyl, or indolinyl.

The expression "optionally substituted" means non-substitution or substitution with 1 to 5 substituents. It is, in a certain embodiment, non-substitution or substitution with 1, 2, or 3 substituents, in another embodiment, non-substitution or substitution with 1 or 2 substituents, in still another embodiment, non-substitution or substitution with one substituent, in a further still another embodiment, substitution with two substituents, in a further still another embodiment, substitution with one substituent, and in a further still another embodiment, non-substitution. If it has a plurality of substituents, the substituents may be the same as or different from each other.

Examples of substituents of the "optionally substituted cycloalkyl", "optionally substituted heterocycloalkyl", "optionally substituted aryl", or "optionally substituted heteroaryl" in $A^1$ include, in a certain embodiment, a group selected from the group consisting of halogen, —CN, lower alkyl, and halogeno-lower alkyl. $A^1$ is, in a certain embodiment, cycloalkyl, heterocycloalkyl optionally substituted with one or more F atoms, aryl optionally substituted with one or more F atoms, or heteroaryl optionally substituted with one or more F atoms. Further, $A^1$ is, in another embodiment, unsubstituted cycloalkyl, unsubstituted heterocycloalkyl, unsubstituted aryl, or unsubstituted heteroaryl.

Examples of the substituents of the "optionally substituted cycloalkyl", "optionally substituted heterocycloalkyl", "optionally substituted aryl", and "optionally substituted heteroaryl" in $A^2$ include in a certain embodiment, a group selected from the group consisting of —OH, oxo, —OR$^0$, —O—R$^{00}$—CO$_2$R$^0$, —O—R$^{00}$—CO$_2$H, CO$_2$H, —CO—R$^0$, —NH$_2$, —NHR$^0$, —N(R$^0$)$_2$, —NH—R$^{00}$—OH, —CO$_2$H, —CO$_2$R$^0$, —SO$_2$—R$^0$, —R$^{00}$—CO$_2$H, CO$_2$H, —R$^{00}$—CO$_2$R$^0$, halogen, phenyl, morpholyl, (piperidyl optionally substituted with carboxy or alkoxycarbonyl), R$^0$, and halogeno-lower alkyl. A substituent is in another embodiment, R$^0$, halogen, or —CO$_2$H, and in still another embodiment, —CO$_2$H.

A substituted examples of the substituent of the "optionally substituted aryl" and "optionally substituted heteroaryl" in Group G$^2$ is, in a certain embodiment, a group selected from the group consisting of R$^0$, —OH, halogen, oxo, —CO$_2$H, and —OR$^0$. The substituent is, in another embodiment, methyl, F, Cl, or methoxy.

Group G$^2$ is, in one embodiment, unsubstituted aryl and unsubstituted heteroaryl.

Certain embodiments of the present invention are shown below.

(1) The compound of formula (I) or a salt thereof, wherein $A^1$ is cycloalkyl, or phenyl optionally substituted with one or more halogen atoms; in another embodiment, the compound of formula (I) or a salt thereof, wherein $A^1$ is cyclohexyl, or phenyl optionally substituted with one or more F atoms; in still another embodiment, the compound of the formula (I) or a salt thereof, wherein $A^1$ is cyclohexyl; in further still another embodiment, the compound of the formula (I) or a salt thereof, wherein $A^1$ is phenyl optionally substituted with one or more F atoms; and in further still another embodiment, the compound of the formula (I) or a salt thereof, wherein $A^1$ is cyclohexyl, 2-fluorophenyl, 2,3-difluorophenyl, 2,6-difluorophenyl, or 2,3,6-trifluorophenyl.

(2) The compound of formula (I) or a salt thereof, wherein $R^1$ is H.

(3) The compound of formula (I) or a salt thereof, wherein $R^2$ is methyl.

(4) The compound of formula (I) or a salt thereof, wherein $R^3$ is H.

(5) The compound of formula (I) or a salt thereof, wherein $R^4$ is —Y-$A^2$; and in another embodiment, the compound of formula (I) or a salt thereof, wherein $R^4$ is $A^3$.

(5-1) The compound of formula (I) or a salt thereof, wherein $R^4$ is —Y-$A^2$, and $A^2$ is H, —OH, or —$CONH_2$, or phenyl, pyridyl, pyrimidinyl, triazinyl, pyrrolyl, pyrazolyl, thienyl, furyl, thiazolyl, oxazolyl, isoxazolyl, isoxadiazolyl, tetrazolyl, quinoxalinyl, piperidyl, piperazyl, morpholyl, thiomorpholyl, tetrahydropyranyl, tetrahydrothiopyranyl, quinuclidyl, or monocyclic $C_{3-8}$ cycloalkyl, each of which is optionally substituted with at least one group selected from the group consisting of —OH, oxo, —$OR^0$, —O—$R^{00}$—$CO_2R^0$, —O—$R^{00}$—$CO_2H$, —CO—$R^0$, —$NH_2$, —$NHR^0$, —$N(R^0)_2$, —NH—$R^{00}$—OH, —$CO_2H$, —$CO_2R^0$, —$SO_2$—$R^0$, —$R^{00}$—$CO_2H$, —$R^{00}$—$CO_2R^0$, halogen, phenyl, morpholyl, (piperidyl optionally substituted with carboxy or alkoxycarbonyl), $R^0$, and halogeno-lower alkyl; in another embodiment, the compound of formula (I) or a salt thereof, wherein $R^4$ is —Y-$A^2$, and $A^2$ is H, pyridyl, or phenyl optionally substituted with at least one group selected from the group consisting of $R^0$, halogen, and —$CO_2H$; and in still another embodiment, the compound of formula (I) or a salt thereof, wherein $R^4$ is —Y-$A^2$, and $A^2$ is H, pyridyl, or phenyl optionally substituted with —$CO_2H$.

(5-2) The compound of formula (I) or a salt thereof, wherein $R^4$ is —Y-$A^2$, and Y is $C_{1-10}$ alkylene optionally substituted with at least one group selected from Group $G^2$, $C_{2-10}$ alkenylene optionally substituted with at least one group selected from Group $G^2$, or —$SO_2$— (lower alkylene optionally substituted with at least one group selected from Group $G^2$)-; in another embodiment, the compound of formula (I) or a salt thereof, wherein $R^4$ is —Y-$A^2$, and Y is $C_{1-10}$ alkylene optionally substituted with at least one group selected from Group $G^2$ or $C_{2-10}$ alkenylene optionally substituted with at least one group selected from Group $G^2$; in still another embodiment, the compound of formula (I) or a salt thereof, wherein $R^4$ is —Y-$A^2$, and Y is $C_{1-6}$ alkylene optionally substituted with at least one group selected from Group $G^2$. Here, Group $G^2$ is, in a certain embodiment, phenyl, pyridyl, thienyl, cyclopentyl, cyclohexyl, —$CO_2H$, —$CO_2R^0$, —OH, and —$OR^0$, each of which is optionally substituted with at least one group selected from the group consisting of halogen, —$OR^0$, and $R^0$; in another embodiment, pyridyl, phenyl, and cyclohexyl; in still another embodiment, —$CO_2H$, —$CO_2R^0$, —OH, and —$OR^0$; and in a further still another embodiment, —$CO_2H$, —$CO_2R^0$, and —OH.

(5-3) The compound of formula (I) or a salt thereof, wherein $R^4$ is $A^3$, and $A^3$ is cycloalkyl or heterocycloalkyl; in another embodiment, the compound of formula (I) or a salt thereof, wherein $R^4$ is $A^3$ and $A^3$ is heterocycloalkyl; in still another embodiment, the compound of formula (I) or a salt thereof, wherein $R^4$ is $A^3$ and $A^3$ is cycloalkyl; in a further still another embodiment, the compound of formula (I) or a salt thereof, wherein $R^4$ is $A^3$, and $A^3$ is pyrrolidyl optionally substituted with at least one group selected from Group $G^1$, piperidyl optionally substituted with at least one group selected from Group $G^1$, or piperazyl optionally substituted with at least one group selected from Group $G^1$; in a further still another embodiment, the compound of formula (I) or a salt thereof, wherein $R^4$ is $A^3$, and $A^3$ is monocyclic $C_{3-8}$ cycloalkyl optionally substituted with at least one group selected from Group $G^1$, or indanyl optionally substituted with at least one group selected from Group $G^1$; in a further still another embodiment, the compound of formula (I) or a salt thereof, wherein $R^4$ is $A^3$, $A^3$ is piperidyl optionally substituted with at least one group selected from Group $G^1$, or pyrrolidyl optionally substituted with at least one group selected from Group $G^1$; and in a further still another embodiment, the compound of formula (I) or a salt thereof, wherein $R^4$ is $A^3$, and $A^3$ is indanyl optionally substituted with at least one group selected from Group $G^1$. Here, the compound of formula (I) or a salt thereof, wherein Group $G^1$ includes, in a certain embodiment, $R^0$, —$R^{00}$—OH, halogen, oxo, —OH, —$OR^0$, —CO—$R^0$, —CO—$R^{00}$—OH, —$CO_2H$, —$CO_2R^0$, —CO—$NH_2$, —$CO_2$—$R^{00}$-(phenyl), —$SO_2$—$R^0$, —$SO_2$—$NH_2$, —$SO_2$—$NHR^0$, —$SO_2$—$R^{00}$—$CO_2H$, —$SO_2$—$R^{00}$—$CO_2R^0$, —$SO_2$-(phenyl), —$R^{00}$—$CO_2H$, —$R^{00}$—$CO_2R^0$, —$R^{00}$-(phenyl), cycloalkyl, phenyl, -(phenylene)-$CO_2R^0$, -(piperidinediyl)-$R^0$, —$R^{00}$-(phenylene)-$CO_2H$, and —$R^{00}$-(phenylene)-$CO_2R^0$; Group $G^1$ is, in another embodiment, halogen, —OH, —$CO_2H$, —$CO_2R^0$, —$CO_2$—$R^{00}$-(phenyl), —$SO_2$—$R^{00}$—$CO_2R^0$, —$R^{00}$—$CO_2H$, —$R^{00}$—$CO_2R^0$, and phenyl; in still another embodiment, $R^0$; in a further still another embodiment, halogen, $R^0$, —$CO_2H$, and —OH; in a further still another embodiment, halogen, $R^0$, —$CO_2H$, and —OH; and in a further still another embodiment, —OH, phenyl, and —$SO_2$—$NH_2$.

(5-4) The compound of formula (I) or a salt thereof, which is selected from a compound group including the following (5-5) and (5-6).

(5-5) The compound of formula (I) or a salt thereof, wherein $R^4$ is $A^3$, $A^3$ is heterocycloalkyl, and Group $G^1$ is $R^0$, —$R^{00}$—OH, halogen, oxo, —OH, —$OR^0$, —CO—$R^0$, —CO—$R^{00}$—OH, —$CO_2H$, —$CO_2R^0$, —CO—$NH_2$, —$CO_2$—$R^{00}$-(phenyl), —$SO_2$—$R^0$, —$SO_2$—$NH_2$, —$SO_2$—$NHR^0$, —$SO_2$—$R^{00}$—$CO_2H$, —$SO_2$—$R^{00}$—$CO_2R^0$, —$SO_2$-(phenyl), —$R^{00}$—$CO_2H$, —$R^{00}$—$CO_2R^0$, —$R^{00}$-(phenyl), cycloalkyl, phenyl, -(phenylene)-$CO_2R^0$, -(piperidinediyl)-$R^0$, —$R^{00}$-(phenylene)-$CO_2H$, and —$R^{00}$-(phenylene)-$CO_2R^0$.

(5-6) The compound of formula (I) or a salt thereof, wherein $R^4$ is $A^3$, $A^3$ is cycloalkyl, and Group $G^1$ is $R^0$, halogen, —OH, —$CO_2H$, —$CO_2R^0$, —$CO_2$—$R^{00}$-(phenyl), —$SO_2$—$R^{00}$—$CO_2R^0$, —$R^{00}$—$CO_2H$, —$R^{00}$—$CO_2R^0$, and phenyl.

(5-7) The compound of formula (I) or a salt thereof, wherein $R^4$ is $A^3$, $A^3$ is cycloalkyl, and Group $G^1$ is halogen and $R^0$.

(5-8) The compound of formula (I) or a salt thereof, wherein $R^4$ is —Y-$A^2$, Y is $C_{1-10}$ alkylene, $C_{2-10}$ alkenylene, or —$SO_2$—$R^{00}$—, Group $G^2$ is —$CO_2H$, —$CO_2R^0$, —OH, and —$OR^0$, and $A^2$ is H, —OH or —$CONH_2$, or phenyl, pyridyl, pyrimidinyl, triazinyl, pyrrolyl, pyrazolyl, thienyl, furyl, thiazolyl, oxazolyl, isoxazolyl, isoxadiazolyl, tetrazolyl, quinoxazolyl, piperidyl, piperazyl, morpholyl, thiomorpholyl, tetrahydropyranyl, tetrahydrothiopyranyl, quinuclidyl, or monocyclic $C_{3-8}$ cycloalkyl, each of which is optionally substituted with at least one group selected from the group consisting of —OH, oxo, —OR$^0$, —O—R$^{00}$—CO$_2$R$^0$, —O—R$^{00}$—CO$_2$H, —CO—R$^0$, —NH$_2$, —CO$_2$H, —CO$_2$R$^0$, —SO$_2$—R$^0$, R$^{00}$—CO$_2$H, halogen, phenyl, morpholyl, 4-carboxypiperidyl, 4-alkoxycarbonylpiperidyl, 3-alkoxycarbonylpiperidyl, 3-carboxypiperidyl, R$^0$, and halogeno-lower alkyl.

(5-9) The compound of formula (I) or a salt thereof, which is selected from the group consisting of the following (5-10), (5-11), and (5-13).

(5-10) The compound of formula (I) or a salt thereof, wherein R$^4$ is A$^3$, A$^3$ is pyrrolidyl optionally substituted with at least one group selected from Group G$^1$, piperidyl optionally substituted with at least one group selected from Group G$^1$, or piperazyl optionally substituted with at least one group selected from Group G$^1$, and Group G$^1$ is R$^0$.

(5-11) The compound of formula (I) or a salt thereof, wherein R$^4$ is A$^3$, A$^3$ is monocyclic $C_{3-8}$ cycloalkyl optionally substituted with at least one group selected from Group G$^1$, or indanyl optionally substituted with at least one group selected from Group G$^1$, and Group G$^1$ is halogen, —CO$_2$H, and —OH.

(5-12-1) The compound of formula (I) or a salt thereof, wherein R$^4$ is A$^3$, A$^3$ is monocyclic $C_{3-8}$ cycloalkyl or indanyl, each optionally substituted with at least one group selected from Group G$^1$, and Group G$^1$ is —CO$_2$H, —OH, halogen, and R$^0$.

(5-12-2) The compound of formula (I) or a salt thereof, wherein R$^4$ is A$^3$, A$^3$ is indanyl optionally substituted with at least one group selected from Group G$^1$, and Group G$^1$ is halogen, —CO$_2$H, —CO$_2$R$^0$, —R$^{00}$—OH, and —OH.

(5-12-3) The compound of formula (I) or a salt thereof, wherein R$^4$ is A$^3$, A$^3$ is tetrahydronaphthyl optionally substituted with at least one group selected from Group G$^1$, and Group G$^1$ is —CO$_2$H and —CO$_2$R$^0$.

(5-12-4) The compound of formula (I) or a salt thereof, wherein R$^4$ is A$^3$, A$^3$ is dihydrobenzofuranyl optionally substituted with at least one group selected from Group G$^1$, and Group G$^1$ is —CO$_2$H and —CO$_2$R$^0$.

(5-13) The compound of formula (I) or a salt thereof, wherein R$^4$ is Y is $C_{1-10}$ alkylene optionally substituted with at least one group selected from Group G$^2$, or $C_{2-10}$ alkenylene optionally substituted with at least one group selected from Group G$^2$, Group G$^2$ is —CO$_2$H, —CO$_2$R$^0$, and —OH, and A$^2$ is H, or phenyl optionally substituted with at least one group selected from the group consisting of R$^0$, halogen, and —CO$_2$H.

(5-14) The compound of formula (I) or a salt thereof, wherein R$^4$ is A$^3$, A$^3$ is a group represented by the following formula (A) or (B):

[Chem. 9]

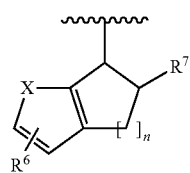

(A)

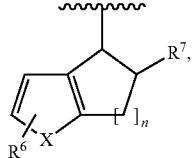

(B)

R$^6$ is H, halogen, or lower alkyl, R$^7$ is —CO$_2$H, —CO$_2$R$^0$, —CN, —NO$_2$, —SO$_3$H, or —SO$_3$R$^0$, X is NH, NR$^0$, O, S, or —HC=CH—, and n is 1 or 2.

(5-14-1) The compound or a salt thereof according to (5-14), wherein R$^4$ is A$^3$ and A$^3$ is a group represented by the formula (A).

(5-14-2) The compound or a salt thereof according to (5-14), wherein R$^4$ is A$^3$ and A$^3$ is a group represented by the formula (B).

(5-14-3) The compound or a salt thereof according to (5-14), wherein R$^4$ is A$^3$, A$^3$ is a group represented by the formula (A) or the formula (B), and X is —HC=CH—.

(5-14-4) The compound or a salt thereof according to (5-14), wherein R$^4$ is A$^3$, A$^3$ is a group represented by the formula (A), and X is S.

(5-14-5) The compound or a salt thereof according to (5-14), wherein R$^4$ is A$^3$, A$^3$ is a group represented by the formula (B), and X is S.

(5-14-6) The compound or a salt thereof according to (5-14), wherein R$^4$ is A$^3$, A$^3$ is a group represented by the formula (A) or the formula (B), X is —HC=CH—, and n is 1.

(5-14-7) The compound or a salt thereof according to (5-14), wherein R$^4$ is A$^3$, A$^3$ is a group represented by the formula (A) or the formula (B), X is —HC=CH—, and n is 2.

(5-14-8) The compound or a salt thereof according to (5-14), wherein R$^4$ is A$^3$, A$^3$ is a group represented by the formula (A) or the formula (B), X is —HC=CH—, and R$^6$ is H, F, or methyl, in another embodiment, R$^6$ is F or methyl, in still another embodiment, R$^6$ is H, in still another embodiment, R$^6$ is F, and in a further still another embodiment, R$^6$ is methyl.

(5-14-9) The compound or a salt thereof according to (5-14), wherein R$^4$ is A$^3$, A$^3$ is a group represented by the formula (A) or the formula (B), X is —HC=CH—, and R$^7$ is —CO$_2$H or —CO$_2$R$^0$, in still another embodiment, R$^7$ is —CO$_2$H, and in a further still another embodiment, R$^7$ is —CO$_2$R$^0$.

(5-14-10) The compound or a salt thereof according to (5-14), wherein X is S or —HC=CH—.

(5-15) The compound of formula (I) or a salt thereof, wherein R$^4$ is —Y-A$^2$, —Y-A$^2$ is a group represented by the following formula (C) or (D):

[Chem. 10]

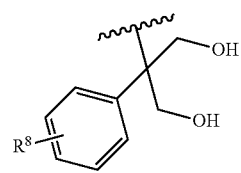

(C)

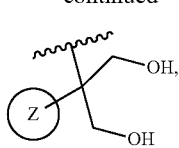

(D)

$R^8$ is H or lower alkyl, and Ring Z is unsubstituted pyridyl.

(5-16) The compound of formula (I) or a salt thereof, wherein $R^4$ is $A^3$, $A^3$ is 1,3-dioxane optionally substituted with at least one group selected from Group $G^1$, and Group $G^1$ is phenyl optionally substituted with $R^0$, $R^0$, and pyridyl.

(5-17) The compound of formula (I) or a salt thereof, wherein $R^4$ is $-Y-A^2$, $-Y-A^2$ is a group represented by the following formula (E):

[Chem. 11]

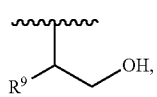

(E)

and $R^9$ is phenyl or lower alkyl.

(5-18) The compound of formula (I) or a salt thereof, wherein $R^4$ is $A^3$, $A^3$ is a group represented by the following formula (F):

[Chem. 12]

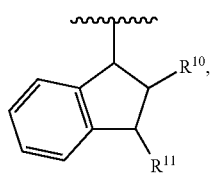

(F)

$R^{10}$ is H or $-$OH, and $R^{11}$ is H or $-$OH.

(5-19) The compound of formula (I) or a salt thereof, wherein $R^4$ is $-Y-A^2$, $-Y-A^2$ is a group represented by the following formula (G):

[Chem. 13]

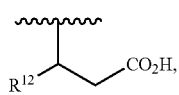

(G)

and $R^{12}$ is lower alkyl, cycloalkyl, or phenyl.

(6) The compound of the formula (I) or a salt thereof, wherein $R^5$ is each H; and in another embodiment, the compound of the formula (I) or a salt thereof, wherein any one of $R^5$'s is H and another one is $R^0$.

(7) The compound or a salt thereof, including the combinations of two or more of the groups as described in (1) to (4), (5) to (5-5), (5-9) to (5-12), (5-13), and (6).

(7-1) The compound or a salt thereof, including the combinations of two or more of the groups as described in (1) to (4), (5-6), (5-7), (5-12-1), (5-14), and (5-14-1) to (5-14-9).

(7-2) The compound or a salt thereof, including the combinations of two or more of the groups as described in (1) to (4), (5-12-2) to (5-12-4), (5-15-1), and (5-16) to (5-18).

Examples of the compound that is a combination of two or more of the groups as described in (1) to (6) include the following compounds or salts thereof.

(8) The compound of the formula (I) or a salt thereof, wherein $R^3$ is H and $R^5$ is each H.

(9) The compound or a salt thereof according to (8), wherein $R^2$ is methyl and $R^1$ is H.

(10) The compound or a salt thereof according to (9), wherein $A^1$ is cyclohexyl or phenyl optionally substituted with one or more F atoms.

(11a) The compound or a salt thereof, which is selected from the compound group consisting of the following (11-1), (11-2), and (11-3).

(11-1) The compound or a salt thereof according to (10), wherein $R^4$ is $A^3$, $A^3$ is pyrrolidyl optionally substituted with at least one group selected from Group $G^1$ or piperidyl optionally substituted with at least one group selected from Group $G^1$, and Group $G^1$ is $R^0$.

(11-2) The compound or a salt thereof according to (10), wherein $R^4$ is $A^3$, $A^3$ is indanyl optionally substituted with at least one group selected from Group $G^1$, and Group $G^1$ is halogen, $-CO_2H$, and $-OH$.

(11-3) The compound or a salt thereof according to (10), wherein $R^4$ is $-Y-A^2$, Y is $C_{1-10}$ alkylene optionally substituted with at least one group selected from Group $G^2$, Group $G^2$ is $-CO_2H$ and $-OH$, and $A^2$ is H, or phenyl optionally substituted with $-CO_2H$.

(11b) The compound or a salt thereof, which is selected from the compound group consisting of (11-1), and the following (11-4) and (11-5).

(11-4) The compound or a salt thereof according to (10), wherein $R^4$ is $A^3$, $A^3$ is indanyl optionally substituted with at least one group selected from Group $G^1$, and Group $G^1$ is halogen, $R^0$, $-CO_2H$, and $-OH$.

(11-5) The compound or a salt thereof according to (10), wherein $R^4$ is $-Y-A^2$, Y is $C_{1-10}$ alkylene optionally substituted with at least one group selected from Group $G^2$, Group $G^2$ is $-CO_2H$ and $-OH$, and $A^2$ is H, or phenyl optionally substituted with at least one group selected from the group consisting of $R^0$, halogen, and $-CO_2H$.

(11-6) The compound or a salt thereof according to (10), wherein $R^4$ is $-Y-A^2$, $-Y-A^2$ is a group represented by the formula (C), and $R^{8a}$ is H.

(11-7) The compound or a salt thereof according to (10), wherein $R^4$ is $A^3$, $A^3$ is cyclopentyl or piperidyl each of which is optionally substituted with at least one group selected from Group $G^1$, and Group $G^1$ is $-OH$, phenyl, and $-SO_2-NH_2$.

(11-8) The compound or a salt thereof according to (10), wherein $R^4$ is $A^3$, $A^3$ is indanyl optionally substituted with at least one group selected from Group $G^1$, and Group $G^1$ is $-CO_2H$ and $-OH$.

(11-9) The compound of formula (I) or a salt thereof, wherein $A^1$ is cyclohexyl, or phenyl optionally substituted with one or more F atom, $R^1$ is H, $R^2$ is $R^0$, $R^3$ is H, $R^5$ is H, $R^4$ is $-Y-A^2$ or $A^3$, Y is $C_{1-10}$ alkylene optionally substituted with at least one group selected from Group $G^2$, Group $G^2$ is $-CO_2H$ and $-OH$, $A^2$ is H, cycloalkyl, pyridyl, or phenyl optionally substituted with a group selected from lower alkyl and $-CO_2H$, $A^3$ is cycloalkyl selected from the group consisting of cyclopentyl, indanyl, dihydrocyclopentathienyl, dihydrocyclopentafuranyl, and dihydrocyclopentapyrrolyl, the above cycloalkyl is optionally substituted with at least one group selected from Group G¹, or piperidyl or pyrrolidyl each optionally substituted with at least one group selected from Group G¹, and Group G¹ is R⁰, halogen, —CO₂H, —OH, —CO₂R⁰, —CN, —NO₂, phenyl, —SO₂—NH₂, —SO₃H, and —SO₃R⁰.

(12) The compound of formula (I) or a salt thereof, wherein A¹ is cycloalkyl optionally substituted or aryl optionally substituted, R¹ is H, R⁰, halogen, —CN, —CO₂H, —CO₂R⁰, or —R⁰⁰—OH, R² is H, R⁰, or halogeno-lower alkyl, R³ is H, R⁰, —R⁰⁰—CO₂H, or —R⁰⁰—CO₂R⁰, R⁴ is A³, A³ is a group represented by the formula (A) or (B), R⁶ is H, halogen, or lower alkyl, R⁷ is —CO₂H, —CO₂R⁰, —CN, —NO₂, —SO₃H, or —SO₃R⁰, X is NH, NR⁰, O, S, or —HC=CH—, and n is 1 or 2.

(12-1) The compound or a salt thereof as described in (11-9), wherein A¹ is cyclohexyl, 2-fluorophenyl, 2,3-difluorophenyl, 2,6-difluorophenyl, or 2,3,6-trifluorophenyl, R⁴ is a group represented by any one of the following formulae (A), (B), (C), (D), (E), (F), or (G):

[Chem. 14]

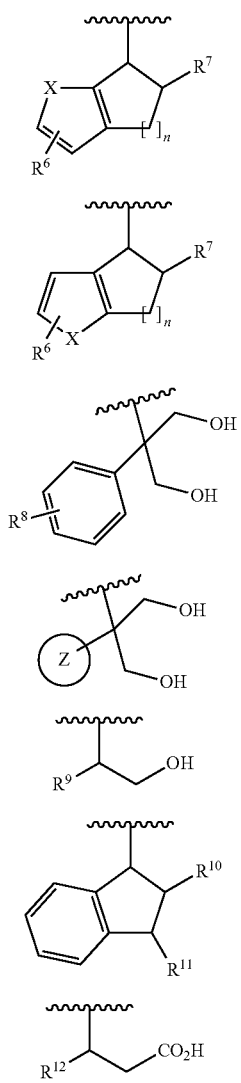

wherein R⁶ is H, halogen, or R⁰, R⁷ is —CO₂H, —CO₂R⁰, —CN, —NO₂, —SO₃H, or —SO₃R⁰, X is NH, NR⁰, O, S, or —HC=CH—, n is 1 or 2, R⁸ is H or lower alkyl, Z is pyridyl, R⁹ is phenyl or lower alkyl, R¹⁰ is H or —OH, R¹¹ is H or —OH, and R¹² is lower alkyl, cycloalkyl, or phenyl.

(12-2) The compound of formula (I) or a salt thereof, wherein A¹ is cyclohexyl, 2-fluorophenyl, 2,3-difluorophenyl, 2,6-difluorophenyl, or 2,3,6-trifluorophenyl, R¹ is H, R² is R⁰, R³ is H, R⁴ is —Y-A², Y is C₁₋₁₀ alkylene optionally substituted with at least one group selected from Group G², Group G² is —CO₂H and —OH, and A² is H, or phenyl optionally substituted with —CO₂H.

(12-2-1) The compound or a salt thereof as described in (12-1), wherein R² is methyl and R⁴ is a group represented by the formula (C) or (D).

(12-2-2) The compound or a salt thereof as described in (12-1), wherein R² is methyl and R⁴ is a group represented by the formula (E).

(12-3) The compound of formula (I) or a salt thereof, wherein A¹ is cyclohexyl, 2-fluorophenyl, 2,3-difluorophenyl, 2,6-difluorophenyl, or 2,3,6-trifluorophenyl, R¹ is H, R² is R⁰, R³ is H, R⁴ is A³, A³ is indanyl optionally substituted with at least one group selected from Group G¹, and Group G¹ is halogen, —CO₂H, and —OH.

(12-4) The compound of formula (I) or a salt thereof, wherein A¹ is cyclohexyl, 2-fluorophenyl, 2,3-difluorophenyl, 2,6-difluorophenyl, or 2,3,6-trifluorophenyl, R¹ is H, R² is R⁰, R³ is H, R⁴ is A³, A³ is cyclopentyl or piperidyl, and Group G¹ is —OH, phenyl, and —SO₂—NH₂.

(12-5) The compound of formula (I) or a salt thereof, wherein A¹ is cyclohexyl, 2-fluorophenyl, 2,3-difluorophenyl, 2,6-difluorophenyl, or 2,3,6-trifluorophenyl, R¹ is H, R² is R⁰, R³ is H, R⁴ is A³, R⁵ is H, A³ is indanyl optionally substituted with at least one group selected from Group G¹, and Group G¹ is —CO₂H and —OH.

(13) The compound or a salt thereof as described in (12-1), wherein A¹ is 2,6-difluorophenyl, R² is methyl, R⁴ is A³, A³ is a group represented by the formula (A) or the formula (B), X is —HC=CH—, n is 1, R⁵ is each H, R⁶ is F or methyl, and R⁷ is —CO₂H.

(14) The compound or a salt thereof as described in (13), wherein R⁶ is F.

(15) The compound or a salt thereof as described in (13), wherein R⁶ is methyl.

(16) The compound or a salt thereof as described in (12), wherein A¹ is cycloalkyl, R¹ is H, R² is methyl, R³ is H, X is —HC=CH—, n is 1, R⁵ is each H, R⁶ is F or methyl, and R⁷ is —CO₂H.

(17) The compound or a salt thereof as described in (16), wherein R⁶ is F.

(17-1) The compound or a salt thereof as described in (12-1), wherein A¹ is cyclohexyl or 2,6-difluorophenyl, R² is methyl, R⁴ is A³, A³ is a group represented by the formula (A) or the formula (B), X is —HC=CH—, n is 1, R⁵ is each H, R⁶ is H, and R⁷ is —CO₂H.

(18) The compound or a salt thereof as described in (16), wherein R⁶ is methyl.

(19) The compound of formula (I) or a salt thereof, wherein A¹ is 2,3,6-trifluorophenyl, R¹ is H, R² is methyl, R³ is H, R⁴ is A³, A³ is a group represented by the formula (A) or the formula (B), X is —HC=CH—, n is 1, R⁵ is each H, R⁶ is H, and R⁷ is —CO₂H.

(20) The compound of formula (I) or a salt thereof, wherein A¹ is cycloalkyl, R¹ is H, R² is methyl, R³ is H, R⁴ is A³, A³ is a group represented by the formula (A) or the formula (B), X is —HC=CH—, n is 1, R⁵ is each H, R⁶ is H, and R⁷ is —CO₂H.

(21) The compound of formula (I) or a salt thereof, wherein A¹ is 2,6-difluorophenyl, R¹ is H, R² is methyl, R³ is H, R⁴ is A³, A³ is a group represented by the formula (A) or the formula (B), X is —HC═CH—, n is 1, R⁵ is each H, R⁶ is H, and R⁷ is —CO₂H.

(22) The compound or a salt thereof as described in (12-1), wherein R² is methyl and R⁴ is a group represented by the formula (F).

(23) The compound of or a salt thereof as described in (12-1), wherein R² is methyl and R⁴ is a group represented by the formula (G).

Examples of the specific compounds included in the present invention are the following compounds.

Compounds or salts thereof selected from the group consisting of:

(3S)-3-({[8-(cyclohexylmethoxy)-2-methylimidazo[1,2-a]pyridin-3-yl]carbonyl}amino)-3-phenylpropanoic acid,
(1S,2R)-1-[({8-[(2,6-difluorobenzyl)oxy]-2-methylimidazo[1,2-a]pyridin-3-yl}carbonyl)amino]indane-2-carboxylic acid,
(1S,2R)-1-({[8-(cyclohexylmethoxy)-2-methylimidazo[1,2-a]pyridin-3-yl]carbonyl}amino)indane-2-carboxylic acid,
(1R,2S)-1-({[8-(cyclohexylmethoxy)-2-methylimidazo[1,2-a]pyridin-3-yl]carbonyl}amino)indane-2-carboxylic acid,
8-[(2,6-difluorobenzyl)oxy]-N-(1,3-dihydroxy-2-phenylpropan-2-yl)-2-methylimidazo[1,2-a]pyridine-3-carboxamide,
(1S,2R)-1-[({8-[(2,6-difluorobenzyl)oxy]-2-methylimidazo[1,2-a]pyridin-3-yl}carbonyl)amino]-7-fluoroindane-2-carboxylic acid,
(1S,2R)-1-[({8-[(2,6-difluorobenzyl)oxy]-2-methylimidazo[1,2-a]pyridin-3-yl}carbonyl)amino]-4-methylindane-2-carboxylic acid,
(1S,2R)-1-({[8-(cyclohexylmethoxy)-2-methylimidazo[1,2-a]pyridin-3-yl]carbonyl}amino)-5-fluoroindane-2-carboxylic acid,
(1S,2R)-1-({[8-(cyclohexylmethoxy)-2-methylimidazo[1,2-a]pyridin-3-yl]carbonyl}amino)-7-fluoroindane-2-carboxylic acid,
(1R,2S)-1-({[8-(cyclohexylmethoxy)-2-methylimidazo[1,2-a]pyridin-3-yl]carbonyl}amino)-7-fluoroindane-2-carboxylic acid,
(1S,2R)-1-({[8-(cyclohexylmethoxy)-2-methylimidazo[1,2-a]pyridin-3-yl]carbonyl}amino)-4-methylindane-2-carboxylic acid,
(1S,2R)-1-[({2-methyl-8-[(2,3,6-trifluorobenzyl)oxy]imidazo[1,2-a]pyridin-3-yl}carbonyl)amino]indane-2-carboxylic acid,
8-[(2,6-difluorobenzyl)oxy]-N-[(1R)-2-hydroxy-1-phenylethyl]-2-methylimidazo[1,2-a]pyridine-3-carboxamide,
8-[(2,6-difluorobenzyl)oxy-N-[(1R,2R)-2-hydroxy-2,3-dihydro-1H-inden-1-yl]-2-methylimidazo[1,2-a]pyridine-3-carboxamide,
8-[(2,3-difluorobenzyl)oxy]-N-(1,3-dihydroxy-2-phenylpropan-2-yl)-2-methylimidazo[1,2-a]pyridine-3-carboxamide,
8-[(2,6-difluorobenzyl)oxy]-N-[1,3-dihydroxy-2-(pyridin-2-yl)propan-2-yl]-2-methylimidazo[1,2-a]pyridine-3-carboxamide,
8-(cyclohexylmethoxy)-N-[(1R)-2-hydroxy-1-phenylethyl]-2-methylimidazo[1,2-a]pyridine-3-carboxamide,
8-[(2,6-difluorobenzyl)oxy]-N-[(2R)-1-hydroxypropan-2-yl]-2-methylimidazo[1,2-a]pyridine-3-carboxamide,
8-[(2,6-difluorobenzyl)oxy]-N-[(2R)-1-hydroxy-3-methylbutan-2-yl]-2-methylimidazo[1,2-a]pyridine-3-carboxamide, and
N-(1,3-dihydroxy-2-phenylpropan-2-yl)-8-[(2-fluorobenzyl)oxy]-2-methylimidazo[1,2-a]pyridine-3-carboxamide.

Furthermore, the following compounds are examples of specific compounds included in the present invention.

Compounds or salts thereof selected from the group consisting of:

8-[(2,6-difluorobenzyl)oxy]-N-[(1R,2S,3S)-2,3-dihydroxy-2,3-dihydro-1H-inden-1-yl]-2-methylimidazo[1,2-a]pyridine-3-carboxamide,
8-[(2,3-difluorobenzyl)oxy]-N-[(1R,2S,3S)-2,3-dihydroxy-2,3-dihydro-1H-inden-1-yl]-2-methylimidazo[1,2-a]pyridine-3-carboxamide, and
N-[(1R,2S,3S)-2,3-dihydroxy-2,3-dihydro-1H-inden-1-yl]-8-[(2-fluorobenzyl)oxy]-2-methylimidazo[1,2-a]pyridine-3-carboxamide.

Still further, the following compounds are examples of specific compounds included in the present invention.

Compounds or salts thereof selected from the group consisting of:

8-[(2,6-difluorobenzyl)oxy]-N-[(1R,2S,3R)-2,3-dihydroxy-2,3-dihydro-1H-inden-1-yl]-2-methylimidazo[1,2-a]pyridine-3-carboxamide,
8-[(2,3-difluorobenzyl)oxy]-N-[(1R,2S,3R)-2,3-dihydroxy-2,3-dihydro-1H-inden-1-yl]-2-methylimidazo[1,2-a]pyridine-3-carboxamide, and
N-[(1R,2S,3R)-2,3-dihydroxy-2,3-dihydro-1H-inden-1-yl]-8-[(2-fluorobenzyl)oxy]-2-methylimidazo[1,2-a]pyridine-3-carboxamide.

Still further, the following compounds are examples of specific compounds included in the present invention.

Compounds or pharmaceutically acceptable salts thereof selected from the group consisting of:

8-[(2,6-difluorobenzyl)oxy]-N-[(1r,3R,4S)-3,4-dihydroxy-1-phenylcyclopentyl]-2-methylimidazo[1,2-a]pyridine-3-carboxamide and
8-[(2,6-difluorobenzyl)oxy]-N-[(1s,3R,4S)-3,4-dihydroxy-1-phenylcyclopentyl]-2-methylimidazo[1,2-a]pyridine-3-carboxamide.

Still further, the following compounds are examples of specific compounds included in the present invention.

Compounds or salts thereof selected from the group consisting of:

8-(cyclohexylmethoxy)-2-methyl-N-[(3S)-1-methylpiperidin-3-yl]imidazo[1,2-a]pyridine-3-carboxamide,
(3R)-3-({[8-(cyclohexylmethoxy)-2-methylimidazo[1,2-a]pyridin-3-yl]carbonyl}amino)-5-methylhexanoic acid,
8-(cyclohexylmethoxy)-N-(1,3-dihydroxypropan-2-yl)-2-methylimidazo[1,2-a]pyridine-3-carboxamide,
8-(cyclohexylmethoxy)-2-methyl-N-[(3S)-1-methylpyrrolidin-3-yl]imidazo[1,2-a]pyridine-3-carboxamide,
3-[(1S)-1-({[8-(cyclohexylmethoxy)-2-methylimidazo[1,2-a]pyridin-3-yl]carbonyl}amino)ethyl]benzoic acid,
8-[(2,6-difluorobenzyl)oxy]-N-(1-hydroxy-2-methylpropan-2-yl)-2-methylimidazo[1,2-a]pyridine-3-carboxamide,
8-[(2,6-difluorobenzyl)oxy]-N-[(1R,2S)-2,3-dihydroxy-1-phenylpropyl]-2-methylimidazo[1,2-a]pyridine-3-carboxamide,
(3R)-4-cyclobutyl-3-({[8-(cyclohexylmethoxy)-2-methylimidazo[1,2-a]pyridin-3-yl]carbonyl}amino)butanoic acid,
8-[(2,6-difluorobenzyl)oxy]-2-methyl-N-[(3S)-1-sulfamoylpiperidin-3-yl]imidazo[1,2-a]pyridine-3-carboxamide, and
8-[(2,6-difluorobenzyl)oxy]-2-methyl-N-[(3S)-piperidin-3-yl]imidazo[1,2-a]pyridine-3-carboxamide.

The compound of formula (I) may exist in the form of tautomers or geometrical isomers depending on the kind of substituents. In the present specification, the compound of formula (I) shall be described in only one isomer form, yet the present invention includes any other isomers, in their isolated form, or as mixtures thereof.

In addition, the compound of formula (I) may have asymmetric carbon atoms or axial asymmetries in some cases, and therefore, optical isomers may exist based thereon. The present invention includes both isolated forms of optical isomers of the compound of formula (I) or any mixture thereof.

Moreover, the present invention also includes a pharmaceutically acceptable prodrugs of the compound of formula (I). Pharmaceutically acceptable prodrugs are compounds having groups that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Drug Design, 163-198.

Furthermore, salts of the compound of formula (I) are pharmaceutically acceptable salts of the compound of formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystalline substances of the compound of formula (I) or d a salt thereof. In addition, the present invention also includes compounds labeled with various radioactive or non-radioactive isotopes.

(Preparation Methods)

The compound of formula (I) and salts thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4$^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, prodrugs of the compound of formula (I) can be prepared by introducing a specific group or by carrying out the reaction using the obtained compound of formula (I) at the stage from a starting material to an intermediate, just as in the case of the above-mentioned protective group. The reaction can be carried out using methods known to a person skilled in the art, such as ordinary esterification, amidation, dehydration, and the like.

Hereinbelow, representative preparation methods for the compound of formula (I) will be described. Each production process may also be carried out with reference to the References appended in the present description. Further, the preparation methods of the present invention are not limited to the examples as shown below.

(General Production Processes)
(Production Process 1)

[Chem. 15]

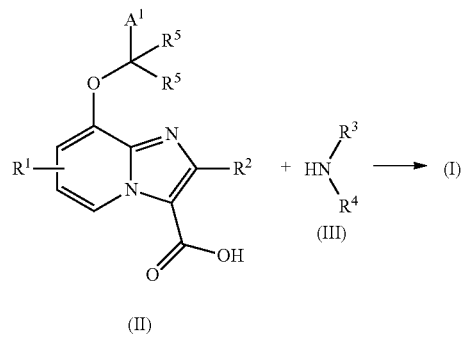

The compound of formula (I) can be prepared by reacting compound (II) with compound (III).

In this production process, compound (II) and compound (III) are used in equivalent amounts, or either thereof in an excess amount, and their mixture is stirred in a range of from cooling to heating, preferably at a temperature from −20° C. to 60° C., usually for about 0.1 hours to 5 days, in a solvent which is inert to the reaction, in the presence of a condensing agent. The solvent hereinused is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran (THF), dioxane, dimethoxyethane, and the like, N,N-dimethylformamide (DMF), dimethylsulfoxide (DMSO), ethyl acetate, acetonitrile, or water, and any mixture thereof. Examples of condensing agents include, but are not limited to, 1-(3-dimethylaminopropyl)-3-ethylcarbodiimide (WSC), dicyclohexylcarbodiimide (DCC), 1,1'-carbonyldiimidazole (CDI), diphenylphosphoryl azide (DPPA), and phosphorous oxychloride. In some cases, it may be preferable for the reaction to use an additive (for example, 1-hydroxybenzotriazole (HOBt)). It is in some cases advantageous for smooth progress of the reaction to carry out the reaction in the presence of organic bases such as triethylamine (TEA), N,N-diisopropylethylamine (DIPEA), N-methylmorpholine (NMM), and the like, or inorganic bases such as potassium carbonate, sodium carbonate, potassium hydroxide, and the like.

Furthermore, it is also possible to use a method in which compound (II) is converted to a reactive derivative and afterward reacted with compound (III). Examples of reactive derivatives of compound (II) include acid halides that can be obtained by the reaction with a halogenating agent such as phosphorus oxychloride, thionyl chloride, and the like, mixed acid anhydrides obtained by the reaction with isobutyl chloroformate or the like, active esters obtained by condensation with 1-hydroxybenzotriazole or the like, etc. The reaction of these reactive derivatives with compound (III) can be carried out in a range of from cooling to heating, and preferably from −20° C. to 60° C., in a solvent which is inert to the reaction, such as halogenated hydrocarbons, aromatic hydrocarbons, ethers, and the like. For this reaction, for example, the following references may be referred to.

"Organic Functional Group Preparations", S. R. Sandler and W. Karo, $2^{nd}$ edition, Vol. 1, Academic Press Inc., 1991

The Chemical Society of Japan, "Courses in Experimental Chemistry ($5^{th}$ edition)" Vol. 16 (2005) (Maruzen)

In addition, further compounds of formula (I) can also be prepared from the compound of formula (I) prepared by this Production Process (for details, Examples as described later may be referred to).

(Production Process 2)

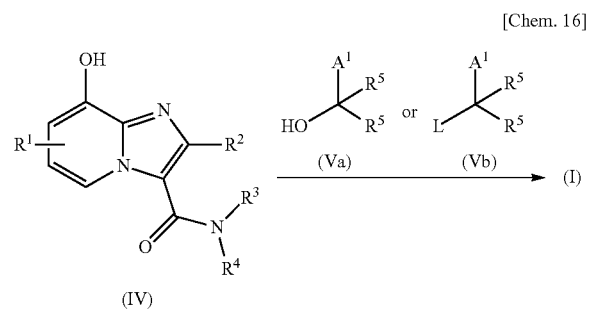

[Chem. 16]

(wherein L represents a leaving group, for example, halogen).

Furthermore, the compound of formula (I) can be prepared by reacting compound (IV) with compound (Va) or compound (Vb).

Examples of the preparation method using compound (Va) include methods in which known diazocarboxylic esters or diazocarboxylic amides are used in combination with phosphines, (tributylphosphoraniliden)acetonitrile (Tsunoda reagent), or the like. These are the so-called Mitsunobu reaction, or any modified method thereof. These reactions are known to the skilled in the art.

In this reaction, compound (IV) and compound (Va) are used in equivalent amounts, or in an excess amount for either thereof, and their mixture is stirred in a range of from cooling to heating under refluxing, preferably at a temperature from 0° C. to 150° C., usually for about 0.1 hours to 5 days, in a solvent which is inert to the reaction. The solvent as used herein is not particularly limited, but examples thereof include, aromatic hydrocarbons, ethers, halogenated hydrocarbons, DMF, DMSO, ethyl acetate, acetonitrile, and a mixture thereof.

For this reaction, for example, the following references may be referred to.

Mitsunobu, O.; Synthesis (1981), 1

Tsunoda, T. et al., Tetrahedron Letters (1995) 36, 2529, ibid, (1996) 37, 2463

On the other hand, when compound (Vb) is used, compound (IV) and compound (Vb) are used in equivalent amounts, or in an excess amount for either thereof, and their mixture is stirred in a range of from cooling to heating and refluxing, preferably at a temperature from 0° C. to 80° C., usually for about 0.1 hours to 5 days, in a solvent which is inert to the reaction, in the presence of a base. The solvent as used herein is not particularly limited, but examples thereof include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and any mixture thereof. Examples of bases include organic bases such as triethylamine, diisopropylethylamine, 1,8-diazabicyclo[5.4.0]-7-undecene, n-butyllithium, and the like, and inorganic bases such as sodium carbonate, potassium carbonate, sodium hydride, potassium tert-butoxide, and the like. It may be advantageous in some cases to carry out the reaction in the presence of a phase transfer catalyst such as tetra-n-butylammonium chloride, and the like.

For this reaction, for example, the following references may be referred to.

"Organic Functional Group Preparations", S. R. Sandler and W. Karo, $2^{nd}$ edition, Vol. 1, Academic Press Inc., 1991

The Chemical Society of Japan, "Courses in Experimental Chemistry ($5^{th}$ edition)" Vol. 14 (2005) (Maruzen)

(Starting Material Synthesis)

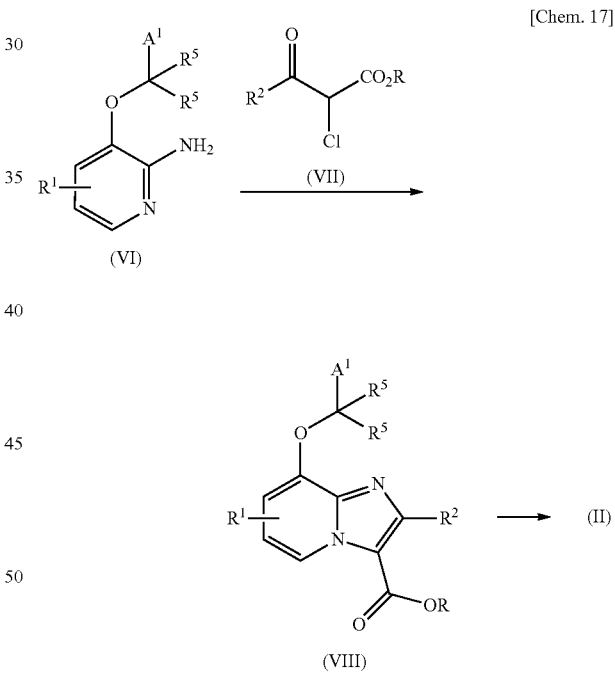

[Chem. 17]

(wherein R is lower alkyl or the like, for example, methyl or ethyl).

The starting material compound (II) can be prepared by hydrolyzing compound (VIII) which is prepared by reacting compound (VI) with compound (VII).

The reaction for preparing the compound (VIII) can be carried out with the same reaction solvent and temperature as in Production Process 1 (for details, Examples as described later may be referred to).

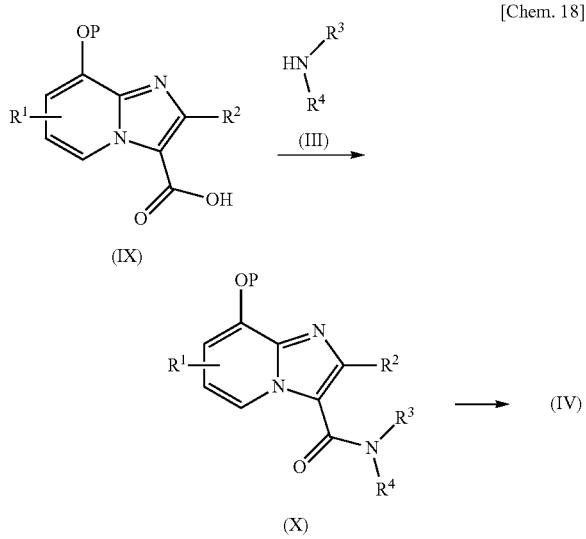

(wherein P is a protective group, for example, benzyl).

The starting material compound (IV) can be prepared by reacting compound (IX) and compound (III) to prepare compound (X), which is thus subjected to deprotection. The reaction of compound (IX) with compound (III) can be carried out in the same way as in Production Process 1. Further, the deprotection can be carried out by known methods or those obvious to the skilled in the art.

The compounds of formula (I) can be isolated and purified as free compounds, salts, hydrates, solvates, or polymorphic crystalline substances thereof. Salts of the compound of formula (I) can be prepared by conventional salt forming reactions.

Isolation and purification are carried out by employing ordinary chemical operations such as extraction, fractional crystallization, fractional chromatography, and the like.

Various isomers can be prepared by selecting appropriate starting compounds or by separation using the difference in physicochemical properties between the isomers. For example, optical isomers can be obtained by means of a general optical resolution method for racemic products (for example, fractional crystallization for inducing diastereomer salts with optically active bases or acids, chromatography using a chiral column or the like, and others), and further, the isomers can also be prepared from an appropriate optically active starting compound.

TEST EXAMPLES

Pharmacological activities of the compound of formula (I) were confirmed in the following tests.

Test Example 1

Measurement of sGC Activation (Enzyme)

The activity of sGC was evaluated by measuring the amount of a cyclic guanosine monophosphate (cGMP) which is produced by human purified sGC.

A test compound was dissolved in DMSO and diluted 20-fold with ultrapure water. 2 μL of the diluted test compound solution (maximum concentration 100 μM), 2 μL of a substrate solution [0.5 μM TEBA, 0.03 μM dithiothreitol, 0.01 μM GTP, 0.04 μM MgCl$_2$, and 0.03 μM sodium nitroprusside (SNP)], and 6 μL of a human enzyme suspension were added to 384-well plates (manufactured by Greiner Bio-One), and incubated at room temperature for one hour. The quantitative determination of cGMP is using HTRF which based on the competition between sample cGMP and fluorescent dye labeled cGMP for binding to a cGMP-specific antibody.

The test results of some Example compounds that are the compounds of the formula (I) of the present invention are shown below. The sGC activation of the test compound was calculated by taking the activation when the compound was not added as 100%. As compared with the activation when the compound was not added, it was recognized that a compound having a sGC activation of more than 300% has sGC activation. In addition, in Tables, Ex represents Example number in which the test compound is described and the sGC activation [%] represents sGC activation (%).

Furthermore, the $EC_{50}$ [μM] value was calculated as another parameter for expressing sGC activation. This parameter indicates the concentration of the evaluated compound giving 50% of a maximum activation, which is calculated based on the maximum activation that compound of Example 102 is added, which is taken as 100%. In this connection, when a known sGC activator, YC-1 (Lificiguat, [5-(1-benzyl-1H-indazol-3-yl)-2-furyl]methanol), was evaluated according to the above Test Example 1, its maximum activation was 52% of the maximum activation for compound of Example 102. Further, "−" means no evaluation.

TABLE 1

| Ex | sGC activation [%] | $EC_{50}$ [μM] |
| --- | --- | --- |
| Ex 12 | — | 3.0 |
| Ex 102 | — | 2.8 |
| Ex 104 | >1000 | — |
| Ex 110 | >1000 | — |
| Ex 119 | — | 2.9 |
| Ex 126 | — | 11 |
| Ex 179 | — | 2.7 |
| Ex 205 | >1000 | — |
| Ex 244 | >1000 | — |
| Ex 226 | >1000 | 6.7 |
| Ex 247 | — | 2.4 |
| Ex 251 | >1000 | 6.1 |
| Ex 259 | >1000 | — |
| Ex 321 | >1000 | 4.5 |
| Ex 323 | — | 13 |
| Ex 341 | 980 | 6.9 |
| Ex 424 | >1000 | 2.4 |
| Ex 430 | — | 2.6 |
| Ex 434 | — | 7.3 |
| Ex 436 | >1000 | — |
| Ex 633 | 830 | — |
| Ex 693 | >1000 | 17 |
| Ex 695 | >1000 | — |
| Ex 698 | >1000 | 19 |
| Ex 699 | >1000 | 15 |
| Ex 702 | >1000 | 6.2 |
| Ex 704 | >1000 | 11 |
| Ex 705 | — | 11 |
| Ex 706 | >1000 | 4.7 |
| Ex 759 | — | 2.2 |
| Ex 760 | — | 5.9 |
| Ex 766 | — | 17 |
| Ex 767 | — | 3.0 |
| Ex 772 | — | 5.4 |
| Ex 776 | — | 15 |
| Ex 778 | — | 6.3 |
| Ex 797 | — | 8.9 |
| Ex 798 | — | 8.6 |
| Ex 822 | — | 5.6 |
| Ex 828 | — | 7.6 |

TABLE 1-continued

| Ex | sGC activation [%] | EC$_{50}$ [μM] |
|---|---|---|
| Ex 829 | — | 2.7 |
| Ex 834 | — | 4.1 |

Test Example 2

Blood Flow Increasing In Vivo

The hind limb blood flow in rats anesthetized with pentobarbital was measured by the following test method.

Wistar male rats were used. An administration liquid was prepared by adding N,N-dimethyl formamide, Polyethylene Glycol 400, TWEEN 80, a 0.5% methyl cellulose aqueous solution, a 0.5 M aqueous sodium bicarbonate solution, and 0.1 M hydrochloric acid to the test compound and dissolving the test compound in an appropriate manner depending on the compound. Thus prepared administration liquid was orally administered, and 2 hours later, the hind limb blood flow was measured using a laser blood flow imaging device (PIM II Integral) under anesthesia with intraperitoneal administration of 60 mg/kg of pentobarbital.

The compounds of Examples 244, 259, and 341 of the present invention each exhibited a blood flow increasing effect at a dose of 30 mg/kg. Further, the compounds of Examples 12, 102, 119, 179, 247, 251, 321, 424, 430, 693, 698, 699, 702, 704, 706, 759, 760, 767, and 834 each exhibited a blood flow increasing effect at a dose of 10 mg/kg.

Test Example 3

Measurement of Antihypertensive Effect In Vivo

Wistar male rats were used. Three days prior to administration of a drug, a cannula (PE-50, Becton, Dickinson and Company, Japan) filled with heparin physiological saline (200 U/mL, Ajinomoto Pharmaceuticals Co., Ltd.) was inserted and placed in the common carotid artery under anesthesia with intraperitoneal administration of 60 mg/kg of pentobarbital. The other end of the cannula was exposed to the back neck through the subcutaneous. After the recovery period, the placed cannula was connected to a pressure transducer (Life Kit DTS DX-100, Nihon Kohden Corporation) to record the blood pressure waveform through a Polygraph (AP-641G, Nihon Kohden Co., Ltd.) and PowerLab (ML870 PowerLab8/30 (AD Instruments Japan)). The heart rate was calculated using a heart rate measuring unit (AT-601G, Nihon Kohden Co., Ltd.). After stabilization of the blood pressure, the drug was orally administered to measure the blood pressure and the heart rates. The test compounds were administered by appropriately adding N,N-dimethylformamide, Polyethylene Glycol 400, TWEEN 80, a 0.5% aqueous methylcellulose solution, and a 0.5 M aqueous sodium bicarbonate solution, and 0.1 M hydrochloric acid therein according to the compounds and dissolving it.

The results from the measurement according to Test Example 3 are shown below according to the following criteria with a maximum value of the mean blood pressure reduction. A: <20 mmHg, B: 20 to 40 mmHg, and C: >40 mmHg

TABLE 1-1

| | Administration dose (mg/kg po) | Blood pressure reduction |
|---|---|---|
| Ex 180 | 30 | B |
| Ex 422 | 30 | C |
| Ex 431 | 10 | B |
| Ex 434 | 30 | C |
| Ex 827 | 10 | B |

In Test Examples 1 and 2 above, it was confirmed in several Example compounds of the present invention that they have sGC activation and blood flow improving action. Accordingly, the compound of formula (I) can be used for treating sGC-related cardiovascular diseases, in particular, peripheral arterial diseases, as well as intermittent claudication and critical limb ischemia caused by the aforesaid peripheral arterial diseases or the like.

In addition, in Test Example 3 above, it was confirmed that in several Example compounds of the present invention that they have antihypertensive effect. Accordingly, the compound of formula (I) can be used for treating hypertension, or the like.

Pharmaceutical compositions containing one or more kinds of compound of formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal solutions, ointments, transdermal patches, transmucosal solutions, transmucosal patches, inhalers, and the like.

Solid compositions for oral administration are used in the form of tablets, powders, granules, or the like. In such solid compositions, one or more active ingredient(s) are mixed with at least one inactive excipient. In a conventional method, the composition may contain inactive additives, such as lubricants, disintegrating agents, stabilizers, or solubilization assisting agents. If necessary, tablets or pills may be coated with sugar or s gastric- or enteric-soluble substances films.

Liquid compositions for oral administration comprises pharmaceutically acceptable emulsions, solutions, suspensions, syrups, elixirs, or the like, and also comprises generally used inert diluents, for example, purified water or ethanol (EtOH). In addition to the inert diluent, liquid compositions may also contain auxiliary agents, such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of non-aqueous solvents include alcohols such as ethanol. Such compositions may further contain tonicity agents, antiseptics, moistening agents, emulsifying agents, dispersing agents, stabilizers, or solubilization assisting agents. These are sterilized, for example, by filtration through bacteria retaining filter, blendings of bactericide, or irradiation. In addition, these can also be used by preparing sterile solid compositions, and dissolving or suspending in sterile water or sterile solvents for injection prior to its use.

Agents for external use includes ointments, plasters, creams, jellies, poultices, sprays, lotions, eye drops, eye ointments, and the like. The agents contain generally used ointment bases, lotion bases, aqueous or non-aqueous solutions, suspensions, emulsions, and the like.

As transmucosal agents such as inhalers, transnasal agents, and the like, those in the form of a solid, liquid, or semi-solid state are used, and can be prepared in accordance with conventionally known methods. For example, known excipients, and furthermore pH adjusting agents, antiseptics, surfactants, lubricants, stabilizers, thickening agents, or the like may be appropriately added thereto. For their administration, appropriate devices for inhalation or blowing can be used. For example, a compound may be administered alone or as a powder of formulated mixture, or as a solution or suspension in combination with pharmaceutically acceptable carriers, using a known device or sprayer, such as a measured administration inhalation device, and the like. Dry powder inhalers or the like may be for single or multiple administration use, and dry powder or powder-containing capsules may be used. Alternatively, these may be pressurized aerosol spray which uses appropriate ejection agents, for example, a suitable gas such as chlorofluoroalkane, hydrofluoroalkane, carbon dioxide, and the like.

For oral administration, daily dose is generally from about 0.001 to 100 mg/kg, preferably from 0.1 to 30 mg/kg, and more preferably from 0.1 to 10 mg/kg, per body weight, administered in one portion or in 2 to 4 separate portions. In the case of intravenous administration, daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. Doses are appropriately determined according to the individual according to the symptoms, age, gender, and the like.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of formula (I) or a salt thereof, as the active ingredient.

The compound of formula (I) can be used in combination with various therapeutic or prophylactic agents for the diseases for which the compound of formula (I) is considered to be effective, as described above. The combined preparation may be administered simultaneously, or separately and continuously, or at a desired time interval. The preparations to be administered simultaneously may be a mixture, or may be prepared individually.

EXAMPLES

Hereinbelow, the preparation methods for the compound of formula (I) will be described in more detail with reference to Examples. The present invention is not limited to the compounds described in Examples as described below. Further, the production processes for the starting compounds will be described in Preparation Examples. The compound of formula (I) is prepared by using a combination of the preparation methods or a method apparent to a person skilled in the art, in addition to Production Processes described in Examples.

Moreover, the following abbreviations may be used in some cases in Examples, Preparation Examples, and Tables as described later.

PEx: Preparation Example number, Ex: Example number, Str: Structural formula, Dat: Physicochemical data (ESI+: ESI-MS [M+H]$^+$ or ESI-MS [M]$^+$; ESI−: ESI-MS [M−H]$^−$; FAB+: FAB-MS [M+H]$^+$ or FAB-MS [M]$^+$; EI+: EI [M]$^+$; APCI/ESI+: APCI/ESI-MS [M+H]$^+$ or APCI/ESI-MS [M]$^+$ (APCI/ESI means simultaneous measurement of APCI and ESI); A/E−:APCI/ESI-MS [M−H]$^−$ (APCI/ESI means simultaneous measurement of APCI and ESI); NMR: δ (ppm) of a peak in $^1$HNMR, and unless otherwise described, 400 MHz), Me: methyl, Et: ethyl, nPr: n-propyl, iPr: isopropyl, nBu: n-butyl, iBu: isobutyl, tBu: tert-butyl, cBu: cyclobutyl, cPr: cyclopropyl, neoPen: neopentyl, cPen: cyclopentyl, nHex: n-hexyl, cHex: cyclohexyl, cHep: cycloheptyl, cOct: cyclooctyl, Ph: phenyl, Bn: benzyl, Ac: acetyl, Boc: tert-butoxycarbonyl, Z: benzyloxycarbonyl, TBS: tert-butyldimethylsilyl, Syn: Preparation method (in which the number in the section of Syn indicates that the compound is prepared by the same method as the compound having the Preparation Example compound number or Example compound number. For example, for example, the compound of Ex2 in the section of Syn is prepared by the same method as the compound of Example 2; the compound of PEx2 in the section of Syn is prepared by the same method as the compound of Preparation Example 2; the compound of PEx1, 16 in the section of Syn is prepared by the same method as the compound of Preparation Example 1 followed by the same method as the Preparation Example 16), (cis) denotes that the relative configuration of the compound is a cis isomer, (trans) denotes that the relative configuration of the compound is a trans isomer, and (rac) denotes that the compound is a racemate, and the racemate is a mixture of an optically active body and its enantiomer (mirror image isomer) at a rate of 1:1, and means an optically inactive compound.

Furthermore, in the present specification, regarding to compounds with asymmetric carbons, when a substituent bonded to a chiral center has no notation regarding to its configuration, then it means that the configuration of the substituent has not been determined.

Furthermore, in the structural formulae in Tables as described later, when any substituent bonded to chiral centers is illustrated with a planar structure, and when there is no notation regarding the configuration of the substituent, then it means that the configuration of the substituent has not been determined.

Furthermore, for convenience, concentration mol/l is expressed as M. For example, a 1 M aqueous sodium hydroxide solution means a 1 mol/l aqueous sodium hydroxide solution.

Furthermore, the compounds of Preparation Example 29 to 100, 103, 108, 118 to 128, 132 to 134, 138, 141 to 164, 177, 202 to 238, and 241 to 277 and 202 to 279 were prepared in the same manner as the methods of Preparation Examples 1 to 28, 101 to 102, 104 to 107, 109 to 117, 129 to 131, 135 to 137, 139 to 140, and 165 to 201 as described later, and thus, they are described only in Tables as described later. For each Preparation Example Compounds, their chemical structures are shown in Tables 2 to 20 as described later and physicochemical data and preparation methods are shown in Tables 21 to 31 as described later.

Preparation Example 1

A suspension of 1 g of 5-methyl-2-nitropyridin-3-ol, 1.35 ml of (bromomethyl)cyclohexane, and 1.79 g of potassium carbonate in 10 ml of DMF was stirred at 78° C. for 12 hours. After leaving to be cooled at room temperature, to the reaction mixture were added water and hexane/ethyl acetate to carry out a layer separation operation. The organic layer was washed with water and saturated brine, and dried over anhydrous magnesium sulfate, and the solvent was evaporated under reduced pressure to obtain 1.8 g of 3-(cyclohexylmethoxy)-5-methyl-2-nitropyridine.

Preparation Example 2

To a solution of 1.8 g of 3-(cyclohexylmethoxy)-5-methyl-2-nitropyridine in 16 ml of THF was added 325 mg of 10% palladium-carbon (wet), followed by stirring for 3 hours under a hydrogen atmosphere. The reaction mixture was filtered over Celite and the solvent was then evaporated under reduced pressure to obtain 1.38 g of 3-(cyclohexylmethoxy)-5-methylpyridin-2-amine.

Preparation Example 3

To a solution of 2 g of 3-(cyclohexylmethoxy)pyridin-2-amine in 10 ml of acetic acid was added 1.90 g of N-bromosuccinimide over 30 minutes under ice-cooling, followed by stirring for 30 minutes under ice-cooling. To the reaction mixture were added water and ethyl acetate to carry out a layer separation operation. The organic layer was washed with water and saturated brine, and dried over anhydrous sodium sulfate, and the solvent was evaporated under reduced pressure. The obtained residue was purified by silica gel column chromatography to obtain 2.25 g of 5-bromo-3-(cyclohexylmethoxy)pyridin-2-amine.

Preparation Example 4

To a solution of 1.38 g of 3-(cyclohexylmethoxy)-5-methylpyridin-2-amine in 24 ml of toluene were added 1.21 ml of ethyl 2-chloro-3-oxobutanoate and 1.23 ml of triethylamine, followed by stirring at 110° C. for 3 days. After leaving to be cooled at room temperature, water and diisopropyl ether were added thereto to carry out a layer separation operation. The organic layer was dried over anhydrous sodium sulfate and the solvent was evaporated under reduced pressure. The obtained residue was purified by silica gel column chromatography to obtain 1.52 g of ethyl 8-(cyclohexylmethoxy)-2,6-dimethylimidazo[1,2-a]pyridine-3-carboxylate.

Preparation Example 5

To 2.16 g of ethyl 8-[(2-fluorobenzyl)oxy]-2-methylimidazo[1,2-a]pyridine-3-carboxylate were added 20 ml of THF, 40 ml of ethanol, and 20 ml of a 1 M aqueous sodium hydroxide solution, followed by stirring for 4 days. The solvent was evaporated under reduced pressure, and water and 1 M hydrochloric acid were added thereto. The insoluble material was collected by filtration and dried to obtain 1.99 g of 8-[(2-fluorobenzyl)oxy]-2-methylimidazo[1,2-a]pyridine-3-carboxylic acid.

Preparation Example 6

To a solution of 5.2 g of 8-(benzyloxy)-N-[(1R)-2-{[tert-butyl(dimethyl)silyl]oxy}-1-phenylethyl]-2-methylimidazo[1,2-a]pyridine-3-carboxamide in 70 ml of ethanol was added 1.0 g of 10% palladium-carbon (wet), followed by stirring for 3 hours under a hydrogen atmosphere. The reaction mixture was filtered over Celite, the solvent was then evaporated under reduced pressure, and the obtained residue was purified by silica gel column chromatography. To the obtained purified product were added hexane and diisopropyl ether, followed by stirring, and the resulting solid was collected by filtration and dried to obtain 3.5 g of N-[(1R)-2-{[tert-butyl(dimethyl)silyl]oxy}-1-phenylethyl]-8-hydroxy-2-methylimidazo[1,2-a]pyridine-3-carboxamide.

Preparation Example 7

To a solution of 2 g of methyl 3-cyclopropyl-3-oxopropanoate in 20 ml of dichloromethane was added dropwise 1.24 ml of sulfuryl chloride under ice-cooling, followed by stirring at room temperature for 5 hours. To the reaction mixture was added water under ice-cooling, and chloroform was further added thereto to carry out a layer separation operation. The organic layer was washed with saturated brine and dried over anhydrous sodium sulfate, and the solvent was evaporated under reduced pressure to obtain 2.48 g of methyl 2-chloro-3-cyclopropyl-3-oxopropanoate.

Preparation Example 8

To a suspension of 300 mg of {4-amino-1-[(benzyloxy)carbonyl]piperidin-4-yl}acetic acid in 6 ml of methanol was added 150 μl of thionyl chloride, followed by stirring for 2 days. The reaction mixture was concentrated under reduced pressure, ether was added thereto, and the resulting solid was collected by filtration and dried to obtain 350 mg of benzyl 4-amino-4-(2-methoxy-2-oxoethyl)piperidine-1-carboxylate hydrochloride.

Preparation Example 9

To a solution of 1.07 g of tert-butyl(diethoxyphosphoryl)acetate in 50 ml of THF was added 3.8 ml of a 1.12 M methylmagnesium bromide/THF solution, followed by stirring for 30 minutes. To the obtained reaction mixture was added a solution of 500 of n-pentanal in 5 ml of THF, followed by heating to reflux for 3 hours. To the reaction mixture were added a saturated aqueous ammonium chloride solution and ether to carry out a layer separation operation. The organic layer was washed with saturated brine and dried over anhydrous magnesium sulfate, and the solvent was evaporated under reduced pressure to obtain 726 mg of tert-butyl (2E)-hepta-2-noate.

Preparation Example 10

To a solution of 1.3 ml of (1R)—N-benzyl-1-phenylethanamine in 15 ml of THF was added 3.7 ml of a 1.65 M n-butyllithium/hexane solution at −78° C., followed by stirring at the same temperature for 1 hour. Then, a solution of 710 mg of tert-butyl (2E)-hepta-2-noate in 5 ml of THF was slowly added dropwise at the same temperature, followed by stirring at the same temperature for 3 hours. To the reaction mixture was added a saturated aqueous ammonium chloride solution, followed by warming to room temperature, and ethyl acetate was added thereto to carry out a layer separation operation. The organic layer was washed with saturated brine and dried over anhydrous magnesium sulfate, and the solvent was evaporated under reduced pressure. The obtained residue was purified by silica gel column chromatography to obtain 1.27 g of tert-butyl (3R)-3-{benzyl[(1R)-1-phenylethyl]amino}heptanoate. Further, the structure of the product was determined in accordance to a reference (Tetrahedron Asymmetry, 17 (2006) 1793-1811, and the like) by S. G. Davis, et al.

Preparation Example 11

To a solution of 1.15 g of tert-butyl (3R)-3-{benzyl[(1R)-1-phenylethyl]amino}heptanoate in 30 ml of methanol was added 450 mg of 10% palladium-carbon, followed by stirring overnight under a hydrogen atmosphere at 4 atm. The reaction mixture was filtered over Celite and the solvent was then evaporated under reduced pressure. The obtained residue was purified by silica gel column chromatography to obtain 460 mg of tert-butyl (3R)-3-aminoheptanoate.

Preparation Example 12

To a suspension of 510 mg of 8-(cyclohexylmethoxy)-2-methylimidazo[1,2-a]pyridine-3-carboxylic acid in dichloromethane were added 0.30 ml of oxalyl dichloride and one drop of DMF under ice-cooling, followed by stirring at room temperature for 30 minutes, and the solvent was evaporated under reduced pressure to obtain 603 mg of 8-(cyclohexylmethoxy)-2-methylimidazo[1,2-a]pyridine-3-carboxylic acid chloride hydrochloride.

Preparation Example 13

To a solution of 2 g of methyl 5-hydroxy-6-nitronicotinate, 1.62 ml of (2-fluorophenyl)methanol, and 3.99 ml of tributylphosphine in 40 ml of THF was added 2.54 ml of diethyl azodicarboxylate under ice-cooling, followed by stirring for 1 hour under ice-cooling and at room temperature for 2 hours. To the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 2.58 g of methyl 5-[(2-fluorobenzyl)oxy]-6-nitronicotinate.

Preparation Example 14

To a solution of 2.5 g of methyl 5-[(2-fluorobenzyl)oxy]-6-nitronicotinate in 25 ml of THF were added 50 ml of ethanol, 25 ml of water, 218 mg of ammonium chloride, and 1.37 g of iron, followed by heating to reflux for 2 hours. After leaving to be cooled at room temperature, the reaction mixture was filtered over Celite, and to the filtrate were added a saturated aqueous sodium hydrogen carbonate solution and chloroform to carry out a layer separation operation. The organic layer was dried over anhydrous sodium sulfate and the solvent was evaporated under reduced pressure to obtain 2.25 g of methyl 6-amino-5-[(2-fluorobenzyl)oxy]nicotinate.

Preparation Example 15

To a suspension of 2.15 g of methyl 6-amino-5-[(2-fluorobenzyl)oxy]nicotinate in 43 ml of ethanol was added 1.09 ml of bromoacetone, followed by stirring at 80° C. for 4 hours. To the reaction mixture was added 1.09 ml of bromoacetone, followed by stirring at 80° C. for 4 hours. To the reaction mixture was added a saturated aqueous sodium hydrogen carbonate solution, and the solvent was evaporated under reduced pressure, followed by extracting with ethyl acetate and washing with saturated brine. After drying over anhydrous magnesium sulfate and then filtering, the solvent was evaporated under reduced pressure. The obtained residue was purified by silica gel column chromatography to obtain 1.39 g of methyl 8-[(2-fluorobenzyl)oxy]-2-methylimidazo[1,2-a]pyridine-6-carboxylate.

Preparation Example 16

To 350 mg of 8-[(2-fluorobenzyl)oxy]-2-methylimidazo[1,2-a]pyridine-6-carboxylic acid were added 18 ml of ethanol and 200 µl of sulfuric acid, followed by heating to reflux overnight. Under reduced pressure, the solvent was removed by filtration to around one third of the amount thereof, and a saturated aqueous sodium hydrogen carbonate solution and chloroform were then added thereto to carry out a layer separation operation. The organic layer was dried over anhydrous sodium sulfate and the solvent was evaporated under reduced pressure. The obtained residue was purified by silica gel column chromatography to obtain 330 mg of ethyl 8-[(2-fluorobenzyl)oxy]-2-methylimidazo[1,2-a]pyridine-6-carboxylate.

Preparation Example 17

A mixture of 1 g of N-methyl-2-nitrobenzenesulfonamide, 2.3 g of tert-butyl [(1R)-2-hydroxy-1-phenylethyl]carbamate, 2.5 g of triphenylphosphine, 4.2 ml of diethyl azodicarboxylate, and 40 ml of toluene was stirred at 80° C. for 2 hours, and the solvent was evaporated under reduced pressure. To a solution of the obtained residue in chloroform was added silica gel, followed by filtration, and the filtrate was concentrated under reduced pressure. To a solution of the obtained residue in 3 ml of dichloromethane was added 3 ml of trifluoroacetic acid, followed by stirring for 1 hour. The solvent was evaporated under reduced pressure, and an aqueous sodium carbonate solution and chloroform were then added thereto to carry out a layer separation operation. The organic layer was dried over anhydrous magnesium sulfate and the solvent was evaporated under reduced pressure. The obtained residue was purified by silica gel column chromatography to obtain 890 mg of N-[(2R)-2-amino-2-phenylethyl]-N-methyl-2-nitrobenzenesulfonamide.

Preparation Example 18

To a solution of 200 mg of 8-(cyclohexylmethoxy)-N-(2,2-dimethoxyethyl)-2-methylimidazolo[1,2-a]pyridine-3-carboxamide in 2 mL of dioxane was added 6 M hydrochloric acid, followed by stirring for 7 hours. To the reaction mixture were added saturated brine and ethyl acetate to carry out a layer separation operation. To the obtained aqueous layer was added a 1 M aqueous sodium hydroxide solution, and the resulting solid was collected by filtration and dried to obtain 165 mg of 8-(cyclohexylmethoxy)-2-methyl-N-(2-oxoethyl)imidazolo[1,2-a]pyridine-3-carboxamide.

Preparation Example 19

To a solution of 160 mg of ethyl 1-{(2R)-2-[(tert-butoxycarbonyl)amino]-2-phenylethyl}piperidine-4-carboxylate in 1.5 mL of dichloromethane was added 0.7 mL of trifluoroacetic acid, followed by stirring for 1 hour. The solvent was evaporated under reduced pressure, and a saturated aqueous sodium carbonate solution and a chloroform-methanol mixed solution were added thereto in this order to carry out a layer separation operation. After drying over anhydrous magnesium sulfate, the solvent was evaporated under reduced pressure to obtain 120 mg of ethyl 1-[(2R)-2-amino-2-phenylethyl]piperidine-4-carboxylate.

Preparation Example 20

To a solution of 1 g of (2R)-2-[(tert-butoxycarbonyl)amino]-2-phenylethyl methanesulfonate in 5 mL of THF were added 0.4 mL of ethyl piperidine-4-carboxylate and 1 mL of diisopropylethylamine, followed by stirring at 70° C. for 14 hours, and the solvent was evaporated under reduced pressure. The obtained residue was purified by silica gel column chromatography to obtain 160 mg of ethyl 1-{(2R)-2-[(tert-butoxycarbonyl)amino]-2-phenylethyl}piperidine-4-carboxylate.

Preparation Example 21

To 223 mg of tert-butyl (2E)-3-(4-cyanophenyl)acrylate were added 12 mL of methanol, 5 ml of THF, 1 ml of an acetic acid solution, and 90 mg of 10% palladium-carbon in this order, followed by stirring for 3 hours under hydrogen at 3 atm. The catalyst was removed by filtration and the filtrate was concentrated under reduced pressure. To the residue were added a saturated aqueous sodium hydrogen carbonate solution and ethyl acetate to carry out a layer separation operation. The organic layer was dried over anhydrous sodium sulfate and the solvent was evaporated under reduced pressure to obtain 177 mg of tert-butyl 3-[4-(aminomethyl)phenyl]propanoate.

Preparation Example 22

To a solution of 280 mg of ethyl 2-(4-cyanophenyl)-2-methylpropanoate in 10 ml of ethanol were added 2 mL of 1 M hydrochloric acid and 120 mg of 10% palladium-carbon in this order, followed by stirring for 3 hours under a hydrogen atmosphere at 3 atm. The catalyst was removed by filtration, and the filtrate was concentrated under reduced pressure and dried to obtain 345 mg of, ethyl 2-[4-(aminomethyl)phenyl]-2-methylpropanoate hydrochloride.

Preparation Example 23

A mixture of 1 g of tert-butyl (2-bromobenzyl)carbamate, 1.12 g of ethyl (2E)-3-(4,4,5,5-tetramethyl-1,3,2-dioxaborolan-2-yl)acrylate, 16 mg of palladium acetate, 72 mg of dicyclohexyl(2',6'-dimethoxybiphenyl-2-yl)phosphine, 1.5 g of potassium phosphate, and 20 mL of toluene was stirred at 100° C. for 5 days. To the reaction mixture was added ether, followed by filtration through silica gel. The filtrate was concentrated under reduced pressure and the obtained residue was purified by silica gel column chromatography to obtain 412 mg of ethyl (2E)-3-(2-{[(tert-butoxycarbonyl)amino]methyl}phenyl)acrylate.

Preparation Example 24

To a suspension of 320 mg of 60% sodium hydride in 4 mL of DMF were added 500 mg of ethyl(4-cyanophenyl)acetate and a solution of 0.41 mL of methyl iodide in 2 mL of DMF under ice-cooling, followed by stirring at room temperature for 1 day. To the reaction mixture were added water and ethyl acetate to carry out a layer separation operation. The organic layer was washed with water and saturated brine in this order, and dried over anhydrous sodium sulfate, and the solvent was evaporated under reduced pressure. The residue was purified by silica gel column chromatography to obtain 280 mg of ethyl 2-(4-cyanophenyl)-2-methylpropanoate.

Preparation Example 25

To a solution of 1 g of (3S)-3-amino-2-hydroxyhexanoic acid hydrochloride in 10 mL of methanol was added 10 mL of a 4 M hydrogen chloride/dioxane solution, followed by stirring overnight, and the solvent was evaporated under reduced pressure. A saturated aqueous sodium hydrogen carbonate solution and chloroform were added thereto to carry out a layer separation operation. The organic layer was washed with saturated brine and dried over anhydrous sodium sulfate and the solvent was evaporated under reduced pressure. The residue was purified by silica gel column chromatography to obtain 425 mg of methyl (2R,3S)-3-amino-2-hydroxyhexanoate and 130 mg of methyl (2S,3S)-3-amino-2-hydroxyhexanoate.

Preparation Example 26

To a solution of 500 mg of tert-butyl (3S)-piperidin-3-yl carbamate and 900 mg of [3-(methoxycarbonyl)phenyl] boric acid in 10 mL of dichloromethane were added Molecular Sieves 4A, 460 mg of copper (II) acetate, and 0.70 mL of triethylamine in this order, followed by stirring overnight. The reaction mixture was filtered over Celite, and then to the filtrate were added a saturated aqueous sodium hydrogen carbonate solution and ethyl acetate to carry out a layer separation operation. The organic layer was washed with saturated brine and then dried over anhydrous magnesium sulfate, and the solvent was evaporated under reduced pressure. The obtained residue was purified by silica gel column chromatography to obtain 380 mg of methyl 3-{(3S)-3-[(tert-butoxycarbonyl)amino]piperidin-1-yl}benzoate.

Preparation Example 27

To a solution of 300 mg of tert-butyl (3S)-piperidin-3-yl carbamate and 6 mL of N-methyl-2-pyrrolidone were added 310 mg of methyl 6-chloropyridine-2-carboxylate and 0.55 mL of diisopropylethylamine, followed by stirring at 130° C. overnight. After leaving to be cooled, to the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 215 mg of methyl 6-{(3S)-3-[(tert-butoxycarbonyl)amino]piperidin-1-yl}pyridine-2-carboxylate.

Preparation Example 28

To 2.02 g of tert-butyl (3S)-piperidin-3-yl carbamate were added 4.86 g of sulfamide and 30 mL of dioxane, followed by stirring at 95° C. overnight. After leaving to be cooled, the solvent was evaporated under reduced pressure, and water and chloroform were added thereto to carry out a layer separation operation. The organic layer was washed with an aqueous citric acid solution and dried over anhydrous magnesium sulfate, and the solvent was evaporated under reduced pressure. To the obtained residue was added 30 mL of a 4 M hydrogen chloride-ethyl acetate solution, followed by stirring for 40 minutes. The resulting solid was collected by filtration and dried to obtain 1.51 g of (3S)-3-aminopiperidine-1-sulfonamide hydrochloride.

Preparation Example 101

To 2.36 g of 2a,3,4,8b-tetrahydronaphtho[1,2-b]azet-2 (1H)-one was added 50 ml of a 10% hydrogen chloride/methanol solution, followed by stirring at 90° C. for 6 hours. After leaving to be cooled, the solvent was evaporated under reduced pressure. To the obtained residue were added methanol and diethyl ether, and the insoluble material was collected by filtration and dried to obtain 3.08 g of methyl rac-(1S,2S)-1-amino-1,2,3,4-tetrahydronaphthalene-2-carboxylate hydrochloride.

Preparation Example 102

To a suspension of 750 mg of rac-(1R,2R)-1-[(tert-butoxycarbonyl)amino]indane-2-carboxylic acid in 15 ml of methanol was added 0.40 ml of thionyl chloride, followed by stirring overnight. The solvent was evaporated to about a half amount thereof under reduced pressure, to the obtained residue was added diethyl ether, and the insoluble material was collected by filtration and dried to obtain 512 mg of methyl rac-(1R,2R)-1-aminoindane-2-carboxylate hydrochloride.

Preparation Example 104

A mixture of 2.64 g of (2-bromo-5-methylphenyl)methanol, 246 mg of bis(dibenzylideneacetone)palladium, 2.95 ml of tert-butylacrylate, 442 mg of tris(2-methylphenyl)phosphine, 2.5 ml of triethylamine, and 24 ml of DMF was stirred at 100° C. for 24 hours. After leaving to be cooled at room temperature, water and ethyl acetate were added thereto to carry out a layer separation operation. The organic layer was washed with saturated brine, dried over anhydrous magnesium sulfate, and the solvent was evaporated under reduced pressure. The obtained residue was purified by silica gel column chromatography to obtain 2.32 g of tert-butyl (2E)-3-[2-(hydroxymethyl)-4-methylphenyl]acrylate.

Preparation Example 105

To a solution of 2.32 g of tert-butyl (2E)-3-[2-(hydroxymethyl)-4-methylphenyl]acrylate in 46 ml of THF were added 4.64 g of carbon tetrabromide and 3.67 g of triphenylphosphine under ice-cooling, followed by stirring at the same temperature for 2.5 hours. To the reaction mixture were added water and ethyl acetate to carry out a layer separation operation. The organic layer was washed with water and saturated brine in this order, and dried over anhydrous magnesium sulfate, and the solvent was evaporated under reduced pressure. The obtained residue was purified by silica gel column chromatography to obtain 2.73 g of tert-butyl (2E)-3-[2-(bromomethyl)-4-methylphenyl]acrylate.

Preparation Example 106

To a solution of 1.5 ml of (1R)—N-benzyl-1-phenylethanamine in 40 ml of THF was added 4.35 ml of n-butyllithium (1.62 M hexane solution) at −78° C., followed by stirring for 30 minutes. At the same temperature, a solution of 1.00 g of tert-butyl (2E)-3-[2-(bromomethyl)-4-methylphenyl]acrylate in 5 ml of THF was added thereto, followed by stirring for 1.5 hours. To the reaction mixture was added water, followed by warming to room temperature. The solvent was evaporated under reduced pressure and ethyl acetate was then added thereto to carry out a layer separation operation. The organic layer was washed with a 1 M aqueous citric acid solution, water, and saturated brine in this order, and dried over anhydrous magnesium sulfate, and the solvent was evaporated under reduced pressure. The obtained residue was purified by silica gel column chromatography to obtain 1.17 g of tert-butyl (1S,2R)-1-{benzyl[(1R)-1-phenylethyl]amino}-5-methylindane-2-carboxylate. Further, the present Preparation Example is in accordance with the method described in a reference (Synlett, 1999, No. 12, 1919-1920 by D. A. Price).

Preparation Example 107

To 1.10 g of tert-butyl (1S,2R)-1-{benzyl[(1R)-1-phenylethyl]amino}-5-methylindane-2-carboxylate was added 30 ml of a 10% hydrogen chloride/methanol solution, followed by stirring at 60° C. for 5 hours. After leaving to be cooled, the solvent was evaporated under reduced pressure, and a saturated aqueous sodium hydrogen carbonate solution and ethyl acetate were added thereto to carry out a layer separation operation. The organic layer was washed with saturated brine and dried over anhydrous magnesium sulfate, and the solvent was evaporated under reduced pressure. The obtained residue was purified by silica gel column chromatography to obtain 828 mg of methyl S,2R)-1-{benzyl[(1R)-1-phenylethyl]amino}-5-methylindane-2-carboxylate.

Preparation Example 109

To a solution of 1.67 g of methyl (1S,2R)-1-{benzyl[(1R)-1-phenylethyl]amino}-6-methylindane-2-carboxylate in 27 ml of acetic acid was added 500 mg of 10% palladium-carbon (wet), followed by stirring for 18 hours under a hydrogen atmosphere at 4 atm. The reaction mixture was filtered over Celite and the solvent was then evaporated under reduced pressure. To the obtained residue were added a saturated aqueous sodium hydrogen carbonate solution, chloroform, and methanol to carry out a layer separation operation. The organic layer was washed with saturated brine and dried over anhydrous magnesium sulfate, the solvent was evaporated under reduced pressure, and the obtained residue was purified by silica gel column chromatography. To a solution of the obtained purified product in methanol was added 3 ml of a 10% hydrogen chloride/methanol solution. The solvent was evaporated under reduced pressure to obtain 803 mg of methyl (1S,2R)-1-amino-6-methylindane-2-carboxylate hydrochloride.

Preparation Example 110

To a solution of 789 mg of tert-butyl (2E)-3-[2-(hydroxymethyl)-3-methylphenyl]acrylate in 16 ml of methanol was added 82 mg of nickel chloride (II). Then, 240 mg of sodium borohydride was added thereto under ice-cooling, followed by stirring for 4 hours under ice-cooling. To the reaction mixture were added water and ethyl acetate to carry out a layer separation operation. The organic layer was washed with saturated brine and dried over anhydrous magnesium sulfate, and the solvent was evaporated under reduced pressure to obtain 790 mg of tert-butyl 3-[2-(hydroxymethyl)-3-methylphenyl]propanoate.

Preparation Example 111

To a solution of 770 mg of tert-butyl 3-[2-(hydroxymethyl)-3-methylphenyl]propanoate in 16 ml of dimethylsulfoxide were added 4 ml of triethylamine and 1.22 g of a sulfur trioxide pyridine complex, followed by stirring at room temperature for 5 hours. To the reaction mixture were added diluted hydrochloric acid and ethyl acetate to carry out a layer separation operation. The organic layer was sequentially washed with water, saturated aqueous sodium hydrogen carbonate solution, water, and saturated brine, dried over anhydrous magnesium sulfate, and the solvent was evaporated under reduced pressure. The obtained residue was purified by silica gel column chromatography to obtain 707 mg of tert-butyl 3-(2-formyl-3-methylphenyl)propanoate.

Preparation Example 112

To a solution of 305 mg of tert-butyl 3-(2-formyl-3-methylphenyl)propanoate in 3 ml of THF 3 ml were added 298 mg of (S)-2-methyl-2-propanesulfinamide and 0.62 ml of tetraethyl orthotitanate, followed by stirring at room temperature for 16 hours. The reaction mixture was poured into ice water and the insoluble material was filtered through Celite. To the filtrate was added chloroform to carry out a layer separation operation. The organic layer was washed with water and subsequentially with saturated brine, dried over anhydrous magnesium sulfate, and the solvent was evaporated under reduced pressure. The obtained residue was purified by silica gel column chromatography to obtain 336 mg of tert-butyl 3-{2-[(E)-{[(S)-tert-butylsulfinyl]imino}methyl]-3-methylphenyl}propanoate.

Preparation Example 113

To a solution of 1.122 g of tert-butyl 3-{2-[(E)-{[(S)-tert-butylsulfinyl]imino}methyl]-3-fluorophenyl}propanoate (compound of Preparation Example 129) in 26.7 ml of THF was added 9.5 ml of lithium bis(trimethylsilyl)amide (1 M THF solution) at −78° C., followed by stirring at the same temperature for 8.5 hours. To the reaction mixture were added a saturated aqueous ammonium chloride solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 390 mg of tert-butyl (1S,2R)-1-{[(S)-tert-butylsulfinyl]amino}-7-fluoroindane-2-carboxylate (Preparation Example 113a), and 130 mg of each of tert-butyl (1R,2R)-1-{[(S)-tert-butylsulfinyl]amino}-7-fluoroindane-2-carboxylate and tert-butyl (1S,2S)-1-{[(S)-tert-butylsulfinyl]amino}-7-fluoroindane-2-carboxylate (Preparation Example 113b and Preparation Example 113c).

Preparation Example 114

To a solution of 140 mg of tert-butyl (1S,2R)-1-{[(S)-tert-butylsulfinyl]amino}-7-methylindane-2-carboxylate in 9.1 ml of ethyl acetate was added 0.88 ml of a 4 M hydrogen chloride/ethyl acetate solution, followed by stirring at room temperature for 2 hours. The solvent was evaporated under reduced pressure, and to the obtained residue were added a saturated aqueous sodium hydrogen carbonate solution and ethyl acetate to carry out a layer separation operation. The organic layer was washed with water and saturated brine, and dried over anhydrous magnesium sulfate, and the solvent was evaporated under reduced pressure to obtain 88 mg of tert-butyl (1S,2R)-1-amino-7-methylindane-2-carboxylate.

Preparation Example 115

To 12 mg of tert-butyl (1S,2R)-1-{[(S)-tert-butylsulfinyl]amino}-7-fluoroindane-2-carboxylate (compound of Preparation Example 113a) was added 0.4 ml of a 10% hydrogen chloride/methanol solution, followed by stirring for 1 hour under ice-cooling. To the reaction mixture was added 1 ml of a 10% hydrogen chloride/methanol solution, followed by stirring at 50° C. for 6 hours. After leaving to be cooled, the solvent was evaporated under reduced pressure, and then to the obtained residue were added a saturated aqueous sodium hydrogen carbonate solution and ethyl acetate to carry out a layer separation operation. The organic layer was washed with saturated brine and dried over anhydrous magnesium sulfate, and the solvent was evaporated under reduced pressure to obtain 6 mg of methyl (1S,2R)-1-amino-7-fluoroindane-2-carboxylate.

Preparation Example 116

A suspension of 1 g of 2-bromothiophene-3-carbaldehyde, 3.8 ml of tert-butyl acrylate, 120 mg of palladium acetate, 420 mg of tetra-n-butylammonium bromide, and 610 mg of potassium carbonate in 10 ml of DMF was stirred at 100° C. overnight. After leaving to be cooled, the insoluble material was filtered through Celite, and to the filtrate were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 660 mg of tert-butyl (2E)-3-(3-formyl-2-thienyl)acrylate.

Preparation Example 117

To a solution of 650 mg of tert-butyl (2E)-3-(3-formyl-2-thienyl)acrylate in 15 ml of methanol was added 150 mg of 10% palladium-carbon, followed by stirring for 5 hours under a hydrogen atmosphere. After filtration through Celite, the solvent was evaporated under reduced pressure. The obtained residue was purified by silica gel column chromatography to obtain 530 mg of tert-butyl 3-(3-formyl-2-thienyl)propanoate.

Preparation Example 129 tert-Butyl 3-{2-[(E)-{[(S)-tert-butylsulfinyl]imino}methyl]-3-fluorophenyl}propanoate was prepared using (S)-2-methyl-2-propanesulfinamide by the same method as in Preparation Example 112 as described above.

Preparation Example 130 tert-Butyl 3-(2-{(E)-[(tert-butylsulfinyl)imino]methyl}-3-fluorophenyl)propanoate as a racemate was prepared using 2-methyl-2-propanesulfinamide as a racemate by the same method as in Preparation Example 112 as described above.

Preparation Example 131 tert-Butyl 3-{2-[(E)-{[(R)-tert-butylsulfinyl]imino}methyl]-3-fluorophenyl}propanoate was prepared using (R)-2-methyl-2-propanesulfinamide by the same method as in Preparation Example 112 as described above.

Preparation Example 135 tert-Butyl rac-(1R,2R)-1-[(tert-butylsulfinyl)amino]-7-fluoroindane-2-carboxylate was prepared using tert-butyl 3-(2-{(E)-[(tert-butylsulfinyl)imino]methyl}-3-fluorophenyl)propanoate (compound of Preparation Example 130) as a racemate by the same method as in Preparation Example 113 as described above.

Preparation Example 136 tert-Butyl (1R,2S)-1-[(R)-tert-butylsulfinyl]amino-7-fluoroindane-2-carboxylate was prepared using tert-butyl 3-{2-[(E)-{[(R)-tert-butylsulfinyl]imino}methyl]-3-fluorophenyl}propanoate (compound of Preparation Example 131) by the same method as in Preparation Example 113 as described above. Further, the compound of Preparation Example 136 and the compound of Preparation Example 113a are enantiomers (mirror image isomers) with respect to each other.

Preparation Example 137

To a solution of 120 mg of tert-butyl (5R,6S)-4-{[(S)-tert-butylsulfinyl]amino}-5,6-dihydro-4H-cyclopenta[b]thiophene-5-carboxylate (compound of Preparation Example 143) in 7 ml of ethyl acetate was added 0.7 ml of a 4 M hydrogen chloride/ethyl acetate solution, followed by stirring for 2 hours. The solvent was evaporated under reduced pressure, and then to the obtained residue was added diisopropyl ether. The insoluble material was collected by filtration and dried to obtain 80 mg of tert-butyl (5R,6S)-6-amino-5,6-dihydro-4H-cyclopenta[b]thiophene-5-carboxylate hydrochloride.

Preparation Example 139

Preparation was carried out using the compound of Preparation Example 135 by the same method as in Preparation Example 115 as described above.

Preparation Example 140

Preparation was carried out using the compound of Preparation Example 136 by the same method as in Preparation Example 115 as described above. Further, the compound of Preparation Example 140 and the compound of Preparation Example 115 are enantiomers (mirror image isomers) with respect to each other.

Preparation Example 165

To 820 mg of tert-butyl[(1S)-1-(3-bromophenyl)ethyl]carbamate were added 113 mg of 1,3-bis(diphenylphosphino)propane, 62 mg of palladium acetate, 0.84 ml of triethylamine, 8 ml of DMF, and 12 ml of methanol, followed by stirring at room temperature for 1 hour. While stirring at room temperature, carbon monooxide was intaken for 10 minutes, followed by stirring at 80° C. overnight under a carbon monooxide atmosphere. 113 mg of 1,3-bis(diphenylphosphino)propane and 62 mg of palladium acetate were added thereto, followed by stirring at 80° C. overnight. To the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 577 mg of methyl 3-{(1S)-1-[(tert-butoxycarbonyl)amino]ethyl}benzoate.

Preparation Example 166

To a solution of 1 g of tert-butyl[(1R,2R)-2-hydroxy-2,3-dihydro-1H-inden-1-yl]carbamate in 10 ml of THF was added 16.9 ml of a 0.5 M potassium hexamethyldisilazane/toluene solution at −78° C., followed by stirring for 30 minutes. 0.92 ml of chlorodimethyl ether was added thereto at −78° C., followed by warming to room temperature for 3 hours. 4 ml of a 0.5 M potassium hexamethyldisilazane/toluene solution and 0.31 ml of chlorodimethyl ether were added thereto at −78° C., followed by stirring at room temperature for 2 hours. To the reaction mixture were added a saturated aqueous ammonium chloride solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 311 mg of tert-butyl [(1R,2R)-2-(methoxymethoxy)-2,3-dihydro-1H-inden-1-yl](methoxymethyl)carbamate.

Preparation Example 167

A solution of 2.75 g of tert-butyl[(1R,2R)-2-(methoxymethoxy)-2,3-dihydro-1H-inden-1-yl](methoxymethyl)carbamate in 55 ml of carbon tetrachloride was heated at an outer temperature of 100° C., and a mixture of 1.53 g of N-bromosuccinimide and 95 mg of 2,2'-azodiisobutyronitrile was added portionwise thereto over 30 minutes at an interval of 5 minutes, followed by stirring at an outer temperature of 100° C. for 1 hour. The insoluble material was filtered, and an aqueous sodium thiosulfate solution and chloroform were added thereto to carry out a layer separation operation. After drying over anhydrous sodium sulfate, the solvent was evaporated under reduced pressure. The obtained residue was purified by silica gel column chromatography to obtain 984 mg of tert-butyl[(1R,2S)-3-bromo-2-(methoxymethoxy)-2,3-dihydro-1H-inden-1-yl](methoxymethyl)carbamate.

Preparation Example 168

To 983 mg of tert-butyl[(1R,2S)-3-bromo-2-(methoxymethoxy)-2,3-dihydro-1H-inden-1-yl](methoxymethyl)carbamate were added 1.39 g of potassium acetate and 15 ml of N-methyl-2-pyrrolidone, followed by stirring at 70° C. for 15 hours. To the reaction mixture were added water and ethyl acetate to carry out a layer separation operation. The organic layer was washed with water and saturated brine, and dried over anhydrous sodium sulfate, and the solvent was evaporated under reduced pressure. The obtained residue was purified by silica gel column chromatography to obtain 436 mg (Preparation Example 168a) and 106 mg (Preparation Example 168b), respectively, of (2S,3R)-3-[(tert-butoxycarbonyl)(methoxymethyl)amino]-2-(methoxymethoxy)-2,3-dihydro-1H-inden-1-yl acetate, as two kinds of single isomers, each having an undetermined configuration at the 1-position of an indane ring.

Preparation Example 169

To 235 mg of tert-butyl (3aR,8aR)-8-acetoxy-2-oxo-8,8a-dihydro-2H-indeno[1,2-d][1,3]oxazole-3(3aH)-carboxylate were added 2.4 ml of THF, 0.24 ml of water, and 229 mg of sodium hydroxide, followed by stirring for 4 hours. To the reaction mixture were added water and chloroform to carry out a layer separation operation. The organic layer was washed with saturated brine and dried over anhydrous magnesium sulfate, and the solvent was evaporated under reduced pressure. The obtained residue was purified by silica gel column chromatography to obtain 66 mg (Preparation Example 169a) and 28 mg (Preparation Example 169b), respectively, of tert-butyl[(1R,2R)-2,3-dihydroxy-2,3-dihydro-1H-inden-1-yl]carbamate, as two kinds of single isomers, each having an undetermined configuration at the 3-position of an indane ring.

Preparation Example 170

To a solution of 700 mg of tert-butyl[(1R,2R)-3-{[tert-butyl(dimethyl)silyl]oxy}-2-hydroxy-1-phenylpropyl]carbamate in 35 ml of THF was added 1.2 g of triphenylphosphine, 766 mg of 4-nitrobenzoic acid, and 2.4 ml of a 1.9 M diisopropyl azodicarboxylate/toluene solution under ice-cooling, followed by stirring at room temperature for 5 hours. To the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 638 mg of (6S,7R)-2,2,3,3,11,11-hexamethyl-9-oxo-7-phenyl-4,10-dioxa-8-aza-3-siladodecan-6-yl 4-nitrobenzoate.

Preparation Example 171

To a solution of 106 mg of the compound of Preparation Example 168b in 6 ml of methanol was added 117 mg of potassium carbonate, followed by stirring for 2 hours. To the reaction mixture were added water and ethyl acetate to carry out a layer separation operation, the organic layer was dried over anhydrous sodium sulfate, and the solvent was evaporated under reduced pressure. The obtained residue was purified by silica gel column chromatography to obtain 82 mg of tert-butyl[(1R,2S)-3-hydroxy-1-(methoxymethoxy)-2,3-dihydro-1H-inden-1-yl](methoxymethyl)carbamate as a single isomer having an undetermined configuration at the 3-position of an indane ring.

Preparation Example 172

To a solution of 190 mg of the compound of Preparation Example 171 in 3 ml of methanol was added 3 ml of 4 M hydrogen chloride/dioxane solution, followed by stirring for 20 hours. The solvent was evaporated under reduced pressure to obtain 110 mg of (2S,3R)-3-aminoindane-1,2-diol hydrochloride as a compound having an undetermined configuration at the 1-position of an indane ring. This was used for the next step without purification.

Preparation Example 173

To a solution of 1 g of methyl 3-oxoindane-1-carboxylate in 10 ml of toluene were added 0.78 ml of (1S)-1-(4-methoxyphenyl)ethanamine and 100 mg of p-toluenesulfonic acid monohydrate, followed by heating to reflux for 5 hours using a Dean-Stark type reflux device. Then, 634 mg of magnesium sulfate was added thereto, followed by heating to reflux for 5 hours using a Dean-Stark type reflux device. Further, 634 mg of magnesium sulfate was added thereto, followed by heating to reflux for 5 hours using a Dean-Stark type reflux device. The insoluble material was removed by filtration and the solvent was then evaporated under reduced pressure to obtain an intermediate product. To a solution of the obtained intermediate product in 17 ml of ethanol was added 209 mg of sodium borohydride under ice-cooling, followed by stirring for 1 hour under ice-cooling. The solvent was evaporated under reduced pressure, and to the obtained residue were added water, a saturated aqueous sodium hydrogen carbonate solution, and ethyl acetate to carry out a layer separation operation. The organic layer was washed with water and saturated brine, and dried over anhydrous magnesium sulfate, and the solvent was evaporated under reduced pressure. The obtained residue was purified by silica gel column chromatography to obtain 1.195 g of methyl (3S)-3-{[(1S)-1-(4-methoxyphenyl)ethyl]amino}indane-1-carboxylate.

Preparation Example 174

To 713 mg of methyl 1-oxoindane-5-carboxylate were added 612 mg of (1S)-1-(4-methoxyphenyl)ethanamine, 0.23 ml of acetic acid, 600 mg of Molecular Sieves 4A, and 12 ml of toluene, followed by heating to reflux using a Dean-Stark type reflux device for 4 hours under reduced pressure (213 mbar). Then, 0.23 ml of acetic acid and 300 mg of Molecular Sieves 4A were added thereto, followed by heating to reflux using a Dean-Stark type reflux device for 4 hours under reduced pressure (213 mbar). The insoluble material was removed by filtration and the solvent was then evaporated under reduced pressure to obtain an intermediate product. To a solution of the obtained intermediate product in 13 ml of ethanol was added 161 mg of sodium borohydride under ice-cooling, followed by stirring for 1 hour under ice-cooling. The solvent was evaporated under reduced pressure, and to the obtained residue were added water, a saturated aqueous sodium hydrogen carbonate solution, and ethyl acetate to carry out a layer separation operation. The organic layer was washed with water and saturated brine in this order, and dried over anhydrous magnesium sulfate, and the solvent was evaporated under reduced pressure. The obtained residue was purified by silica gel column chromatography to obtain 452 mg of methyl (1S)-1-{[(1S)-1-(4-methoxyphenyl)ethyl]amino}indane-5-carboxylate.

Preparation Example 175

To a solution of 850 mg of tert-butyl[2-(3-bromophenyl)propan-2-yl]carbamate in 8.5 ml of THF was added 4.1 ml of a 1.65 M n-butyllithium/hexane solution at −78° C., followed by stirring at the same temperature for 30 minutes. Then, 0.85 ml of methyl chloroformate was added dropwise thereto at −78° C., followed by stirring at the same temperature for 1 hour. To the reaction mixture were added a saturated aqueous ammonium chloride solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 199 mg of methyl 3-{2-[(tert-butoxycarbonyl)amino]propan-2-yl}benzoate.

Preparation Example 176

To 452 mg of methyl (1S)-1-{[(1S)-1-(4-methoxyphenyl)ethyl]amino}indane-5-carboxylate were added 34 ml of trifluoroacetic acid and 1.03 g of pentamethylbenzene, followed by stirring at 70° C. for 4 days, and the solvent was evaporated under reduced pressure. To the obtained residue were added a saturated aqueous sodium hydrogen carbonate solution and chloroform to carry out a layer separation operation. The organic layer was washed with saturated brine and dried over anhydrous magnesium sulfate, and the solvent was evaporated under reduced pressure. The obtained residue was purified by silica gel column chromatography to obtain 165 mg of methyl (1S)-1-aminoindane-5-carboxylate.

Preparation Example 178

To a mixed solution of 1.55 g of 1-methyl-3-(nitromethyl)benzene in 15 ml of ethanol and 6 ml of dioxane were added 0.05 ml of a 1 M aqueous sodium hydroxide solution and 1.89 ml of a 37% aqueous formalin solution, followed by stirring for 15 hours. 0.05 ml of a 1 M aqueous sodium hydroxide solution and 0.83 ml of a 37% aqueous formalin solution were added thereto, followed by stirring at 50° C. for 2 hours, and the solvent was evaporated under reduced pressure. To the obtained residue was added ethyl acetate, followed by washing with saturated brine and drying over anhydrous magnesium sulfate, and the solvent was evaporated under reduced pressure. The obtained residue was purified by silica gel column chromatography to obtain 1.91 g of 2-(3-methylphenyl)-2-nitropropane-1,3-diol.

Preparation Example 179

To a solution of 2 g of ethylpyridin-3-yl acetate in 40 ml of DMF were added 1.09 g of paraformaldehyde and 165 mg of sodium ethoxide, followed by stirring for 19 hours. Acetic acid was added thereto under ice-cooling and the solvent was evaporated under reduced pressure. The obtained residue was purified by silica gel column chromatography to obtain 1.29 g of ethyl 3-hydroxy-2-(hydroxymethyl)-2-(pyridin-3-yl)propanoate.

Preparation Example 180

To a mixture of 1.25 g of ethyl 3-hydroxy-2-(hydroxymethyl)-2-(pyridin-3-yl)propanoate in 13 ml of acetone were added 0.75 ml of 2,2-dimethoxypropane and 105 mg of p-toluenesulfonic acid monohydrate, followed by stirring for 12 hours. Then, 1.06 g of p-toluenesulfonic acid monohydrate was added thereto, followed by stirring for 6 hours. Further, 0.75 ml of 2,2-dimethoxypropane was added thereto, followed by stirring at 50° C. for 30 minutes, and the solvent was evaporated under reduced pressure. To the obtained residue were added 13 ml of acetone and 0.78 ml of 2-methoxy-1-propene at room temperature, followed by stirring for 30 minutes. To the reaction mixture were added a saturated aqueous sodium hydrogen carbonate solution and ethyl acetate to carry out a layer separation operation. The organic layer was washed with a saturated aqueous sodium hydrogen carbonate solution, water, and saturated brine in this order, and dried over anhydrous magnesium sulfate, and the solvent was evaporated under reduced pressure. The obtained residue was purified by silica gel column chromatography to obtain 1.16 g of ethyl 2,2-dimethyl-5-(pyridin-3-yl)-1,3-dioxane-5-carboxylate.

Preparation Example 181

To a mixed solution of 0.86 g of tert-butyl (1-phenylcyclopenta-3-en-1-yl)carbamate and 0.47 g of 4-methylmorpholine N-oxide in 22 ml of THF and 8.7 ml of water was added 0.42 ml of a 2.5% osmium tetraoxide/tert-butanol solution, followed by stirring for 2 hours and leaving to stand for 4 days. To the reaction mixture were added an aqueous sodium thiosulfate solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 512 mg (Preparation Example 181a) and 126 mg (Preparation Example 181b), respectively, of tert-butyl [(3R,4S)-3,4-dihydroxy-1-phenylcyclopentyl]carbamate, as two kinds of single isomers, each having an undetermined configuration at the 1-position.

Preparation Example 182

A mixture of 620 mg of tert-butyl[(1R,2R)-2,3-dihydroxy-1-phenylpropyl]carbamate, 0.37 g of tert-butyldimethylchlorosilane, 0.19 g of imidazole, and 9.3 ml of dichloromethane was stirred for 2 hours. To the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 705 mg of tert-butyl[(1R,2R)-3-{[tert-butyl(dimethyl)silyl]oxy}-2-hydroxy-1-phenylpropyl]carbamate.

Preparation Example 183

To 500 mg of methyl 6,6a-dihydro-1aH-indeno[1,2-b]oxirene-1a-carboxylate were added 860 mg of sodium azide, 309 mg of ammonium chloride, 4 ml of methanol, and 0.5 ml of water, followed by stirring at 80° C. for 2 hours. To the reaction mixture were added a saturated aqueous sodium hydrogen carbonate solution, water, and ethyl acetate to carry out a layer separation operation, and the organic layer was dried over anhydrous magnesium sulfate. To a solution of the obtained intermediate product in ethyl acetate-methanol was added 61 mg of 10% palladium-carbon (wet), followed by stirring for 6 hours under a hydrogen atmosphere. The reaction mixture was filtered over Celite and the solvent was then evaporated under reduced pressure to obtain 0.51 g of methyl rac-(1R,2R)-1-amino-2-hydroxyindane-1-carboxylate.

Preparation Example 184

To 1.09 g of 2,2-dimethyl-5-(pyridin-3-yl)-1,3-dioxane-5-carboxylic acid were added 20 ml of toluene, 0.9 ml of triethylamine, 2.4 ml of benzyl alcohol, and 1.3 ml of diphenylphosphoryl azide, followed by stirring at 100° C. for 17 hours. After leaving to be cooled, to the reaction mixture were added a saturated aqueous sodium hydrogen carbonate solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 1.01 g of benzyl[2,2-dimethyl-5-(pyridin-3-yl)-1,3-dioxan-5-yl]carbamate.

Preparation Example 185

To a solution of 340 mg of sodium 2,2-dimethyl-5-(pyridin-2-yl)-1,3-dioxane-5-carboxylate in 5 ml of dioxane and 1 ml of water was added 0.21 ml of isobutyl chloroformate under ice-cooling, followed by stirring for 1 hour. A solution of 850 mg of sodium azide in 3 ml of water was added thereto, followed by stirring for 10 minutes under ice-cooling. To the reaction mixture were added water and diethyl ether to carry out a layer separation operation. The organic layer was washed with saturated brine and dried over anhydrous magnesium sulfate, and the solvent was evaporated under reduced pressure. To the obtained residue was added 5 ml of toluene, followed by stirring at 100° C. for 5 minutes. After leaving to be cooled, 0.7 ml of benzyl alcohol was added thereto at room temperature, followed by stirring at 100° C. for 19 hours. After leaving to be cooled, the solvent was evaporated under reduced pressure. The obtained residue was purified by silica gel column chromatography to obtain 223 mg of benzyl[2,2-dimethyl-5-(pyridin-2-yl)-1,3-dioxan-5-yl]carbamate.

Preparation Example 186

To a mixture of 1.6 g of 2,2-dimethyl-5-(3-methylphenyl)-5-nitro-1,3-dioxane in 24 ml of ethanol was added a suspension of a Raney nickel (manufactured by Aldrich, product obtained by washing 1 ml of an aqueous suspension with water and ethanol) in 9 ml of ethanol, followed by stirring for 22 hours under a hydrogen atmosphere at 4 atm. The reaction mixture was filtered over Celite and the solvent was then evaporated under reduced pressure. The obtained residue was purified by silica gel column chromatography to obtain 1.55 g of 2,2-dimethyl-5-(3-methylphenyl)-1,3-dioxan-5-amine.

Preparation Example 187

A suspension of 3.0 g of methyl 3-formylbenzoate, 2.25 g of (R)-2-methyl-2-propanesulfinamide, and 6.0 g of copper (II) sulfate in 50 ml of dichloromethane was stirred overnight. The reaction mixture was filtered over Celite and the solvent was then evaporated under reduced pressure. The obtained residue was purified by silica gel column chromatography to obtain 700 mg of methyl 3-[(E)-{[(R)-tert-butylsulfinyl]imino}methyl]benzoate.

Preparation Example 188

A suspension of 3.0 g of methyl 3-formylbenzoate, 2.5 g of (S)-2-methyl-2-propanesulfinamide, 250 mg of pyridinium paratoluene sulfonate, and 11 g of magnesium sulfate in 50 ml of dichloromethane was stirred overnight. The reaction mixture was filtered over Celite and the solvent was then evaporated under reduced pressure. The obtained residue was purified by silica gel column chromatography to obtain 3.0 g of methyl 3-[(E)-{[(S)-tert-butylsulfinyl]imino}methyl]benzoate.

Preparation Example 189

To a solution of 500 mg of methyl 3-[(E)-{[(S)-tert-butylsulfinyl]imino}methyl]benzoate in 12 ml of THF was added 0.50 ml of a 1 M diethylzinc/hexane solution at −78° C., followed by stirring at the same temperature for 5 minutes. 0.80 ml of a 3 M ethylmagnesium bromide/diethyl ether solution was added thereto at −78° C., followed by stirring at the same temperature for 2 hours. To the reaction mixture were added a saturated aqueous ammonium chloride solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 447 mg of methyl 3-[(1S)-1-{[(S)-tert-butylsulfinyl]amino}propyl]benzoate.

Preparation Example 190

To a solution of 1 ml of diisopropylamine in 5 ml of THF was added 4.4 ml of a 1.6 M n-butyllithium/hexane solution under ice-cooling, followed by stirring at the same temperature for 15 minutes. 0.6 ml of methyl acetate was added thereto at −78° C., followed by stirring at the same temperature for 20 minutes. A solution of 3.6 g of chlorotitanium (IV) triisopropoxide in 7 ml of THF was added thereto, followed by stirring at the same temperature for 20 minutes. A solution of 500 mg of N-[(E)-(2,3-dimethylphenyl)methylene]-2-methylpropane-2-(R)-sulfinamide in 5 ml of THF was added thereto at −78° C., followed by stirring at the same temperature for 4 hours. To the reaction mixture were added a saturated aqueous ammonium chloride solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 592 mg of methyl (3S)-3-{[(R)-tert-butylsulfinyl]amino}-3-(2,3-dimethylphenyl)propanoate.

Preparation Example 191

A suspension of 1 g of 2,2-dimethylspiro[1,3-dioxane-5,2'-inden]-1'(3'H)-one, 329 mg of hydroxylamine hydrochloride, and 388 mg of sodium acetate in 5 ml of ethanol was stirred for 12 hours. Then, 1.2 ml of triethylamine was added thereto, followed by stirring at room temperature for 3 days and further stirring at 50° C. for 1 hour. To the reaction mixture were added water and ethyl acetate to carry out a layer separation operation. The organic layer was washed with water and saturated brine, and dried over anhydrous magnesium sulfate, and the solvent was evaporated under reduced pressure. The obtained residue was purified by silica gel column chromatography to obtain 1.0 g of N-hydroxy-2,2-dimethylspiro[1,3-dioxane-5,2'-inden]-1'(3'H)-imine.

Preparation Example 192

To a suspension of 384 mg of lithium aluminum hydride in 22 ml of diethyl ether were added 0.5 g of N-hydroxy-2,2-dimethylspiro[1,3-dioxane-5,2'-inden]-1'(3'H)-imine and 5 ml of THF under ice-cooling, followed by stirring at 40° C. for 8 hours. 0.55 ml of water, 0.55 ml of a 15% aqueous sodium hydroxide solution, and 1.65 ml of water were added thereto under ice-cooling. After filtration through Celite, the solvent was evaporated under reduced pressure. The obtained residue was purified by silica gel column chromatography to obtain 146 mg of 2,2-dimethyl-1',3'-dihydrospiro[1,3-dioxane-5,2'-inden]-1'-amine.

Preparation Example 193

A mixture of 1 g of tert-butyl[(1S)-1-(3-bromophenyl)ethyl]carbamate, 18 mg of bis(tri-tert-butylphosphine)palladium (0), 180 mg of zinc fluoride, 1 ml of [(1-methoxy-2-methylpropa-1-en-1-yl)oxy](trimethyl)silane, and 10 ml of DMF was stirred at 80° C. overnight and at 100° C. for 5 hours. 25 mg of bis(tri-tert-butylphosphine)palladium (0)

and 0.34 ml of [(1-methoxy-2-methylpropa-1-en-1-yl)oxy] (trimethyl)silane were added thereto, followed by stirring at 80° C. for 3 days. To the reaction mixture were added water and ethyl acetate to carry out a layer separation operation. The organic layer was washed with water and dried over anhydrous magnesium sulfate, and the solvent was evaporated under reduced pressure. The obtained residue was purified by silica gel column chromatography to obtain 281 mg of methyl 2-(3-{(1S)-1-[(tert-butoxycarbonyl)amino]ethyl}phenyl)-2-methylpropanoate.

Preparation Example 194

To a solution of 130 mg of 2-(trimethylsilyl)ethyl rac-[(2R,3S)-2,3-dihydroxy-1-methyl-2,3-dihydro-1H-inden-1-yl]carbamate in 4 ml of THF was added 70 mg of 55% sodium hydride under ice-cooling, followed by stirring at the same temperature for 1 hour. To the reaction mixture were added a saturated aqueous ammonium chloride solution and ethyl acetate to carry out a layer separation operation, followed by drying over anhydrous magnesium sulfate, and the solvent was evaporated under reduced pressure. The obtained residue was purified by silica gel column chromatography to obtain 70 mg of 2-(trimethylsilyl)ethyl rac-[(1R,2S,3R)-2,3-dihydroxy-1-methyl-2,3-dihydro-1H-inden-1-yl]carbamate and 45 mg of rac-(3aR,8S,8aR)-8-hydroxy-3a-methyl-3,3a,8,8a-tetrahydro-2H-indeno[1,2-d][1,3]oxazol-2-one.

Preparation Example 195

To a solution of 3.4 g of 1-methyl-1H-indene in 136 ml of ether was added 16.2 ml of a 1.62 M n-butyllithium/hexane solution at −78° C., followed by stirring at room temperature for 30 minutes. To the reaction mixture were added 15.5 ml of tetra-iso-propyl titanate and 2.41 ml of methyl chloroformate at −78° C., followed by stirring at −78° C. for 2 hours. To the reaction mixture were added 1 M hydrochloric acid and ethyl acetate to carry out a layer separation operation, followed by drying over anhydrous magnesium sulfate, and the solvent was evaporated under reduced pressure. The obtained residue was purified by silica gel column chromatography to obtain 1.57 g of methyl 1-methyl-1H-indene-1-carboxylate.

Preparation Example 196

To a solution of 1.0 g of tert-butyl (3S)-piperidin-3-yl carbamate in 20 ml of DMF were added 0.77 ml of methyl 2-fluorobenzoate and 1.4 g of potassium carbonate, followed by stirring at 130° C. overnight. After leaving to be cooled, to the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 590 mg of methyl 2-{(3S)-3-[(tert-butoxycarbonyl)amino]piperidin-1-yl}benzoate.

Preparation Example 197

To a solution of 280 mg of methyl 3-[(2S)-2-{[(1S)-1-phenylethyl]amino}propyl]benzoate in 6.8 ml of ethanol were added 30 mg of 20% palladium-carbon hydroxide (wet) and 320 mg of ammonium formate, followed by stirring at 80° C. for 4 hours. The reaction mixture was filtered over Celite and the solvent was then evaporated under reduced pressure. To the obtained residue were added a saturated aqueous sodium hydrogen carbonate solution and chloroform to carry out a layer separation operation, followed by drying over anhydrous magnesium sulfate. The solvent was evaporated under reduced pressure to obtain 180 mg of methyl 3-[(2S)-2-aminopropyl]benzoate.

Preparation Example 198

To a solution of 300 mg of tert-butyl[(1R,2S)-3-{[tert-butyl(dimethyl)silyl]oxy}-2-hydroxy-1-phenylpropyl]carbamate and 5 ml of methanol was added 5 ml of a 4 M hydrogen chloride/dioxane solution, followed by stirring for 2 hours. The solvent was evaporated under reduced pressure to obtain 171 mg of (2S,3R)-3-amino-3-phenylpropane-1,2-diol hydrochloride.

Preparation Example 199

To 448 mg of (2R,3R)-3-amino-3-phenylpropane-1,2-diol hydrochloride were added 18 ml of dichloromethane, 0.77 ml of triethylamine, and 0.53 g of di-tert-butyl dicarbonate, followed by stirring for 3 hours, and the solvent was evaporated under reduced pressure. The obtained residue was purified by silica gel column chromatography to obtain 620 mg of tert-butyl[(1R,2R)-2,3-dihydroxy-1-phenylpropyl]carbamate.

Preparation Example 200

To a solution of 300 mg of N-[(2E)-1-{[tert-butyl(dimethyl)silyl]oxy}propan-2-ylidene]-2-methylpropane-2-(S)-sulfinamide in 2 ml of toluene was added 0.62 ml of a 2.0 M trimethylaluminum/toluene solution at −78° C., followed by stirring for 30 minutes. Further, 3.2 ml of a 0.5 Methyllithium/benzene-cyclohexane solution was added thereto at −78° C., followed by stirring for 1 hour. To the reaction mixture were added a saturated aqueous ammonium chloride solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 160 mg of N-[(2R)-1-{[tert-butyl(dimethyl)silyl]oxy}-2-methylbutan-2-yl]-2-methylpropane-2-(S)-sulfinamide.

Preparation Example 201

To a solution of 97 mg of N-[(2R)-1-{[tert-butyl(dimethyl)silyl]oxy}-2-methylbutan-2-yl]-2-methylpropane-2-(S)-sulfinamide in 1 ml of methanol was added 1.3 ml of a 4 M hydrogen chloride/dioxane solution, followed by stirring for 2 hours. The solvent was evaporated under reduced pressure to obtain 63 mg of (2R)-2-amino-2-methylbutan-1-ol hydrochloride.

Preparation Example 239

Preparation was carried out using the compound of Preparation Example 168a by the same method as in Preparation Example 171 as described above.

Preparation Example 240

Preparation was carried out using the compound of Preparation Example 239 by the same method as in Preparation Example 172 as described above.

Preparation Example 278

Preparation was carried out using the compound of Preparation Example 181a by the same method as in Example 5 as described below.

Preparation Example 279

Preparation was carried out using the compound of Preparation Example 181b by the same method as in Example 5 as described below.

Hereinafter, Preparation Examples for the compounds of the formula (I) of the present invention are shown as Examples. Further, for the respective Example Compounds, the structures are shown in Tables 32 to 99, and the physicochemical data and preparation methods are shown in Tables 100 to 131. Since the compounds of Examples 36 to 660, 662, 664 to 668, 670 to 672, 675 to 682, 686 to 692, 694, 696 to 697, 700 to 701, 706 to 708, and 715 to 757, 760 to 765, 768 to 796 and 799 to 885 were prepared in the same manner as the methods of Examples 1 to 35, 661, 663 and 709 to 714, they are described only in Tables as described later.

Example 1

To a solution of 600 mg of 8-(cyclohexylmethoxy)-2-methylimidazo[1,2-a]pyridine-3-carboxylic acid in 10 ml of DMF were added 500 mg of tert-butyl (3S)-3-aminopiperidine-1-carboxylate, 518 mg of N-[3-(dimethylamino)propyl]-N'-ethylcarbodiimide hydrochloride, and 366 mg of 1-hydroxybenzotriazole, followed by stirring overnight. To the reaction mixture were added water and ethyl acetate to carry out a layer separation operation. The organic layer was washed with water and saturated brine, dried over anhydrous sodium sulfate, and the solvent was evaporated under reduced pressure. The obtained residue was purified by silica gel column chromatography to obtain 808 mg of tert-butyl (3S)-3-({[8-(cyclohexylmethoxy)-2-methylimidazo[1,2-a]pyridin-3-yl]carbonyl}amino)piperidine-1-carboxylate.

Example 2

A mixture of 120 mg of N-[(1R)-2-{[tert-butyl(dimethyl)silyl]oxy}-1-phenylethyl]-8-hydroxy-2-methylimidazo[1,2-a]pyridine-3-carboxamide, 60 µl of cyclopentylmethanol, 156 µl of (tributylphosphoranylidene)acetonitrile, and 2.4 ml of toluene was stirred at 110° C. for 16 hours, followed by purification using silica gel chromatography, to obtain 100 mg of N-[(1R)-2-{[tert-butyl(dimethyl)silyl]oxy}-1-phenylethyl]-8-(cyclopentylmethoxy)-2-methylimidazo[1,2-a]pyridine-3-carboxamide.

Example 3

To a solution of 370 mg of ethyl 3-{[(1R)-2-{[tert-butyl(dimethyl)silyl]oxy}-1-phenylethyl]carbamoyl}-8-[(2-fluorobenzyl)oxy]-2-methylimidazo[1,2-a]pyridine-6-carboxylate in 12 ml of THF was added 1.22 ml of a 1 M tetrabutylammonium fluoride/THF solution, followed by stirring for 30 minutes. To the reaction mixture were added water and ethyl acetate to carry out a layer separation operation. The organic layer was dried over anhydrous magnesium sulfate and the solvent was evaporated under reduced pressure. The obtained residue was purified by silica gel column chromatography to obtain 220 mg of ethyl 8-[(2-fluorobenzyl)oxy]-3-{[(1R)-2-hydroxy-1-phenylethyl]carbamoyl}-2-methylimidazo[1,2-a]pyridine-6-carboxylate.

Example 4

To a solution of 90 mg of 6-bromo-8-(cyclohexylmethoxy)-N-[(1R)-2-hydroxy-1-phenylethyl]-2-methylimidazo[1,2-a]pyridine-3-carboxamide in 1.8 ml of N-methyl-2-pyrrolidone were added 54 mg of zinc cyanide and 27 mg of [1,1-bis(diphenylphosphino)ferrocene]dichloropalladium (II), followed by stirring at 180° C. for 30 minutes under a condition for microwave irradiation. To the reaction mixture was added 46 mg of zinc cyanide, followed by further stirring at 180° C. for 30 minutes under a condition for microwave irradiation. To the reaction mixture were added ethyl acetate and a saturated aqueous sodium hydrogen carbonate solution, followed by filtration through Celite. A layer separation operation of the obtained filtrate was carried out, the organic layer was washed with a saturated aqueous sodium hydrogen carbonate solution and saturated brine, and dried over anhydrous sodium sulfate, and the solvent was evaporated under reduced pressure. The obtained residue was purified by silica gel column chromatography to obtain 7 mg of 6-cyano-8-(cyclohexylmethoxy)-N-[(1R)-2-hydroxy-1-phenylethyl]-2-methylimidazo[1,2-a]pyridine-3-carboxamide.

Example 5

To a solution of 1.44 g of tert-butyl 4-({[8-(cyclohexylmethoxy)-2-methylimidazo[1,2-a]pyridin-3-yl]carbonyl}amino)piperidine-1-carboxylate in 15 ml of ethyl acetate was added 3.8 ml of a 4 M hydrogen chloride/ethyl acetate solution, followed by stirring for 1 day. The reaction mixture was concentrated under reduced pressure, and to the obtained residue were added ethyl acetate and ethanol. The resulting solid was collected by filtration and dried to obtain 1.29 g of 8-(cyclohexylmethoxy)-2-methyl-N-(piperidin-4-yl)imidazo[1,2-a]pyridine-3-carboxamide dihydrochloride.

Example 6

To a suspension of 400 mg of 8-(cyclohexylmethoxy)-2-methyl-N-[(3S)-pyrrolidin-3-yl]imidazo[1,2-a]pyridine-3-carboxamide dihydrochloride, 0.26 ml of triethylamine, and 0.23 ml of a 37% aqueous formaldehyde solution in 11 ml of dichloroethane was added 592 mg of sodium triacetoxyborohydride under ice-cooling, followed by stirring at room temperature for 1 hour. To the reaction mixture were added a saturated aqueous sodium hydrogen carbonate solution and chloroform to carry out a layer separation operation. The organic layer was dried over anhydrous sodium sulfate and the solvent was evaporated under reduced pressure. The obtained residue was purified by silica gel column chromatography to obtain 249 mg of 8-(cyclohexylmethoxy)-2-methyl-N-[(3S)-1-methylpyrrolidin-3-yl]imidazo[1,2-a]pyridine-3-carboxamide.

Example 7

To a suspension of 307 mg of 8-(cyclohexylmethoxy)-2-methyl-N-[(3S)-piperidin-3-yl]imidazo[1,2-a]pyridine-3-carboxamide dihydrochloride, 335 mg of potassium carbonate, 5 ml of acetonitrile, and 5 ml of DMF was added 92 μl of bromoethyl acetate under ice-cooling, followed by stirring for 3 hours under ice-cooling. To the reaction mixture were added water and chloroform to carry out a layer separation operation. The organic layer was dried over anhydrous sodium sulfate and the solvent was evaporated under reduced pressure. The obtained residue was purified by silica gel column chromatography to obtain 299 mg of ethyl[(3S)-3-({[8-(cyclohexylmethoxy)-2-methylimidazo[1, 2-a]pyridin-3-yl]carbonyl}amino)piperidin-1-yl]acetate.

Example 8

To a mixture of 150 mg of methyl 4-[({[8-(cyclohexylmethoxy)-2-methylimidazo[1,2-a]pyridin-3-yl] carbonyl}amino)methyl]piperidine-4-carboxylate dihydrochloride, 150 μl of triethylamine, and 5 ml of dichloromethane was added 25 μl of acetyl chloride under ice-cooling, followed by stirring at room temperature for 2 hours. To the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 135 mg of methyl 1-acetyl-4-[({[8-(cyclohexylmethoxy)-2-methylimidazo[1,2-a]pyridin-3-yl]carbonyl}amino)methyl] piperidine-4-carboxylate.

Example 9

To a mixture of 150 mg of methyl 4-[({[8-(cyclohexylmethoxy)-2-methylimidazo[1,2-a]pyridin-3-yl] carbonyl}amino)methyl]piperidine-4-carboxylate dihydrochloride, 150 μl of triethylamine, and 5 ml of dichloromethane was added 35 μl of methanesulfonyl chloride under ice-cooling, followed by stirring at room temperature for 2 hours. To the reaction mixture were added water and ethyl acetate to carry out a layer separation operation. The organic layer was washed with saturated brine and dried over anhydrous magnesium sulfate, and the solvent was evaporated under reduced pressure. The obtained residue was purified by silica gel column chromatography to obtain 85 mg of methyl 4-[({[8-(cyclohexylmethoxy)-2-methylimidazo[1,2-a]pyridin-3-yl] carbonyl}amino)methyl]-1-(methylsulfonyl)piperidine-4-carboxylate.

Example 10

To a solution of 200 mg of 8-(cyclohexylmethoxy)-2-methyl-N-[(3S)-piperidin-3-yl]imidazo[1,2-a]pyridine-3-carboxamide dihydrochloride in 5 ml of isopropylalcohol were added 220 μl of triethylamine and 72 μl of (trimethylsilyl)isocyanate, followed by stirring for 6 hours. To the reaction mixture were added water and ethyl acetate to carry out a layer separation operation. The organic layer was washed with water, a saturated aqueous sodium hydrogen carbonate solution, and saturated brine in this order, and dried over anhydrous sodium sulfate, the solvent was evaporated under reduced pressure, and the obtained residue was purified by silica gel column chromatography. The obtained solid was suspended in ethyl acetate, and 120 μl of 4 M hydrogen chloride/ethyl acetate solution was added thereto, followed by stirring. The resulting solid was collected by filtration and dried to obtain 170 mg of N-[(3S)-1-carbamoylpiperidin-3-yl]-8-(cyclohexylmethoxy)-2-methylimidazo[1,2-a]pyridine-3-carboxamide hydrochloride.

Example 11

To 200 mg of 8-(cyclohexylmethoxy)-2-methyl-N-[(3S)-piperidin-3-yl]imidazo[1,2-a]pyridine-3-carboxamide dihydrochloride were added 5 ml of pyridine and 217 mg of sulfamide, followed by heating to reflux for 4 hours. After leaving to be cooled at room temperature, to the reaction mixture were added water and chloroform to carry out a layer separation operation. The organic layer was dried over anhydrous sodium sulfate, the solvent was evaporated under reduced pressure, and the obtained residue was purified by silica gel column chromatography. The obtained solid was suspended in ethyl acetate, and 120 μl of a 4 M hydrogen chloride/ethyl acetate solution was added thereto. The resulting solid was collected by filtration and dried to obtain 151 mg of N-[(3S)-1-(aminosulfonyl)piperidin-3-yl]-8-(cyclohexylmethoxy)-2-methylimidazo[1,2-a]pyridine-3-carboxamide hydrochloride.

Example 12

To a solution of 216 mg of tert-butyl (3R)-3-({[8-(cyclohexylmethoxy)-2-methylimidazo[1,2-a]pyridin-3-yl] carbonyl}amino)-5-methylhexanoate in 2 ml of dichloromethane was added 2 ml of trifluoroacetic acid, followed by stirring overnight. The solvent was evaporated under reduced pressure, and water, a saturated aqueous sodium hydrogen carbonate solution, 1 M hydrochloric acid, and chloroform were added thereto to carry out a layer separation operation. The organic layer was dried over anhydrous sodium sulfate, the solvent was evaporated under reduced pressure, and the obtained residue was purified by silica gel column chromatography. To the obtained purified product were added ethyl acetate and diisopropyl ether, and the resulting solid was collected by filtration and dried to obtain 147 mg of (3R)-3-({[8-(cyclohexylmethoxy)-2-methylimidazo[1,2-a]pyridin-3-yl]carbonyl}amino)-5-methylhexanoic acid.

Example 13

To a solution of 290 mg of 8-(cyclohexylmethoxy)-N-[(1S)-1-(2-fluorophenyl)-3-hydroxypropyl]-2-methylimidazo[1,2-a]pyridine-3-carboxamide in dichloromethane was added 300 mg of 1,1,1-triacetoxy-1,1-dihydro-1,2-benziodoxol-3(1H)-one, followed by stirring overnight. To the reaction mixture were added saturated aqueous sodium bicarbonate, an aqueous sodium thiosulfate solution, and ethyl acetate to carry out a layer separation operation. The organic layer was washed with saturated aqueous sodium bicarbonate and dried over anhydrous magnesium sulfate, and the solvent was evaporated under reduced pressure. To a solution of the obtained residue and 230 μl of 2-methyl-2-butene in 6.5 ml of dioxane was added 1.7 ml of an aqueous solution of 93 mg of sodium chlorite and 315 mg of sodium dihydrogen phosphate in a water bath, followed by stirring for 30 minutes in a water bath. To the reaction mixture were added water, 1 M hydrochloric acid, and chloroform to carry out a layer separation operation. The organic layer was dried over anhydrous magnesium sulfate, the solvent was evaporated under reduced pressure, and the obtained residue was purified by silica gel column chromatography. To the obtained purified product was added diisopropyl ether, and the resulting solid was filtered and dried to obtain 80 mg of (3S)-3-({[8-(cyclohexylmethoxy)-2-methylimidazo[1,2-a]pyridin-3-yl]carbonyl}amino)-3-(2-fluorophenyl)propanoic acid.

Example 14

To a suspension of 20 mg of lithium aluminum hydride in 5 ml of THF was added a solution of 220 mg of methyl (2R)-2-({[8-(cyclohexylmethoxy)-2-methylimidazo[1,2-a]pyridin-3-yl]carbonyl}amino)-3-(2-methylphenyl)propanoate in 2 ml of THF under ice-cooling, followed by stirring for 7 hours under ice-cooling. To the reaction mixture was added 180 mg of sodium sulfate decahydrate, followed by stirring for a while. The reaction mixture was filtered over Celite, the solvent was then evaporated under reduced pressure, and the obtained residue was purified by silica gel column chromatography. The obtained purified product was dissolved in ethyl acetate and a 4 M hydrogen chloride/ethyl acetate solution was added thereto. The solvent was evaporated under reduced pressure, and then diisopropyl ether was added thereto, followed by stirring. The resulting solid was collected by filtration and dried to obtain 72 mg of 8-(cyclohexylmethoxy)-N-[(1R)-2-hydroxy-1-(2-methylbenzyl)ethyl]-2-methylimidazo[1,2-a]pyridine-3-carboxamide hydrochloride.

Example 15

To a solution of 185 mg of methyl (2E,4S)-4-({[8-(cyclohexylmethoxy)-2-methylimidazo[1,2-a]pyridin-3-yl]carbonyl}amino)-4-phenylbuta-2-enoate in 3.7 ml of ethyl acetate was added 20 mg of 10% palladium-carbon, followed by stirring for 8 hours under a hydrogen atmosphere. The reaction mixture was filtered over Celite and the solvent was evaporated under reduced pressure to obtain 165 mg of methyl (4S)-4-({[8-(cyclohexylmethoxy)-2-methylimidazo[1,2-a]pyridin-3-yl]carbonyl}amino)-4-phenylbutanoate.

Example 16

To 245 mg of 8-(cyclohexylmethoxy)-2-methyl-N-[(3S)-1-methylpyrrolidin-3-yl]imidazo[1,2-a]pyridine-3-carboxamide were added 12 ml of ethyl acetate and 364 µl of a 4 M hydrogen chloride/ethyl acetate solution, followed by stirring. The resulting solid was collected by filtration and dried to obtain 258 mg of 8-(cyclohexylmethoxy)-2-methyl-N-[(3S)-1-methylpyrrolidin-3-yl]imidazo[1,2-a]pyridine-3-carboxamide hydrochloride.

Example 17

To a solution of 280 mg of ethyl 8-[(2-fluorobenzyl)oxy]-2-methylimidazo[1,2-a]pyridine-6-carboxylate, 208 mg of 4-(dimethylamino)pyridine, and 5 ml of chloroform was added 191 µl of trichloroacetyl chloride under ice-cooling, followed by stirring at room temperature for 1 hour and at 65° C. overnight. After leaving to be cooled at room temperature, the solvent was evaporated under reduced pressure, and to the obtained residue were added acetonitrile and 429 mg of (1R)-2-{[tert-butyl(dimethyl)silyl]oxy}-1-phenylethanamine, followed by stirring overnight. To the reaction mixture were added water and chloroform to carry out a layer separation operation. The organic layer was dried over anhydrous sodium sulfate and the solvent was evaporated under reduced pressure. The obtained residue was purified by silica gel column chromatography to obtain 370 mg of ethyl 3-{[(1R)-2-{[tert-butyl(dimethyl)silyl]oxy}-1-phenyl ethyl]carbamoyl}-8-[(2-fluorobenzyl)oxy]-2-methylimidazo[1,2-a]pyridine-6-carboxylate.

Example 18

To a mixture of 100 mg of 8-[(2-fluorobenzyl)oxy]-3-{[(1R)-2-hydroxy-1-phenylethyl]carbamoyl}-2-methylimidazo[1,2-a]pyridine-6-carboxylic acid, 28 µl of 4-methylmorpholine, and 0.7 ml of dimethoxyethane was added 34 µl of isobutyl chloroformate under ice-cooling, followed by stirring at room temperature overnight. The insoluble material was removed by filtration, and then to the filtrate were added 16 mg of sodium borohydride and 210 µl of methanol under ice-cooling, followed by stirring for 30 minutes under ice-cooling. To the reaction mixture were added a saturated aqueous ammonium chloride solution and chloroform to carry out a layer separation operation. The organic layer was dried over anhydrous magnesium sulfate and the solvent was evaporated under reduced pressure. The obtained residue was purified by silica gel column chromatography to obtain 21 mg of 8-[(2-fluorobenzyl)oxy]-6-(hydroxymethyl)-N-[(1R)-2-hydroxy-1-phenylethyl]-2-methylimidazo[1,2-a]pyridine-3-carboxamide.

Example 19

To a suspension of 300 mg of 8-(cyclohexylmethoxy)-N-[(1R)-2-(1,3-dioxo-1,3-dihydro-2H-isoindol-2-yl)-1-phenylethyl]-2-methylimidazo[1,2-a]pyridine-3-carboxamide in 6 ml of ethanol was added 0.13 ml of hydrazine monohydrate, followed by stirring at 85° C. for 1 hour. The solvent was evaporated under reduced pressure and the obtained residue was purified by silica gel column chromatography to obtain 200 mg of N-[(1R)-2-amino-1-phenylethyl]-8-(cyclohexylmethoxy)-2-methylimidazo[1,2-a]pyridine-3-carboxamide.

Example 20

To a solution of 1.2 g of benzyl 4-({[8-(cyclohexylmethoxy)-2-methylimidazo[1,2-a]pyridin-3-yl]carbonyl}amino)-4-(2-methoxy-2-oxoethyl)piperidine-1-carboxylate in 30 ml of methanol was added 300 mg of 10% palladium-carbon, followed by stirring overnight under a hydrogen atmosphere. The reaction mixture was filtered over Celite and the solvent was then evaporated under reduced pressure to obtain 900 mg of methyl[4-({[8-(cyclohexylmethoxy)-2-methylimidazo[1,2-a]pyridin-3-yl]carbonyl}amino)piperidin-4-yl]acetate.

Example 21

To a suspension of 300 mg of 8-(cyclohexylmethoxy)-2-methylimidazo[1,2-a]pyridine-3-carboxylic acid in 5 ml of THF was added 253 mg of 1,1'-carbonyldiimidazole, followed by stirring at 60° C. for 1 hour. Subsequently, 283 mg of 3-(aminosulfonyl)propyl acetate and 389 µl of 1,8-diazabicyclo[5.4.0]-7-undecene were added thereto under ice-cooling, followed by stirring at room temperature overnight. To the reaction mixture were added water and ethyl acetate to carry out a layer separation operation. The organic layer was washed with saturated brine and dried over anhydrous sodium sulfate, the solvent was evaporated under reduced pressure, and the obtained residue was purified by silica gel column chromatography. Since the reaction was not completed, to the obtained purified product were added again 57 mg of 3-(aminosulfonyl)propyl acetate, 60 mg of N-[3-(dimethylamino)propyl]-N'-ethylcarbodiimide hydrochloride, 38 mg of 4-(dimethylamino)pyridine, and 2 ml of DMF, followed by stirring at room temperature overnight. To the reaction mixture were added a saturated aqueous ammonium chloride solution and chloroform to carry out a layer separation operation. The organic layer was dried over anhydrous sodium sulfate, the solvent was evaporated under reduced pressure, and the obtained residue was purified by silica gel column chromatography. To the obtained product were added ethyl acetate and ethanol, followed by stirring. The resulting solid was collected by filtration and dried to obtain 149 mg of 3-[({[8-(cyclohexylmethoxy)-2-methylimidazo[1,2-a]pyridin-3-yl]carbonyl}amino)sulfonyl]propyl acetate.

Example 22

To 130 mg of 3-[({[8-(cyclohexylmethoxy)-2-methylimidazo[1,2-a]pyridin-3-yl]carbonyl}amino)sulfonyl]propyl acetate were added 2 ml of methanol, 2 ml of THF, and 1 ml of a 1 M aqueous sodium hydroxide solution, followed by stirring for 8.5 hours. The solvent was evaporated under reduced pressure and to the obtained residue were added water and 1 M hydrochloric acid. The solvent was evaporated under reduced pressure and the obtained residue was purified by silica gel column chromatography. To the obtained purified product were added ethyl acetate and hexane, followed by stirring. The resulting solid was collected by filtration and dried to obtain 41 mg of 8-(cyclohexylmethoxy)-N-[(3-hydroxypropyl)sulfonyl]-2-methylimidazo[1,2-a]pyridine-3-carboxamide.

Example 23

To a mixture of 8.7 mg of 8-(cyclohexylmethoxy)-2-methylimidazo[1,2-a]pyridine-3-carboxylic acid, 5.1 mg of cyclopropylamine, 4.1 mg of 1-hydroxybenzotriazole, 1 ml of DMF, and 28 µl of diisopropylethylamine was added 50 mg of polystyrene N-cyclohexylcarbodiimide-N'-propyloxymethyl (PS-Carbodiimide manufactured by Biotage), followed by stirring at room temperature for 16 hours. Subsequently, 1 ml of DMF, 50 mg of macroporious triethylammonium methylpolystyrene carbonate (MP-Carbonate manufactured by Biotage) and 50 mg of polystyrene methyl isocyanate (PS-Isocyanate manufactured by Biotage), followed by stirring at room temperature for 3 hours. The resin of the reaction mixture was removed by filtration and the filtrate was concentrated under reduced pressure. The obtained residue was purified by preparative HPLC (high performance liquid chromatography) to obtain 8.7 mg of 8-(cyclohexylmethoxy)-N-cyclopropyl-2-methylimidazo[1,2-a]pyridine-3-carboxamide.

Example 24

To a mixture of 5.8 mg of 8-(cyclohexylmethoxy)-2-methylimidazo[1,2-a]pyridine-3-carboxylic acid, 6.1 mg of (S)-(+)-2-phenylglycine methyl ester hydrochloride, 2.7 mg of 1-hydroxybenzotriazole, 700 µl of DMF, and 19 µl of diisopropylethylamine was added 50 mg of polystyrene N-cyclohexylcarbodiimide-N'-propyloxymethyl (PS-Carbodiimide manufactured by Biotage), followed by stirring at room temperature for 20 hours. Subsequently, 50 mg of macroporous triethylammonium methylpolystyrene carbonate (MP-Carbonate manufactured by Biotage) and 50 mg of polystyrene methyl isocyanate (PS-Isocyanate manufactured by Biotage) were added thereto, followed by stirring at room temperature for 2 hours. The resin was removed by filtration, the filtrate was concentrated under reduced pressure, and to the obtained residue were added 100 µl of THF, 200 µl of methanol, and 50 µl of a 1 M aqueous sodium hydroxide solution, followed by stirring at 50° C. for 20 hours. To the reaction mixture that had been left to be cooled to room temperature were added 0.5 ml of water and 50 µl of 1 M hydrochloric acid, followed by concentration under reduced pressure. The obtained residue was purified by preparative HPLC to obtain 6.7 mg of (2S)-({[8-(cyclohexylmethoxy)-2-methylimidazo[1,2-a]pyridin-3-yl]carbonyl}amino)(phenyl)acetic acid.

Example 25

To a mixture of 5.8 mg of 8-(cyclohexylmethoxy)-2-methylimidazo[1,2-a]pyridine-3-carboxylic acid, 7.1 mg of tert-butyl (3R)-3-amino-4-phenylbutanoate, 2.7 mg of 1-hydroxybenzotriazole, 700 µl of DMF, and 19 µl of diisopropylethylamine was added 50 mg of polystyrene N-cyclohexylcarbodiimide-N'-propyloxymethyl (PS-Carbodiimide manufactured by Biotage), followed by stirring at room temperature for 20 hours. To the reaction mixture were added 50 mg of macroporous triethylammonium methylpolystyrene carbonate (MP-Carbonate manufactured by Biotage) and 50 mg of polystyrene methyl isocyanate (PS-Isocyanate manufactured by Biotage), followed by stirring at room temperature for 2 hours. The resin was removed by filtration, the filtrate was concentrated under reduced pressure, and to the obtained residue were added 100 µl of 1,4-dioxane and 200 µl of a 4 M hydrogen chloride/1,4-dioxane solution, followed by stirring at room temperature for 20 hours. The reaction mixture was concentrated under reduced pressure and the obtained residue was purified by preparative HPLC to obtain 5.6 mg of (3R)-3-({[8-(cyclohexylmethoxy)-2-methylimidazo[1,2-a]pyridin-3-yl]carbonyl}amino)-4-phenylbutanoic acid.

Example 26

A mixture of 8.5 mg of N-[(1R)-2-{[tert-butyl(dimethyl)silyl]oxy}-1-phenylethyl]-8-hydroxy-2-methylimidazo[1,2-a]pyridine-3-carboxamide, 5.6 mg of α-bromo-2,5-difluorotoluene, 5.0 mg of potassium carbonate, and 700 µl of DMF was stirred at 30° C. for 28 hours. To the reaction mixture were added 1 ml of water, 0.5 ml of saturated brine, and 4 ml of chloroform to carry out a layer separation operation. The organic layer was concentrated under reduced pressure, and to the residue were added 300 µl of THF and 300 µl of 1 M hydrochloric acid, followed by stirring at room temperature for 6 hours. To the reaction mixture were added 300 µl of a 1 M aqueous sodium hydroxide solution and 100 of saturated aqueous sodium bicarbonate, followed by extraction with 3 ml of chloroform. The solvent was evaporated under reduced pressure and the obtained residue was purified by preparative HPLC to obtain 6.3 mg of 8-[(2,5-difluorobenzyl)oxy]-N-[(1R)-2-hydroxy-1-phenylethyl]-2-methylimidazo[1,2-a]pyridine-3-carboxamide.

Example 27

To a solution of 250 mg of 8-(cyclohexylmethoxy)-2-methyl-N-[(3S)-piperidin-3-yl]imidazo[1,2-a]pyridine-3-carboxamide dihydrochloride in 10 ml of methanol were added 157 µl of triethylamine, 300 mg of Molecular Sieves 3A, 323 µl of acetic acid, 1.53 ml of [(1-ethoxy cyclopropyl)oxy](trimethyl)silane, and 146 mg of sodium cyanoborohydride under ice-cooling, followed by stirring for 6 hours under heating to reflux. The insoluble material was removed by filtration and the filtrate was concentrated under reduced pressure. To the obtained residue were added saturated aqueous sodium bicarbonate and chloroform to carry out a layer separation operation. The organic layer was dried over anhydrous sodium sulfate, the solvent was evaporated under reduced pressure, and the obtained residue was purified by silica gel column chromatography. To a mixture of the obtained purified product, ethyl acetate, and methanol was added a 4 M hydrogen chloride/ethyl acetate solution under ice-cooling, and the solvent was evaporated under reduced pressure. To the obtained residue was added ethyl acetate and hexane, followed by stirring. The resulting solid was collected by filtration and dried to obtain 136 mg of 8-(cyclohexylmethoxy)-N-[(3S)-1-cyclopropylpiperidin-3-yl]-2-methylimidazo[1,2-a]pyridine-3-carboxamide dihydrochloride.

Example 28

To a solution of 200 mg of 8-(cyclohexylmethoxy)-2-methyl-N-[(1R)-2-{methyl[(2-nitrophenyl)sulfonyl]amino}-1-phenylethyl]imidazo[1,2-a]pyridine-3-carboxamide in 3 ml of DMF were added 140 mg of potassium carbonate and 50 mg of 4-methylbenzenethiol, followed by stirring for 3 hours. To the reaction mixture were added water and chloroform/methanol (9/1) to carry out a layer separation operation. The organic layer was washed with saturated brine and dried over anhydrous magnesium sulfate, and the solvent was evaporated under reduced pressure. The obtained residue was purified by silica gel column chromatography to obtain 80 mg of 8-(cyclohexylmethoxy)-2-methyl-N-[(1R)-2-(methylamino)-1-phenylethyl]imidazo[1,2-a]pyridine-3-carboxamide.

Example 29

To a solution of 150 mg of methyl (2S,4S)-4-({[8-(cyclohexylmethoxy)-2-methylimidazo[1,2-a]pyridin-3-yl]carbonyl}amino)-1-methylpyrrolidine-2-carboxylate and 4 ml of dichloromethane was added dropwise 1.5 ml of a 1 M diisobutylaluminum hydride/toluene solution under ice-cooling, followed by stirring for 2 hours under ice-cooling. Subsequently, 1 M hydrochloric acid was added thereto, the reaction mixture was filtered over Celite, and to the filtrate were added ethyl acetate to carry out a layer separation operation. The organic layer was washed with water and saturated brine, and dried over anhydrous magnesium sulfate. The solvent was evaporated under reduced pressure and the obtained residue was purified by silica gel column chromatography. To a solution of the obtained purified product in ethyl acetate was added a hydrogen chloride/ethyl acetate solution, and the resulting solid was collected by filtration and dried to obtain 25 mg of 8-(cyclohexylmethoxy)-N-[(3S,5S)-5-(hydroxymethyl)-1-methylpyrrolidin-3-yl]-2-methylimidazo[1,2-a]pyridine-3-carboxamide dihydrochloride.

Example 30

To a solution of 32 mg of N-[(6-chloropyridin-3-yl)methyl]-8-(cyclohexylmethoxy)-2-methylimidazo[1,2-a]pyridine-3-carboxamide in 0.6 ml of N-methyl-2-pyrrolidone was added 0.05 ml of ethyl piperidine-4-carboxylate to carry out a reaction at 150° C. for 30 minutes and further at 200° C. for 30 minutes under microwave irradiation. 24 mg of potassium carbonate was added thereto to carry out a reaction at 240° C. for 2 hours under microwave irradiation. To the reaction mixture were added a saturated aqueous ammonium chloride solution and ethyl acetate to carry out a layer separation operation. The organic layer was washed with water and saturated brine, and dried over anhydrous sodium sulfate. The solvent was evaporated under reduced pressure and the obtained residue was purified by silica gel column chromatography. To the obtained purified product were added hexane and isopropyl ether, and the resulting solid was collected by filtration and dried to obtain 14 mg of 1-{4-[({[8-(cyclohexylmethoxy)-2-methylimidazo[1,2-a]pyridin-3-yl]carbonyl}amino)methyl]pyridin-2-yl}piperidine-4-carboxylic acid.

Example 31

To a solution of 70 mg of N-[(6-chloropyridin-3-yl)methyl]-8-(cyclohexylmethoxy)-2-methylimidazolo[1,2-a]pyridine-3-carboxamide in 1 mL of N-methyl-2-pyrrolidone was added 0.12 mL of ethyl piperidine-3-carboxylate to carry out a reaction at 240° C. for 50 minutes under microwave irradiation. To the reaction mixture were added a saturated aqueous ammonium chloride solution and ethyl acetate to carry out a layer separation operation. The organic layer was washed with saturated brine and dried over anhydrous magnesium sulfate. The solvent was evaporated under reduced pressure and the obtained residue was purified by silica gel column chromatography to obtain 43 mg of ethyl 1-{5-[({[8-(cyclohexylmethoxy)-2-methylimidazolo[1,2-a]pyridin-3-yl]carbonyl}amino)methyl]pyridin-2-yl}piperidine-3-carboxylate.

Example 32

To a solution of 270 mg of methyl N-{[8-(cyclohexylmethoxy)-2-methylimidazo[1,2-a]pyridin-3-yl]carbonyl}serinate in 7 mL of methanol were added 210 mg of bisguanidine and 115 mg of sodium methoxide, followed by stirring at 65° C. for 8 hours. After leaving to be cooled, the insoluble material was collected by filtration, and washed with methanol, water, and hexane in this order to obtain 75 mg of 8-(cyclohexylmethoxy)-N-[1-(4,6-diamino-1,3,5-triazin-2-yl)-2-hydroxyethyl]-2-methylimidazo[1,2-a]pyridine-3-carboxamide.

Example 33

A mixture of 860 mg of 8-(cyclohexylmethoxy)-2-methylimidazo[1,2-a]pyridine-3-carboxylic acid, 992 mg of 1-benzyl-4-methylpiperidine-4-amine dihydrochloride, 170 mg of O-(7-azabenzotriazole-1-yl)-N,N,N',N',-tetramethyluronium hexafluorophosphate, 3 mL of diisopropylethylamine, and 10 mL of DMF was stirred for 1 day. To the reaction mixture were added water and ethyl acetate to carry out a layer separation operation. The organic layer was washed with water and saturated brine in this order, and dried over anhydrous sodium sulfate. The solvent was evaporated under reduced pressure and the obtained residue was purified by silica gel column chromatography to obtain 1.25 g of N-(1-benzyl-4-methylpiperidin-4-yl)-8-(cyclohexylmethoxy)-2-methylimidazolo[1,2-a]pyridine-3-carboxamide.

Example 34

A mixture of 1.15 g of N-(1-benzyl-4-methylpiperidin-4-yl)-8-(cyclohexylmethoxy)-2- methylimidazolo[1,2-a]pyridine-3-carboxamide, 0.4 mL of 1-chloroethyl chloroformate, and 15 mL of dichloroethane was heated to reflux overnight. After leaving to be cooled at room temperature, the solvent was evaporated under reduced pressure, and to the residue was added 15 mL of methanol, followed by heating to reflux for 6 hours. After leaving to be cooled at room temperature, the solvent was evaporated under reduced pressure, and to the residue were added a saturated aqueous sodium hydrogen carbonate solution and chloroform to carry out a layer separation operation. The organic layer was dried over anhydrous magnesium sulfate and the solvent was evaporated under reduced pressure. The residue was purified by silica gel column chromatography to obtain 426 mg of 8-(cyclohexylmethoxy)-2-methyl-N-(4-methyl-piperidin-4-yl)imidazolo[1,2-a]pyridine-3-carboxamide.

Example 35

To a solution of 100 mg of (3S)-3-({[8-(cyclohexylmethoxy)-2-methylimidazolo[1,2-a]pyridin-3-yl]carbonyl}amino)-3-phenylpropanoic acid in 1 mL of DMF was added 43 mg of 1,1'-carbonyldiimidazole, followed by stirring for 30 minutes. To the reaction solution were added 24 mg of methanesulfonamide and 0.039 mL of 1,8-diazabicyclo[5.4.0]-7-undecene, followed by stirring for 5 hours. To the reaction mixture were added 1 M hydrochloric acid and ethyl acetate to carry out a layer separation operation. The obtained organic layer was washed with water and saturated brine, and dried over anhydrous sodium sulfate. The solvent was evaporated under reduced pressure and the residue was purified by silica gel column chromatography. To the purified product were added ethyl acetate and hexane, and the resulting solid was collected by filtration and dried to obtain 41 mg of 8-(cyclohexylmethoxy)-2-methyl-N-{(1S)-3-[(methylsulfonyl)amino]-3-oxo-1-phenylpropyl}imidazolo[1,2-a]pyridine-3-carboxamide.

Example 661

To a suspension of 149 mg of methyl (1S,2R)-1-({[8-(cyclohexylmethoxy)-2-methylimidazo[1,2-a]pyridin-3-yl]carbonyl}amino)-5-methylindane-2-carboxylate in 6 ml of dioxane was added 6 ml of 3 M hydrochloric acid, followed by stirring at 80° C. for 4 hours. After leaving to be cooled, the solvent was evaporated under reduced pressure, and then to the obtained residue were added a saturated aqueous sodium hydrogen carbonate solution, an aqueous citric acid solution, and chloroform to carry out a layer separation operation. The organic layer was dried over anhydrous magnesium sulfate and the solvent was evaporated under reduced pressure. To the obtained residue was added diisopropyl ether, and the insoluble material was collected by filtration and dried to obtain 126 mg of (1S,2R)-1-({[8-(cyclohexylmethoxy)-2-methylimidazo[1,2-a]pyridin-3-yl]carbonyl}amino)-5-methylindane-2-carboxylic acid.

Example 663

4.5 mg of sodium was added to and dissolved in 6 ml of methanol. To the reaction mixture was added 300 mg of methyl rac-(1R,2R)-1-({[8-(cyclohexylmethoxy)-2-methyl-imidazo[1,2-a]pyridin-3-yl]carbonyl}amino)-1,2,3,4-tetrahydronaphthalene-2-carboxylate, followed by stirring at 90° C. for 5 hours. After leaving to be cooled, the solvent was evaporated under reduced pressure, and then to the obtained residue were added a 10% aqueous citric acid solution and ethyl acetate to carry out a layer separation operation. The organic layer was washed with saturated brine and dried over anhydrous magnesium sulfate, and the solvent was evaporated under reduced pressure. The obtained residue was purified by silica gel column chromatography and washed with ethyl acetate-hexane to obtain 139 mg of methyl rac-(1R,2S)-1-({[8-(cyclohexylmethoxy)-2-methyl-imidazo[1,2-a]pyridin-3-yl]carbonyl}amino)-1,2,3,4-tetrahydronaphthalene-2-carboxylate.

Example 669

Methyl (1S,2R)-1-({[8-(cyclohexylmethoxy)-2-methyl-imidazo[1,2-a]pyridin-3-yl]carbonyl}amino)-4-methylindane-2-carboxylate was prepared using the compound of Preparation Example 123 by the same method as in Example 1 as described above.

Example 673

Methyl (1S,2R)-1-[({8-[(2,6-difluorobenzyl)oxy]-2-methylimidazo[1,2-a]pyridin-3-yl}carbonyl)amino]-4-methylindane-2-carboxylate was prepared using the compound of Preparation Example 123 by the same method as in Example 1 as described above.

Example 674

Methyl (1S,2R)-1-[({8-[(2,6-difluorobenzyl)oxy]-2-methylimidazo[1,2-a]pyridin-3-yl}carbonyl)amino]-7-fluoroindane-2-carboxylate was prepared using the compound of Preparation Example 115 by the same method as in Example 1 as described above.

Example 683

Methyl rac-(1R,2R)-1-({[8-(cyclohexylmethoxy)-2-methylimidazo[1,2-a]pyridin-3-yl]carbonyl}amino)-7-fluoroindane-2-carboxylate as a racemate of cis isomers was prepared using the compound of Preparation Example 139 by the same method as in Example 1 as described above.

Example 684

Methyl (1S,2R)-1-({[8-(cyclohexylmethoxy)-2-methyl-imidazo[1,2-a]pyridin-3-yl]carbonyl}amino)-7-fluoroindane-2-carboxylate was prepared using the compound of Preparation Example 115 by the same method as in Example 1 as described above.

Example 685

Methyl (1R,2S)-1-({[8-(cyclohexylmethoxy)-2-methyl-imidazo[1,2-a]pyridin-3-yl]carbonyl}amino)-7-fluoroindane-2-carboxylate was prepared using the compound of Preparation Example 140 by the same method as in Example 1 as described above. Further, the compound of Example 684 and the present compound of Example 685 are enantiomers (mirror image isomers) with respect to each other.

Example 693

Preparation was carried out by the same method as in Example 661 as described above using the compound of Example 669.

Example 695

Preparation was carried out by the same method as in Example 661 as described above using the compound of Example 663.

Example 698

Preparation was carried out by the same method as in Example 661 as described above using the compound of Example 673.

Example 699

Preparation was carried out by the same method as in Example 661 as described above using the compound of Example 674.

Example 702

Preparation was carried out by the same method as in Example 661 as described above using the compound of Example 678.

Example 703

Preparation was carried out by the same method as in Example 661 as described above using the compound of Example 683.

Example 704

Preparation was carried out by the same method as in Example 661 as described above using the compound of Example 684.

Example 705

Preparation was carried out by the same method as in Example 661 as described above using the compound of Example 685.

Example 709

To 301 mg of 8-[(2,6-difluorobenzyl)oxy]-N-[2,2-dimethyl-5-(3-methylphenyl)-1,3-dioxan-5-yl]-2-methylimidazo[1,2-a]pyridine-3-carboxamide were added 3 ml of dioxane, 3 ml of methanol, and 6 ml of 1 M hydrochloric acid, followed by stirring for 14 hours. To the reaction mixture were added a saturated aqueous sodium hydrogen carbonate solution, water, and ethyl acetate under ice-cooling to carry out a layer separation operation. The organic layer was washed with a saturated aqueous sodium hydrogen carbonate solution and saturated brine in this order, and dried over anhydrous magnesium sulfate. The solvent was evaporated under reduced pressure and the obtained residue was purified by silica gel column chromatography. To the obtained purified product were added hexane and ethyl acetate, and the insoluble material was collected by filtration and dried to obtain 172 mg of 8-[(2,6-difluorobenzyl)oxy]-N-[1,3-dihydroxy-2-(3-methylphenyl)propan-2-yl]-2-methylimidazo[1,2-a]pyridine-3-carboxamide.

Example 710

To 252 mg of diethyl[({8-[(2,6-difluorobenzyl)oxy]-2-methylimidazo[1,2-a]pyridin-3-yl}carbonyl)amino]malonate were added 4 ml of ethanol, 0.23 ml of a 20% sodium ethoxide/ethanol solution, and 0.31 ml of 1-iodobutane, followed by stirring at 70° C. for 3 hours. Subsequently, 11 mg of sodium ethoxide was added thereto, followed by stirring at 70° C. for 1 hour. To the reaction mixture were added an aqueous citric acid solution, a saturated aqueous sodium hydrogen carbonate solution, and chloroform to carry out a layer separation operation. The organic layer was dried over anhydrous sodium sulfate and the solvent was evaporated under reduced pressure. The obtained residue was purified by silica gel column chromatography to obtain 69 mg of diethyl butyl[({8-[(2,6-difluorobenzyl)oxy]-2-methylimidazo[1,2-a]pyridin-3-yl}carbonyl)amino]malonate.

Example 711

To a mixture of 68 mg of diethyl butyl[({8-[(2,6-difluorobenzyl)oxy]-2-methylimidazo[1,2-a]pyridin-3-yl}carbonyl)amino]malonate in 1.4 ml of ethanol was added a solution of 35 mg of calcium chloride in 0.34 ml of water. Subsequently, 24 mg of sodium borohydride was added thereto under ice-cooling, followed by stirring for 1 hour under ice-cooling and at room temperature for 4 hours. Further, 2 ml of ethanol, a solution of 35 mg of calcium chloride in 0.34 ml of water, and 24 mg of sodium borohydride were added thereto followed by stirring at room temperature for 15 hours. Further, a solution of 35 mg of calcium chloride in 0.34 ml of water and 24 mg of sodium borohydride were added thereto, followed by stirring at room temperature for 15 hours. To the reaction mixture were added 1 M hydrochloric acid and ethyl acetate to carry out a layer separation operation. The organic layer was washed with saturated brine and dried over anhydrous sodium sulfate, and the solvent was evaporated under reduced pressure. The obtained residue was purified by silica gel column chromatography to obtain 32 mg of 8-[(2,6-difluorobenzyl)oxy]-N-[1-hydroxy-2-(hydroxymethyl)hexan-2-yl]-2-methylimidazo[1,2-a]pyridine-3-carboxamide.

Example 712

To a solution of 229 mg of methyl rac-(1R,2R)-1-[({8-[(2,6-difluorobenzyl)oxy]-2-methylimidazo[1,2-a]pyridin-3-yl}carbonyl)amino]-2-hydroxyindane-1-carboxylate in 3.4 ml of ethanol and 0.68 ml of THF was added 68 mg of sodium borohydride under ice-cooling, followed by stirring at room temperature for 4 hours. To the reaction mixture were added 1 M hydrochloric acid and ethyl acetate to carry out a layer separation operation. The organic layer was washed with saturated brine and dried over anhydrous magnesium sulfate, and the solvent was evaporated under reduced pressure. The obtained residue was purified by silica gel column chromatography. To the obtained purified product was added diisopropyl ether, and the resulting solid was collected by filtration and dried to obtain 74 mg of rac-8-[(2,6-difluorobenzyl)oxy]-N-[(1R,2S)-2-hydroxy-1-(hydroxymethyl)-2,3-dihydro-1H-indan-1-yl]-2-methylimidazo[1,2-a]pyridine-3-carboxamide.

Example 713

To 100 mg of 1-({[8-(cyclohexylmethoxy)-2-methylimidazo[1,2-a]pyridin-3-yl]carbonyl}oxy)-1H-benzotriazole were 1.7 ml of dichloromethane, 0.065 ml of (S)-(−)-1-phenylethylamine, and 0.07 ml of triethylamine, followed by stirring overnight. To the reaction mixture were added water and chloroform to carry out a layer separation operation, followed by drying over anhydrous sodium sulfate, and the solvent was evaporated under reduced pressure. The obtained residue was purified by silica gel column chromatography. To the obtained purified product was added diisopropyl ether, and the resulting solid was collected by filtration and dried to obtain 80 mg of 8-(cyclohexylmethoxy)-2-methyl-N-[(1S)-1-phenylethyl]imidazo[1,2-a]pyridine-3-carboxamide.

Example 714

To a mixture of 100 mg of the compound of Example 766 in 3.3 ml of THF and 1.7 ml of water was added 65 mg of sodium periodate under ice-cooling, followed by stirring at room temperature for 2 hours and at 50° C. for 3 hours. To the reaction mixture were added water and ethyl acetate to carry out a layer separation operation. The organic layer was washed with saturated brine and dried over anhydrous sodium sulfate, and the solvent was evaporated under reduced pressure. To a mixture of the obtained residue in 2 ml of THF and 2 ml of methanol was added 39 mg of sodium borohydride under ice-cooling, followed by stirring for 1 hour under ice-cooling and at room temperature for 1 hour. To the reaction mixture were added a saturated aqueous ammonium chloride solution, ethyl acetate, and water to carry out a layer separation operation. The organic layer was washed with saturated brine and dried over anhydrous magnesium sulfate, the solvent was evaporated under reduced pressure, and the obtained residue was purified by silica gel column chromatography. The obtained purified product was washed with ethyl acetate and hexane to obtain 33 mg of 8-[(2,6-difluorobenzyl)oxy]-N-(1,5-dihydroxy-3-phenylpentan-3-yl)-2-methylimidazo[1,2-a]pyridine-3-carboxamide.

Example 758

Preparation was carried out using the compound of Preparation Example 240 by the same method as in Example 1 as described above.

Example 759

Preparation was carried out using the compound of Preparation Example 172 by the same method as in Example 1 as described above.

Example 766

Preparation was carried out using the compound of Preparation Example 278 by the same method as in Example 1 as described above.

Example 767

Preparation was carried out using the compound of Preparation Example 279 by the same method as in Example 1 as described above.

Example 797

Preparation was carried out using the compound of Preparation Example 172 by the same method as in Example 1 as described above.

Example 798

Preparation was carried out using the compound of Preparation Example 172 by the same method as in Example 1 as described above.

TABLE 2

| PEx | Str |
|---|---|
| 1 | ![structure] cyclohexyl-CH2-O-pyridine with NO2 and Me |
| 2 | ![structure] cyclohexyl-CH2-O-pyridine with NH2 and Me |
| 3 | ![structure] cyclohexyl-CH2-O-pyridine with NH2 and Br |
| 4 | ![structure] cyclohexyl-CH2-O-imidazo[1,2-a]pyridine with Me, CO2Et, Me |
| 5 | ![structure] 2-fluorobenzyl-O-imidazo[1,2-a]pyridine with Me, CO2H |
| 6 | ![structure] HO-imidazo[1,2-a]pyridine-Me-C(O)NH-CH(Ph)-CH2-OTBS |
| 7 | ![structure] cyclopropyl-C(O)-CH(Cl)-CO2Me |
| 8 | ![structure] Z-N-piperidine-4-(NH2)(CO2Me)·HCl |

TABLE 2-continued

| PEx | Str |
|---|---|
| 9 | (structure: Me-CH2CH2CH2-CH=CH-C(=O)-OtBu) |
| 10 | (structure: (Ph)(Me)CH-N(CH2Ph)-CH(nBu)-CH2-C(=O)-OtBu) |
| 11 | (structure: Me-CH2CH2CH2-CH(NH2)-CH2-C(=O)-OtBu) |
| 12 | (structure: 8-(cyclohexylmethoxy)-2-methylimidazo[1,2-a]pyridine-3-carbonyl chloride · HCl) |
| 13 | (structure: methyl 5-(2-fluorobenzyloxy)-6-nitropyridine-3-carboxylate) |
| 14 | (structure: methyl 6-amino-5-(2-fluorobenzyloxy)pyridine-3-carboxylate) |
| 15 | (structure: methyl 8-(2-fluorobenzyloxy)-2-methylimidazo[1,2-a]pyridine-6-carboxylate) |
| 16 | (structure: ethyl 8-(2-fluorobenzyloxy)-2-methylimidazo[1,2-a]pyridine-6-carboxylate) |

TABLE 3

| PEx | Str |
|---|---|
| 17 | (structure: N-methyl-N-(2-amino-2-phenylethyl)-2-nitrobenzenesulfonamide) |
| 18 | (structure: 8-(cyclohexylmethoxy)-2-methyl-N-(2-oxoethyl)imidazo[1,2-a]pyridine-3-carboxamide) |
| 19 | (structure: ethyl 1-(2-amino-2-phenylethyl)piperidine-4-carboxylate) |
| 20 | (structure: ethyl 1-(2-(Boc-amino)-2-phenylethyl)piperidine-4-carboxylate) |
| 21 | (structure: tert-butyl 3-(4-(aminomethyl)phenyl)propanoate) |
| 22 | (structure: ethyl 2-(4-(aminomethyl)phenyl)-2-methylpropanoate · HCl) |
| 23 | (structure: ethyl (E)-3-(2-((Boc-amino)methyl)phenyl)acrylate) |
| 24 | (structure: ethyl 2-(4-cyanophenyl)-2-methylpropanoate) |
| 25 | (structure: methyl (2R,3S)-3-amino-2-hydroxyhexanoate) |
| 26 | (structure: methyl 3-((3R)-3-(Boc-amino)piperidin-1-yl)benzoate) |
| 27 | 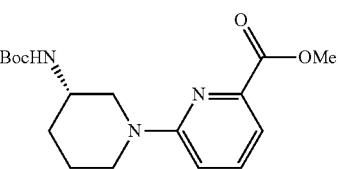 [SMILES: COC(=O)c1cccc(N2CCC[C@H](NC(=O)OC(C)(C)C)C2)n1] |

TABLE 3-continued

| PEx | Str |
|---|---|
| 28 | H2N-S(=O)2-N(piperidine)-NH2·HCl (3-amino-piperidine-1-sulfonamide HCl) |
| 29 | cyclopentyl-CH2-CH(NH2)-CH2-C(=O)-OtBu |
| 30 | cyclobutyl-CH2-CH(NH2)-CH2-C(=O)-OtBu |
| 31 | 8-(cyclohexylmethoxy)imidazo[1,2-a]pyridine-3-carboxylic acid ethyl ester |
| 32 | 3-(cyclohexylmethoxy)-5-chloropyridin-2-amine |
| 33 | ethyl 8-(cyclohexylmethoxy)-2-methylimidazo[1,2-a]pyridine-3-carboxylate |
| 34 | ethyl 8-((2-fluorobenzyl)oxy)-2-methylimidazo[1,2-a]pyridine-3-carboxylate |
| 35 | ethyl 8-(benzyloxy)-2-methylimidazo[1,2-a]pyridine-3-carboxylate |
| 36 | ethyl 8-(cyclohexylmethoxy)-2-ethylimidazo[1,2-a]pyridine-3-carboxylate |

TABLE 4

| PEx | Str |
|---|---|
| 37 | ethyl 8-(cyclohexylmethoxy)-2-(trifluoromethyl)imidazo[1,2-a]pyridine-3-carboxylate |
| 38 | methyl 8-(cyclohexylmethoxy)-2-cyclopropylimidazo[1,2-a]pyridine-3-carboxylate |
| 39 | ethyl 8-((2,6-difluorobenzyl)oxy)-2-methylimidazo[1,2-a]pyridine-3-carboxylate |
| 40 | ethyl 8-(cyclohexylmethoxy)-6-chloro-2-methylimidazo[1,2-a]pyridine-3-carboxylate |
| 41 | 8-((2-fluorobenzyl)oxy)-2-methylimidazo[1,2-a]pyridine-6-carboxylic acid |
| 42 | 8-(cyclohexylmethoxy)-2-methylimidazo[1,2-a]pyridine-3-carboxylic acid |
| 43 | 8-(cyclohexylmethoxy)-2-(trifluoromethyl)imidazo[1,2-a]pyridine-3-carboxylic acid |
| 44 | 8-(benzyloxy)-2-methylimidazo[1,2-a]pyridine-3-carboxylic acid |
| 45 | 8-((2,6-difluorobenzyl)oxy)-2-methylimidazo[1,2-a]pyridine-3-carboxylic acid |
| 46 | 8-(cyclohexylmethoxy)imidazo[1,2-a]pyridine-3-carboxylic acid |
| 47 | 8-(cyclohexylmethoxy)-2,6-dimethylimidazo[1,2-a]pyridine-3-carboxylic acid |

TABLE 4-continued

| PEx | Str |
|---|---|
| 48 | 8-(cyclohexylmethoxy)-6-bromo-2-methyl-imidazo[1,2-a]pyridine-3-carboxylic acid |
| 49 | 8-(cyclohexylmethoxy)-6-chloro-2-methyl-imidazo[1,2-a]pyridine-3-carboxylic acid |
| 50 | 8-(cyclohexylmethoxy)-2-ethyl-imidazo[1,2-a]pyridine-3-carboxylic acid |
| 51 | 8-(cyclohexylmethoxy)-2-cyclopropyl-imidazo[1,2-a]pyridine-3-carboxylic acid |
| 52 | tert-butyl (E)-3-cyclopentylacrylate |
| 53 | tert-butyl (E)-5,5-dimethylhex-2-enoate |
| 54 | tert-butyl (E)-4-cyclohexylbut-2-enoate |

TABLE 5

| PEx | Str |
|---|---|
| 55 | tert-butyl (E)-4-cyclopentylbut-2-enoate |
| 56 | tert-butyl (E)-4-cyclobutylbut-2-enoate |
| 57 | 8-(pyrimidin-4-ylmethoxy)-2-methyl-N-[(S)-2-(TBS-oxy)-1-phenylethyl]imidazo[1,2-a]pyridine-3-carboxamide |

TABLE 5-continued

| PEx | Str |
|---|---|
| 58 | tert-butyl (S)-3-[N-benzyl-N-(1-phenylethyl)amino]-5,5-dimethylhexanoate |
| 59 | 8-[(3-fluoropyridin-2-yl)methoxy]-2-methyl-N-[(S)-2-(TBS-oxy)-1-phenylethyl]imidazo[1,2-a]pyridine-3-carboxamide |
| 60 | ethyl 1-[(S)-2-(Boc-amino)-2-phenylethyl]piperidine-3-carboxylate |
| 61 | 8-(pyrimidin-5-ylmethoxy)-2-methyl-N-[(S)-2-(TBS-oxy)-1-phenylethyl]imidazo[1,2-a]pyridine-3-carboxamide |
| 62 | tert-butyl (S)-3-[N-benzyl-N-(1-phenylethyl)amino]-3-cyclopentylpropanoate |
| 63 | 8-(pyridazin-3-ylmethoxy)-2-methyl-N-[(S)-2-(TBS-oxy)-1-phenylethyl]imidazo[1,2-a]pyridine-3-carboxamide |
| 64 | 8-(cyclohexylmethoxy)-2-methyl-N-(2,2-dimethoxyethyl)imidazo[1,2-a]pyridine-3-carboxamide |
| 65 | tert-butyl (R)-3-[N-benzyl-N-(1-phenylethyl)amino]-3-cyclopentylpropanoate |
| 66 | ethyl 1-[(S)-2-amino-2-phenylethyl]piperidine-3-carboxylate |

TABLE 5-continued
| PEx | Str |
|---|---|
| 67 | 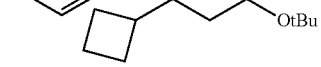 |
| 68 | 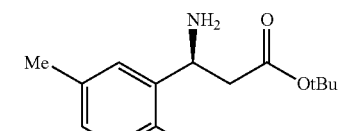 |
| 69 | 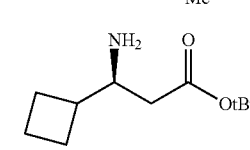 |
| 70 | 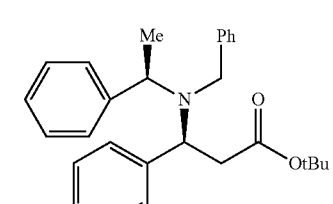 |
TABLE 6
| PEx | Str |
|---|---|
| 71 | 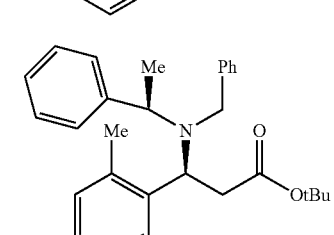 |
| 72 | 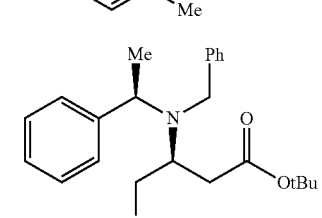 |
| 73 | 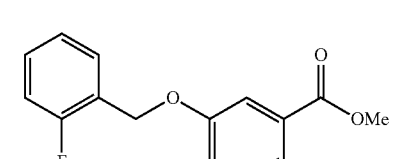 |
TABLE 6-continued
| PEx | Str |
|---|---|
| 74 | 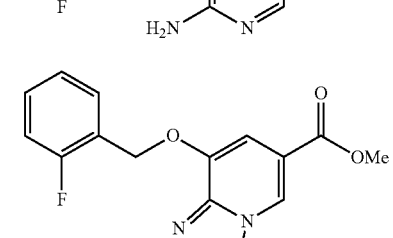 |
| 75 | |
| 76 | |
| 77 | |
| 78 | |
| 79 | |
| 80 | |
| 81 | |

TABLE 6-continued
| PEx | Str |
|---|---|
| 82 | 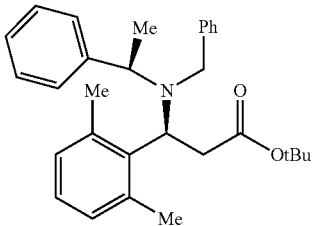 [SMILES: Cc1cccc(C)c1[C@H](CC(=O)OC(C)(C)C)N(Cc1ccccc1)[C@H](C)c1ccccc1] |
| 83 | 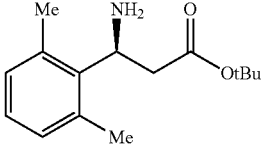 [SMILES: Cc1cccc(C)c1[C@@H](N)CC(=O)OC(C)(C)C] |
| 84 | 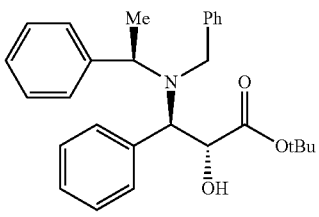 [SMILES: C[C@H](c1ccccc1)N(Cc1ccccc1)[C@H](c1ccccc1)[C@@H](O)C(=O)OC(C)(C)C] |
TABLE 7
| PEx | Str |
|---|---|
| 85 | 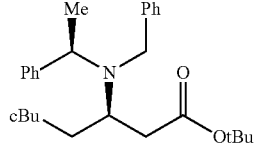 |
| 86 | 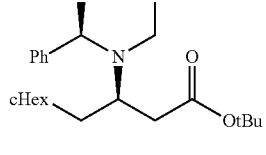 |
| 87 | 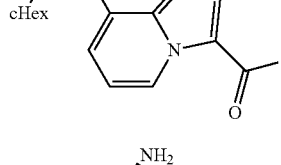 |
| 88 | 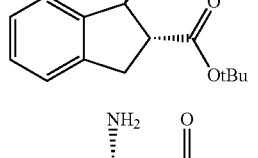 |
| 89 | 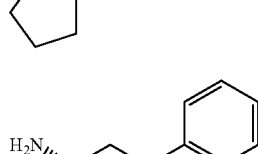 |
TABLE 7-continued
| PEx | Str |
|---|---|
| 90 | 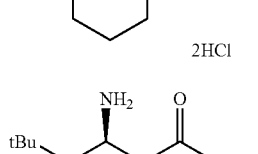 |
| 91 | 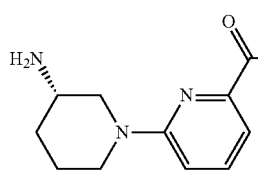 |
| 92 | 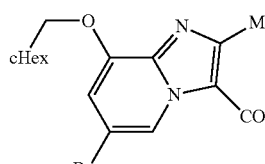 |
| 93 | 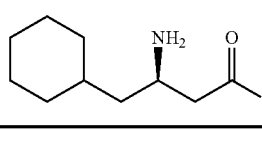 |
| 94 |  |
| 95 | 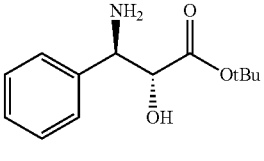 [SMILES: CC(C)(C)OC(=O)[C@H](O)[C@H](N)c1ccccc1] |
| 96 | 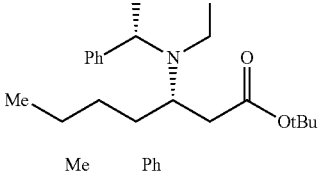 |
| 97 | 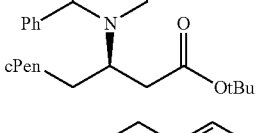 |
| 98 | 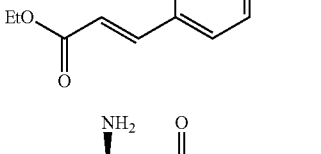 |
| 99 |  |

TABLE 8

| PEx | Str |
|---|---|
| 100 | ethyl 8-((2,3,6-trifluorobenzyl)oxy)-2-methylimidazo[1,2-a]pyridine-3-carboxylate |
| 101 | methyl 1-amino-1,2,3,4-tetrahydronaphthalene-2-carboxylate HCl (cis) |
| 102 | methyl 1-amino-2,3-dihydro-1H-indene-2-carboxylate HCl (cis) |
| 104 | tert-butyl (E)-3-(2-(hydroxymethyl)-4-methylphenyl)acrylate |
| 105 | tert-butyl (E)-3-(2-(bromomethyl)-4-methylphenyl)acrylate |
| 106 | tert-butyl 1-(benzyl((R)-1-phenylethyl)amino)-5-methyl-2,3-dihydro-1H-indene-2-carboxylate |
| 107 | methyl 1-(benzyl((R)-1-phenylethyl)amino)-5-methyl-2,3-dihydro-1H-indene-2-carboxylate |
| 108 | methyl 1-amino-5-methyl-2,3-dihydro-1H-indene-2-carboxylate |
| 109 | methyl 1-amino-6-methyl-2,3-dihydro-1H-indene-2-carboxylate HCl |

TABLE 8-continued

| PEx | Str |
|---|---|
| 110 | tert-butyl 3-(2-(hydroxymethyl)-3-methylphenyl)propanoate |
| 111 | tert-butyl 3-(2-formyl-3-methylphenyl)propanoate |
| 112 | tert-butyl 3-(2-((tert-butylsulfinylimino)methyl)-3-methylphenyl)propanoate |
| 113a | tert-butyl 1-((tert-butylsulfinyl)amino)-7-fluoro-2,3-dihydro-1H-indene-2-carboxylate |

TABLE 9

| PEx | Str |
|---|---|
| 113b | tert-butyl 1-((tert-butylsulfinyl)amino)-7-fluoro-2,3-dihydro-1H-indene-2-carboxylate or |
| 113c | tert-butyl 1-((tert-butylsulfinyl)amino)-7-fluoro-2,3-dihydro-1H-indene-2-carboxylate |
| 114 | tert-butyl 1-amino-7-methyl-2,3-dihydro-1H-indene-2-carboxylate |

TABLE 9-continued

| PEx | Str |
|---|---|
| 115 | (1-amino-7-fluoro-2,3-dihydro-1H-indene-2-carboxylic acid methyl ester, stereo) |
| 116 | (E)-tert-butyl 3-(3-formylthiophen-2-yl)acrylate |
| 117 | tert-butyl 3-(3-formylthiophen-2-yl)propanoate |
| 118 | tert-butyl 3-(2-formylthiophen-3-yl)propanoate |
| 119 | ethyl 8-((2,3-difluorobenzyl)oxy)-2-methylimidazo[1,2-a]pyridine-3-carboxylate |
| 120 | tert-butyl 1-amino-2,3-dihydro-1H-indene-2-carboxylate (stereo) |
| 121 | methyl 1-amino-5-fluoro-2,3-dihydro-1H-indene-2-carboxylate (stereo) |
| 122 | 8-((2,3,6-trifluorobenzyl)oxy)-2-methylimidazo[1,2-a]pyridine-3-carboxylic acid |
| 123 | methyl 1-amino-7-methyl-2,3-dihydro-1H-indene-2-carboxylate HCl (stereo) |
| 124 | methyl 1-amino-4-fluoro-2,3-dihydro-1H-indene-2-carboxylate HCl (stereo) |

TABLE 9-continued

| PEx | Str |
|---|---|
| 125 | tert-butyl 3-(2-fluoro-6-(hydroxymethyl)phenyl)propanoate |

TABLE 10

| PEx | Str |
|---|---|
| 127 | tert-butyl 3-(2-((((tert-butylsulfinyl)imino)methyl)thiophen-3-yl)propanoate |
| 128 | tert-butyl 3-(3-((((tert-butylsulfinyl)imino)methyl)thiophen-2-yl)propanoate |
| 129 | tert-butyl 3-(2-((((tert-butylsulfinyl)imino)methyl)-3-fluorophenyl)propanoate |
| 130 | tert-butyl 3-(2-((((tert-butylsulfinyl)imino)methyl)-3-fluorophenyl)propanoate (rac) |
| 131 | tert-butyl 3-(2-((((tert-butylsulfinyl)imino)methyl)-3-fluorophenyl)propanoate |

TABLE 10-continued

| PEx | Str |
|---|---|
| 132 | (structure: 7-methyl-indane with HN-S(O)-tBu sulfinamide and CO-OtBu) |
| 133 | (structure: thieno-cyclopentane with HN-S(O)-tBu sulfinamide and CO-OtBu) |
| 134 | (structure: 3-fluoro-2-formyl-phenyl propanoate OtBu) |
| 135 | (structure: 7-fluoro-indane with HN-S(O)-tBu and CO-OtBu, cis) |
| 136 | (structure: 7-fluoro-indane with HN-S(O)-tBu and CO-OtBu) |
| 137 | (structure: thieno-cyclopentane with NH₂ and CO-OtBu, HCl) |
| 138 | (structure: thieno-cyclopentane with NH₂ and CO-OtBu, HCl) |
| 139 | (structure: 7-fluoro-indane with NH₂ and CO-OMe, cis) |

TABLE 10-continued

| PEx | Str |
|---|---|
| 140 | (structure: 7-fluoro-indane with NH₂ and CO-OMe) |

TABLE 11

| PEx | Str |
|---|---|
| 141 | (structure: 2-formyl-thiophene with acrylate OtBu) |
| 142 | (structure: 8-(2,3-difluorobenzyloxy)-2-methyl-imidazo[1,2-a]pyridine-3-carboxylic acid) |
| 143 | (structure: thieno-cyclopentane with HN-S(O)-tBu and CO-OtBu) |
| 144 | (structure: 4-fluoro-2-(hydroxymethyl)phenyl acrylate OtBu) |
| 145 | (structure: 3-methyl-2-(hydroxymethyl)phenyl acrylate OtBu) |
| 146 | (structure: 5-fluoro-2-(hydroxymethyl)phenyl acrylate OtBu) |
| 147 | (structure: 5-methyl-2-(hydroxymethyl)phenyl acrylate OtBu) |

TABLE 11-continued
| PEx | Str |
|---|---|
| 148 | 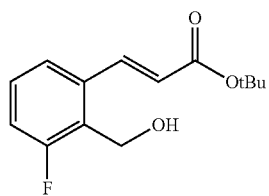 [SMILES: CC(C)(C)OC(=O)/C=C/c1cccc(F)c1CO] |
| 149 | 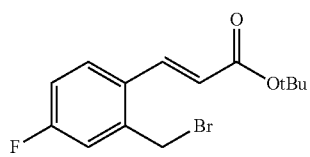 [SMILES: CC(C)(C)OC(=O)/C=C/c1ccc(F)cc1CBr] |
| 150 | 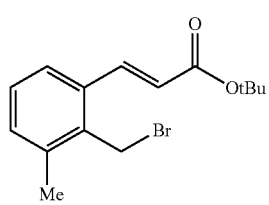 [SMILES: Cc1cccc(/C=C/C(=O)OC(C)(C)C)c1CBr] |
| 151 | 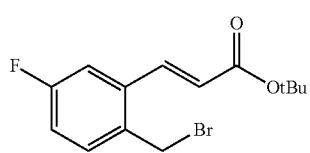 [SMILES: CC(C)(C)OC(=O)/C=C/c1cc(F)ccc1CBr] |
| 152 | 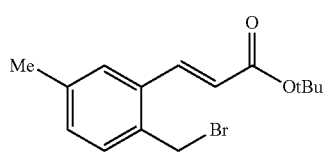 [SMILES: Cc1ccc(CBr)c(/C=C/C(=O)OC(C)(C)C)c1] |
| 153 | 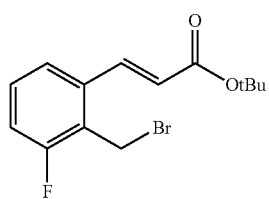 [SMILES: CC(C)(C)OC(=O)/C=C/c1cccc(F)c1CBr] |
| 154 | 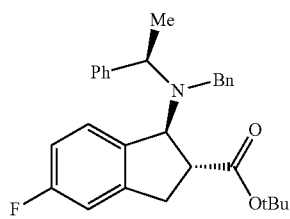 [SMILES: C[C@H](c1ccccc1)N(Cc1ccccc1)[C@@H]1c2ccc(F)cc2C[C@H]1C(=O)OC(C)(C)C] |
| 155 | 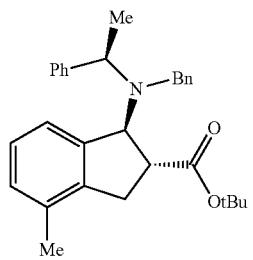 [SMILES: Cc1cccc2c1C[C@@H](C(=O)OC(C)(C)C)[C@@H]2N(Cc1ccccc1)[C@H](C)c1ccccc1] |
TABLE 11-continued
| PEx | Str |
|---|---|
| 156 | 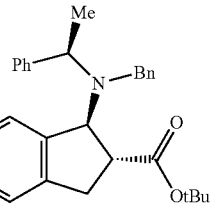 |
TABLE 12
| PEx | Str |
|---|---|
| 157 | 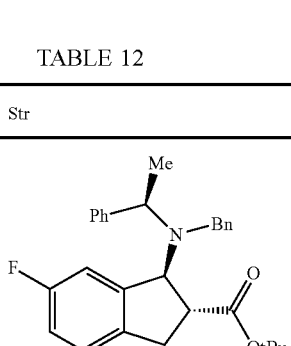 |
| 158 | 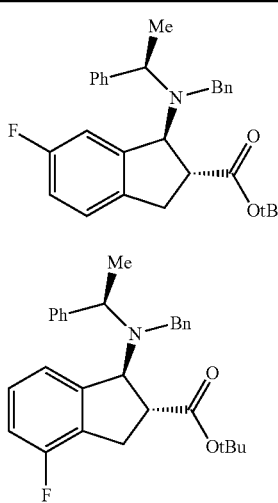 |
| 159 | 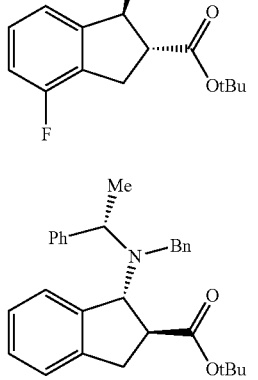 |
| 160 | 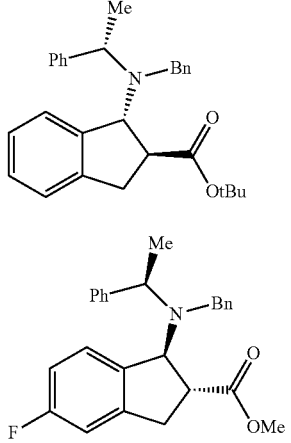 |
| 161 | 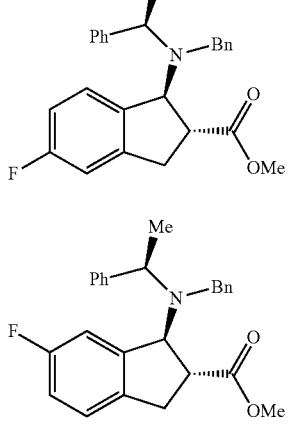 |

TABLE 12-continued

| PEx | Str |
|---|---|
| 162 | (1-phenylethyl-N-benzyl)amino 6-methyl indane-2-carboxylic acid methyl ester |
| 163 | (1-phenylethyl-N-benzyl)amino 4-methyl indane-2-carboxylic acid methyl ester |
| 164 | (1-phenylethyl-N-benzyl)amino 4-fluoro indane-2-carboxylic acid methyl ester |

TABLE 13

| PEx | Str |
|---|---|
| 165 | tBuO-C(O)-NH-CH(Me)-(3-methoxycarbonylphenyl) |
| 166 | N-Boc, N-MOM 2-OMOM indane |
| 167 | N-Boc, N-MOM 2-OMOM 3-Br indane |
| 168a | N-Boc, N-MOM 2-OMOM 3-OAc indane |
| 168b | N-Boc, N-MOM 2-OMOM 3-OAc indane (diastereomer) |
| 169a | NHBoc 2-OH 3-OH indane |
| 169b | NHBoc 2-OH 3-OH indane (diastereomer) |
| 170 | 4-nitrobenzoate of BocNH-CH(Ph)-CH(O-)-CH2-OTBS |
| 171 | N-Boc, N-MOM 2-OMOM 3-OH indane |
| 172 | NH2·HCl 2-OH 3-OH indane |
| 173 | (1-(4-methoxyphenyl)ethyl)-NH-indan-3-yl-CO2Me |

TABLE 13-continued

| PEx | Str |
|---|---|
| 174 | (structure: MeO-C6H4-CH(Me)-NH-indane-CO2Me) |
| 175 | (structure: MeO2C-C6H4-C(Me)2-NH-C(O)-OtBu) |

TABLE 14

| PEx | Str |
|---|---|
| 176 | (structure: MeO-C(O)-indane-NH2) |
| 177 | (structure: Me, NH2, OH, OH indane, HCl, rac) |
| 178 | (structure: HOCH2-C(NO2)(m-tolyl)-CH2OH) |
| 179 | (structure: EtO-C(O)-C(CH2OH)2-pyridyl) |
| 180 | (structure: dimethyl dioxane with CO2Et and 3-pyridyl) |

TABLE 14-continued

| PEx | Str |
|---|---|
| 181a | (structure: phenyl, NHBoc, cyclopentane diol) |
| 181b | (structure: phenyl, NHBoc, cyclopentane diol, diastereomer) |
| 182 | (structure: BocHN-CH(Ph)-CH(OH)-CH2-OTBS) |
| 183 | (structure: H2N, CO2Me, OH indane, rac) |
| 184 | (structure: dimethyl dioxane with ZHN and 3-pyridyl) |
| 185 | (structure: dimethyl dioxane with ZHN and 2-pyridyl) |
| 186 | (structure: dimethyl dioxane with H2N and m-tolyl) |
| 187 | (structure: tBu-S(O)-N=CH-C6H4-CO2Me) |

TABLE 14-continued

| PEx | Str |
|---|---|
| 188 | 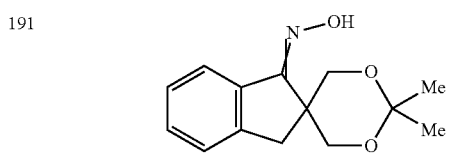 |

TABLE 15

| PEx | Str |
|---|---|
| 189 | 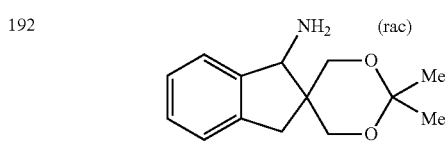 |
| 190 | 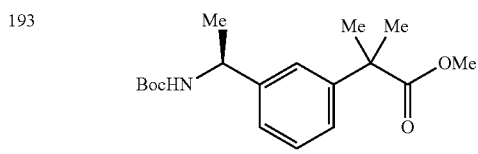 |
| 191 | 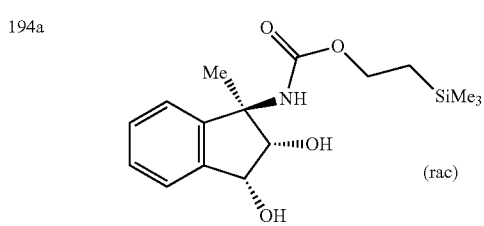 |
| 192 | 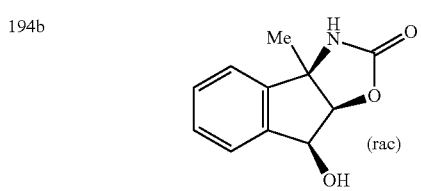 |
| 193 | ![](Me, BocHN, Me Me, OMe, O structure) |
| 194a | (rac) structure with Me, NH, O, SiMe3, OH, OH |
| 194b | (rac) structure with Me, H, N, O, O, OH |

TABLE 15-continued

| PEx | Str |
|---|---|
| 195 | Me, CO2Me indene (rac) |
| 196 | BocHN, piperidine, CO2Me phenyl |
| 197 | H2N, Me, CO2Me phenyl |
| 198 | H2N, OH, OH, Ph · HCl |
| 199 | BocHN, OH, OH, Ph |
| 200 | tBu, S(=O), NH, Me, Et, OTBS |
| 201 | H2N, OH, Et, Me · HCl |
| 202 | cHex-O, imidazopyridine, Me, C(=O)O-benzotriazole |
| 203 | H2N, OH, Ph, CO2Me (rac) |
| 204 | Me, Me, O, O, H2N, pyridin-3-yl |

TABLE 16

| PEx | Str |
|---|---|
| 205 | (2,2-dimethyl-1,3-dioxan-5-yl)(pyridin-2-yl) with NH2 |
| 206 | (3R)-3-amino-1-[4-(methoxycarbonyl)phenyl]piperidine · 2HCl |
| 207 | (3R)-3-amino-1-[2-(methoxycarbonyl)phenyl]piperidine · 2HCl |
| 208 | methyl 6-[(3R)-3-aminopiperidin-1-yl]pyridine-3-carboxylate · 2HCl |
| 209 | methyl 2-[(3R)-3-aminopiperidin-1-yl]pyridine-4-carboxylate · HCl |
| 210 | methyl 2-[3-((1R)-1-aminoethyl)phenyl]-2-methylpropanoate · HCl |
| 211 | (1S,2R,3S)-1-amino-2,3-dihydroxyindane · HCl |
| 212 | (1R,2S,3R)-1-amino-2,3-dihydroxyindane · HCl |
| 213 | methyl 3-(1-amino-1-methylethyl)benzoate · HCl |

TABLE 16-continued

| PEx | Str |
|---|---|
| 214 | 1-methyl-1-amino-2,3-dihydroxyindane · HCl (rac) |
| 215 | 1-methyl-1-amino-2,3-dihydroxyindane · HCl (rac) (diastereomer) |
| 216 | methyl 3-[(2R)-2-{[(1R)-1-phenylethyl]amino}propyl]benzoate |
| 217 | (2S)-methyl 2-{[(4-nitrophenyl)sulfonyl]oxy}propanoate |
| 218 | ethyl 8-[(2-chloro-6-fluorobenzyl)oxy]-2-methylimidazo[1,2-a]pyridine-3-carboxylate |
| 219 | ethyl 2-methyl-8-[(2,4,6-trifluorobenzyl)oxy]imidazo[1,2-a]pyridine-3-carboxylate |
| 230 | tert-butyl (3R)-3-cycloheptyl-3-{benzyl[(1R)-1-phenylethyl]amino}propanoate |

TABLE 17

| PEx | Str |
|---|---|
| 221 | (structure: cycloheptyl with chiral -CH(NH2)-CH2-C(=O)-OtBu) |
| 222 | (structure: 2-(methoxycarbonylmethoxy)benzaldehyde N-tert-butylsulfinyl imine) |
| 223 | (structure: tBu-S(=O)-N=C(Me)-CH2-OTBS) |
| 224a | (structure: methyl 3-((tert-butylsulfinyl)amino)-2,3-dihydrobenzofuran-2-carboxylate, single stereoisomer) |
| 224b | (structure: methyl 3-((tert-butylsulfinyl)amino)-2,3-dihydrobenzofuran-2-carboxylate, diastereomer) or (another diastereomer) |
| 225a | (structure: methyl 3-((tert-butylsulfinyl)amino)-2,3-dihydrobenzofuran-2-carboxylate stereoisomer) |
| 225b | (structure: methyl 3-((tert-butylsulfinyl)amino)-2,3-dihydrobenzofuran-2-carboxylate) or (other diastereomer) |
| 226 | (structure: methyl 3-(2,3-dimethylphenyl)-3-aminopropanoate) |
| 227 | (structure: 8-((2,6-difluorobenzyl)oxy)-2-methylimidazo[1,2-a]pyridine-3-carbonyl chloride, HCl) |
| 228 | (structure: methyl 3-(1-amino-2-methylpropyl)benzoate, HCl) |
| 229 | (structure: methyl 3-(1-aminopropyl)benzoate with Et, HCl) |
| 230 | (structure: methyl 3-(amino(cyclopropyl)methyl)benzoate, HCl) |
| 231 | (structure: methyl 3-amino-2,3-dihydrobenzofuran-2-carboxylate, HCl) |
| 232 | (structure: methyl 3-amino-2,3-dihydrobenzofuran-2-carboxylate, HCl, diastereomer) |

TABLE 18

| PEx | Str |
|---|---|
| 233 | 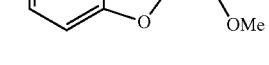 HCl, methyl 3-amino-2,3-dihydrobenzofuran-2-carboxylate or |
| 234 | HCl, methyl 3-amino-2,3-dihydrobenzofuran-2-carboxylate |
| 235 | Boc-N, oxazolidinone fused indane with OAc |
| 236 | Me, NH₂, OH, OH indane (rac) |
| 237a | Me, NH-C(O)O-CH₂CH₂SiMe₃, OH, OH indane (rac) |
| 237b | Me, NH-C(O)O-CH₂CH₂SiMe₃, OH, OH indane (rac) |
| 238 | BocHN, OH, OTBS, Ph |
| 239 | MeOCH₂-N(Boc), OMOM, OH indane |

TABLE 18-continued

| PEx | Str |
|---|---|
| 240 | NH₂, OH, OH indane · HCl |
| 241 | (p-tolyl)CH(Me)-NH-indane-CO₂Me |
| 242 | (p-tolyl)CH(Me)-NH-indane-CO₂Me |
| 243 | MeO₂C-indane-NH₂ · HCl |
| 244 | MeO₂C-indane-NH₂ · HCl |
| 245 | NH₂-indane-CO₂Me · HCl |

TABLE 19

| PEx | Str |
|---|---|
| 246 | HO-CH₂-C(NO₂)(o-tolyl)-CH₂-OH |

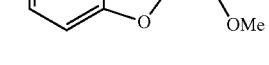
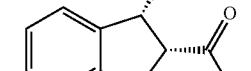
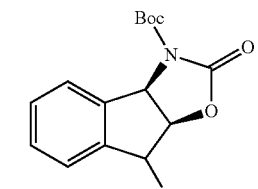
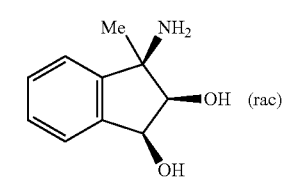
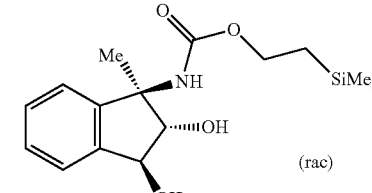
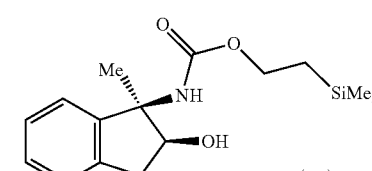
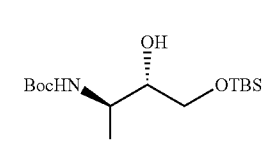
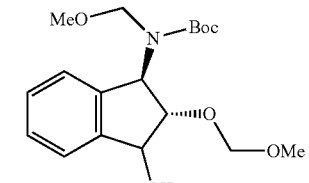

TABLE 19-continued

| PEx | Str |
|---|---|
| 247 | (structure) |
| 248 | (structure) |
| 249 | (structure) |
| 250 | (structure) |
| 251 | (structure) |
| 252 | (structure) |
| 253 | (structure) |
| 254 | (structure) |
| 255 | (structure) |
| 256 | (structure) |
| 257 | (structure) |
| 258 | (structure) |
| 259 | (structure) |
| 260 | (structure) |
| 261 | (structure) |

TABLE 20

| PEx | Str |
|---|---|
| 262 | (structure) |

TABLE 20-continued
| PEx | Str |
|---|---|
| 263 | 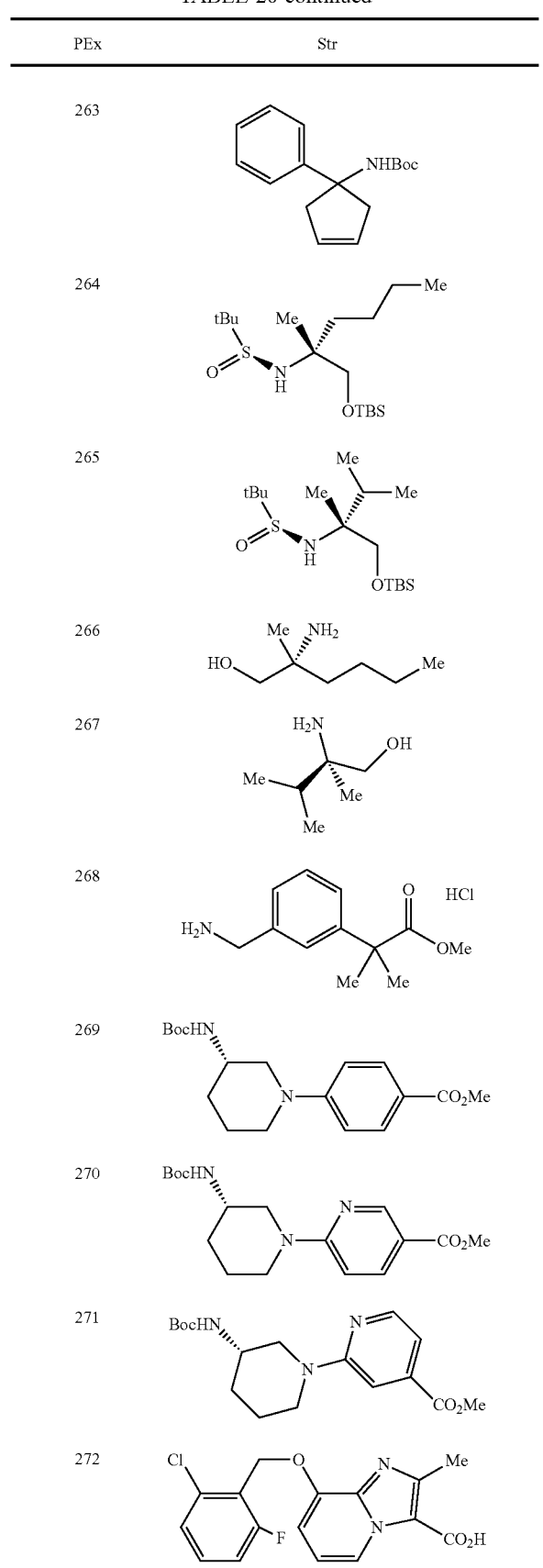 |
| 264 | |
| 265 | |
| 266 | |
| 267 | |
| 268 | |
| 269 | |
| 270 | |
| 271 | |
| 272 | |
TABLE 20-continued
| PEx | Str |
|---|---|
| 273 | 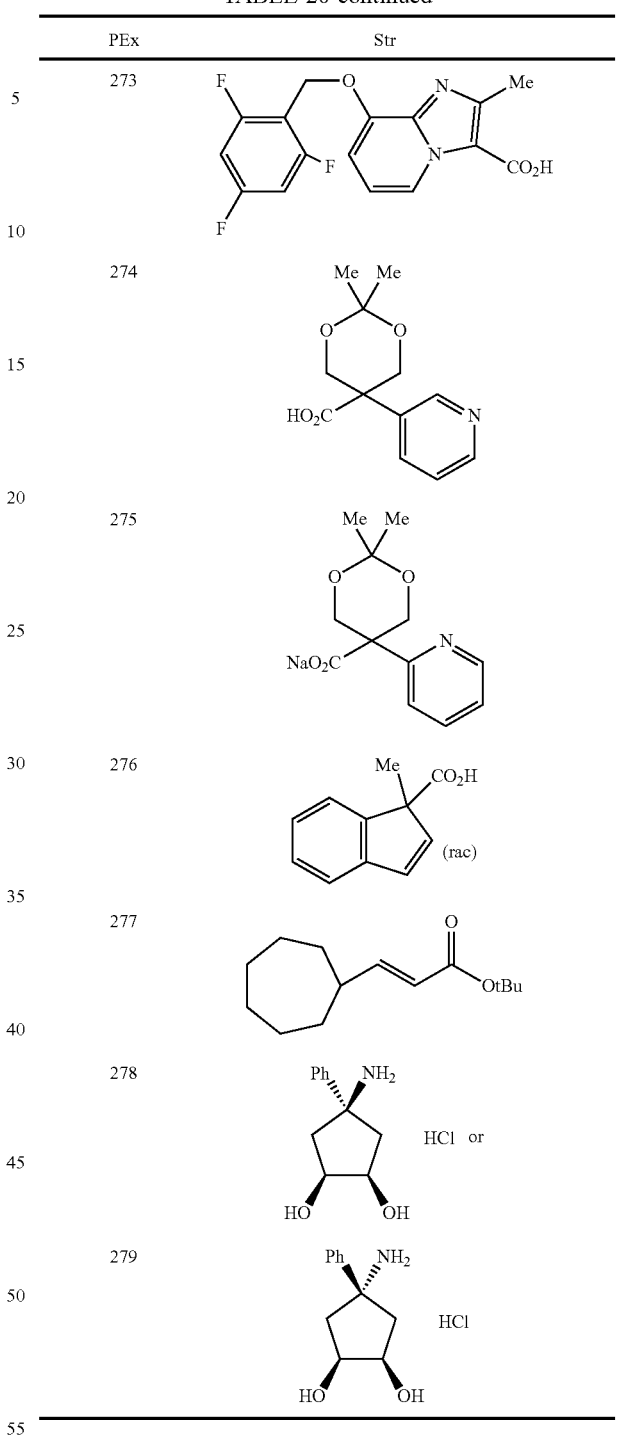 |
| 274 | |
| 275 | |
| 276 | |
| 277 | |
| 278 | |
| 279 | |
TABLE 21
| PEx | Syn | Dat |
|---|---|---|
| 1 | PEx1 | ESI+: 251 |
| 2 | PEx2 | ESI+: 221 |
| 3 | PEx3 | ESI+: 285 |
| 4 | PEx4 | ESI+: 331 |
| 5 | PEx5 | ESI+: 301 |
| 6 | PEx6 | ESI+: 426 |
| 7 | PEx7 | CI+: 177, 179 |
| 8 | PEx8 | ESI+: 307 |

TABLE 21-continued

| PEx | Syn | Dat |
|---|---|---|
| 9 | PEx9 | ESI+: 185 |
| 10 | PEx10 | ESI+: 396 |
| 11 | PEx11 | ESI+: 202 |
| 12 | PEx12 | NMR(DMSO-$d_6$): 1.07-1.36 (5H, m), 1.63-1.80 (2H, m), 1.82-1.96 (2H, m), 2.76 (3H, s), 4.13 (2H, d, J = 6 Hz), 7.52-7.47 (1H, m), 7.58 (1H, d, J = 8 Hz), 9.08 (1H, d, J = 6 Hz) |
| 13 | PEx13 | FAB+: 307 |
| 14 | PEx14 | EI: 276 |
| 15 | PEx15 | EI: 314 |
| 16 | PEx16 | ESI+: 329 |
| 17 | PEx17 | ESI+: 336 |
| 18 | PEx18 | ESI+: 330 |
| 19 | PEx19 | ESI+: 277 |
| 20 | PEx20 | ESI+: 377 |
| 21 | PEx21 | NMR(CDCl$_3$): 1.42 (9H, s), 2.52 (2H, t, J = 8 Hz), 2.89 (2H, t, J = 8 Hz), 3.84 (2H, s), 7.17 (2H, d, J = 8 Hz), 7.23 (2H, d, J = 8 Hz) |
| 22 | PEx22 | NMR(DMSO-$d_6$): 1.12 (3H, t, J = 8 Hz), 1.49 (6H, s), 3.98 (2H, s), 4.06 (2H, q, J = 7 Hz), 7.34 (2H, d, J = 8 Hz), 7.46 (2H, d, J = 8 Hz), 8.44 (3H, br s) |
| 23 | PEx23 | NMR(CDCl$_3$): 1.34 (3H, t, J = 7 Hz), 1.46 (9H, s), 4.27 (2H, q, J = 7 Hz), 4.46 (2H, d, J = 5 Hz), 4.73 (1H, brs), 6.37 (1H, d, J = 16 Hz), 7.28-7.36 (3H, m), 7.57 (1H, d, J = 8 Hz), 7.95 (1H, d, J = 16 Hz) |
| 24 | PEx24 | NMR(CDCl$_3$): 1.18 (3H, t, J = 7 Hz), 1.58 (6H, s), 4.13 (2H, q, J = 7 Hz), 7.45 (2H, dt, J = 9, 2 Hz), 7.62 (2H, dt, J = 9, 2 Hz) |

TABLE 22

| PEx | Syn | Dat |
|---|---|---|
| 25 | PEx25 | ESI+: 162 |
| 26 | PEx 26 | ESI+: 335 |
| 27 | PEx 27 | ESI+: 336 |
| 28 | PEx28 | ESI+: 180 |
| 29 | PEx11 | CI+: 228 |
| 30 | PEx11 | ESI+: 214 |
| 31 | PEx15 | ESI+: 303 |
| 32 | PEx3 | ESI+: 241 |
| 33 | PEx4 | ESI+: 317 |
| 34 | PEx4 | ESI+: 329 |
| 35 | PEx4 | ESI+: 311 |
| 36 | PEx4 | ESI+: 317 |
| 37 | PEx4 | ESI+: 371 |
| 38 | PEx4 | ESI+: 329 |
| 39 | PEx4 | ESI+: 347 |
| 40 | PEx4 | ESI+: 351 |
| 41 | PEx5 | ESI+: 301 |
| 42 | PEx5 | ESI+: 289 |
| 43 | PEx5 | ESI+: 343 |
| 44 | PEx5 | ESI+: 283 |
| 45 | PEx5 | ESI+: 319 |
| 46 | PEx5 | ESI+: 275 |
| 47 | PEx5 | ESI+: 303 |
| 48 | PEx5 | ESI+: 367 |
| 49 | PEx5 | ESI+: 323, 325 |
| 50 | PEx5 | ESI+: 303 |
| 51 | PEx5 | ESI+: 315 |
| 52 | PEx9 | ESI+: 197 |
| 53 | PEx9 | CI+: 199 |
| 54 | PEx9 | CI+: 225 |
| 55 | PEx9 | EI: 210 |
| 56 | PEx9 | ESI+: 197 |
| 57 | Ex2 | ESI+: 518 |
| 58 | PEx10 | ESI+: 410 |

TABLE 23

| PEx | Syn | Dat |
|---|---|---|
| 59 | Ex2 | ESI+: 535 |
| 60 | PEx20 | ESI+: 377 |
| 61 | Ex2 | ESI+ 518 |
| 62 | PEx10 | ESI+: 408 |
| 63 | Ex2 | ESI+: 518 |
| 64 | Ex1 | ESI+: 376 |
| 65 | PEx10 | ESI+: 408 |
| 66 | PEx19 | ESI+: 277 |
| 67 | PEx11 | ESI+: 202 |
| 68 | PEx10 | ESI+: 408 |
| 69 | PEx10 | ESI+: 410 |
| 70 | PEx12 | NMR(DMSO-$d_6$): 1.07-1.36 (5H, m), 1.63-1.80 (2H, m), 1.82-1.96 (2H, m), 2.49-2.53 (2H, m), 2.76 (3H, s), 4.13 (2H, d, J = 6 Hz), 7.52-7.47 (1H, m), 7.58 (1H, d, J = 8 Hz), 9.08 (1H, d, J = 6 Hz) |
| 71 | PEx9, 10 | ESI+: 394 |
| 72 | PEx9, 10 | ESI+: 443 |
| 73 | PEx 11 | ESI+: 200 |
| 74 | PEx9, 10 | ESI+: 394 |
| 75 | PEx11 | ESI+: 250 |
| 76 | PEx11 | ESI+: 200 |
| 77 | PEx10 | ESI+: 416 |
| 78 | PEx10 | ESI+: 444 |
| 79 | PEx10 | ESI+: 370 |
| 80 | PEx14 | EI: 276 |
| 81 | PEx15 | EI: 314 |
| 82 | PEx10 | ESI+: 444 |
| 83 | PEx11 | ESI+: 250 |
| 84 | PEx10 | ESI+: 432 |
| 85 | PEx11 | ESI+: 238 |
| 86 | PEx10 | ESI+: 396 |
| 87 | PEx10 | ESI+: 422 |
| 88 | Ex5 | ESI+: 206 |
| 89 | PEx11 | ESI+: 214 |
| 90 | PEx10 | ESI+: 408 |

TABLE 24

| PEx | Syn | Dat |
|---|---|---|
| 91 | PEx10 | ESI+: 436 |
| 92 | PEx5 | ESI+: 289 |
| 93 | PEx11 | ESI+: 234 |
| 94 | PEx11 | ESI+: 214 |
| 95 | Ex5 | ESI+: 235 |
| 96 | PEx11 | ESI+: 216 |
| 97 | Ex5 | ESI+: 236 |
| 98 | PEx4 | ESI+: 395 |
| 99 | PEx11 | ESI+: 242 |

TABLE 25

| PEx | Syn | Dat |
|---|---|---|
| 100 | PEx1 | ESI+: 365 |
| 101 | PEx101 | APCI/ESI+: 206 |
| 102 | PEx 102 | ESI+: 192 |
| 104 | PEx104 | ESI+: 249 |
| 105 | PEx105 | ESI+: 311, 313 |
| 106 | PEx106 | ESI+: 442 |
| 107 | PEx107 | ESI+: 400 |
| 108 | PEx11 | ESI+: 206 |
| 109 | PEx109 | ESI+: 206 |
| 110 | PEx110 | ESI+: 273 [M + Na]+ |
| 111 | PEx111 | ESI+: 249 |
| 112 | PEx112 | ESI+: 352 |
| 113a | PEx113 | ESI+: 356<br>NMR(CDCl$_3$): 1.21 (9H, s), 1.48 (9H, s), 3.15 (1 H, dd, J = 6.6, 16.4 Hz), 3.40 (1H, dd, J = 9.0, 16.4 Hz), 3.50 (1H, ddd, J = 5.4, 6.6, 9.0 Hz), 3.98 (1H, d, J = 3.4 Hz), 5.38 (1H, dd, J = 3.4, 5.0 Hz), 6.89 (1H, dt, Jd = 0.5 Hz, Jt = 9.0 Hz), 7.02 (1H, d, J = 7.5 Hz), 7.23-7.28 (1H, m) |

TABLE 25-continued

| PEx | Syn | Dat |
|---|---|---|
| 113b | PEx113 | ESI+: 356<br>NMR(CDCl$_3$): 1.15 (9H, s), 1.52 (9H, s), 3.08 (1H, dd, J = 8.2, 16.1 Hz), 3.33 (1H, ddd, J = 6.8, 8.2, 10.2 Hz), 3.59 (1H, dd, J = 10.2, 16.1 Hz), 4.38 (1H, d, J = 3.9 Hz), 5.18 (1H, dd, J = 3.9, 6.8 Hz), 6.90 (1H, t, J = 8.6 Hz), 7.05 (1H, d, J = 7.6 Hz), 7.25-7.30 (1H, m) |
| 113c | PEx113 | ESI+: 356<br>NMR(CDCl$_3$): 1.14 (9H, s), 1.51 (9H, s), 3.10 (1H, dd, J = 8.1, 16.1 Hz), 3.27 (1H, dd, J = 8.0, 16.0 Hz), 3,42 (1H, dt, Jd = 6,3 Hz, Jt = 8.1 Hz), 4.50 (1H, d, J = 6.0 Hz), 5.22 (1H, t, J = 6.2 Hz), 6.91 (1H, t, J = 8.7 Hz), 7.02 (1H, d, J = 7.4 Hz), 7.22-7.27 (1H, m) |
| 114 | PEx114 | ESI+: 248 |
| 115 | PEx115 | ESI+: 210 |
| 116 | PEx116 | ESI+: 239 |
| 117 | PEx117 | ESI+: 241 |
| 118 | Ex15 | NMR(CDCl$_3$): 1.41 (9H, s), 2.60 (2H, t, J = 7 Hz), 3.26 (2H, t, J = 7 Hz), 7.04 (1H, dd, J = 1, 5 Hz), 7.65 (1H, d, J = 5 Hz), 10.07 (1H, d, J = 1 Hz) |
| 119 | PEx1 | ESI+: 347 |
| 120 | PEx11 | ESI+: 234 |
| 121 | PEx11 | ESI+: 210 |
| 122 | PEx5 | ESI+: 337 |
| 123 | PEx109 | ESI+: 206 |
| 124 | PEx109 | ESI+: 210 |
| 125 | PEx110 | ESI+: 277 [M + Na]+ |

TABLE 26

| PEx | Syn | Dat |
|---|---|---|
| 127 | PEx112 | ESI+: 344 |
| 128 | PEx112 | ESI+: 344 |
| 129 | PEx112 | APCI/ESI+: 356 |
| 130 | PEx112 | ESI+: 356 |
| 131 | PEx112 | ESI+: 356 |
| 132 | PEx113 | ESI+: 352 |
| 133 | PEx113 | ESI+: 344 |
| 134 | PEx111 | ESI+: 275 [M + Na]+ |
| 135 | PEx113 | ESI+: 356 |
| 136 | PEx113 | ESI+: 356 |
| 137 | PEx137 | ESI+: 240 |
| 138 | PEx137 | ESI+: 240 |
| 139 | PEx115 | ESI+: 210 |
| 140 | PEx115 | ESI+: 210 |
| 141 | PEx116 | NMR(CDCl$_3$): 1.55 (9H, s), 6.39 (1H, d, J = 16 Hz), 7.37 (1H, d, J = 5 Hz), 7.68 (1H, d, J = 5 Hz), 8.07 (1H, d, J = 16 Hz), 10.22 (1H, d, J = 1 Hz) |
| 142 | PEx5 | ESI+: 319 |
| 143 | PEx113 | ESI+: 344 |
| 144 | PEx104 | ESI+: 253 |
| 145 | PEx104 | ESI+: 249 |
| 146 | PEx104 | ESI+: 253 |
| 147 | PEx104 | EI: 248 |
| 148 | PEx104 | EI: 252 |
| 149 | PEx105 | EI: 314 |
| 150 | PEx105 | EI: 310, 312 |
| 151 | PEx105 | ESI+: 315, 317 |
| 152 | PEx105 | EI: 310, 312 |
| 153 | PEx105 | ESI+: 337, 339 [M + Na]+ |
| 154 | PEx106 | ESI+: 446 |
| 155 | PEx106 | ESI+: 442 |

TABLE 27

| PEx | Syn | Dat |
|---|---|---|
| 156 | PEx106 | ESI+: 442 |
| 157 | PEx106 | ESI+: 446 |
| 158 | PEx106 | ESI+: 446 |

TABLE 27-continued

| PEx | Syn | Dat |
|---|---|---|
| 159 | PEx106 | ESI+: 428 |
| 160 | PEx107 | ESI+: 404 |
| 161 | PEx107 | ESI+: 404 |
| 162 | PEx107 | ESI+: 400 |
| 163 | PEx107 | ESI+: 400 |
| 164 | PEx107 | APCI/ESI+: 404 |

TABLE 28

| PEx | Syn | Dat |
|---|---|---|
| 165 | PEx165 | ESI−: 324[M + HCOO]− |
| 166 | PEx166 | ESI+: 360 [M + Na]+ |
| 167 | PEx167 | ESI+: 438, 440 [M + Na]+ |
| 168a | PEx168 | ESI+: 418 [M + Na]+ |
| 168b | PEx168 | ESI+: 418 [M + Na]+ |
| 169a | PEx169 | ESI+: 266 |
| 169b | PEx169 | ESI+: 266 |
| 170 | PEx170 | ESI+: 531 |
| 171 | PEx171 | ESI+: 376 [M + Na]+ |
| 172 | PEx172 | ESI+: 166 |
| 173 | PEx173 | APCI/ESI+: 326 |
| 174 | PEx174 | ESI+: 326 |
| 175 | PEx175 | ESI+: 294 |
| 176 | PEx176 | ESI+: 192 |
| 177 | Ex5 | ESI+: 180 |
| 178 | PEx178 | APCI/ESI+: 212 |
| 179 | PEx179 | APCI/ESI+: 226 |
| 180 | PEx180 | APCI/ESI+: 266 |
| 181a | PEx 181 | ESI+: 294<br>NMR(CDCl$_3$): 1.43 (9H, brs), 2.50-2.59 (4H, m), 4.02 (4H, brs), 5.12 (1H, brs), 7.27-7.30 (1H, m), 7.35-7.43 (4H, m) |
| 181b | PEx 181 | ESI+: 294<br>NMR(CDCl$_3$): 1.39 (9H, brs), 2.24-2.32 (4H, m), 2.64 (2H, brs), 4.37-4.43 (2H, m), 4.80 (1H, brs), 7.19-7.23 (1H, m), 7.32 (2H, t, J = 7.4 Hz), 7.41-7.43 (2H, m) |
| 182 | PEx182 | ESI+: 382 |
| 183 | PEx183 | ESI+: 208 |
| 184 | PEx184 | APCI/ESI+: 343 |
| 185 | PEx185 | APCI/ESI+: 343 |
| 186 | PEx186 | APCI/ESI+: 222 |
| 187 | PEx187 | ESI+: 268 |
| 188 | PEx188 | ESI+: 268 |
| 189 | PEx189 | ESI+: 298 |
| 190 | PEx190 | ESI+: 312 |
| 191 | PEx191 | ESI+: 248 |
| 192 | PEx192 | ESI+: 234 |
| 193 | PEx193 | ESI+: 322 |
| 194a | PEx194 | ESI+: 324 |
| 194b | PEx194 | EI: 205 |
| 195 | PEx195 | EI: 188 |

TABLE 29

| PEx | Syn | Dat |
|---|---|---|
| 196 | PEx196 | ESI+: 335 |
| 197 | PEx197 | ESI+: 194 |
| 198 | PEx198 | ESI+: 168 |
| 199 | PEx199 | ESI+: 268 |
| 200 | PEx200 | ESI+: 322 |
| 201 | PEx201 | ESI+: 104 |
| 202 | Ex1 | ESI+: 406 |
| 203 | Ex19 | ESI+: 196 |
| 204 | Ex20 | APCI/ESI+: 209 |
| 205 | Ex20 | APCI/ESI+: 209 |
| 206 | Ex5 | ESI+: 235 |
| 207 | Ex5 | ESI+: 235 |
| 208 | Ex5 | ESI+: 236 |
| 209 | Ex5 | ESI+: 236 |
| 210 | Ex5 | ESI+: 222 |

TABLE 29-continued

| PEx | Syn | Dat |
|---|---|---|
| 211 | Ex5 | ESI+: 166 |
| 212 | Ex5 | ESI+: 166 |
| 213 | Ex5 | ESI+: 194 |
| 214 | Ex5 | ESI+: 180 |
| 215 | Ex5 | ESI+: 180 |
| 216 | Ex6 | ESI+: 298 |
| 217 | Ex9 | CI+: 290 |
| 218 | PEx1 | ESI+: 363 |
| 219 | PEx1 | ESI+: 365 |
| 220 | PEx10 | ESI+: 436 |
| 221 | PEx11 | NMR(CDCl$_3$): 1.22-1.74 (22H, m), 2.16 (1H, dd, J = 9.8 Hz, 15.4 Hz), 2.35 (1H, dd, J = 3.5 Hz, 15.4 Hz), 3.03-3.13 (1H, m) |
| 222 | PEx188 | ESI+: 298 |
| 223 | PEx112 | ESI+: 292 |
| 224a | PEx113 | ESI+: 298<br>NMR(CDCl$_3$): 1.24 (9H, s), 3.65 (1H, d, J = 7.0 Hz), 3.82 (3H, s), 5.03 (1H, d, J = 4.7 Hz), 5.30 (1H, dd, J = 4.9, 7.0 Hz), 6.96 (1H, d, J = 8.1 Hz), 7.01 (1H, t, J = 7.5 Hz), 7.25-7.31 (1H, m), 7.48 (1H, d, J = 7.5 Hz) |
| 224b | PEx113 | ESI+: 298<br>NMR(CDCl$_3$): 1.18 (9H, s), 3.50 (1H, d, J = 9.1 Hz), 3.82 (3H, s), 5.21 (1H, d, J = 8.4 Hz), 5.31 (1H, t, J = 8.7 Hz), 6.93 (1H, d, J = 8.2 Hz), 7.01 (1H, t, J = 7.5 Hz), 7.24-7.30 (1H, m), 7.57 (1H, d, J = 7.3 Hz) |
| 225a | PEx113 | ESI+: 298<br>NMR(CDCl$_3$): 1.24 (9H, s), 3.68 (1H, d, J = 7.1 Hz), 3.82 (3H, s), 5.03 (1H, d, J = 4.8 Hz), 5.30 (1H, dd, J = 4.8, 7.0 Hz), 6.95 (1H, d, J = 8.1 Hz), 7.00 (1H, dt, J = 0.8, 7.5 Hz), 7.26-7.31 (1H, m), 7.48 (1H, d, J = 7.5 Hz) |
| 225b | PEx113 | ESI+: 298<br>NMR(CDCl$_3$): 1.18 (9H, s), 3.51 (1H, d, J = 9.1 Hz), 3.82 (3H, s), 5.21 (1H, d, J = 8.3 Hz), 5.31 (1H, t, J = 8.7 Hz), 6.93 (1H, d, J = 8.1 Hz), 7.01 (1H, dt, J = 0.9, 7.5 Hz), 7.27 (1H, dt, J = 1.3, 7.8 Hz), 7.57 (1H, d, J = 7.5 Hz) |

TABLE 30

| PEx | Syn | Dat |
|---|---|---|
| 226 | PEx114 | ESI+: 208 |
| 227 | PEx12 | ESI+: 337, 339 |
| 228 | PEx137 | ESI+: 208 |
| 229 | PEx137 | ESI+: 194 |
| 230 | PEx137 | ESI+: 206 |
| 231 | PEx137 | ESI+: 194 |
| 232 | PEx137 | ESI+: 194 |
| 233 | PEx137 | ESI+: 194 |
| 234 | PEx137 | ESI+: 194 |
| 235 | PEx168 | ESI+: 356[M + Na]+ |
| 236 | PEx169 | ESI+: 180 |
| 237a | PEx170, 171 | ESI+: 324 |
| 237b | PEx170, 171 | ESI+: 324 |
| 238 | PEx171 | ESI+: 382 |
| 239 | PEx171 | ESI+: 376[M + Na]+ |
| 240 | PEx172 | ESI+: 166 |
| 241 | PEx174 | ESI+: 326 |
| 242 | PEx174 | ESI+: 326 |
| 243 | PEx176, Ex16 | ESI+: 192 |
| 244 | PEx176, Ex16 | ESI+: 192 |
| 245 | PEx176, Ex16 | ESI+: 192 |
| 246 | PEx178 | ESI+: 234 (M + Na)+ |
| 247 | PEx179 | APCI/ESI+: 226 |
| 248 | PEx179 | ESI+: 326 |
| 249 | PEx180 | APCI/ESI+: 274 [M + Na]+ |
| 250 | PEx180 | APCI/ESI+: 274 [M + Na]+ |
| 251 | PEx178 | ESI+: 193 |
| 252 | PEx180 | CI+: 233 |
| 253 | PEx180 | APCI/ESI+: 266 |
| 254 | PEx181 | ESI+: 324 |
| 255 | PEx184 | ESI+: 290 |
| 256 | PEx186 | APCI/ESI+: 222 |
| 257 | PEx186 | ESI+: 208 |
| 258 | PEx186 | APCI/ESI+: 222 |

TABLE 31

| PEx | Syn | Dat |
|---|---|---|
| 259 | PEx187 | ESI+: 238 |
| 260 | PEx188 | ESI+: 298 |
| 261 | PEx189 | ESI+: 312 |
| 262 | PEx189 | ESI+: 310 |
| 263 | PEx199 | ESI+: 260 |
| 264 | PEx200 | ESI+: 350 |
| 265 | PEx200 | ESI+: 336 |
| 266 | PEx201 | ESI+: 132 |
| 267 | PEx201 | ESI+: 118 |
| 268 | PEx22 | NMR(DMSO-d$_6$): 1.52 (6H, s), 3.60 (3H, s), 4.03 (2H, s), 7.28-7.42 (3H, m), 7.45 (1H, s), 8.10-8.35 (3H, br) |
| 269 | PEx26 | ESI+: 335 |
| 270 | PEx27 | ESI+: 336 |
| 271 | PEx27 | ESI+: 336 |
| 272 | PEx5 | ESI+: 335 |
| 273 | PEx5 | ESI+: 337 |
| 274 | PEx5 | APCI/ESI+: 238 |
| 275 | PEx5 | APCI/ESI+: 238 |
| 276 | PEx5 | ESI+: 175 |
| 277 | PEx9 | NMR(CDCl$_3$): 1.29-1.82 (21H, m), 2.24-2.36 (1H, m), 5.67 (1H, dd, J = 1.2 Hz, 15.7 Hz), 6.85 (1H, dd, J = 7.6 Hz, 15.7 Hz) |
| 278 | Ex5 | ESI+: 194<br>NMR(DMSO-d$_6$): 2.22 (2H, dd, J = 4.2, 14.8 Hz), 2.38 (2H, dd, J = 6.5, 14.8 Hz), 4.09-4.14 (2H, m), 4.80-5.60 (2H, br), 7.33-7.38 (1H, m), 7.43 (2H, t, J = 7.2 Hz), 7.47-7.51 (2H, m), 8.34 (3H, brs) |
| 279 | Ex5 | ESI+: 194<br>NMR(DMSO-d$_6$): 2.21 (2H, dd, J = 5.7, 14.6 Hz), 2.31 (2H, dd, J = 6.1, 14.6 Hz), 4.23 (2H, t, J = 4.4 Hz), 4.81 (2H, brs), 7.32-7.36 (1H, m), 7.43 (2H, t, J = 7.4 Hz), 7.53-7.57 (2H, m), 8.46 (3H, brs) |

TABLE 32

| Ex | Str |
|---|---|
| 1 | cHex-O-[imidazopyridine, 2-Me]-C(=O)NH-[piperidin-3-yl]-N-Boc |
| 2 | cPen-O-[imidazopyridine, 2-Me]-C(=O)NH-CH(CH$_2$OTBS)-Ph |
| 3 | (2-F-C$_6$H$_4$)-CH$_2$-O-[imidazopyridine, 2-Me, 6-CO$_2$Et]-C(=O)NH-CH(CH$_2$OH)-Ph |

TABLE 32-continued

| Ex | Str |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE 32-continued

| Ex | Str |
|---|---|
| 12 | (structure) |
| 13 | (structure) |
| 14 | (structure) |

TABLE 33

| Ex | Str |
|---|---|
| 15 | (structure) |
| 16 | (structure) |
| 17 | (structure) |
| 18 | (structure) |

TABLE 33-continued

| Ex | Str |
|---|---|
| 19 | (structure) |
| 20 | (structure) |
| 21 | (structure) |
| 22 | (structure) |
| 23 | (structure) |
| 24 | (structure) |
| 25 | (structure) |
| 26 | (structure) |
| 27 | (structure) |
| 28 | (structure) |

TABLE 34

| Ex | Str |
|---|---|
| 29 | (structure) |
| 30 | (structure) |
| 31 | (structure) |

TABLE 34-continued
| Ex | Str |
|---|---|
| 32 |  |
| 33 | 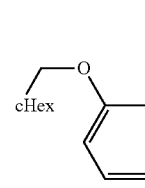 |
| 34 | 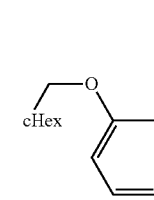 |
| 35 | 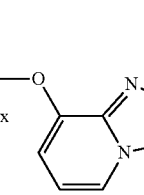 |
| 36 | 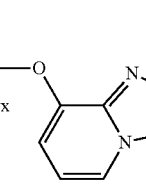 |
| 37 | 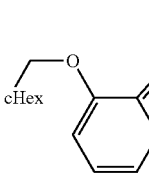 |
| 38 | 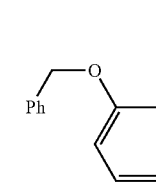 |
TABLE 34-continued
| Ex | Str |
|---|---|
| 39 | |
| 40 | |
TABLE 35
| Ex | Str |
|---|---|
| 41 | |
| 42 | |
| 43 | |
| 44 | |
| 45 | |
| 46 | |

TABLE 35-continued
| Ex | Str |
|---|---|
| 47 | 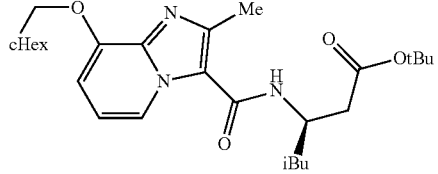 |
| 48 | 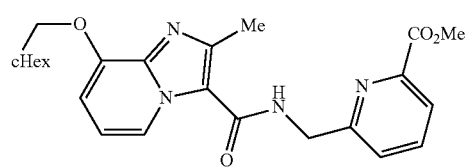 |
| 49 | 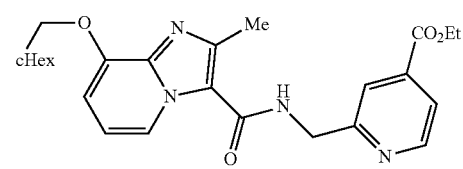 |
| 50 | 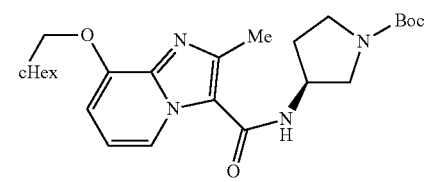 |
| 51 | 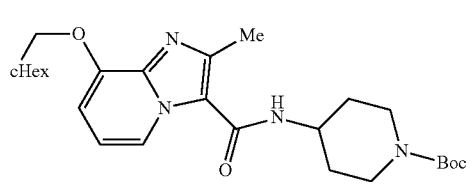 |
| 52 | 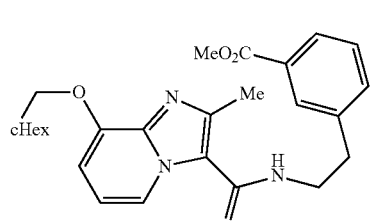 |
| 53 | 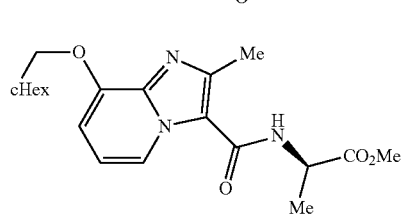 |
| 54 | 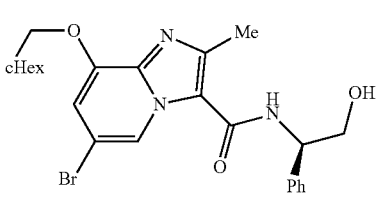 |
| 55 | 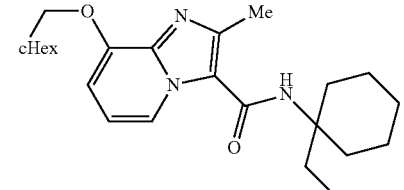 |
| 56 | 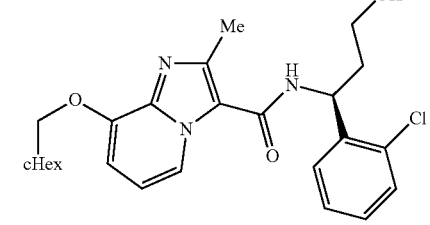 |
TABLE 36
| Ex | Str |
|---|---|
| 57 | 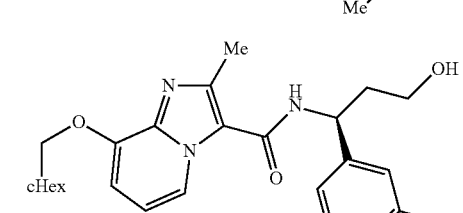 |
| 58 | 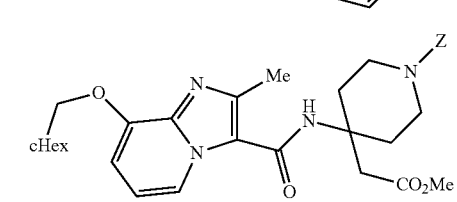 |
| 59 | 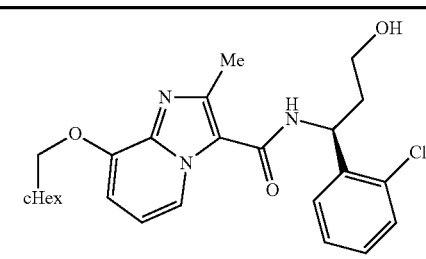 |
| 60 | 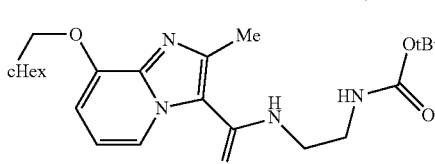 |
| 61 | 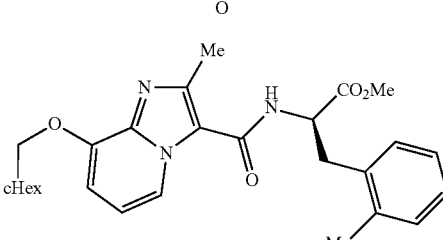 |

TABLE 36-continued

| Ex | Str |
|---|---|
| 62 | (structure) |
| 63 | (structure) |
| 64 | (structure) |
| 65 | (structure) |
| 66 | (structure) |
| 67 | (structure) |
| 68 | (structure) |
| 69 | (structure) |
| 70 | (structure) |

TABLE 37

| Ex | Str |
|---|---|
| 71 | (structure) |
| 72 | (structure) |
| 73 | (structure) |
| 74 | (structure) |
| 75 | (structure) |

TABLE 37-continued

| Ex | Str |
|---|---|
| 76 | (structure: 8-cHex-O-2-Me-imidazopyridine-3-C(O)NH-CH2-[4-(CO2Me)-piperidine-N-Boc]) |
| 77 | (structure: 8-cHex-O-2-Me-imidazopyridine-3-C(O)NH-CH(cPen)-CH2-CO-OtBu) |
| 78 | (structure: 8-cHex-O-2-Me-imidazopyridine-3-C(O)NH-[1-(CH2CO2Me)-cyclobutyl]) |
| 79 | (structure: 8-cHex-O-2-Me-imidazopyridine-3-C(O)NH-[3-Et-piperidine-N-Boc]) |
| 80 | (structure: 8-cHex-O-2-Me-imidazopyridine-3-C(O)NH-C(Me)(Ph)-CH2-CO2Me) |
| 81 | (structure: 8-cHex-O-2-Me-imidazopyridine-3-C(O)NH-CH(2-thienyl)-CH2-CO2Me) |
| 82 | (structure: 8-cHex-O-2-Me-imidazopyridine-3-C(O)NH-CH(3-thienyl)-CH2-CO2Me) |

TABLE 37-continued

| Ex | Str |
|---|---|
| 83 | (structure: 8-cHex-O-2-Me-imidazopyridine-3-C(O)NH-CH(neoPen)-CH2-CO-OtBu) |
| 84 | (structure: 8-cHex-O-2-Me-imidazopyridine-3-C(O)NH-[1-(CH2CO2Me)-cycloheptyl]) |
| 85 | (structure: 8-cHex-O-2-Me-imidazopyridine-3-C(O)NH-CH(nBu)-CH2-CO-OtBu) |
| 86 | (structure: 8-cHex-O-2-Me-imidazopyridine-3-C(O)NH-[3-piperidine-N-Boc]) |

TABLE 38

| Ex | Str |
|---|---|
| 87 | (structure: 8-cHex-O-2-Me-imidazopyridine-3-C(O)NH-CH(cHex)-CH2-CO-OtBu) |
| 88 | (structure: 8-cHex-O-2-Me-imidazopyridine-3-C(O)NH-[4-amino-2-CO2Me-pyrrolidine-N-Boc]) |
| 89 | (structure: 8-cHex-O-2-Me-imidazopyridine-3-C(O)NH-[3-amino-4-MeO-pyrrolidine-N-Boc]) |

TABLE 38-continued

| Ex | Str |
|---|---|
| 90 | *structure* |
| 91 | *structure* |
| 92 | *structure* |
| 93 | *structure* |
| 94 | *structure* |
| 95 | *structure* |
| 96 | *structure* |

TABLE 38-continued

| Ex | Str |
|---|---|
| 97 | *structure* |
| 98 | *structure* |
| 99 | *structure* |
| 100 | *structure* |

TABLE 39

| Ex | Str |
|---|---|
| 101 | *structure* |
| 102 | *structure* |

TABLE 39-continued

| Ex | Str |
|---|---|
| 103 | 8-(cyclohexylmethoxy)-2-methyl-N-(1-hydroxy-2-methylpropan-2-yl)imidazo[1,2-a]pyridine-3-carboxamide · HCl |
| 104 | 8-(cyclohexylmethoxy)-2-methyl-N-(cyclopropylmethyl)imidazo[1,2-a]pyridine-3-carboxamide · HCl |
| 105 | 8-(cyclohexylmethoxy)-2-methyl-N-(2-morpholinoethyl)imidazo[1,2-a]pyridine-3-carboxamide · 2HCl |
| 106 | 8-(cyclohexylmethoxy)-2-methyl-N-(1-(hydroxymethyl)cyclopentyl)imidazo[1,2-a]pyridine-3-carboxamide · HCl |
| 107 | 8-(cyclohexylmethoxy)-2-methyl-N-((S)-1-methoxy-3-phenylpropan-2-yl)imidazo[1,2-a]pyridine-3-carboxamide · HCl |
| 108 | 8-(cyclohexylmethoxy)-2-(trifluoromethyl)-N-((S)-1-hydroxy-3-phenylpropan-2-yl)imidazo[1,2-a]pyridine-3-carboxamide · HCl |
| 109 | 8-(cyclohexylmethoxy)-2-methyl-N-((S)-1-hydroxy-3-methylbutan-2-yl)imidazo[1,2-a]pyridine-3-carboxamide · HCl |
| 110 | 8-(cyclohexylmethoxy)-2-methyl-N-((S)-1-hydroxy-4-methylpentan-2-yl)imidazo[1,2-a]pyridine-3-carboxamide · HCl |

TABLE 39-continued

| Ex | Str |
|---|---|
| 111 | 8-(cyclohexylmethoxy)-2-methyl-N-((S)-1-hydroxy-3-phenylpropan-2-yl)imidazo[1,2-a]pyridine-3-carboxamide · HCl |
| 112 | 8-(cyclohexylmethoxy)-2-methyl-N-(2-hydroxy-2-methylpropyl)imidazo[1,2-a]pyridine-3-carboxamide · HCl |
| 113 | 8-(cyclohexylmethoxy)-2-methyl-N-((S)-1-hydroxypropan-2-yl)imidazo[1,2-a]pyridine-3-carboxamide · HCl |
| 114 | 8-(cyclohexylmethoxy)-2-methyl-N-((S)-1-hydroxy-3,3-dimethylbutan-2-yl)imidazo[1,2-a]pyridine-3-carboxamide · HCl |

TABLE 40

| Ex | Str |
|---|---|
| 115 | 8-((2-fluorobenzyl)oxy)-2-methyl-N-((S)-1-hydroxy-3-phenylpropan-2-yl)imidazo[1,2-a]pyridine-3-carboxamide · HCl |
| 116 | 8-(cyclohexylmethoxy)-2-methyl-N-(2-hydroxyethyl)imidazo[1,2-a]pyridine-3-carboxamide · HCl |
| 117 | 8-(cyclohexylmethoxy)-2-methyl-N-(3-hydroxypropyl)imidazo[1,2-a]pyridine-3-carboxamide · HCl |

TABLE 40-continued
| Ex | Str |
|---|---|
| 118 | 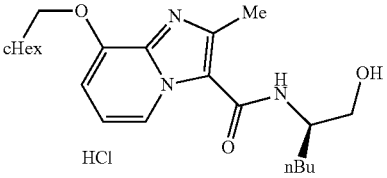 |
| 119 | 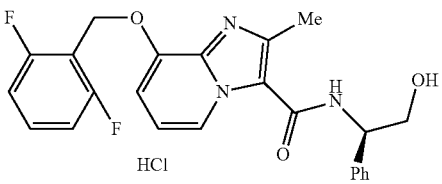 [SMILES: Cc1nc2c(OCc3c(F)cccc3F)cccn2c1C(=O)N[C@@H](CO)c1ccccc1 ; Cl] |
| 120 | 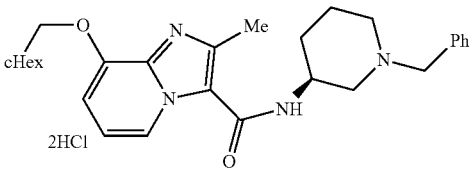 |
| 121 | 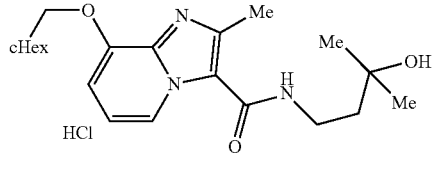 |
| 122 | 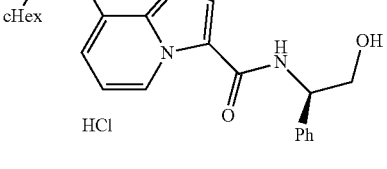 |
| 123 | 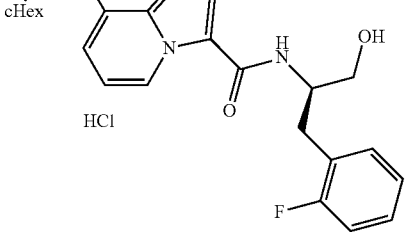 |
| 124 | 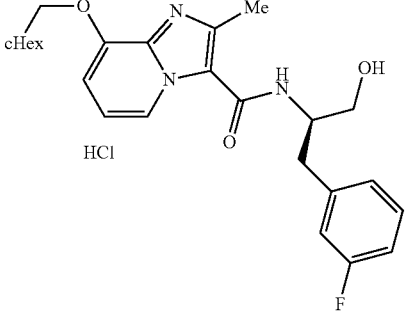 |
| 125 | 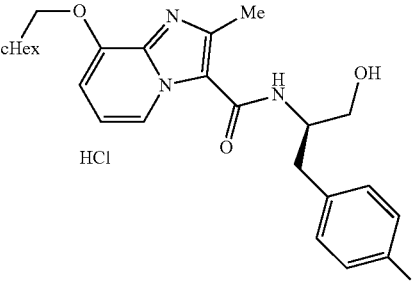 |
| 126 | 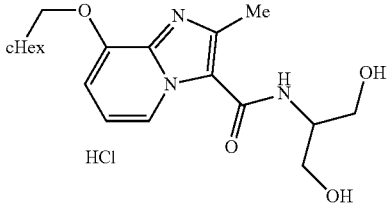 |
TABLE 41
| Ex | Str |
|---|---|
| 127 | 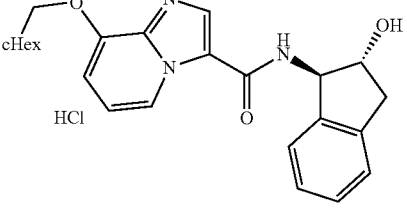 |
| 128 | 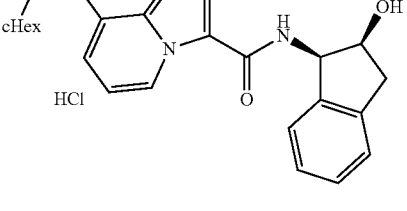 |
| 129 | 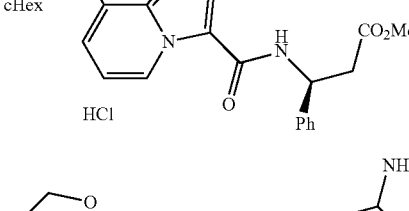 |
| 130 | 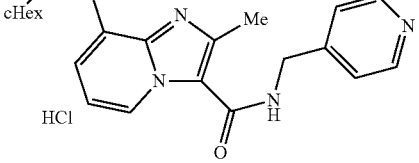 |

TABLE 41-continued

| Ex | Str |
|---|---|
| 131 | (structure: 8-cHex-O-, 2-Me imidazopyridine-3-carboxamide, N-CH2-(2-aminopyrimidin-4-yl); HCl) |
| 132 | (structure: 8-cHex-O-, 6-Me, 2-Me imidazopyridine-3-carboxamide, N-CH(Ph)-CH2OH; HCl) |
| 133 | (structure: 8-cHex-O-, 2-Me imidazopyridine-3-carboxamide, N-CH(CH2OH)-CH2-(4-Cl-Ph); HCl) |
| 134 | (structure: 8-cHex-O-, 2-Me imidazopyridine-3-carboxamide, N-CH(CH2OH)-CH2-(4-OMe-Ph); HCl) |
| 135 | (structure: 8-cHex-O-, 2-Me imidazopyridine-3-carboxamide, N-CH2CH2OH; HCl) |
| 136 | (structure: 8-cHex-O-, 2-Me imidazopyridine-3-carboxamide, N-CH2CH2-(pyridine with MeO2C); HCl) |
| 137 | (structure: 8-cHex-O-, 2-Me imidazopyridine-3-carboxamide, N-(2-hydroxyindanyl); HCl) |
| 138 | (structure: 8-cHex-O-, 2-Me imidazopyridine-3-carboxamide, N-(2-hydroxyindanyl), stereo; HCl) |
| 139 | (structure: 8-cHex-O-, 2-Me imidazopyridine-3-carboxamide, N-(2-hydroxyindanyl), stereo; HCl) |
| 140 | (structure: 8-cHex-O-, 2-Me imidazopyridine-3-carboxamide, N-(2-hydroxyindanyl), stereo; HCl) |

TABLE 42

| Ex | Str |
|---|---|
| 141 | (structure: 8-cHex-O-, 2-Me imidazopyridine-3-carboxamide, N-CH2CH2-CONH2; HCl) |
| 142 | (structure: 8-cHex-O-, 2-Me imidazopyridine-3-carboxamide, N-CH(CH2OH)-CH(OH)Me; HCl) |
| 143 | (structure: 8-cHex-O-, 2-Me imidazopyridine-3-carboxamide, N-CH(CH2OH)-CH(OH)Me; HCl) |
| 144 | (structure: 8-cHex-O-, 6-Cl, 2-Me imidazopyridine-3-carboxamide, N-CH(Ph)-CH2OH; HCl) |

TABLE 42-continued

| Ex | Str |
|---|---|
| 145 | (structure: 8-cHex-O-imidazo[1,2-a]pyridine-2-Me-3-carboxamide with N-H-CH(4-F-phenyl)-CH2-CH2-OH; HCl) |
| 146 | (structure: 8-cHex-O-imidazo[1,2-a]pyridine-2-Me-3-carboxamide with N-H-CH(3-F-phenyl)-CH2-CH2-OH; HCl) |
| 147 | (structure: 8-cHex-O-imidazo[1,2-a]pyridine-2-Me-3-carboxamide with N-H-CH2-CH2-(4-piperidinyl)-N-Ac; HCl) |
| 148 | (structure: 8-cHex-O-imidazo[1,2-a]pyridine-2-Me-3-carboxamide with N-H-CH2-CH(OH)-CH2-OH; HCl) |
| 149 | (structure: 8-cHex-O-imidazo[1,2-a]pyridine-2-Me-3-carboxamide with N-H-CH2-CH(OH)-CH2-OH, other enantiomer; HCl) |
| 150 | (structure: 8-cHex-O-imidazo[1,2-a]pyridine-2-Me-3-carboxamide with N-H-CH(4-Cl-phenyl)-CH2-OH; HCl) |
| 151 | (structure: 8-cHex-O-imidazo[1,2-a]pyridine-2-Me-3-carboxamide with N-H-CH(3-thienyl)-CH2-OH; HCl) |

TABLE 42-continued

| Ex | Str |
|---|---|
| 152 | (structure: 8-cHex-O-imidazo[1,2-a]pyridine-2-Me-3-carboxamide with N-H-(3-piperidinyl)-N-C(O)-CH2-OH; HCl) |

TABLE 43

| Ex | Str |
|---|---|
| 153 | (structure: 8-cHex-O-imidazo[1,2-a]pyridine-2-Me-3-carboxamide with N-H-C(Me)(CH2OH)2; HCl) |
| 154 | (structure: 8-cHex-O-imidazo[1,2-a]pyridine-2-Me-3-carboxamide with N-H-CH(3-F-phenyl)-CH2-OH; HCl) |
| 155 | (structure: 8-cHex-O-imidazo[1,2-a]pyridine-2-Me-3-carboxamide with N-H-CH(2-F-phenyl)-CH2-OH; HCl) |
| 156 | (structure: 8-cHex-O-imidazo[1,2-a]pyridine-2-Me-3-carboxamide with N-H-CH(CH2OH)-CH(OH)-Ph; HCl) |
| 157 | (structure: 8-cHex-O-imidazo[1,2-a]pyridine-2-Me-3-carboxamide with N-H-CH(CH2OH)-CH(OH)-Ph, diastereomer; HCl) |
| 158 | (structure: 8-cHex-O-imidazo[1,2-a]pyridine-2-Me-3-carboxamide with N-H-C(Ph)(CH2OH)2; HCl) |

TABLE 43-continued
| Ex | Str |
|---|---|
| 159 | 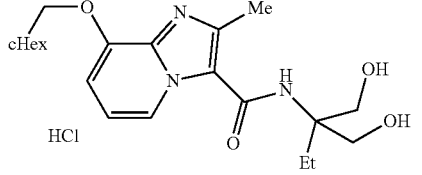 |
| 160 | 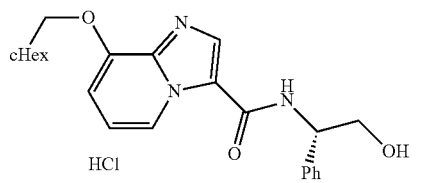 |
| 161 | 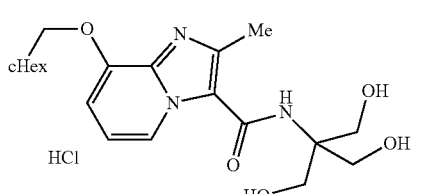 |
| 162 | 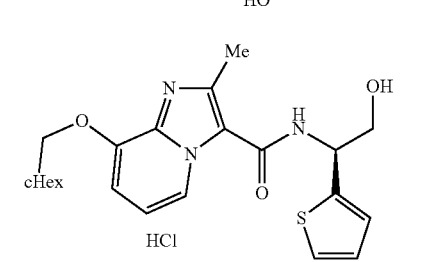 |
| 163 | 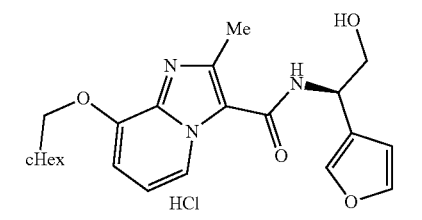 |
| 164 | 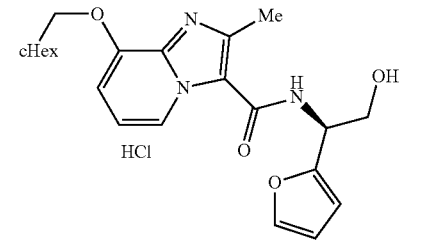 |
| 165 | 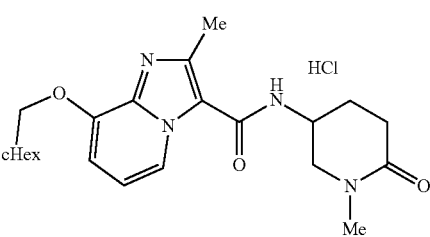 |
TABLE 43-continued
| Ex | Str |
|---|---|
| 166 | 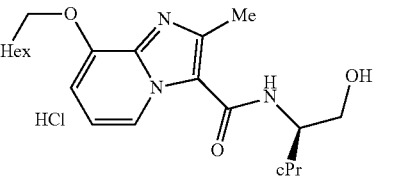 |
TABLE 44
| Ex | Str |
|---|---|
| 167 | 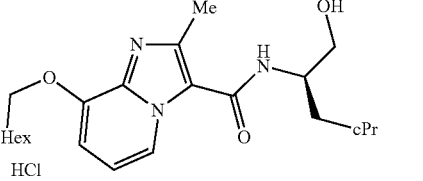 |
| 168 | 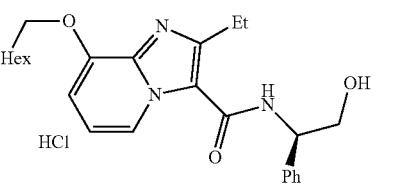 [SMILES: Cc1nc2c(OCc3ccccc3)cccn2c1C(=O)N[C@@H](CO)c1ccccc1 ; Cl] |
| 169 | 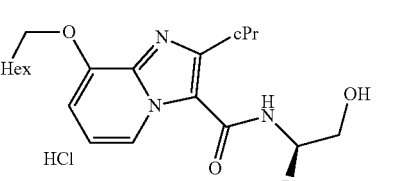 |
| 170 | 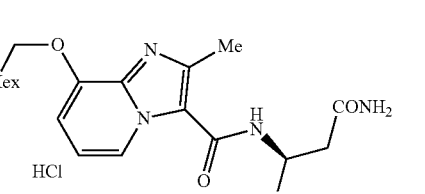 |
| 171 | 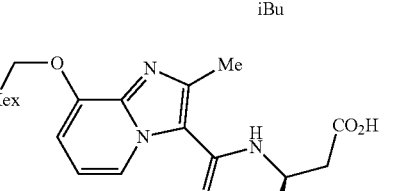 |
| 172 | 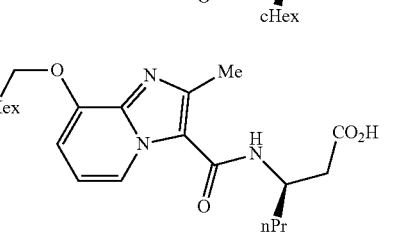 |

TABLE 44-continued

| Ex | Str |
|---|---|
| 173 | 8-(cyclohexylmethoxy)-2-methylimidazo[1,2-a]pyridine-3-carboxamide with (S)-3-amino-heptanoic acid (nBu side chain), CO₂H |
| 174 | analogous, cPen side chain |
| 175 | analogous, cPen side chain (different stereochem) |
| 176 | analogous, nBu side chain |
| 177 | analogous, neoPen side chain |
| 178 | analogous, cHex side chain |
| 179 | analogous, cBu side chain |
| 180 | analogous, cPen side chain |

TABLE 44-continued

| Ex | Str |
|---|---|
| 181 | 8-(cyclohexylmethoxy)-2-methylimidazo[1,2-a]pyridine-3-carboxamide with (S)-3-aminobutanoic acid, HCl salt |
| 182 | analogous, with 2-chlorophenyl substituent |

TABLE 45

| Ex | Str |
|---|---|
| 183 | 8-(cyclohexylmethoxy)-2-methylimidazo[1,2-a]pyridine-3-carboxamide with (S)-3-amino-3-(3-chlorophenyl)propanoic acid |
| 184 | analogous, 4-chlorophenyl |
| 185 | analogous, 3-fluorophenyl |
| 186 | analogous, 4-fluorophenyl |

TABLE 45-continued

| Ex | Str |
|---|---|
| 187 | (structure with cHex-CH2-O-, imidazopyridine-Me, C(O)NH-CH(Ph)-CH2-CO2Me, HCl) |
| 188 | (structure with Ph-CH2-O-, imidazopyridine-Me, C(O)NH-CH(Ph)-CH2-OH, HCl) |
| 189 | (structure with cHex-CH2-O-, imidazopyridine-Me, C(O)-indoline-CO2Et, HCl) |
| 190 | (structure with 4,4-difluorocyclohexyl-CH2-O-, imidazopyridine-Me, C(O)NH-CH(Ph)-CH2-OTBS) |
| 191 | (structure with F3C-CH2-CH2-O-, imidazopyridine-Me, C(O)NH-CH(Ph)-CH2-OTBS) |
| 192 | (structure with tBu-CH2-CH2-O-, imidazopyridine-Me, C(O)NH-CH(Ph)-CH2-OTBS) |
| 193 | (structure with spiro[3.5]-CH2-O-, imidazopyridine-Me, C(O)NH-CH(Ph)-CH2-OTBS) |
| 194 | (structure with cHep-CH2-O-, imidazopyridine-Me, C(O)NH-CH(Ph)-CH2-OH) |

TABLE 46

| Ex | Str |
|---|---|
| 195 | (structure with cOct-CH2-O-, imidazopyridine-Me, C(O)NH-CH(Ph)-CH2-OTBS) |
| 196 | (structure with 1-F-cyclohexyl-CH2-O-, imidazopyridine-Me, C(O)NH-CH(Ph)-CH2-OTBS) |
| 197 | (structure with 3-fluorothiophen-2-yl-CH2-O-, imidazopyridine-Me, C(O)NH-CH(Ph)-CH2-OTBS) |
| 198 | (structure with 3-chlorothiophen-2-yl-CH2-O-, imidazopyridine-Me, C(O)NH-CH(Ph)-CH2-OTBS) |
| 199 | (structure with F3C-CF2-CH2-CH2-O-, imidazopyridine-Me, C(O)NH-CH(Ph)-CH2-OTBS) |
| 200 | (structure with 1-F-cyclohexyl-CH2-O-, imidazopyridine-Me, C(O)NH-CH(Ph)-CH2-OH) |
| 201 | (structure with F3C-CF2-CH2-CH2-O-, imidazopyridine-Me, C(O)NH-CH(Ph)-CH2-OH, HCl) |
| 202 | (structure with 4,4-difluorocyclohexyl-CH2-O-, imidazopyridine-Me, C(O)NH-CH(Ph)-CH2-OH, HCl) |

TABLE 46-continued

| Ex | Str |
|---|---|
| 203 | (structure: 8-(3,3,3-trifluoropropoxy)-2-methylimidazo[1,2-a]pyridine-3-carboxamide with (S)-2-hydroxy-1-phenylethyl, HCl) |
| 204 | (structure: 8-(cPen-methoxy) analog, HCl) |
| 205 | (structure: 8-(tBu-ethoxy) analog, HCl) |
| 206 | (structure: 8-(spiro[3.5]nonyl-methoxy) analog) |
| 207 | (structure: 8-(cHep-methoxy) analog, HCl) |
| 208 | (structure: 8-(cOct-methoxy) analog, HCl) |

TABLE 47

| Ex | Str |
|---|---|
| 209 | (structure: 8-((3-fluorothiophen-2-yl)methoxy) analog, HCl) |
| 210 | (structure: 8-((3-chlorothiophen-2-yl)methoxy) analog, HCl) |
| 211 | (structure: 8-(cHex-methoxy), (R)-piperidin-3-yl amide, 2HCl) |
| 212 | (structure: 8-(cHex-methoxy), (R)-pyrrolidin-3-yl amide, 2HCl) |
| 213 | (structure: 8-(cHex-methoxy), 2-aminoethyl amide, 2HCl) |
| 214 | (structure: 8-(cHex-methoxy), (S)-pyrrolidin-3-yl amide, 2HCl) |
| 215 | (structure: 8-(cHex-methoxy), 4-(CO₂Me)piperidin-4-ylmethyl amide, 2HCl) |
| 216 | (structure: 8-(cHex-methoxy), 3-ethyl-piperidin-3-yl amide, 2HCl) |
| 217 | (structure: 8-(cHex-methoxy), (S)-piperidin-3-yl amide, 2HCl) |

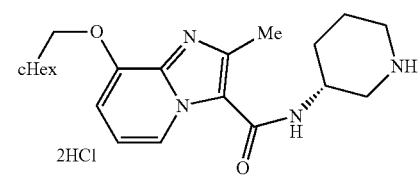

TABLE 47-continued

| Ex | Str |
|---|---|
| 218 | (structure) |
| 219 | (structure) |
| 220 | (structure) |
| 221 | (structure) |
| 222 | (structure) |
| 223 | (structure) |
| 224 | (structure) |

TABLE 48

| Ex | Str |
|---|---|
| 225 | (structure) |
| 226 | (structure) |
| 227 | (structure) |
| 228 | (structure) |
| 229 | (structure) |
| 230 | (structure) |
| 231 | (structure) |
| 232 | (structure) |

TABLE 48-continued

| Ex | Str |
|---|---|
| 233 | (structure) |
| 234 | (structure) |
| 235 | (structure) |
| 236 | (structure) |
| 237 | (structure) |
| 238 | (structure) |

TABLE 49

| Ex | Str |
|---|---|
| 239 | (structure) |
| 240 | (structure) |
| 241 | (structure) |
| 242 | (structure) |
| 243 | (structure) |
| 244 | (structure) |
| 245 | (structure) |
| 246 | (structure) |
| 247 | (structure) |

TABLE 49-continued

| Ex | Str |
|---|---|
| 248 | |
| 249 | |
| 250 | |
| 251 | |
| 252 | |
| 253 | |
| 254 | |

TABLE 50

| Ex | Str |
|---|---|
| 255 | |
| 256 | |
| 257 | |
| 258 | |
| 259 | |
| 260 | |
| 261 | |
| 262 | |

TABLE 50-continued
| Ex | Str |
|---|---|
| 263 | |
| 264 | |
| 265 | |
| 266 | |
| 267 | |
| 268 | |
TABLE 51
| Ex | Str |
|---|---|
| 269 | |
TABLE 51-continued
| Ex | Str |
|---|---|
| 270 | |
| 271 | |
| 272 | |
| 273 | |
| 274 | |
| 275 | |
| 276 | 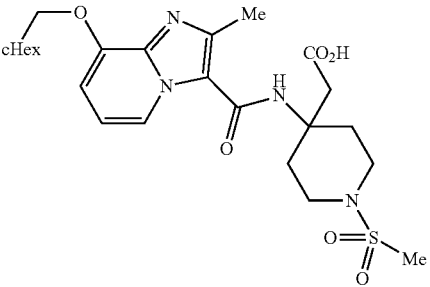 |

TABLE 51-continued
| Ex | Str |
|---|---|
| 277 | 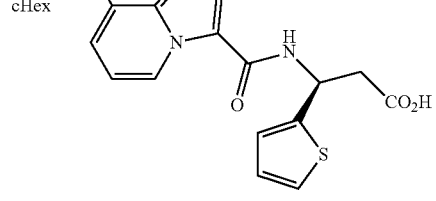 |
| 278 | |
| 279 | |
| 280 | |
TABLE 52
| Ex | Str |
|---|---|
| 281 | 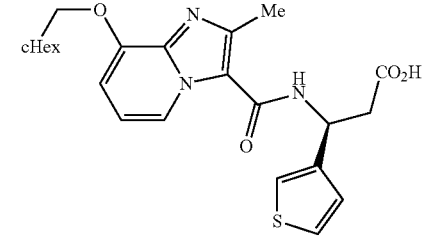 |
| 282 | |
TABLE 52-continued
| Ex | Str |
|---|---|
| 283 | 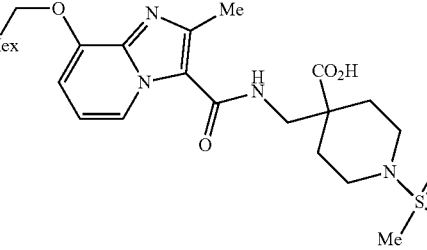 |
| 284 | |
| 285 | |
| 286 | |
| 287 | |
| 288 | 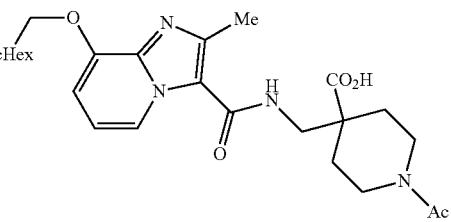 |
| 289 | |

TABLE 52-continued

| Ex | Str |
|---|---|
| 290 | (structure) |
| 291 | (structure) |
| 292 | (structure) |
| 293 | (structure) |
| 294 | (structure) |

TABLE 53

| Ex | Str |
|---|---|
| 295 | (structure) |
| 296 | (structure) |
| 297 | (structure) |
| 298 | (structure) |
| 299 | (structure) |
| 300 | (structure) |
| 301 | (structure) |
| 302 | (structure) |
| 303 | (structure) |

TABLE 53-continued
| Ex | Str |
|---|---|
| 304 | 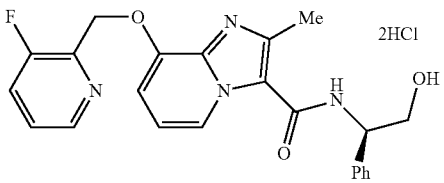 [SMILES: Cc1nc2c(OCc3ncccc3F)cccn2c1C(=O)N[C@@H](CO)c1ccccc1 ; "2HCl"] 2HCl |
| 305 | 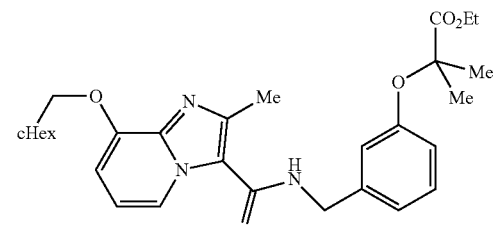 |
| 306 | 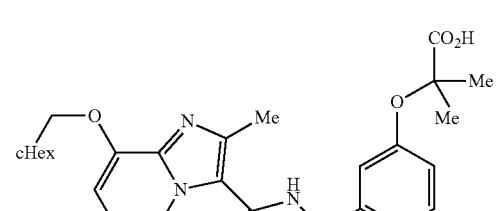 |
TABLE 54
| Ex | Str |
|---|---|
| 307 | 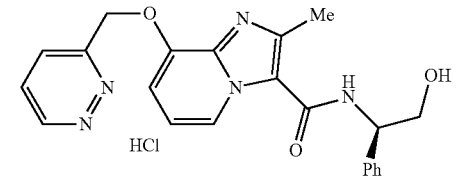 [SMILES: Cc1nc2c(OCc3cccnn3)cccn2c1C(=O)N[C@@H](CO)c1ccccc1 ; Cl] HCl |
| 308 | 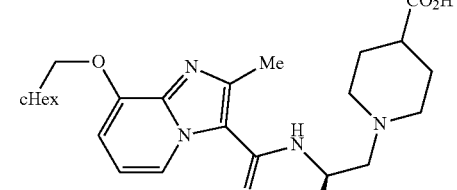 |
| 309 | 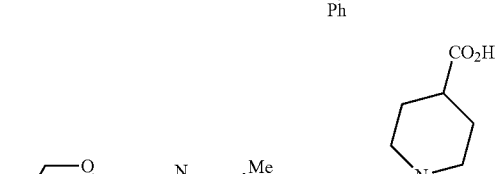 |
TABLE 54-continued
| Ex | Str |
|---|---|
| 310 | 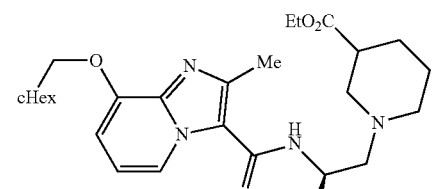 |
| 311 | 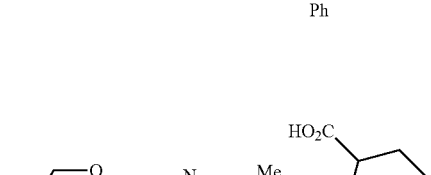 |
| 312 | 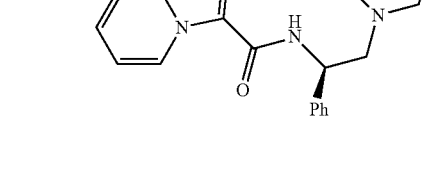 |
| 313 | 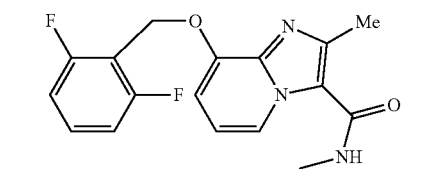 |
| 314 | 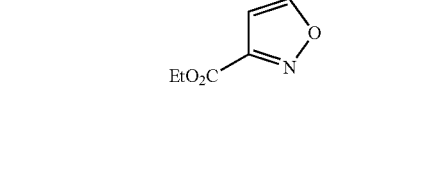 |

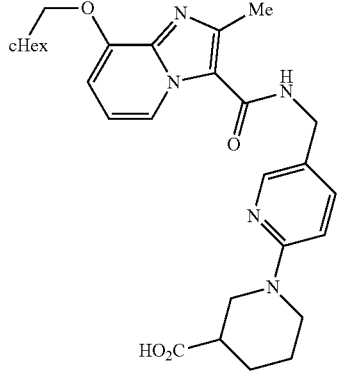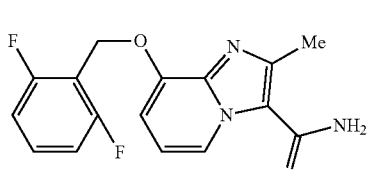

TABLE 55-continued
| Ex | Str |
|---|---|
| 328 | 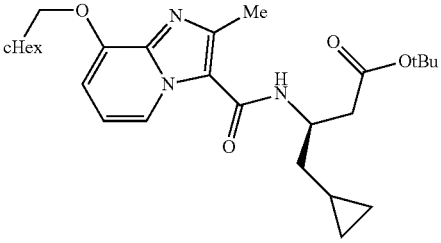 |
TABLE 56
| Ex | Str |
|---|---|
| 329 | |
| 330 | |
| 331 | |
| 332 | |
| 333 | |
TABLE 56-continued
| Ex | Str |
|---|---|
| 334 | |
| 335 | |
| 336 | |
| 337 | |
| 338 | |
| 339 | |

TABLE 56-continued
| Ex | Str |
|---|---|
| 340 | 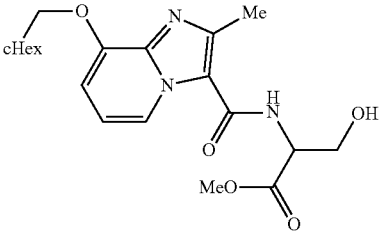 |
TABLE 57
| Ex | Str |
|---|---|
| 341 | 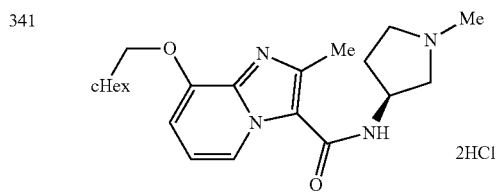 2HCl |
| 342 | 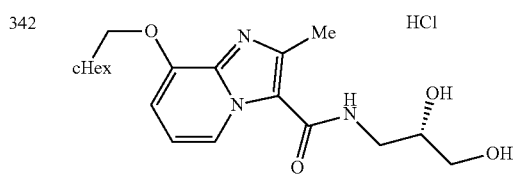 HCl |
| 343 | HCl 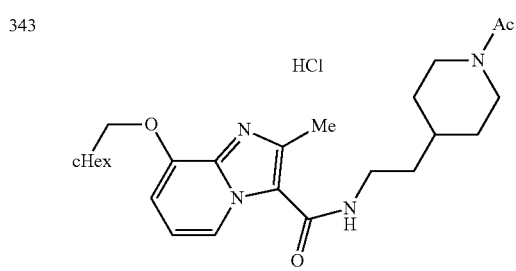 |
| 344 | 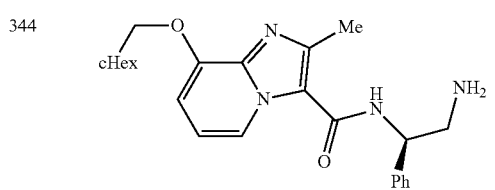 |
| 345 | 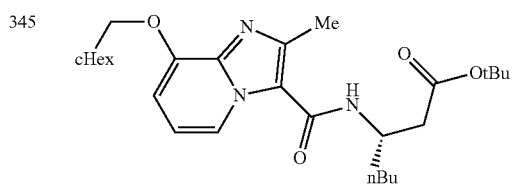 |
TABLE 57-continued
| Ex | Str |
|---|---|
| 346 | 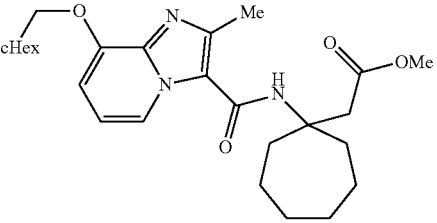 |
| 347 | 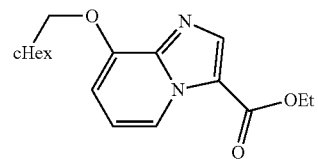 |
| 348 | 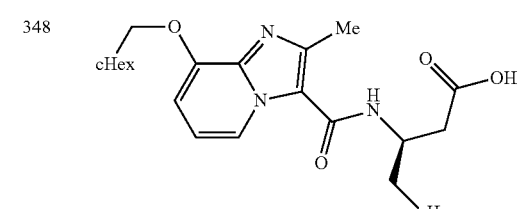 |
| 349 | 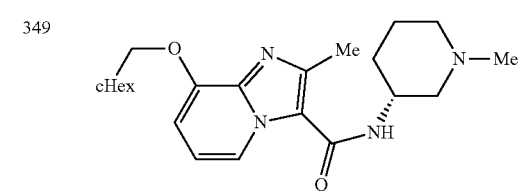 |
| 350 | 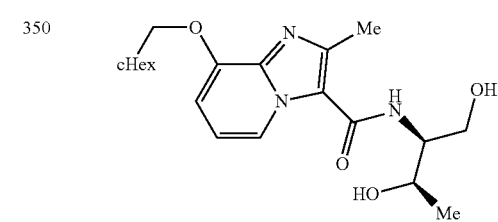 |
| 351 | 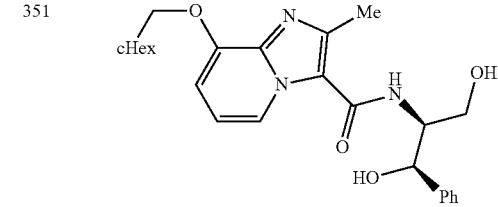 |
| 352 | 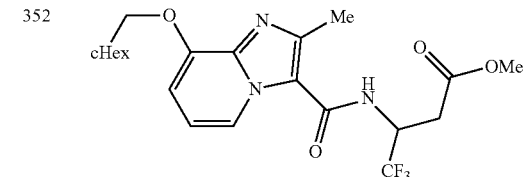 |

TABLE 57-continued
| Ex | Str |
|---|---|
| 353 | 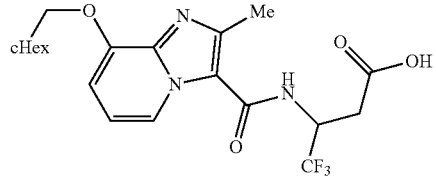 |
| 354 | 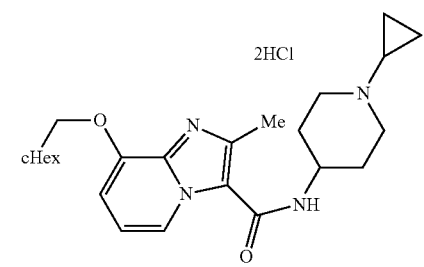 |
TABLE 58
| Ex | Str |
|---|---|
| 355 | 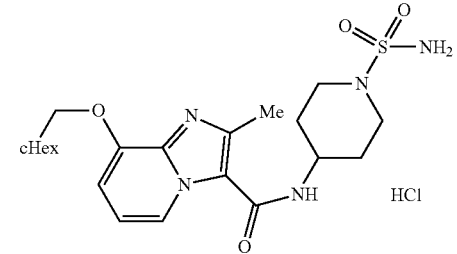 |
| 356 | 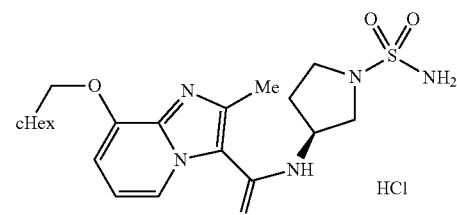 |
| 357 | 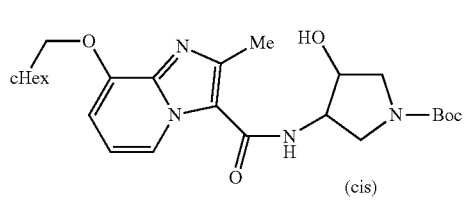 |
| 358 | 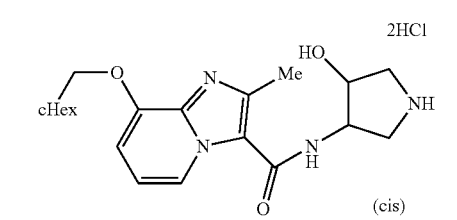 |
TABLE 58-continued
| Ex | Str |
|---|---|
| 359 | 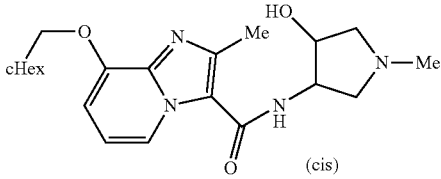 |
| 360 | 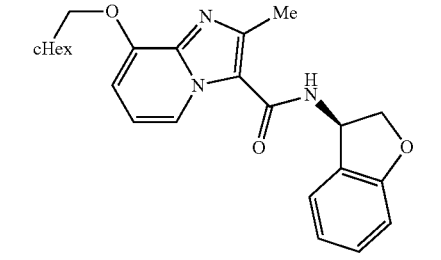 |
| 361 | 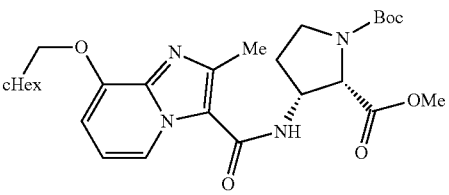 |
| 362 | 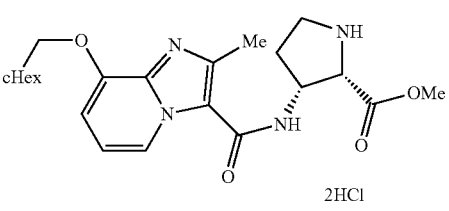 |
| 363 | 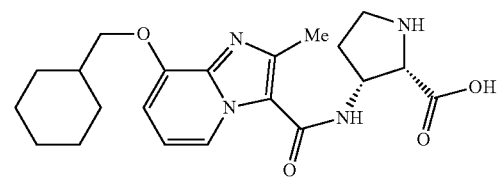 [SMILES: Cc1nc2c(OCC3CCCCC3)cccn2c1C(=O)N[C@@H]1CCN[C@@H]1C(=O)O] |
| 364 | 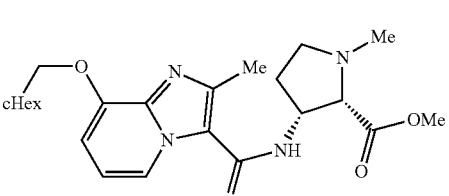 |
| 365 | 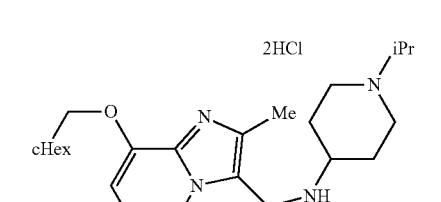 |

TABLE 58-continued

| Ex | Str |
|---|---|
| 366 | (8-(cyclohexylmethoxy)-2-methylimidazo[1,2-a]pyridine-3-carboxamide with N-(1-isopropylpiperidin-3-yl), 2HCl) |

TABLE 59

| Ex | Str |
|---|---|
| 367 | (8-(cyclohexylmethoxy)-2-methylimidazo[1,2-a]pyridine-3-carboxamide with 1-(cyclopropylsulfonyl)piperidin-3-yl, HCl) |
| 368 | (8-(cyclohexylmethoxy)-2-methylimidazo[1,2-a]pyridine-3-carboxamide with 1-methylpyrrolidine-2-carboxylic acid) |
| 369 | (8-(cyclohexylmethoxy)-2-methylimidazo[1,2-a]pyridine-3-carboxamide with 3-hydroxy-1-(o-tolyl)propyl) |
| 370 | (8-(cyclohexylmethoxy)-2-methylimidazo[1,2-a]pyridine-3-carboxamide with 2-carboxy-1-(o-tolyl)ethyl) |
| 371 | (8-(cyclohexylmethoxy)-2-methylimidazo[1,2-a]pyridine-3-carboxamide with 1-sulfamoylpyrrolidin-3-yl, HCl) |

TABLE 59-continued

| Ex | Str |
|---|---|
| 372 | (8-((2,6-difluorobenzyl)oxy)-2-methylimidazo[1,2-a]pyridine-3-carboxamide with 1-methylpiperidin-4-yl, 2HCl) |
| 373 | (8-((2-fluorobenzyl)oxy)-2-methylimidazo[1,2-a]pyridine-3-carboxamide with 1-methylpiperidin-4-yl, 2HCl) |
| 374 | (8-(cyclohexylmethoxy)-2-methylimidazo[1,2-a]pyridine-3-carboxamide with 1-cyclopropylpyrrolidin-3-yl, 2HCl) |
| 375 | (8-(cyclohexylmethoxy)-2-methylimidazo[1,2-a]pyridine-3-carboxamide with 1-((carboxymethyl)sulfonyl)piperidin-3-yl) |
| 376 | (8-(cyclohexylmethoxy)-2-methylimidazo[1,2-a]pyridine-3-carboxamide with 1-(methylsulfonyl)piperidin-4-yl, HCl) |
| 377 | (8-(cyclohexylmethoxy)-2-methylimidazo[1,2-a]pyridine-3-carboxamide with 1-Boc-4-hydroxypyrrolidin-3-yl) |

TABLE 59-continued
| Ex | Str |
|---|---|
| 378 | 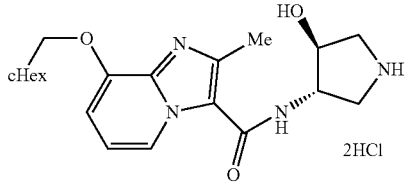 2HCl |
TABLE 60
| Ex | Str |
|---|---|
| 379 | |
| 380 | |
| 381 | 2HCl |
| 382 | |
| 383 | |
| 384 | 2HCl |
TABLE 60-continued
| Ex | Str |
|---|---|
| 385 | |
| 386 | |
| 387 | |
| 388 | 2HCl |
| 389 | |
| 390 | 2HCl |
| 391 | HCl |

TABLE 60-continued

| Ex | Str |
|---|---|
| 392 | (structure) |

TABLE 61

| Ex | Str |
|---|---|
| 393 | (structure) |
| 394 | (structure) |
| 395 | (structure) |
| 396 | (structure, trans) |
| 397 | (structure, 2HCl, trans) |

TABLE 61-continued

| Ex | Str |
|---|---|
| 398 | (structure, trans) |
| 399 | (structure, HCl) |
| 400 | (structure) |
| 401 | (structure, trans) |
| 402 | (structure, trans) |
| 403 | (structure) |
| 404 | (structure, 2HCl) |

TABLE 62
| Ex | Str |
|---|---|
| 405 | 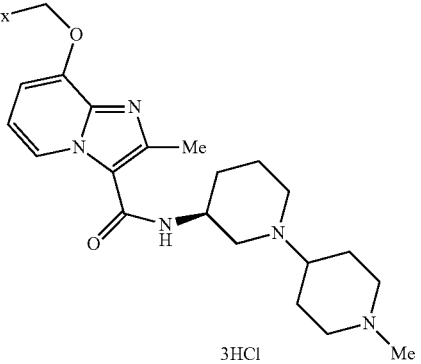 3HCl |
| 406 | 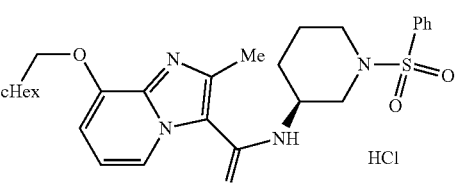 HCl |
| 407 | 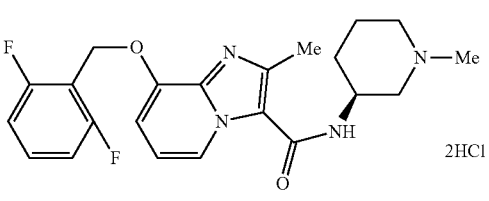 [SMILES: Cc1nc2c(OCc3c(F)cccc3F)cccn2c1C(=O)N[C@H]1CCCN(C)C1 ; "2HCl"] 2HCl |
| 408 | 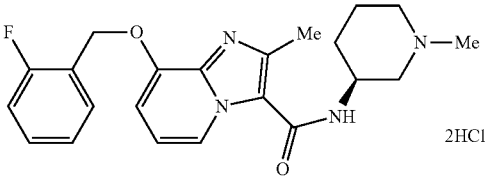 [SMILES: Cc1nc2c(OCc3ccccc3F)cccn2c1C(=O)N[C@H]1CCCN(C)C1 ; "2HCl"] 2HCl |
| 409 | 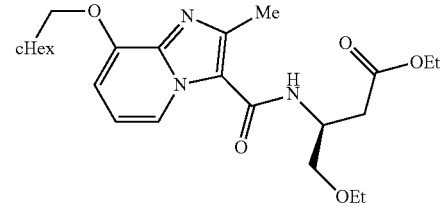 |
| 410 | 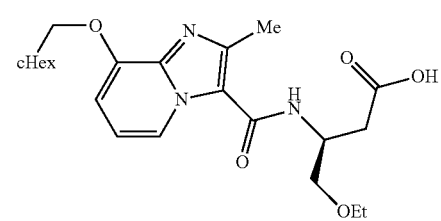 |
| 411 | 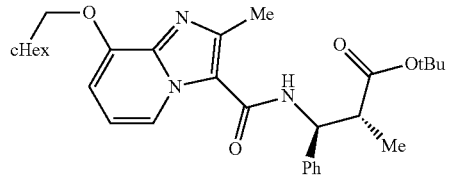 |
TABLE 62-continued
| Ex | Str |
|---|---|
| 412 | 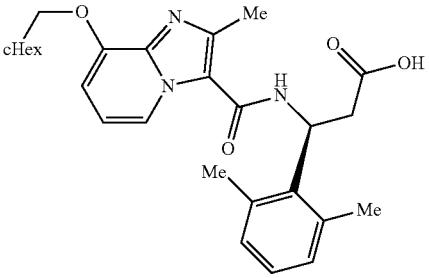 |
| 413 | 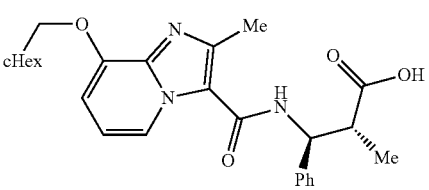 |
| 414 | 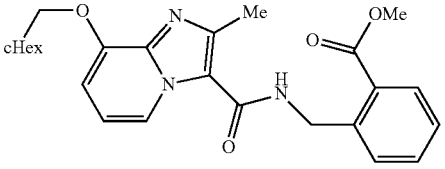 |
| 415 | 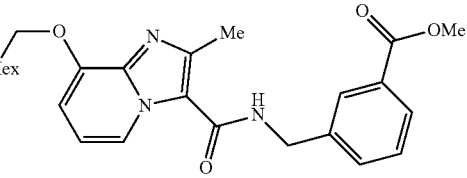 |
| 416 | 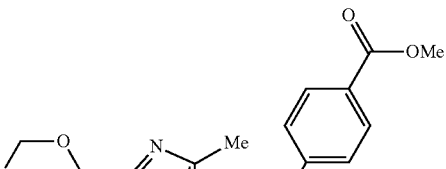 |
| 417 | 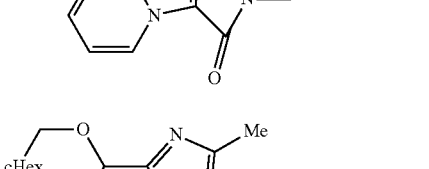 |
| 418 | 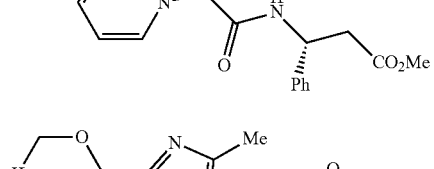 |

TABLE 63

| Ex | Str |
|---|---|
| 419 | (structure) |
| 420 | (structure) |
| 421 | (structure) |
| 422 | (structure) |
| 423 | (structure) |
| 424 | (structure) |

TABLE 63-continued

| Ex | Str |
|---|---|
| 425 | (structure) |
| 426 | (structure) |
| 427 | (structure) |
| 428 | (structure) |
| 429 | (structure) |
| 430 | (structure) |

TABLE 64

| Ex | Str |
|---|---|
| 431 | 2,6-difluorobenzyloxy-2-methyl-imidazo[1,2-a]pyridine-3-carboxamide with (1S,2R)-2-hydroxy-2,3-dihydro-1H-inden-1-yl; HCl |
| 432 | 2,6-difluorobenzyloxy-2-methyl-imidazo[1,2-a]pyridine-3-carboxamide with (1R,2S)-2-hydroxy-2,3-dihydro-1H-inden-1-yl; HCl |
| 433 | 2,6-difluorobenzyloxy-2-methyl-imidazo[1,2-a]pyridine-3-carboxamide with 2-(tert-butoxycarbonyl)-2,3-dihydro-1H-inden-1-yl |
| 434 | 2,6-difluorobenzyloxy-2-methyl-imidazo[1,2-a]pyridine-3-carboxamide with 2-carboxy-2,3-dihydro-1H-inden-1-yl |
| 435 | 2,6-difluorobenzyloxy-2-methyl-imidazo[1,2-a]pyridine-3-carboxamide with (1S)-2-hydroxy-1-(thiophen-2-yl)ethyl; HCl |
| 436 | 2,6-difluorobenzyloxy-2-methyl-imidazo[1,2-a]pyridine-3-carboxamide with (1S)-1-(3-fluorophenyl)-2-hydroxyethyl; HCl |

TABLE 64-continued

| Ex | Str |
|---|---|
| 437 | cHex-O-2-methyl-imidazo[1,2-a]pyridine-3-carboxamide with 4-methyl-1-methylpiperidin-4-yl; 2HCl |
| 438 | cHex-O-2-methyl-imidazo[1,2-a]pyridine-3-carboxamide with 1-(N,N-dimethylsulfamoyl)piperidin-3-yl; HCl |
| 439 | cHex-O-2-methyl-imidazo[1,2-a]pyridine-3-carboxamide with (S)-1-hydroxypropan-2-yl; HCl |
| 440 | cHex-O-2-methyl-imidazo[1,2-a]pyridine-3-carboxamide with 2-(2-(ethoxycarbonyl)ethyl)benzyl |
| 441 | cHex-O-2-methyl-imidazo[1,2-a]pyridine-3-carboxamide with 2-((E)-2-(ethoxycarbonyl)vinyl)benzyl |
| 442 | cHex-O-2-methyl-imidazo[1,2-a]pyridine-3-CONHMe |

TABLE 65
| Ex | Str |
|---|---|
| 443 | 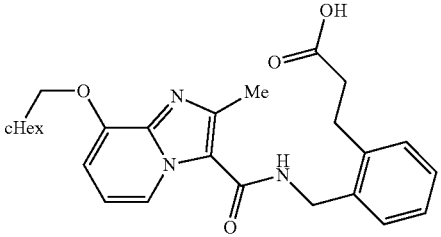 |
| 444 | 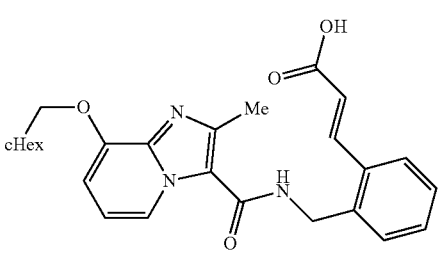 |
| 445 | 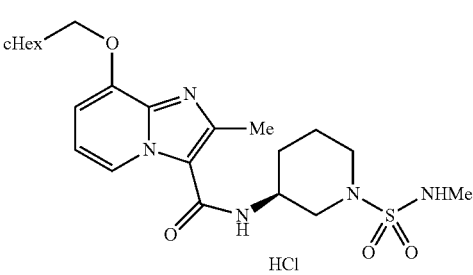 |
| 446 | 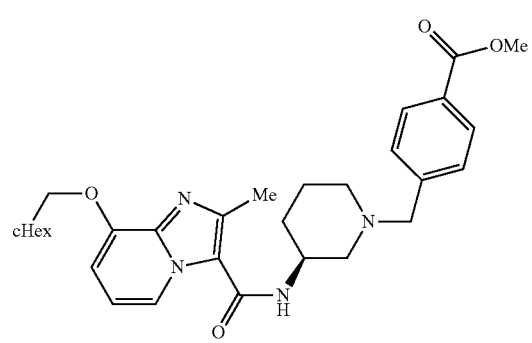 |
| 447 | 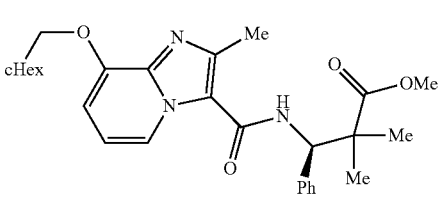 |
| 448 | 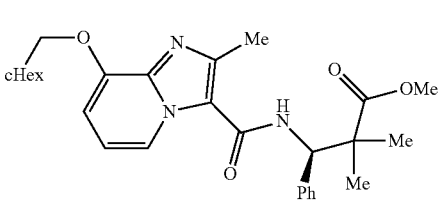 |
TABLE 65-continued
| Ex | Str |
|---|---|
| 449 | 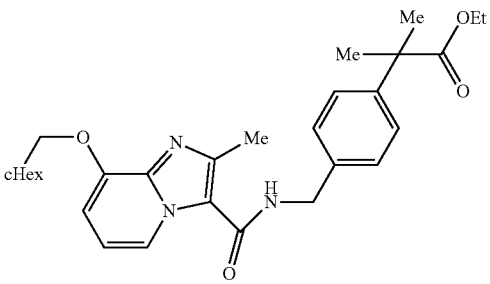 |
| 450 | 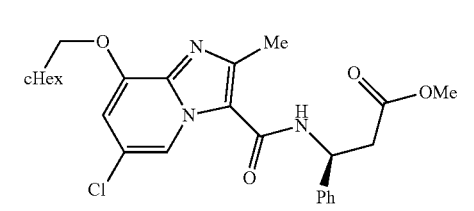 |
| 451 | 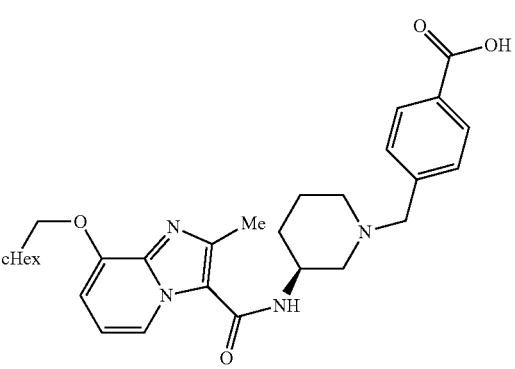 |
| 452 | 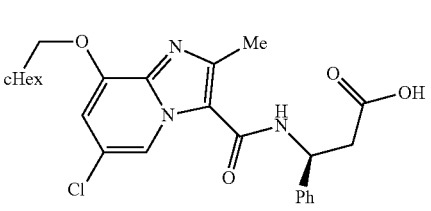 |
TABLE 66
| Ex | Str |
|---|---|
| 453 | 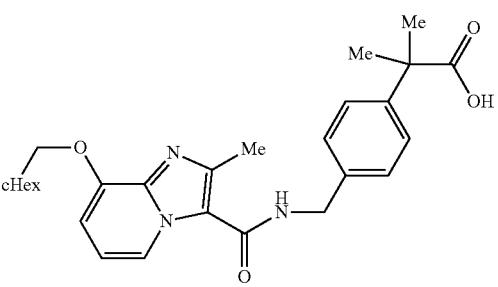 |

TABLE 66-continued

| Ex | Str |
|---|---|
| 454 | (structure: 8-cyclohexylmethoxy-2-methylimidazo[1,2-a]pyridine-3-carboxamide with trans-4-(methoxycarbonyl)cyclohexylmethyl) |
| 455 | (structure: 8-cyclohexylmethoxy-2-methylimidazo[1,2-a]pyridine-3-carboxamide with trans-4-carboxycyclohexylmethyl) |
| 456 | (structure: carboxamide with NH-CH(Ph)-CH(Me)-C(O)OtBu) |
| 457 | (structure: carboxamide with NH-CH(Ph)-CH(Me)-COOH) |
| 458 | (structure: carboxamide with NH-CH2CH2-(3-hydroxyphenyl)) |
| 459 | (structure: carboxamide with 3-(methoxycarbonyl)benzyl-piperidinyl) |
| 460 | (structure: 8-((5-chloro-1,2,3-thiadiazol-4-yl)methoxy)-2-methylimidazo[1,2-a]pyridine-3-carboxamide with (S)-2-hydroxy-1-phenylethyl, HCl) |

TABLE 66-continued

| Ex | Str |
|---|---|
| 461 | (structure: carboxamide with 3-(3-carboxybenzyl)piperidinyl) |
| 462 | (structure: carboxamide with 3-((S)-1-methoxycarbonylethoxy)benzyl) |

TABLE 67

| Ex | Str |
|---|---|
| 463 | (structure: carboxamide with 3-hydroxybenzyl) |
| 464 | (structure: carboxamide with (4-methoxycarbonyloxazol-2-yl)methyl) |
| 465 | (structure: carboxamide with (3-ethoxycarbonylisoxazol-5-yl)methyl) |
| 466 | (structure: carboxamide with (4-carboxyoxazol-2-yl)methyl) |

TABLE 67-continued

| Ex | Str |
|---|---|
| 467 | (structure) |
| 468 | (structure) |
| 469 | (structure) |
| 470 | (structure) |
| 471 | (structure) |
| 472 | (structure) |

TABLE 68

| Ex | Str |
|---|---|
| 473 | (structure) |
| 474 | (structure) |
| 475 | (structure) |
| 476 | (structure) |
| 477 | (structure) |
| 478 | (structure) |

TABLE 68-continued

| Ex | Str |
|---|---|
| 479 | (structure: 8-cHexO-2-Me-imidazo[1,2-a]pyridine-3-C(=O)NH-cPen) |
| 480 | (structure: 8-cHexO-2-Me-imidazo[1,2-a]pyridine-3-C(=O)NH-cHex) |
| 481 | (structure: 8-cHexO-2-Me-imidazo[1,2-a]pyridine-3-C(=O)NH-CH2-cHex) |
| 482 | (structure: 8-cHexO-2-Me-imidazo[1,2-a]pyridine-3-C(=O)NH-CH2-tBu) |
| 483 | (structure: 8-cHexO-2-Me-imidazo[1,2-a]pyridine-3-C(=O)NH-CH2-(2-OMe-phenyl)) |
| 484 | (structure: 8-cHexO-2-Me-imidazo[1,2-a]pyridine-3-C(=O)NH-(CH2)4-OH) |
| 485 | (structure: 8-cHexO-2-Me-imidazo[1,2-a]pyridine-3-C(=O)NH-(3-hydroxyadamantyl)) |
| 486 | (structure: 8-cHexO-2-Me-imidazo[1,2-a]pyridine-3-C(=O)NH-CH2-CH(OH)-CH2-OMe) |
| 487 | (structure: 8-cHexO-2-Me-imidazo[1,2-a]pyridine-3-C(=O)NH-CH2-C(Me)2-CH2-OH) |

TABLE 68-continued

| Ex | Str |
|---|---|
| 488 | (structure: 8-cHexO-2-Me-imidazo[1,2-a]pyridine-3-C(=O)NH-CH(CH2OH)-CH2-(1H-imidazol-4-yl)) |

TABLE 69

| Ex | Str |
|---|---|
| 489 | (structure: 8-cHexO-2-Me-imidazo[1,2-a]pyridine-3-C(=O)NH-CH(CH2OH)-CH2-(1H-imidazol-4-yl), stereo) |
| 490 | (structure: 8-cHexO-2-Me-imidazo[1,2-a]pyridine-3-C(=O)NH-CH2-(tetrahydropyran-4-yl)) |
| 491 | (structure: 8-cHexO-2-Me-imidazo[1,2-a]pyridine-3-C(=O)NH-CH2CH2-OMe) |
| 492 | (structure: 8-cHexO-2-Me-imidazo[1,2-a]pyridine-3-C(=O)NH-CH2CH2-OEt) |
| 493 | (structure: 8-cHexO-2-Me-imidazo[1,2-a]pyridine-3-C(=O)NH-(CH2)3-OMe) |
| 494 | (structure: 8-cHexO-2-Me-imidazo[1,2-a]pyridine-3-C(=O)NH-(tetrahydropyran-4-yl)) |

TABLE 69-continued
| Ex | Str |
|---|---|
| 495 | 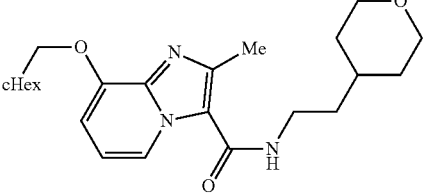 |
| 496 | 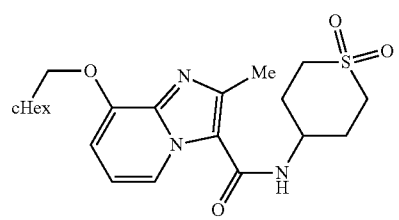 |
| 497 | 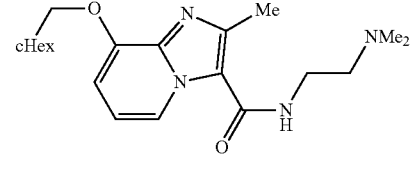 |
| 498 | 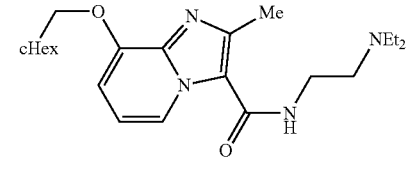 |
| 499 | 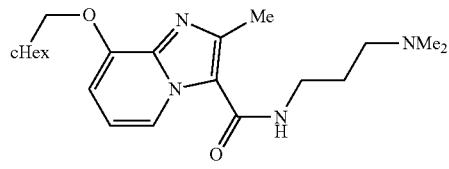 |
| 500 | 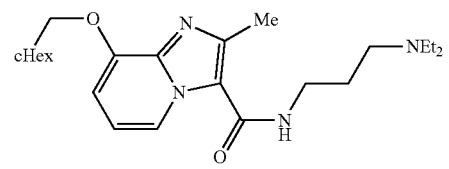 |
| 501 | 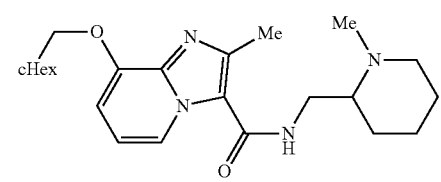 |
| 502 | 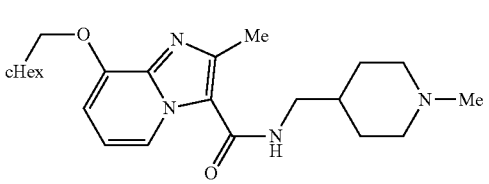 |
TABLE 69-continued
| Ex | Str |
|---|---|
| 503 | 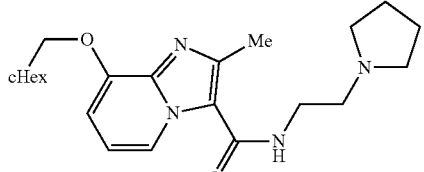 |
| 504 | 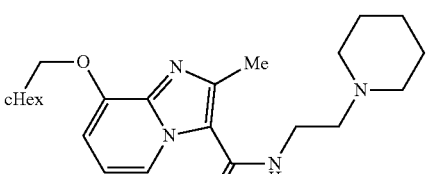 |
TABLE 70
| Ex | Str |
|---|---|
| 505 | 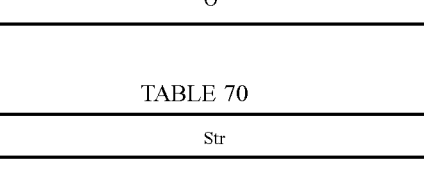 |
| 506 | 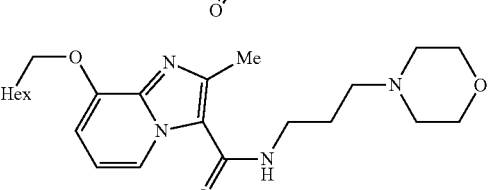 |
| 507 | 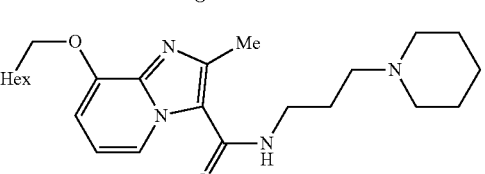 |
| 508 | 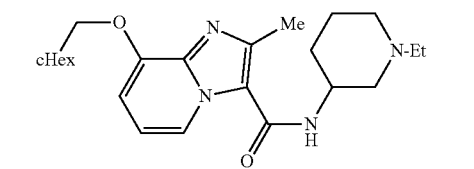 |
| 509 | 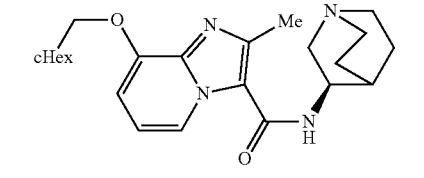 |
| 510 | 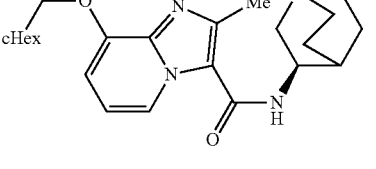 |

TABLE 70-continued
| Ex | Str |
|---|---|
| 511 | 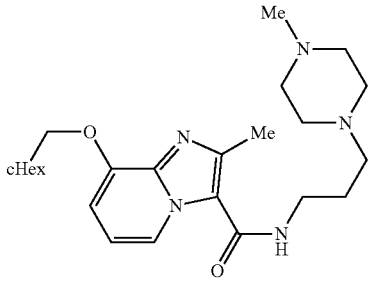 |
| 512 | 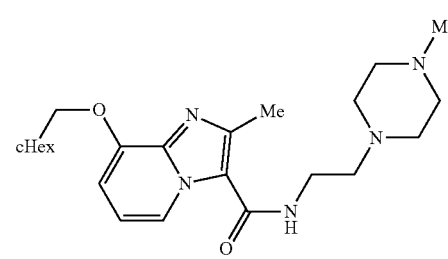 |
| 513 | 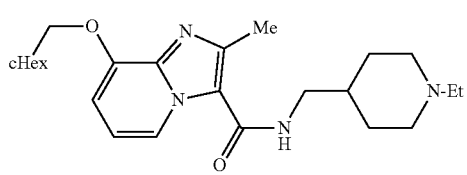 |
| 514 | 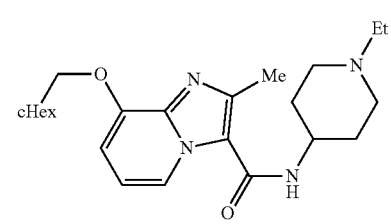 |
| 515 | 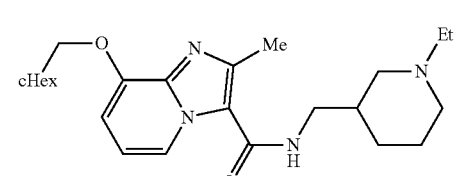 |
| 516 | 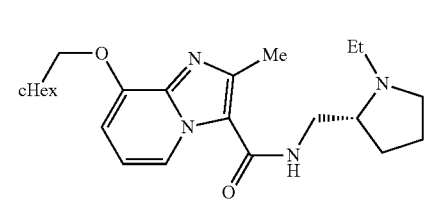 |
| 517 | 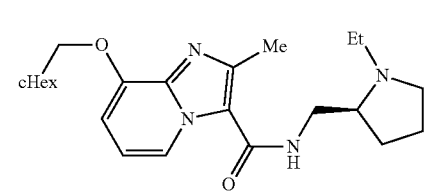 |
| 518 | 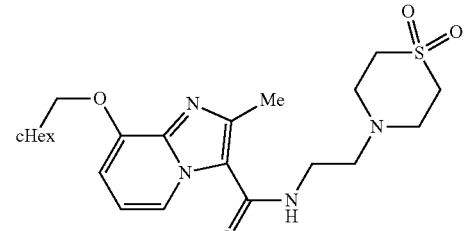 |
TABLE 71
| Ex | Str |
|---|---|
| 519 | 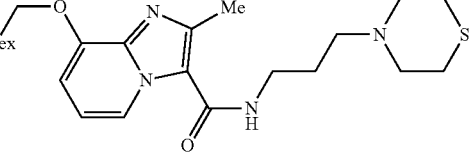 |
| 520 | 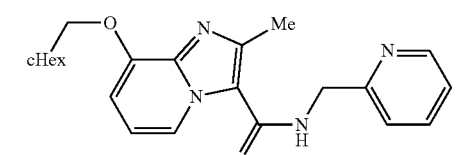 |
| 521 | 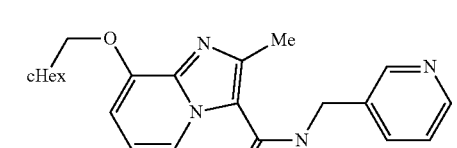 |
| 522 | 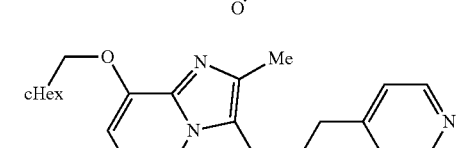 |
| 523 | 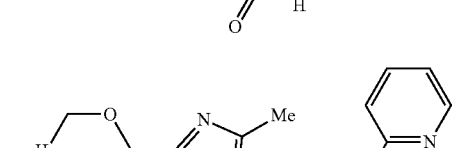 |
| 524 | 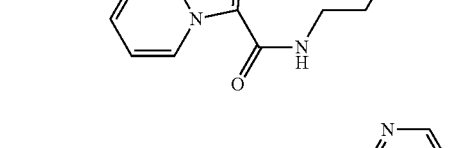 |

TABLE 71-continued
| Ex | Str |
|---|---|
| 525 | 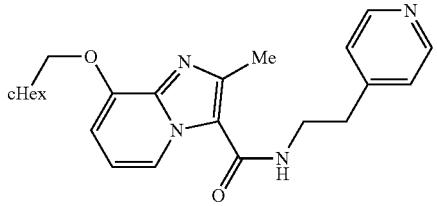 |
| 526 | 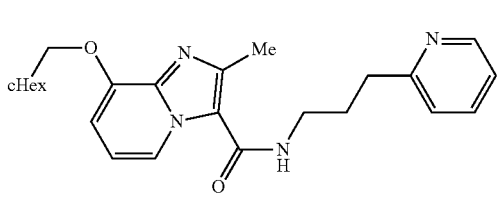 |
| 527 | 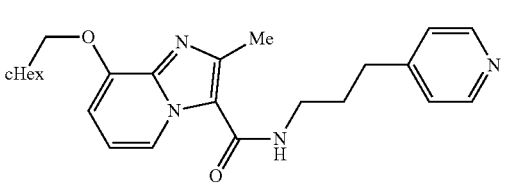 |
| 528 | 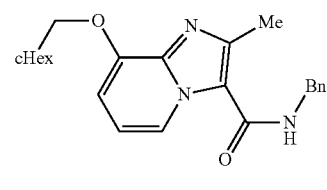 |
| 529 | 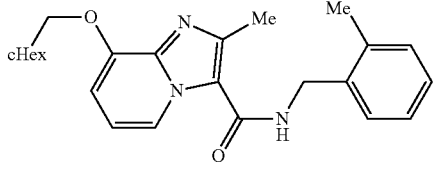 |
| 530 | 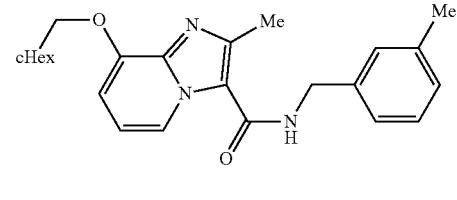 |
| 531 | 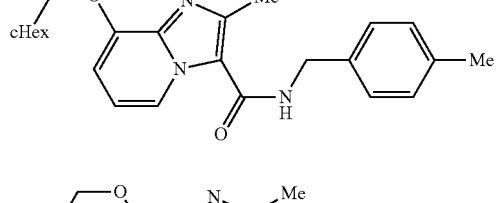 |
| 532 | 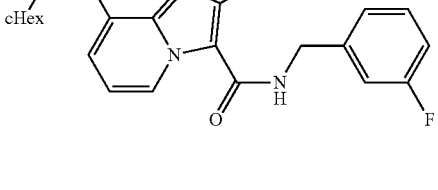 |
| 533 | 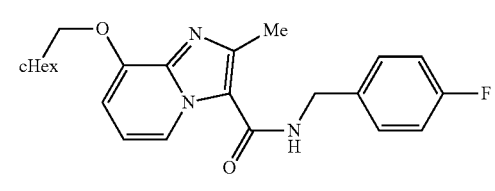 |
| 534 | 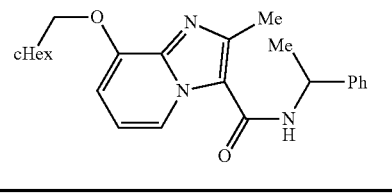 |
TABLE 72
| Ex | Str |
|---|---|
| 535 | 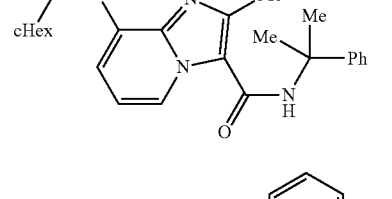 |
| 536 | 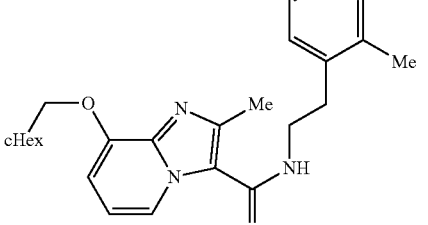 |
| 537 | 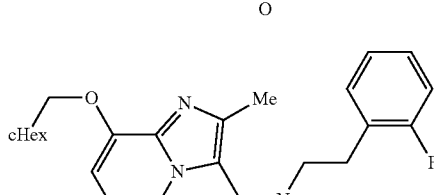 |
| 538 | 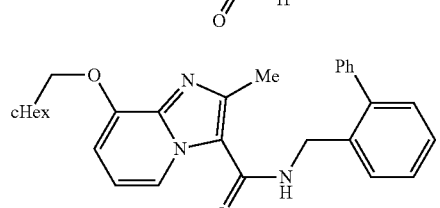 |
| 539 | 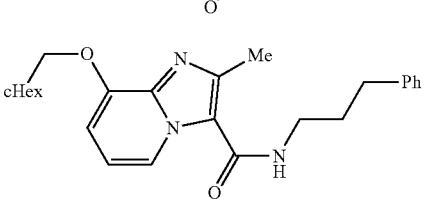 |

TABLE 72-continued

| Ex | Str |
|---|---|
| 540 | (structure) |
| 541 | (structure) |
| 542 | (structure) |
| 543 | (structure) |
| 544 | (structure) |
| 545 | (structure) |
| 546 | (structure) |
| 547 | (structure) |
| 548 | (structure) |
| 549 | (structure) |
| 550 | (structure) |

TABLE 73

| Ex | Str |
|---|---|
| 551 | (structure) |
| 552 | (structure) |
| 553 | (structure) |
| 554 | (structure) |
| 555 | (structure) |

TABLE 73-continued
| Ex | Str |
|---|---|
| 556 | 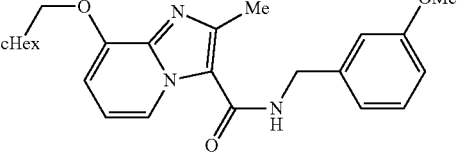 |
| 557 | 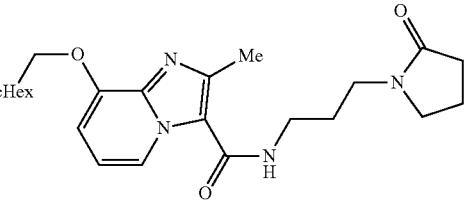 |
| 558 | 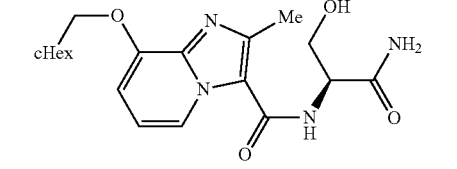 |
| 559 | 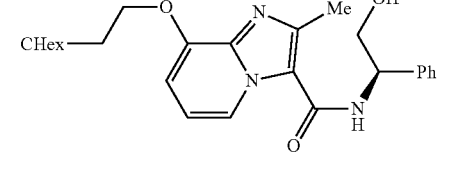 |
| 560 | 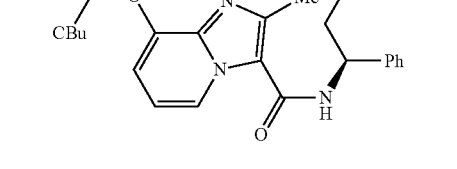 |
| 561 | 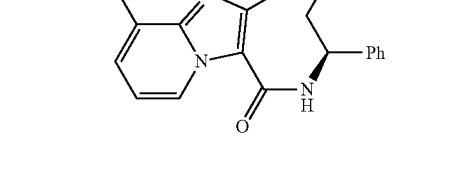 |
| 562 | 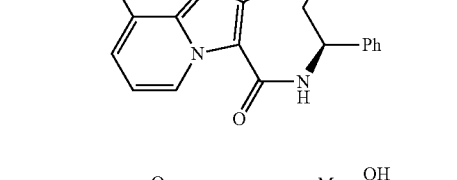 |
| 563 | 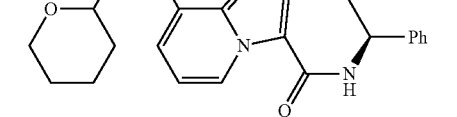 |
TABLE 73-continued
| Ex | Str |
|---|---|
| 564 | 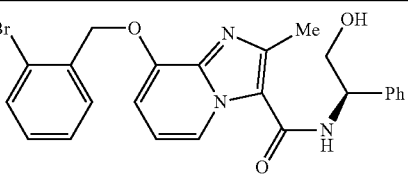 |
| 565 | 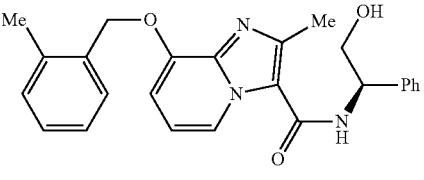 |
| 566 | 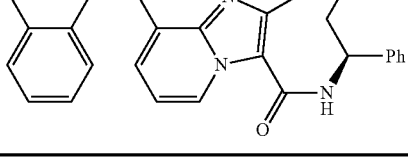 |
TABLE 74
| Ex | Str |
|---|---|
| 567 | 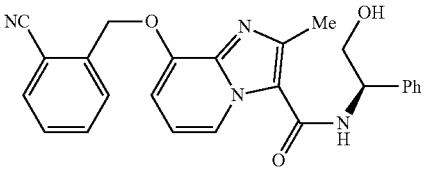 [SMILES: Cc1nc2c(OCc3ccccc3Br)cccn2c1C(=O)N[C@@H](CO)c1ccccc1] |
| 568 | 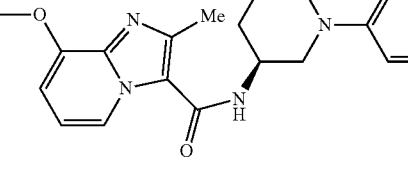 |
| 569 | 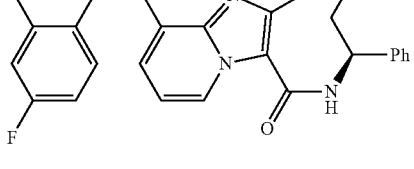 |
| 570 | 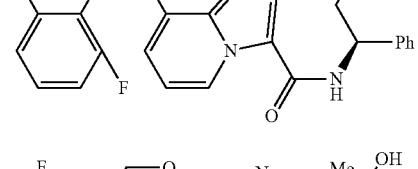 |
| 571 | 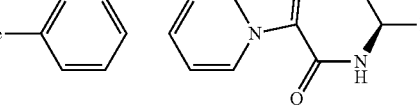 |

TABLE 74-continued

| Ex | Str |
|---|---|
| 572 | |
| 573 | |
| 574 | |
| 575 | |
| 576 | |
| 577 | |
| 578 | |
| 579 | |

TABLE 74-continued

| Ex | Str |
|---|---|
| 580 | |
| 581 | |
| 582 | |

TABLE 75

| Ex | Str |
|---|---|
| 583 | |
| 584 | |
| 585 | |
| 586 | |
| 587 | |

TABLE 75-continued

| Ex | Str |
|---|---|
| 588 | (structure) |
| 589 | (structure) |
| 590 | (structure) |
| 591 | (structure) |
| 592 | (structure) |
| 593 | (structure) |
| 594 | (structure) |
| 595 | (structure) |

TABLE 75-continued

| Ex | Str |
|---|---|
| 596 | (structure) |

TABLE 76

| Ex | Str |
|---|---|
| 597 | (structure) |
| 598 | (structure) |
| 599 | (structure) |
| 600 | (structure) |
| 601 | (structure) |
| 602 | (structure) |

TABLE 76-continued

| Ex | Str |
|---|---|
| 603 | (structure: 8-cHex-methoxy-2-methylimidazo[1,2-a]pyridine-3-carboxamide with N-(1-iPr-2-carboxyethyl), stereo) |
| 604 | (structure: 8-cHex-methoxy-2-methylimidazo[1,2-a]pyridine-3-carboxamide with N-CH(2-methylphenyl)CH₂CO₂H) |
| 605 | (structure: 8-cHex-methoxy-2-methylimidazo[1,2-a]pyridine-3-carboxamide with N-CH(2-bromophenyl)CH₂CO₂H) |
| 606 | (structure: 8-cHex-methoxy-2-methylimidazo[1,2-a]pyridine-3-carboxamide with N-CH(2-ethoxyphenyl)CH₂CO₂H) |
| 607 | (structure: 8-cHex-methoxy-2-methylimidazo[1,2-a]pyridine-3-carboxamide with N-CH(2-iPr-phenyl)CH₂CO₂H) |
| 608 | (structure: 8-cHex-methoxy-2-methylimidazo[1,2-a]pyridine-3-carboxamide with N-CH(2-ethylphenyl)CH₂CO₂H) |
| 609 | (structure: 8-cHex-methoxy-2-methylimidazo[1,2-a]pyridine-3-carboxamide with N-CH(2-CF₃-phenyl)CH₂CO₂H, stereo) |

TABLE 76-continued

| Ex | Str |
|---|---|
| 610 | (structure: 8-cHex-methoxy-2-methylimidazo[1,2-a]pyridine-3-carboxamide with N-CH(3-nitrophenyl)CH₂CO₂H) |

TABLE 77

| Ex | Str |
|---|---|
| 611 | (structure: 8-cHex-methoxy-2-methylimidazo[1,2-a]pyridine-3-carboxamide with N-CH(3-hydroxyphenyl)CH₂CO₂H) |
| 612 | (structure: 8-cHex-methoxy-2-methylimidazo[1,2-a]pyridine-3-carboxamide with N-CH(3-CF₃-phenyl)CH₂CO₂H) |
| 613 | (structure: 8-cHex-methoxy-2-methylimidazo[1,2-a]pyridine-3-carboxamide with N-CH(3-ethoxyphenyl)CH₂CO₂H) |
| 614 | (structure: 8-cHex-methoxy-2-methylimidazo[1,2-a]pyridine-3-carboxamide with N-CH(3-bromophenyl)CH₂CO₂H) |
| 615 | (structure: 8-cHex-methoxy-2-methylimidazo[1,2-a]pyridine-3-carboxamide with N-CH(3-methylphenyl)CH₂CO₂H) |

TABLE 77-continued

| Ex | Str |
|---|---|
| 616 | (structure) |
| 617 | (structure) |
| 618 | (structure) |
| 619 | (structure) |
| 620 | (structure) |
| 621 | (structure) |huh TABLE 77-continued

| Ex | Str |
|---|---|
| 622 | (structure) |
| 623 | (structure) |
| 624 | (structure) |

TABLE 78

| Ex | Str |
|---|---|
| 625 | (structure) |
| 626 | (structure) |
| 627 | (structure) |
| 628 | (structure) |

TABLE 78-continued

| Ex | Str |
|---|---|
| 629 | (structure) |
| 630 | (structure) |
| 631 | (structure, cis) |
| 632 | (structure, trans) |
| 633 | (structure) |
| 634 | (structure) |
| 635 | (structure) |
| 636 | (structure) |

TABLE 79

| Ex | Str |
|---|---|
| 637 | (structure) |
| 638 | (structure) |
| 639 | (structure) |
| 640 | (structure) |
| 641 | (structure) |
| 642 | (structure) |
| 643 | (structure) |

TABLE 79-continued
| Ex | Str |
|---|---|
| 644 | 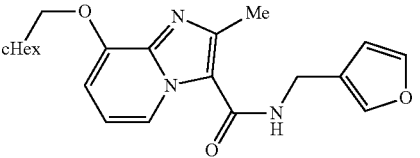 |
| 645 | 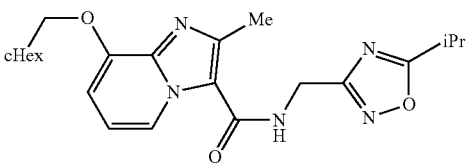 |
| 646 | 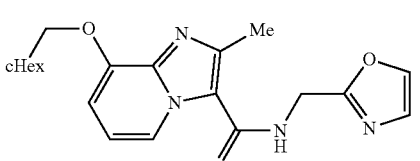 |
| 647 | 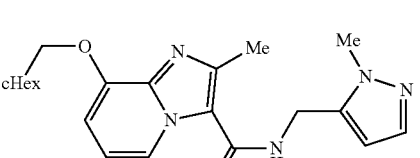 |
| 648 | 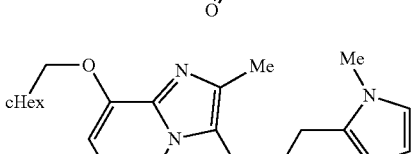 |
| 649 | 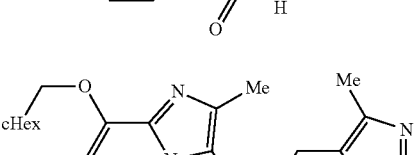 |
| 650 | 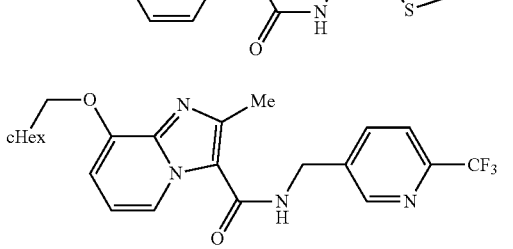 |
TABLE 80
| Ex | Str |
|---|---|
| 651 | 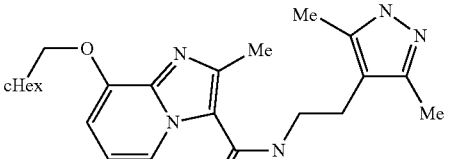 |
| 652 | 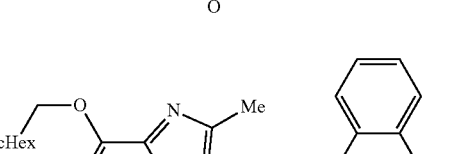 |
| 653 | 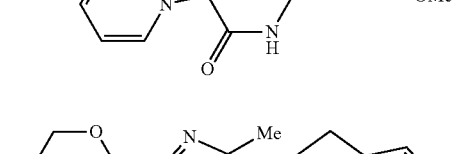 |
| 654 | 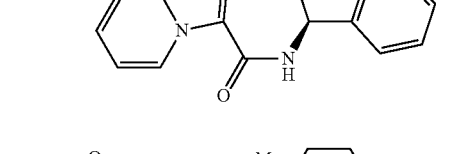 |
| 655 | 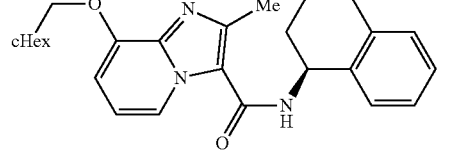 |
| 656 | 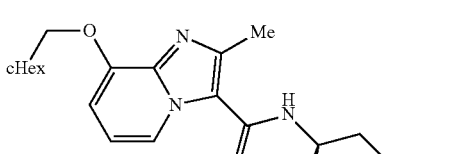 |
| 657 | 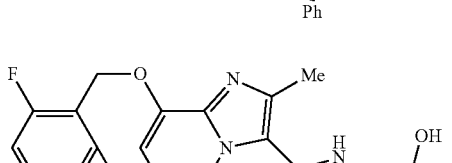 |
| 658 | 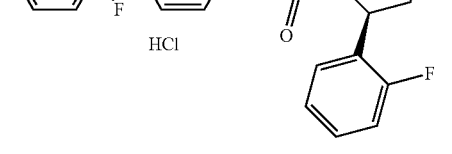 |

TABLE 81
| Ex | Str |
|---|---|
| 659 | |
| 660 | |
| 661 | |
| 662 | |
| 663 | |
| 664 | |
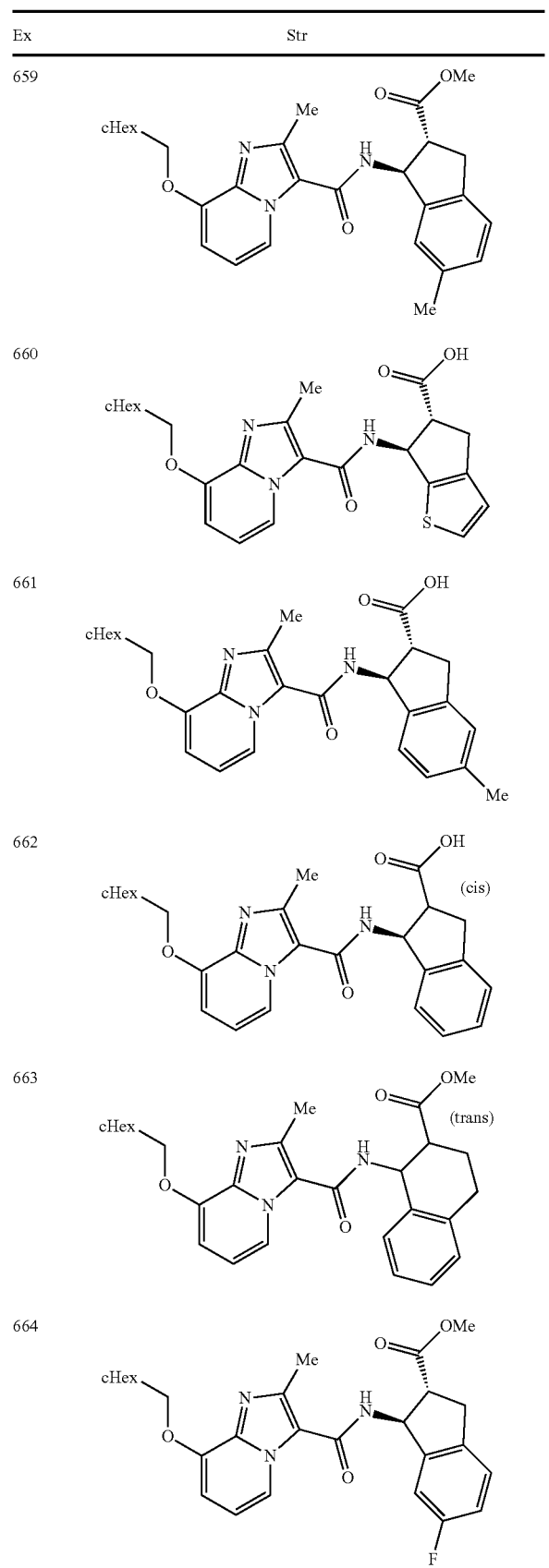
TABLE 81-continued
| Ex | Str |
|---|---|
| 665 | |
| 666 | |
| 667 | |
| 668 | |
| 669 | |
| 670 | |
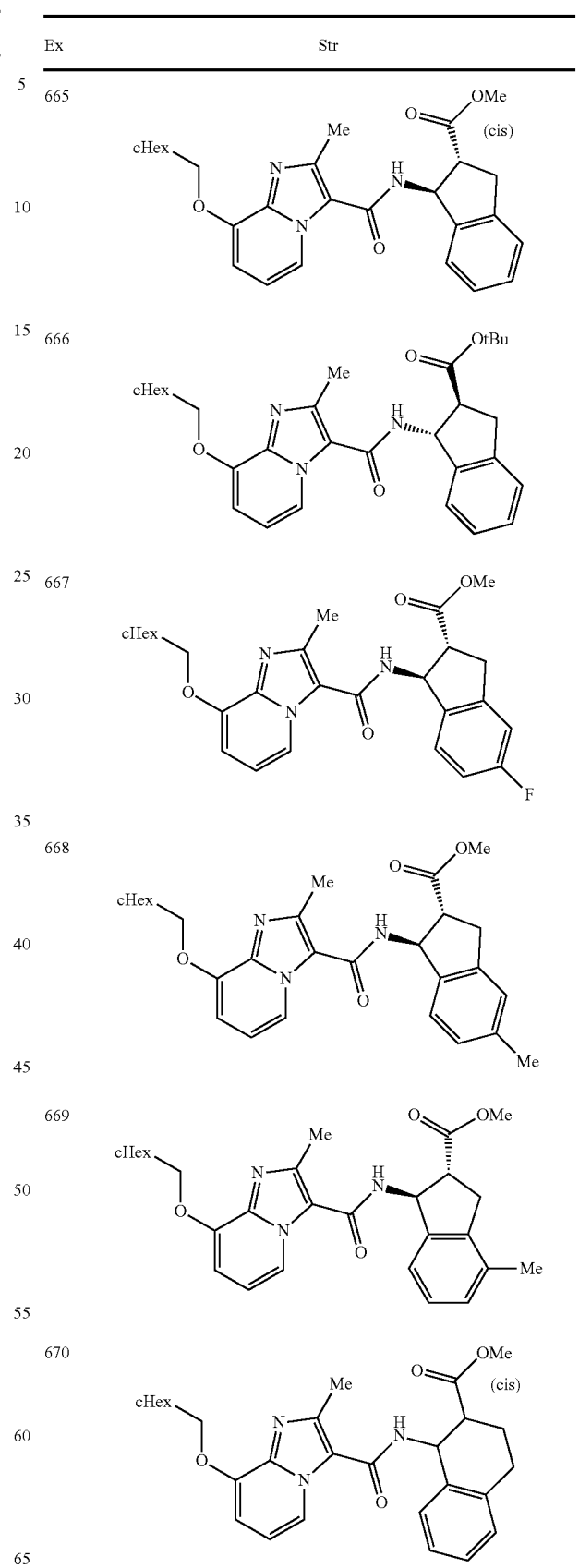

TABLE 81-continued

| Ex | Str |
|---|---|
| 671 | (structure) |
| 672 | (structure) |

TABLE 82

| Ex | Str |
|---|---|
| 673 | (structure) |
| 674 | (structure) |
| 675 | (structure) |
| 676 | (structure) |
| 677 | (structure) |
| 678 | (structure) |
| 679 | (structure) |
| 680 | (structure) |
| 681 | (structure) |
| 682 | (structure) |

TABLE 82-continued

| Ex | Str |
|---|---|
| 683 | (structure) |
| 684 | (structure) |
| 685 | (structure) |
| 686 | (structure) |

TABLE 83

| Ex | Str |
|---|---|
| 687 | (structure) |
| 688 | (structure) |
| 689 | (structure) |
| 690 | (structure) |
| 691 | (structure) |
| 692 | (structure) |
| 693 | (structure) |
| 694 | (structure) |

TABLE 83-continued

| Ex | Str |
|---|---|
| 695 | (trans) |
| 696 | |
| 697 | |
| 698 | |

TABLE 84

| Ex | Str |
|---|---|
| 699 | |
| 700 | |
| 701 | |
| 702 | |
| 703 | (cis) |
| 704 | |
| 705 | |

TABLE 84-continued

| Ex | Str |
|---|---|
| 706 | (structure) |
| 707 | (structure) |
| 708 | (structure) |
| 709 | (structure) |
| 710 | (structure) |

TABLE 85

| Ex | Str |
|---|---|
| 711 | (structure) |
| 712 | (structure) |
| 713 | (structure) |
| 714 | (structure) |
| 715 | (structure) |
| 716 | (structure) |
| 717 | (structure) |

TABLE 85-continued

| Ex | Str |
|---|---|
| 718 | |
| 719 | |
| 720 | |
| 721 | |
| 722 | |

TABLE 86

| Ex | Str |
|---|---|
| 723 | |
| 724 | |
| 725 | |
| 726 | |
| 727 | |

TABLE 86-continued

| Ex | Str |
|---|---|
| 728 | |
| 729 | |
| 730 | |

TABLE 87

| Ex | Str |
|---|---|
| 731 | |

TABLE 87-continued

| Ex | Str |
|---|---|
| 732 | |
| 733 | |
| 734 | |
| 735 | |
| 736 | |

TABLE 87-continued
| Ex | Str |
|---|---|
| 737 | 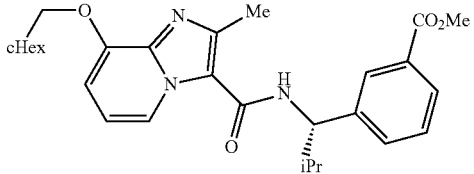 |
| 738 | 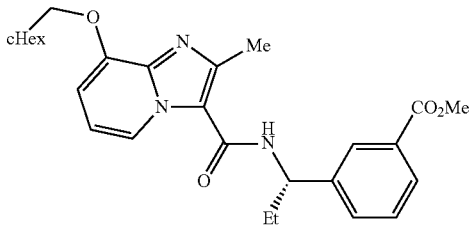 |
| 739 | 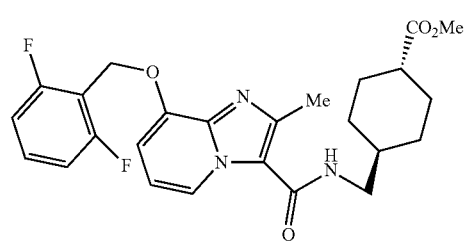 [SMILES: COC(=O)[C@H]1CC[C@H](CNC(=O)c2c(C)nc3c(OCc4c(F)cccc4F)cccn23)CC1] |
| 740 | 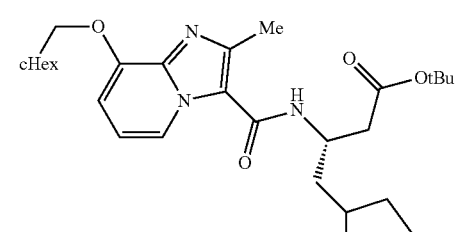 |
TABLE 88
| Ex | Str |
|---|---|
| 741 | 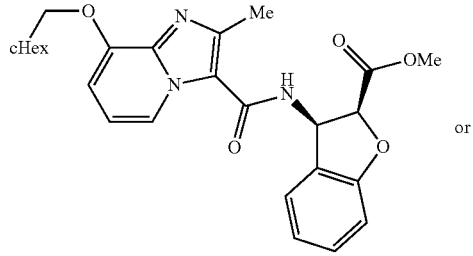 |
| 742 |  |
TABLE 88-continued
| Ex | Str |
|---|---|
| 743 744 |  or 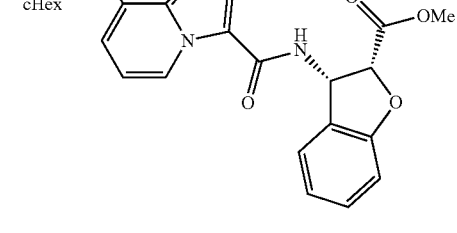 |
| 745 |  |
| 746 |  |
| 747 |  |
| 748 |  |

TABLE 88-continued
| Ex | Str |
|---|---|
| 749 | 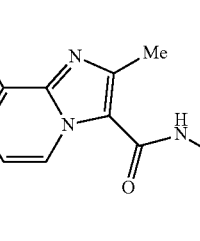 |
| 750 | |
| 751 | |
| 752 | |
TABLE 89
| Ex | Str |
|---|---|
| 753 | 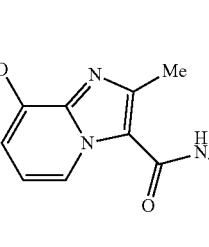 |
TABLE 89-continued
| Ex | Str |
|---|---|
| 754 | 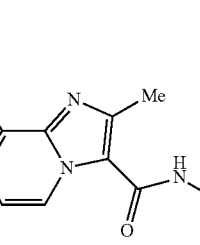 |
| 755 756 | |
| 757 | |
| 758 759 | 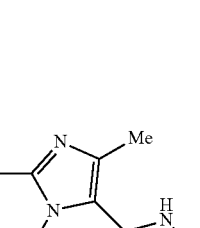 |

TABLE 89-continued

| Ex | Str |
|---|---|
| | (structure) |
| 760 | (structure) |
| 761 | (structure) |
| 762 | (structure) |

TABLE 90

| Ex | Str |
|---|---|
| 763 | (structure) |
| 764 | (structure) |
| 765 | (structure) |
| 766 767 | (structure) or (structure) |
| 768 | (structure) (rac) |
| 769 770 | (structure) or |

TABLE 90-continued
| Ex | Str |
|---|---|
| | 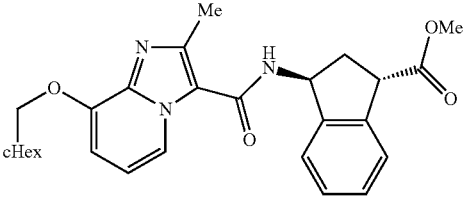 |
| 771 | 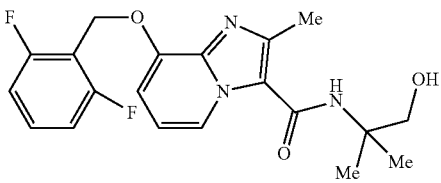 [SMILES: Cc1nc2c(OCc3c(F)cccc3F)cccn2c1C(=O)NC(C)(C)CO] |
| 772 | 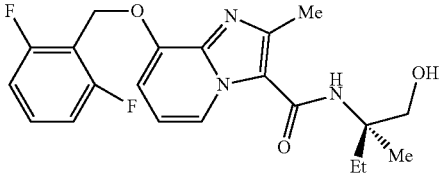 [SMILES: CC[C@](C)(CO)NC(=O)c1c(C)nc2c(OCc3c(F)cccc3F)cccn12] |
| 773 | 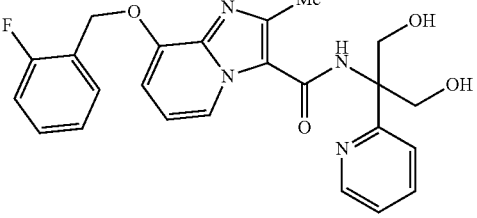 |
| 774 | 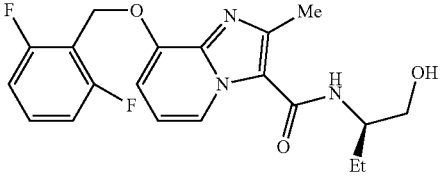 [SMILES: CC[C@H](CO)NC(=O)c1c(C)nc2c(OCc3c(F)cccc3F)cccn12] |
TABLE 91
| Ex | Str |
|---|---|
| 775 | 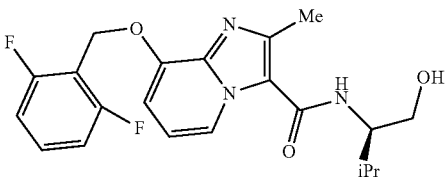 [SMILES: Cc1nc2c(OCc3c(F)cccc3F)cccn2c1C(=O)N[C@@H](CO)C(C)C] |
| 776 | 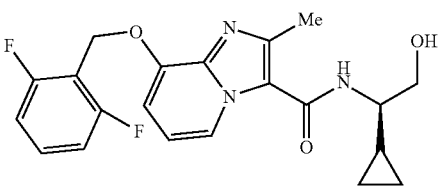 [SMILES: Cc1nc2c(OCc3c(F)cccc3F)cccn2c1C(=O)N[C@@H](CO)C1CC1] |
TABLE 91-continued
| Ex | Str |
|---|---|
| 777 | 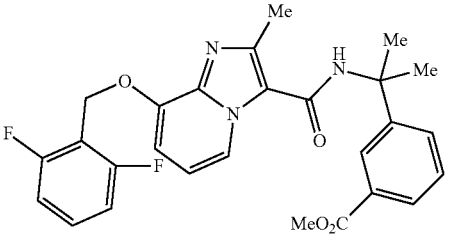 [SMILES: COC(=O)c1cccc(C(C)(C)NC(=O)c2c(C)nc3c(OCc4c(F)cccc4F)cccn23)c1] |
| 778 | 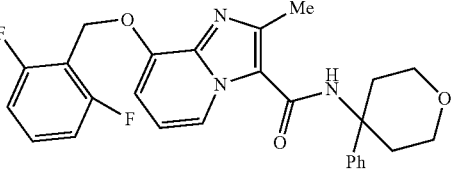 |
| 779 | 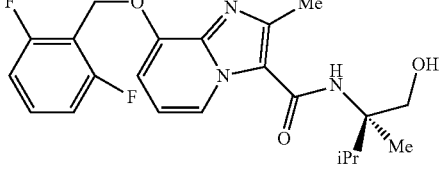 |
| 780 | 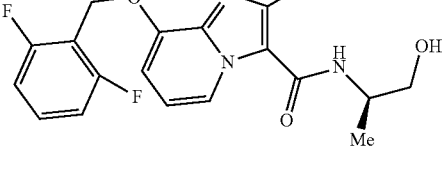 |
| 781 | 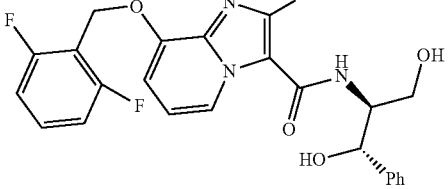 |
| 782 | 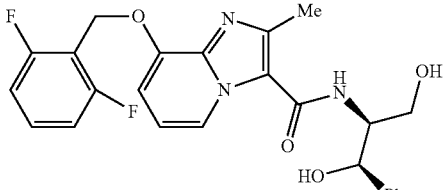 |
| 783 | |

TABLE 91-continued
| Ex | Str |
|---|---|
| 784 | 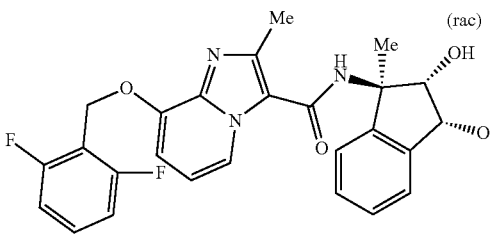 (rac) |
| 785 | 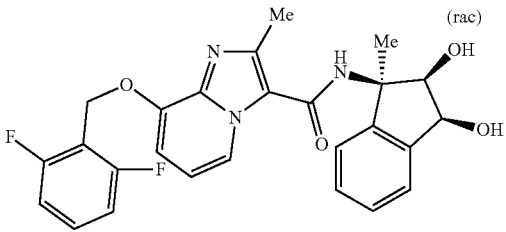 [SMILES: Cc1nc2c(OCc3c(F)cccc3F)cccn2c1C(=O)N[C@]1(C)c2ccccc2[C@H](O)[C@@H]1O] (rac) |
| 788 | 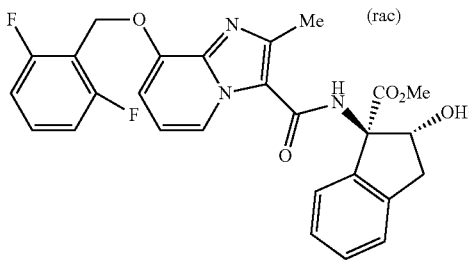 (rac) |
| 786 | 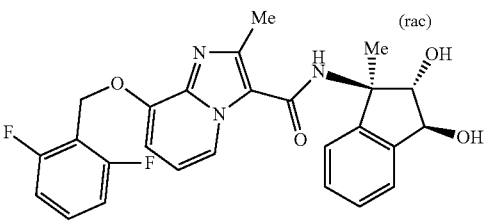 [SMILES: Cc1nc2c(OCc3c(F)cccc3F)cccn2c1C(=O)N[C@@]1(C)c2ccccc2[C@H](O)[C@H]1O] (rac) or |
| | 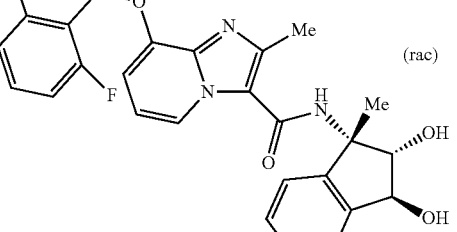 (rac) |
TABLE 92
| Ex | Str |
|---|---|
| 787 | 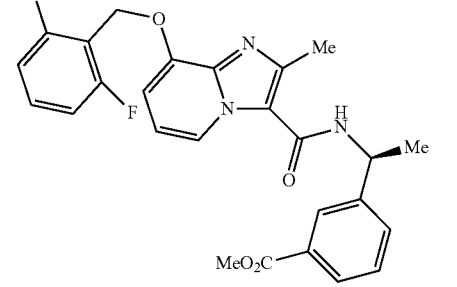 (rac) or |
| | 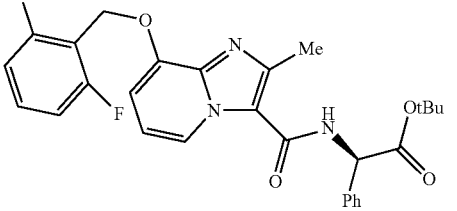 (rac) |
| 789 | 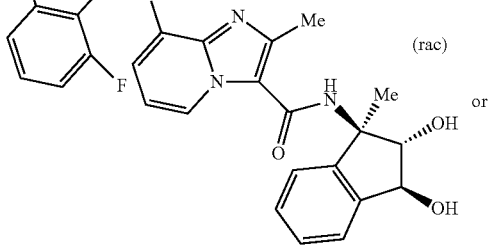 |
| 790 | 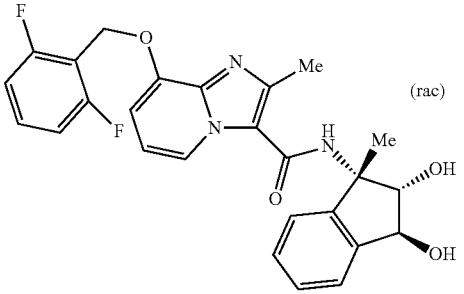 [SMILES: Cc1nc2c(OCc3c(F)cccc3F)cccn2c1C(=O)N[C@@]1(C)c2ccccc2[C@H](O)[C@H]1O] |
| 791 | 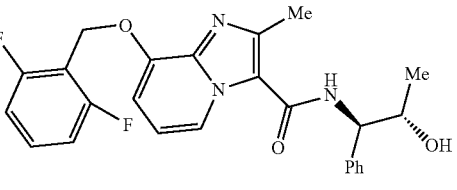 |
| 792 | 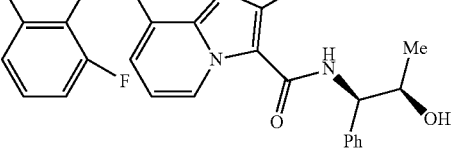 |

TABLE 92-continued

| Ex | Str |
|---|---|
| 793 | (structure) |
| 794 | (structure) |
| 795 | (structure) |
| 796 | (structure) |
| 797 | (structure) |

TABLE 92-continued

| Ex | Str |
|---|---|
| | (structure) |
| 798 | (structure) or (structure) |

TABLE 93

| Ex | Str |
|---|---|
| 799 | (structure) 2HCl |
| 800 | (structure) HCl |

TABLE 93-continued

| Ex | Str |
|---|---|
| 801 | (2,3-difluorobenzyl)oxy-imidazo[1,2-a]pyridine-3-carboxamide with 2-hydroxyindanyl; Me; HCl |
| 802 | (2,3-difluorobenzyl)oxy-imidazo[1,2-a]pyridine-3-carboxamide with 2-hydroxyindanyl (diastereomer); Me; HCl |
| 803 | (2,4,5-trifluorobenzyl)oxy-imidazo[1,2-a]pyridine-3-carboxamide with 2-hydroxyindanyl; Me; HCl |
| 804 | (2,3,6-trifluorobenzyl)oxy-imidazo[1,2-a]pyridine-3-carboxamide with 2-hydroxyindanyl; Me; HCl |
| 805 | (2-fluorobenzyl)oxy-imidazo[1,2-a]pyridine-3-carboxamide with (1-(4-fluorophenyl)-2-hydroxyethyl); Me; HCl |
| 806 | (2,3-difluorobenzyl)oxy-imidazo[1,2-a]pyridine-3-carboxamide with (1-(4-fluorophenyl)-2-hydroxyethyl); Me; HCl |
| 807 | (2,4,6-trifluorobenzyl)oxy-imidazo[1,2-a]pyridine-3-carboxamide with (1-(4-fluorophenyl)-2-hydroxyethyl); Me; HCl |
| 808 | (2,3,6-trifluorobenzyl)oxy-imidazo[1,2-a]pyridine-3-carboxamide with (1-(4-fluorophenyl)-2-hydroxyethyl); Me; HCl |
| 809 | (2,6-difluorobenzyl)oxy-imidazo[1,2-a]pyridine-3-carboxamide with (2,3-dihydroxy-1-phenylpropyl); Me; HCl |
| 810 | (2,6-difluorobenzyl)oxy-imidazo[1,2-a]pyridine-3-carboxamide with 2-(hydroxymethyl)indanyl; Me; HCl (rac) |

TABLE 94

| Ex | Str |
|---|---|
| 811 | (cyclohexylmethoxy)-imidazo[1,2-a]pyridine-3-carboxamide with indanyl-CO$_2$Me; Me |

TABLE 94-continued

| Ex | Str |
|---|---|
| 812 | (structure) |
| 813 | (structure) |
| 814 | (structure) |
| 815 | (structure) |
| 816 | (structure) |
| 817 | (structure) |
| 818 | (structure) |
| 819 | (structure) |
| 820 | (structure) |
| 821 | (structure) |
| 822 | (structure) |
| 823 | (structure) |
| 824 | (structure) |

TABLE 95

| Ex | Str |
|---|---|
| 825 | (structure) |
| 826 | (structure) |
| 827 | (structure) |
| 828 | (structure) |
| 829 | (structure) |
| 830 | (structure) |

TABLE 95-continued

| Ex | Str |
|---|---|
| 831 | (structure) |
| 832 | (structure) |
| 833 | (structure) (rac) |
| 834 | (structure) |
| 835 | (structure) |
| 836 | (structure) |

TABLE 96
| Ex | Str |
|---|---|
| 837 | 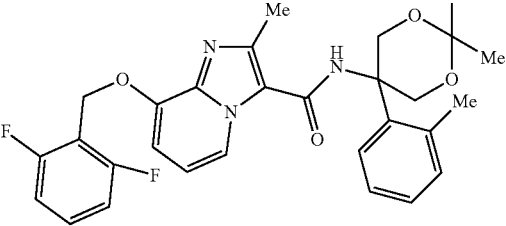 |
| 838 | 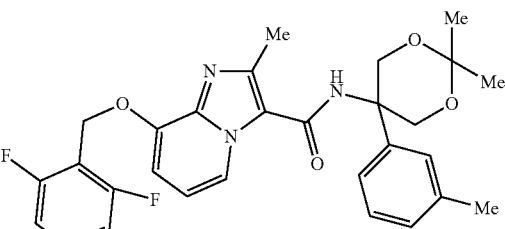 |
| 839 | 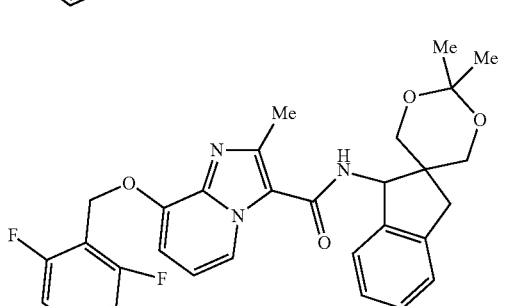 |
| 840 | 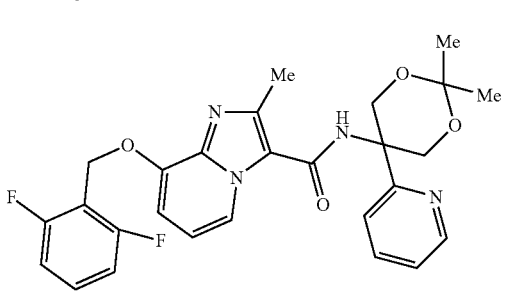 [SMILES: Cc1nc2c(OCc3c(F)cccc3F)cccn2c1C(=O)NC1(c2ccccn2)COC(C)(C)OC1] |
| 841 | 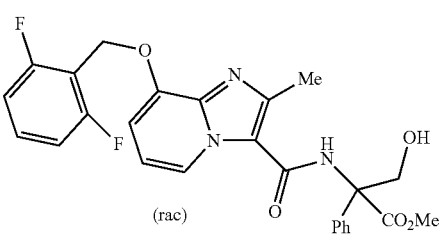 [SMILES: COC(=O)C(CO)(NC(=O)c1c(C)nc2c(OCc3c(F)cccc3F)cccn12)c1ccccc1] |
| 842 | 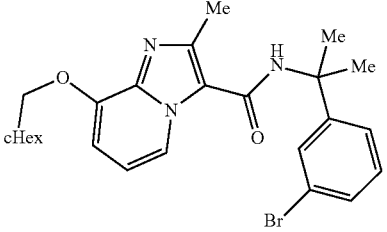 |
| 843 | 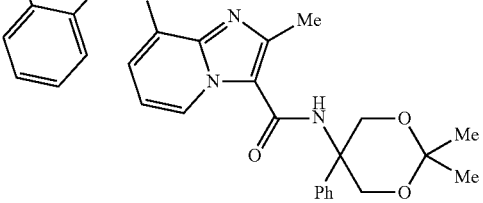 |
| 844 | 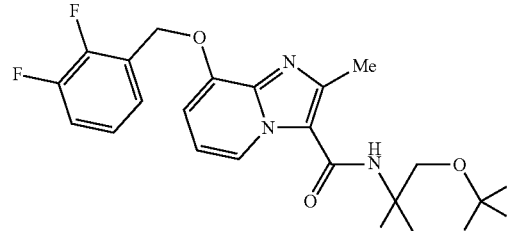 |
| 845 | 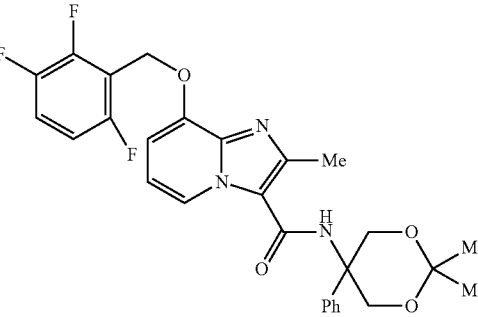 |
| 846 | 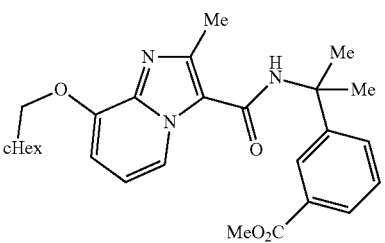 |
| 847 | 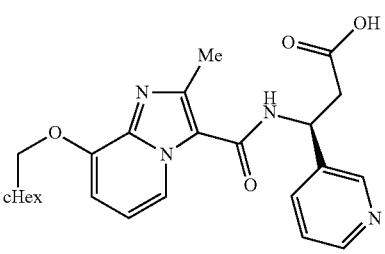 |
| 848 | 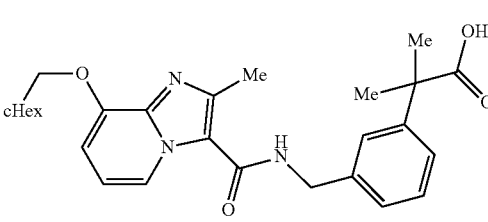 |

TABLE 97
| Ex | Str |
|---|---|
| 849 | 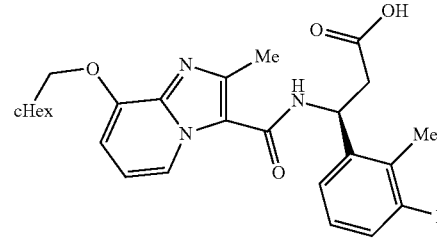 |
| 850 | 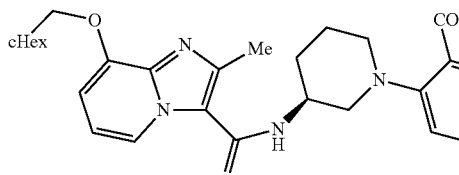 |
| 851 | 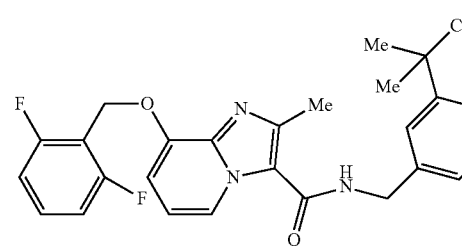 |
| 852 | 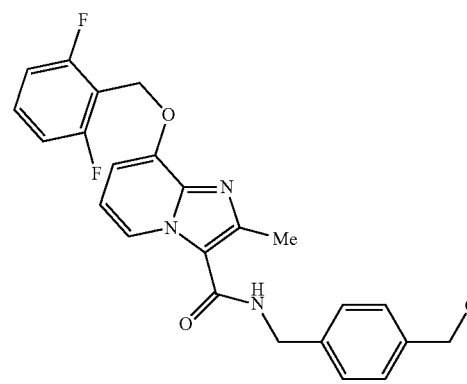 |
| 853 | 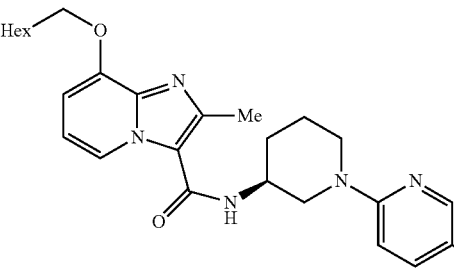 |
| 854 | 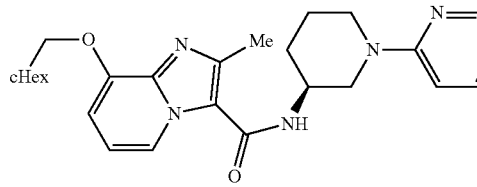 |
TABLE 97-continued
| Ex | Str |
|---|---|
| 855 | |
| 856 | |
| 857 | |
| 858 | |
| 859 | |
| 860 | |

TABLE 98

| Ex | Str |
|---|---|
| 861 | |
| 862 | |
| 863 | |
| 864 | |
| 865 | |

TABLE 98-continued

| Ex | Str |
|---|---|
| 866 | |
| 867 | |
| 868 | |
| 869 | |
| 870 871 | (or) |

TABLE 98-continued

| Ex | Str |
|---|---|
| 872 | (structure) |

TABLE 99

| Ex | Str |
|---|---|
| 873 | (structure) |
| 874 | (structure) |
| 875 | (structure) |
| 876 | (structure) |
| 877 | (structure) |
| 878 | (structure) |

TABLE 99-continued

| Ex | Str |
|---|---|
| 879 | (structure) |
| 880 | (structure) |
| 881 | (structure) |
| 882 | (structure) |
| 883 | (structure) |
| 884 | (structure) |

TABLE 99-continued

| Ex | Str |
|---|---|
| 885 | (structure) |
| 886 | (structure) |
| 887 | (structure) |
| 888 | (structure) |
| 889 | (structure) |
| 890 | (structure) |
| 891 | (structure) |
| 892 | (structure) |

TABLE 100

| Ex | Syn | Dat |
|---|---|---|
| 1 | Ex1 | ESI+: 471 |
| 2 | Ex2 | ESI+: 508 |
| 3 | Ex3 | ESI+: 492 |
| 4 | Ex4 | ESI+: 433 |
| 5 | Ex5 | ESI+: 371 |
| 6 | Ex6 | ESI+: 371 |
| 7 | Ex7 | ESI+: 457 |
| 8 | Ex8 | ESI+: 485 |
| 9 | Ex9 | ESI+: 521 |
| 10 | Ex10 | ESI+: 414 |
| 11 | Ex11 | ESI+: 450 |
| 12 | Ex12 | NMR(DMSO-d$_6$): 0.91 (3H, d, J = 6.6 Hz), 0.93 (3H, d, J = 6.5 Hz), 1.01-1.36 (6H, m), 1.53-1.90 (8H, m), 2.43-2.56 (2H, m), 2.51 (3H, s), 3.95 (2H, d, J = 6.1 Hz), 4.37-4.48 (1H, m), 6.77 (1H, d, J = 7.0 Hz), 6.85 (1H, t, J = 7.2 Hz), 7.71 (1H, d, J = 9.0 Hz), 8.46 (1H, d, J = 6.1 Hz), 12.22 (1H, s); ESI+: 416 |
| 13 | Ex13 | ESI+: 454 |
| 14 | Ex14 | ESI+: 436 |
| 15 | Ex15 | ESI+: 464 |
| 16 | Ex16 | ESI+: 371 |
| 17 | Ex17 | ESI+: 606 |
| 18 | Ex18 | ESI+: 450 |
| 19 | Ex19 | ESI+: 407 |
| 20 | Ex20 | ESI+: 443 |

TABLE 100-continued

| Ex | Syn | Dat |
|---|---|---|
| 21 | Ex21 | ESI+: 452 |
| 22 | Ex22 | ESI+: 410 |
| 23 | Ex23 | ESI+: 328 |
| 24 | Ex24 | ESI+: 422 |
| 25 | Ex25 | ESI+: 450 |
| 26 | Ex26 | ESI+: 438 |
| 27 | Ex27 | ESI+: 411 |
| 28 | Ex28 | ESI+: 421 |
| 29 | Ex29 | ESI+: 401 |
| 30 | Ex30 | ESI+: 506 |

TABLE 101

| Ex | Syn | Dat |
|---|---|---|
| 31 | Ex31 | ESI+: 534 |
| 32 | Ex32 | ESI+: 441 |
| 33 | Ex33 | ESI+: 475 |
| 34 | Ex34 | ESI+: 385 |
| 35 | Ex35 | ESI+: 513 |
| 36 | Ex1 | ESI+: 462 |
| 37 | Ex1 | ESI+: 504 |
| 38 | Ex1 | ESI+: 402 |
| 39 | Ex1 | ESI+: 416 |
| 40 | Ex1 | ESI+: 374 |
| 41 | Ex1 | ESI+: 388 |
| 42 | Ex1 | ESI+: 402 |
| 43 | Ex1 | ESI+: 402 |
| 44 | Ex1 | ESI+: 456 |
| 45 | Ex1 | ESI+: 516 |
| 46 | Ex1 | ESI+: 480 |
| 47 | Ex1 | ESI+: 472 |
| 48 | Ex1 | ESI+: 437 |
| 49 | Ex1 | ESI+: 451 |
| 50 | Ex1 | ESI+: 457 |
| 51 | Ex1 | ESI+: 471 |
| 52 | Ex1 | ESI+: 450 |
| 53 | Ex1 | ESI+: 374 |
| 54 | Ex1 | ESI+: 486 |
| 55 | Ex1 | ESI+: 442 |
| 56 | Ex1 | ESI+: 430 |
| 57 | Ex1 | ESI+: 456, 458 |
| 58 | Ex1 | ESI+: 431 |
| 59 | Ex1 | ESI+: 464 |
| 60 | Ex1 | ESI+: 456, 458 |

TABLE 102

| Ex | Syn | Dat |
|---|---|---|
| 61 | Ex1 | ESI+: 577 |
| 62 | Ex1 | ESI+: 518 |
| 63 | Ex1 | ESI+: 456, 458 |
| 64 | Ex1 | ESI+: 458 |
| 65 | Ex1 | ESI+: 472 |
| 66 | Ex1 | ESI+: 457 |
| 67 | Ex1 | ESI+: 440 |
| 68 | Ex1 | ESI+: 440 |
| 69 | Ex1 | ESI+: 440 |
| 70 | Ex1 | ESI+: 498 |
| 71 | Ex1 | ESI+: 415 |
| 72 | Ex1 | ESI+: 484 |
| 73 | Ex1 | ESI+: 537 |
| 74 | Ex1 | ESI+: 458 |
| 75 | Ex1 | ESI+: 428 |
| 76 | Ex1 | ESI+: 543 |
| 77 | Ex1 | ESI+: 484 |
| 78 | Ex1 | ESI+: 414 |
| 79 | Ex1 | ESI+: 499 |
| 80 | Ex1 | ESI+: 464 |
| 81 | Ex1 | ESI+: 456 |
| 82 | Ex1 | ESI+: 456 |
| 83 | Ex1 | ESI+: 486 |

TABLE 102-continued

| Ex | Syn | Dat |
|---|---|---|
| 84 | Ex1 | ESI+: 456 |
| 85 | PEx11, Ex1 | ESI+: 472 |
| 86 | Ex1 | ESI+: 471 |
| 87 | Ex1 | ESI+: 498 |
| 88 | Ex1 | ESI+: 515 |
| 89 | Ex1 | ESI+: 487 |
| 90 | Ex1 | ESI+: 357 |

TABLE 103

| Ex | Syn | Dat |
|---|---|---|
| 91 | Ex1 | ESI+: 512 |
| 92 | Ex1 | ESI+: 498 |
| 93 | Ex1 | ESI+: 484 |
| 94 | Ex1 | ESI+: 606 |
| 95 | Ex1 | ESI+: 473 |
| 96 | Ex1, 16 | ESI+: 360 |
| 97 | Ex1, 16 | ESI+: 374 |
| 98 | Ex1, 16 | ESI+: 409 |
| 99 | Ex1, 16 | ESI+: 409 |
| 100 | Ex1, 16 | ESI+: 409 |
| 101 | Ex1, 16 | ESI+: 435 |
| 102 | Ex1, 16 | ESI+: 408 |
| 103 | Ex1, 16 | ESI+: 360 |
| 104 | Ex1, 16 | ESI+: 342 |
| 105 | Ex1, 16 | ESI+: 401 |
| 106 | Ex1, 16 | ESI+: 386 |
| 107 | Ex1, 16 | ESI+: 422 |
| 108 | Ex1, 16 | ESI+: 462 |
| 109 | Ex1, 16 | ESI+: 374 |
| 110 | Ex1, 16 | ESI+: 388 |
| 111 | Ex1, 16 | ESI+: 422 |
| 112 | Ex1, 16 | ESI+: 360 |
| 113 | Ex1, 16 | ESI+: 346 |
| 114 | Ex1, 16 | ESI+: 388 |
| 115 | Ex1, 16 | ESI+: 420 |
| 116 | Ex1, 16 | ESI+: 332 |
| 117 | Ex1, 16 | ESI+: 346 |
| 118 | Ex1, 16 | ESI+: 388 |
| 119 | Ex1, 16 | ESI+: 438 |
| 120 | Ex1, 16 | ESI+: 461 |

TABLE 104

| Ex | Syn | Dat |
|---|---|---|
| 121 | Ex1, 16 | ESI+: 374 |
| 122 | Ex1, 16 | ESI+: 394 |
| 123 | Ex1, 16 | ESI+: 440 |
| 124 | Ex1, 16 | ESI+: 440 |
| 125 | Ex1, 16 | ESI+: 440 |
| 126 | Ex1, 16 | NMR(DMSO-$d_6$): 1.05-1.36 (5H, m), 1.63-1.79 (3H, m), 1.82-1.95 (3H, m), 2.66 (3H, s), 3.53-3.63 (4H, m), 3.97-4.07 (1H, m), 4.11 (2H, d, J = 6.1 Hz), 7.37 (1H, t, J = 7.3 Hz), 7.44 (1H, d, J = 7.9 Hz), 8.29 (1H, d, J = 6.7 Hz), 8.63 (1H, d, J = 6.5 Hz); ESI+: 362 |
| 127 | Ex1, 16 | ESI+: 406 |
| 128 | Ex1, 16 | ESI+: 406 |
| 129 | Ex1, 16 | ESI+: 436 |
| 130 | Ex1, 16 | ESI+: 394 |
| 131 | Ex1, 16 | ESI+: 395 |
| 132 | Ex1, 16 | ESI+: 422 |
| 133 | Ex1, 16 | ESI+: 456, 458 |
| 134 | Ex1, 16 | ESI+: 452 |
| 135 | Ex1, 16 | ESI+: 318 |
| 136 | Ex1, 16 | ESI+: 450 |
| 137 | Ex1, 16 | ESI+: 420 |
| 138 | Ex1, 16 | ESI+: 420 |
| 139 | Ex1, 16 | ESI+: 420 |
| 140 | Ex1, 16 | ESI+: 420 |
| 141 | Ex1, 16 | ESI+: 359 |
| 142 | Ex1, 16 | ESI+: 376 |

TABLE 104-continued

| Ex | Syn | Dat |
|---|---|---|
| 143 | Ex1, 16 | ESI+: 376 |
| 144 | Ex1, 16 | ESI+: 442, 444 |
| 145 | Ex1, 16 | ESI+: 440 |
| 146 | Ex1, 16 | ESI+: 440 |
| 147 | Ex1, 16 | ESI+: 441 |
| 148 | Ex1, 16 | ESI+: 362 |
| 149 | Ex1, 16 | ESI+: 362 |
| 150 | Ex1, 16 | ESI+: 442, 444 |

TABLE 105

| Ex | Syn | Dat |
|---|---|---|
| 151 | Ex1, 16 | ESI+: 414 |
| 152 | Ex1, 16 | ESI+: 429 |
| 153 | Ex1, 16 | ESI+: 376 |
| 154 | Ex1, 16 | ESI+: 426 |
| 155 | Ex1, 16 | ESI+: 426 |
| 156 | Ex1, 16 | ESI+: 438 |
| 157 | Ex1, 16 | ESI+: 438 |
| 158 | Ex1, 16 | ESI+: 438 |
| 159 | Ex1, 16 | ESI+: 390 |
| 160 | Ex1, 16 | ESI+: 394 |
| 161 | Ex1, 16 | ESI+: 392 |
| 162 | Ex1, 16 | ESI+: 414 |
| 163 | Ex1, 16 | ESI+: 398 |
| 164 | Ex1, 16 | ESI+ 398 |
| 165 | Ex1, 16 | ESI+: 399 |
| 166 | Ex1, 16 | ESI+: 372 |
| 167 | Ex1, 16 | ESI+: 386 |
| 168 | Ex1, 16 | ESI+: 422 |
| 169 | Ex1, 16 | ESI+: 434 |
| 170 | Ex1, 16 | ESI+: 415 |
| 171 | Ex12 | ESI+: 442 |
| 172 | Ex12 | ESI+: 402 |
| 173 | Ex12 | ESI+: 416 |
| 174 | Ex12 | ESI+: 428 |
| 175 | Ex12 | ESI+: 428 |
| 176 | Ex12 | ESI+: 416 |
| 177 | Ex12 | ESI+: 430 |
| 178 | Ex12 | ESI+: 442 |
| 179 | Ex12 | ESI+: 428 |
| 180 | Ex12 | ESI+: 442 |

TABLE 106

| Ex | Syn | Dat |
|---|---|---|
| 181 | Ex12, 16 | ESI+: 374 |
| 182 | Ex13 | ESI+: 470, 472 |
| 183 | Ex13 | ESI+: 470, 472 |
| 184 | Ex13 | ESI+: 470, 472 |
| 185 | Ex13 | ESI+: 454 |
| 186 | Ex13 | ESI+: 454 |
| 187 | Ex16 | ESI+: 464 |
| 188 | Ex16 | ESI+: 402 |
| 189 | Ex16 | ESI+: 462 |
| 190 | Ex2 | ESI+: 558 |
| 191 | Ex2 | ESI+: 522 |
| 192 | Ex2 | ESI+: 510 |
| 193 | Ex2 | ESI+: 562 |
| 194 | Ex2 | ESI+: 536 |
| 195 | Ex2 | ESI+: 550 |
| 196 | Ex2 | ESI+: 540 |
| 197 | Ex2 | ESI+: 540 |
| 198 | Ex2 | ESI+: 556, 558 |
| 199 | Ex2 | ESI+: 572 |
| 200 | Ex3 | ESI+: 426 |
| 201 | Ex3, 16 | ESI+: 458 |
| 202 | Ex3, 16 | ESI+: 444 |
| 203 | Ex3, 16 | ESI+: 408 |
| 204 | Ex3, 16 | ESI+: 394 |
| 205 | Ex3, 16 | ESI+: 396 |

TABLE 106-continued

| Ex | Syn | Dat |
|---|---|---|
| 206 | Ex3, 16 | ESI+: 448 |
| 207 | Ex3, 16 | ESI+: 422 |
| 208 | Ex3, 16 | ESI+: 436 |
| 209 | Ex3, 16 | ESI+: 426 |
| 210 | Ex3, 16 | ESI+: 442, 444 |

TABLE 107

| Ex | Syn | Dat |
|---|---|---|
| 211 | Ex5 | ESI+: 371 |
| 212 | Ex5 | ESI+: 357 |
| 213 | Ex5 | ESI+: 331 |
| 214 | Ex5 | ESI+: 357 |
| 215 | Ex5 | ESI+: 443 |
| 216 | Ex5 | ESI+: 399 |
| 217 | Ex5 | ESI+: 371 |
| 218 | Ex5 | ESI+: 415 |
| 219 | Ex5 | ESI+: 387 |
| 220 | Ex5 | ESI+: 373 |
| 221 | Ex6 | ESI+: 457 |
| 222 | Ex6 | ESI+: 457 |
| 223 | Ex6 | ESI+: 429 |
| 224 | Ex6 | ESI+: 387 |
| 225 | Ex6, 16 | ESI+: 401 |
| 226 | Ex6, 16 | ESI+: 385 |
| 227 | Ex6, 16 | ESI+: 385 |
| 228 | Ex6, 16 | ESI+: 371 |
| 229 | Ex6, 16 | ESI+: 415 |
| 230 | Ex6, 16 | ESI+: 413 |
| 231 | Ex7, 16 | ESI+: 399 |
| 232 | Ex8 | ESI+: 462 |
| 233 | Ex8 | ESI+: 485 |
| 234 | Ex8, 16 | ESI+: 413 |
| 235 | Ex8, 16 | ESI+: 399 |
| 236 | Ex8, 16 | ESI+: 413 |
| 237 | Ex9 | ESI+: 521 |
| 238 | Ex9, 16 | ESI+: 449 |
| 239 | PEx1, Ex3, 16 | ESI+: 382 |
| 240 | PEx1, Ex3, 16 | ESI+: 396 |

TABLE 108

| Ex | Syn | Dat |
|---|---|---|
| 241 | PEx1, Ex3, 16 | ESI+: 396 |
| 242 | PEx1, Ex3, 16 | ESI+: 394 |
| 243 | PEx1, Ex3, 16 | ESI+: 396 |
| 244 | PEx1, Ex3, 16 | ESI+: 456 |
| 245 | PEx1, Ex3, 16 | ESI+: 456 |
| 246 | PEx12, Ex8 | ESI+: 450 |
| 247 | Ex1 | ESI+: 480 |
| 248 | PEx5 | ESI+: 422 |
| 249 | PEx5 | ESI+: 436 |
| 250 | PEx5 | ESI+: 422 |
| 251 | PEx5 | NMR(DMSO-$d_6$): 1.01-1.34 (5H, m), 1.63-1.77 (3H, m), 1.77-1.90 (3H, m), 2.55 (3H, s), 2.82 (1H, dd, J = 5.9, 15.7 Hz), 2.91 (1H, dd, J = 8.7, 15.7 Hz), 3.95 (2H, d, J = 6.2 Hz), 5.41-5.49 (1H, m), 6.77 (1H, dd, J = 0.9, 7.8 Hz), 6.84 (1H, dd, J = 6.9, 7.6 Hz), 7.25 (1H, t, J = 7.3 Hz), 7.35 (2H, t, J = 7.6 Hz), 7.45 (2H, d, J = 7.3 Hz), 8.38 (1H, d, J = 8.4 Hz), 8.43 (1H, dd, J = 0.9, 6.8 Hz), 12.39 (1H, s); ESI+: 436 |
| 252 | PEx5 | ESI+: 448 |
| 253 | PEx5 | ESI+: 450 |
| 254 | PEx5 | ESI+: 490 |
| 255 | PEx5 | ESI+: 388 |
| 256 | PEx5 | ESI+: 346 |
| 257 | PEx5 | ESI+: 360 |
| 258 | PEx5 | ESI+: 374 |
| 259 | PEx5 | ESI+: 388 |
| 260 | PEx5 | ESI+: 442 |

TABLE 108-continued

| Ex | Syn | Dat |
|---|---|---|
| 261 | PEx5 | ESI+: 466 |
| 262 | PEx5 | ESI+: 429 |
| 263 | PEx5 | ESI+: 360 |
| 264 | PEx5 | ESI+: 428 |
| 265 | PEx5 | ESI+: 464 |
| 266 | PEx5 | ESI+: 504 |
| 267 | PEx5 | ESI+: 563 |
| 268 | PEx5 | ESI+: 429 |
| 269 | PEx5 | ESI+: 507 |
| 270 | PEx5 | ESI+: 471 |

TABLE 109

| Ex | Syn | Dat |
|---|---|---|
| 271 | PEx5 | ESI+: 443 |
| 272 | PEx5 | ESI+: 430 |
| 273 | PEx5 | ESI+: 414 |
| 274 | PEx5 | ESI+: 400 |
| 275 | PEx5 | ESI+: 450 |
| 276 | PEx5 | ESI+: 429 |
| 277 | PEx5 | ESI+: 442 |
| 278 | PEx5 | ESI+: 442 |
| 279 | PEx5 | ESI+: 507 |
| 280 | PEx5 | ESI+: 471 |
| 281 | PEx5 | ESI+: 443 |
| 282 | PEx5 | ESI+: 442 |
| 283 | PEx5 | ESI+: 401 |
| 284 | PEx5 | ESI+: 415 |
| 285 | PEx5, Ex16 | ESI+: 423 |
| 286 | PEx5, Ex16 | ESI+: 423 |
| 287 | PEx5, Ex16 | ESI+: 436 |
| 288 | PEx5, Ex16 | ESI+: 450 |
| 289 | PEx5, Ex16 | ESI+: 434 |
| 290 | Ex 6 | ESI+: 519 |
| 291 | PEx5 | ESI+: 505 |
| 292 | Ex1, 16 | ESI+: 477 |
| 293 | Ex1 | ESI+: 440 |
| 294 | PEx5 | ESI+: 412 |
| 295 | Ex1 | ESI+: 413, 415 |
| 296 | Ex1 | ESI+: 288 |
| 297 | Ex1 | ESI+: 413 |
| 298 | Ex31, 16 | ESI+: 534.5 |
| 299 | Ex3, 16 | ESI+: 404 |
| 300 | Ex1 | ESI+: 547 |
| 301 | Ex1 | ESI+: 464 |
| 302 | PEx5 | ESI+: 450 |
| 303 | Ex3, 16 | ESI+: 404 |
| 304 | Ex3, 16 | ESI+: 421 |

TABLE 110

| Ex | Syn | Dat |
|---|---|---|
| 305 | PEx1 | ESI+: 508 |
| 306 | PEx5 | ESI+: 480 |
| 307 | Ex3, 16 | ESI+: 404 |
| 308 | PEx5 | ESI+: 519 |
| 309 | PEx5 | ESI+: 506 |
| 310 | Ex 1 | ESI+: 547 |
| 311 | PEx5 | ESI+: 519 |
| 312 | Ex1 | ESI+: 471 |
| 313 | PEx 5 | ESI+: 443 |
| 314 | Ex1 | ESI+: 408 |
| 315 | PEx5 | ESI+: 506 |
| 316 | PEx12, Ex8 | ESI+: 318 |
| 317 | PEx12, Ex8 | ESI+: 332 |
| 318 | Ex6 | ESI+: 471 |
| 319 | PEx5 | ESI+: 443 |
| 320 | Ex1 | ESI+: 504 |
| 321 | Ex12 | NMR(DMSO-$d_6$): 1.01-1.36 (5H, m), 1.62-1.77 (3H, m), 1.78-1.91 (3H, m), 2.55 (3H, s), 3.10 (1H, dd, J = 9.0, 15.3 Hz), 3.22-3.37 (2H, m), 3.96 (2H, d, J = 6.2 Hz), 5.79 (1H, t, J = 8.5 Hz), 6.80 (1H, d, J = 7.1 Hz), 6.90 (1H, t, J = 7.3 Hz), 7.21-7.32 (4H, m), 8.43 (1H, d, J = 8.7 Hz), 8.55 (1H, d, J = 6.1 Hz), 12.00-12.80 (1H, br); ESI+: 448 |
| 322 | Ex1 | ESI+: 450 |
| 323 | PEx5 | NMR(DMSO-$d_6$): 1.01-1.34 (5H, m), 1.53 (3H, d, J = 7.0 Hz), 1.63-1.77 (3H, m), 1.78-1.90 (3H, m), 2.58 (3H, s), 3.95 (2H, d, J = 6.1 Hz), 5.18-5.27 (1H, m), 6.77 (1H, d, J = 7.2 Hz), 6.83 (1H, t, J = 7.2 Hz), 7.48 (1H, t, J = 7.7 Hz), 7.69 (1H, d, J = 7.8 Hz), 7.83 (1H, d, J = 7.7 Hz), 8.05 (1H, s), 8.41 (2H, d, J = 6.7 Hz), 12.93 (1H, s); ESI+: 436 |
| 324 | PEx5 | ESI+: 422 |
| 325 | Ex1 | ESI+: 502 |
| 326 | Ex1 | ESI+: 484 |
| 327 | Ex9 | ESI+: 521 |
| 328 | Ex1 | ESI+: 470 |
| 329 | Ex1 | ESI+: 520 |
| 330 | Ex1 | ESI+: 470 |

TABLE 111

| Ex | Syn | Dat |
|---|---|---|
| 331 | Ex1 | ESI+: 520 |
| 332 | Ex1 | ESI+: 508 |
| 333 | Ex1 | ESI+: 450 |
| 334 | Ex1 | ESI+: 506 |
| 335 | Ex1 | ESI+: 466 |
| 336 | Ex1 | ESI+: 528 |
| 337 | Ex1 | ESI+: 478 |
| 338 | Ex1 | ESI+: 432 |
| 339 | Ex1 | ESI+: 432 |
| 340 | Ex1 | ESI+: 390 |
| 341 | Ex6, 16 | ESI+: 371 |
| 342 | Ex1, 16 | ESI+: 362 |
| 343 | Ex1, 16 | ESI+: 441 |
| 344 | Ex19 | ESI+: 407 |
| 345 | Ex1 | ESI+: 472 |
| 346 | Ex1 | ESI+: 456 |
| 347 | PEx15 | ESI+: 303 |
| 348 | Ex12 | ESI+: 456 |
| 349 | Ex6 | ESI+: 385 |
| 350 | Ex1 | ESI+: 376 |
| 351 | Ex1 | ESI+: 438 |
| 352 | Ex1 | ESI+: 442 |
| 353 | PEx5 | ESI+: 428 |
| 354 | Ex1, 16 | ESI+: 411 |
| 355 | Ex11 | ESI+: 450 |
| 356 | Ex11 | ESI+: 436 |
| 357 | Ex1 | ESI+: 473 |
| 358 | Ex5 | ESI+: 373 |
| 359 | Ex6, 16 | ESI+: 387 |
| 360 | Ex1 | ESI+: 406 |

TABLE 112

| Ex | Syn | Dat |
|---|---|---|
| 361 | Ex1 | ESI+: 515 |
| 362 | Ex5 | ESI+: 415 |
| 363 | PEx5 | ESI+: 401 |
| 364 | Ex6 | ESI+: 429 |
| 365 | Ex1, 16 | ESI+: 413 |
| 366 | Ex6, 16 | ESI+: 413 |
| 367 | Ex9, 16 | ESI+: 475 |
| 368 | PEx5 | ESI+: 415 |
| 369 | Ex1 | ESI+: 436 |
| 370 | Ex13 | ESI+: 450 |
| 371 | Ex11 | ESI+: 436 |
| 372 | Ex1, 16 | ESI+: 415 |
| 373 | Ex1, 16 | ESI+: 397 |

TABLE 112-continued

| Ex | Syn | Dat |
|---|---|---|
| 374 | Ex27, 16 | ESI+: 397 |
| 375 | PEx5 | ESI+: 493 |
| 376 | Ex9, 16 | ESI+: 449 |
| 377 | Ex1 | ESI+: 473 |
| 378 | Ex5 | ESI+: 373 |
| 379 | Ex6 | ESI+: 387 |
| 380 | Ex1 | ESI+: 473 |
| 381 | Ex5 | ESI+: 373 |
| 382 | Ex6 | ESI+: 387 |
| 383 | Ex1, 16 | ESI+: 430 |
| 384 | Ex1, 16 | ESI+: 413 |
| 385 | Ex12 | ESI+: 446 |
| 386 | Ex12 | ESI+: 428 |
| 387 | Ex1 | ESI+: 471 |
| 388 | Ex5 | ESI+: 371 |
| 389 | Ex12 | ESI+: 414 |
| 390 | Ex27, 16 | ESI+: 397 |

TABLE 113

| Ex | Syn | Dat |
|---|---|---|
| 391 | Ex9, 16 | ESI+: 435 |
| 392 | Ex12 | ESI+: 464 |
| 393 | Ex9, 16 | ESI+: 449 |
| 394 | Ex8, 16 | ESI+: 413 |
| 395 | Ex6 | ESI+: 385 |
| 396 | Ex1 | ESI+: 529 |
| 397 | Ex5 | ESI+: 429 |
| 398 | PEx5 | ESI+: 401 |
| 399 | Ex9, 16 | ESI+: 435 |
| 400 | Ex12 | ESI+: 414 |
| 401 | Ex6 | ESI+: 443 |
| 402 | PEx5 | ESI+: 415 |
| 403 | Ex1 | ESI+: 436 |
| 404 | Ex6, 16 | ESI+: 425 |
| 405 | Ex6, 16 | ESI+: 468 |
| 406 | Ex9, 16 | ESI+: 511 |
| 407 | Ex1, 16 | ESI+: 415 |
| 408 | Ex1, 16 | ESI+: 397 |
| 409 | PEx11, Ex1 | ESI+: 446 |
| 410 | PEx5 | ESI−: 418 |
| 411 | Ex1 | ESI+: 506 |
| 412 | Ex12 | ESI+: 464 |
| 413 | Ex12 | ESI+: 450 |
| 414 | Ex1 | ESI+: 436 |
| 415 | Ex1 | ESI+: 436 |
| 416 | Ex1 | ESI+: 436 |
| 417 | Ex1 | ESI+: 450 |
| 418 | Ex12 | ESI+: 452 |
| 419 | PEx5 | ESI+: 436 |
| 420 | Ex1, 16 | ESI+: 438 |

TABLE 114

| Ex | Syn | Dat |
|---|---|---|
| 421 | Ex12 | ESI+: 450 |
| 422 | Ex1, 16 | ESI+: 426 |
| 423 | Ex1, 16 | ESI+: 456 |
| 424 | Ex1, 16 | ESI+: 468 |
| | | NMR(DMSO-$d_6$): 2.70 (3H, s), 3.99 (4H, s), 5.45 (2H, s), 7.19-7.37 (6H, m), 7.39-7.43 (2H, m), 7.45-7.66 (2H, m), 7.85-8.10 (1H, m), 8.65 (1H, d, J = 6.9 Hz) |
| 425 | PEx5 | ESI+: 418 |
| 426 | PEx5 | ESI+: 418 |
| 427 | Ex12 | ESI+: 472 |
| 428 | PEx5 | ESI+: 452 |
| 429 | PEx5 | ESI+: 450 |
| 430 | Ex1, 16 | ESI+: 450 |
| | | NMR(DMSO-$d_6$): 2.63 (3H, s), 2.79 (1H, dd, J = 7.9, 15.5 Hz), 3.19 (1H, dd, J = 7.3, 15.5 Hz), 4.40-4.50 (1H, m), 5.33 (1H, t, J = 7.8 Hz), 5.47 (2H, s), 7.18-7.30 (6H, m), 7.37-7.50 (1H, m), 7.55-7.70 (2H, m), 8.79 (1H, d, J = 6.7 Hz), 8.84-8.96 (1H, m) |
| 431 | Ex1, 16 | ESI+: 450 |
| 432 | Ex1, 16 | ESI+: 450 |
| 433 | Ex1 | ESI+: 534 |
| 434 | Ex12 | ESI+: 478 |
| 435 | Ex1, 16 | ESI+: 444 |
| 436 | Ex1, 16 | ESI+: 456 |
| 437 | Ex6, 16 | ESI+: 399 |
| 438 | Ex9, 16 | ESI+: 478 |
| 439 | Ex1, 16 | ESI+: 346 |
| 440 | Ex1 | ESI+: 478 |
| 441 | Ex1 | ESI+: 476 |
| 442 | Ex1 | ESI+: 302 |
| 443 | PEx5 | ESI+: 450 |
| 444 | PEx5 | ESI+: 448 |
| 445 | Ex9, 16 | ESI+: 464 |
| 446 | Ex6 | ESI+: 519 |
| 447 | PEx5 | ESI+: 464 |
| 448 | Ex1 | ESI+: 478 |
| 449 | Ex1 | ESI+: 492 |
| 450 | Ex1 | ESI+: 484 |

TABLE 115

| Ex | Syn | Dat |
|---|---|---|
| 451 | PEx5 | ESI+: 505 |
| 452 | PEx5 | ESI+: 470 |
| 453 | PEx5 | ESI+: 464 |
| 454 | Ex1 | ESI+: 442 |
| 455 | PEx5 | ESI+: 428 |
| 456 | Ex1 | ESI+: 506 |
| 457 | Ex12 | ESI+: 450 |
| 458 | Ex1 | ESI+: 408 |
| 459 | Ex6 | ESI+: 519 |
| 460 | PEx1, Ex3, 16 | ESI+: 444 |
| 461 | PEx5 | ESI+: 505 |
| 462 | Ex1 | ESI+: 480 |
| 463 | Ex1 | ESI+: 394 |
| 464 | Ex1 | ESI+: 427 |
| 465 | Ex1 | ESI+: 441 |
| 466 | PEx5 | ESI+: 413 |
| 467 | PEx5 | ESI+: 466 |
| 468 | PEx5 | ESI+: 413 |
| 469 | PEx1 | ESI+: 480 |
| 470 | PEx5 | ESI+: 452 |
| 471 | PEx1 | ESI+: 494 |
| 472 | PEx5 | ESI+: 466 |
| 473 | Ex23 | ESI+: 330 |
| 474 | Ex23 | ESI+: 344 |
| 475 | Ex23 | ESI+: 330 |
| 476 | Ex23 | ESI+: 344 |
| 477 | Ex1 | ESI+: 505 |
| 478 | Ex23 | ESI+: 342 |
| 479 | Ex23 | ESI+: 356 |
| 480 | Ex23 | ESI+: 370 |

TABLE 116

| Ex | Syn | Dat |
|---|---|---|
| 481 | Ex23 | ESI+: 384 |
| 482 | Ex23 | ESI+: 358 |
| 483 | Ex23 | ESI+: 408 |
| 484 | Ex23 | ESI+: 360 |
| 485 | Ex23 | ESI+: 438 |
| 486 | Ex23 | ESI+: 376 |
| 487 | Ex23 | ESI+: 374 |
| 488 | Ex23 | ESI+: 412 |
| 489 | Ex23 | ESI+: 412 |
| 490 | Ex23 | ESI+: 386 |
| 491 | Ex23 | ESI+: 346 |

TABLE 116-continued

| Ex | Syn | Dat |
|---|---|---|
| 492 | Ex23 | ESI+: 360 |
| 493 | Ex23 | ESI+: 360 |
| 494 | Ex23 | ESI+: 372 |
| 495 | Ex23 | ESI+: 400 |
| 496 | Ex23 | ESI+: 420 |
| 497 | Ex23 | ESI+: 359 |
| 498 | Ex23 | ESI+: 387 |
| 499 | Ex23 | ESI+: 373 |
| 500 | Ex23 | ESI+: 401 |
| 501 | Ex23 | ESI+: 399 |
| 502 | Ex23 | ESI+: 399 |
| 503 | Ex23 | ESI+: 385 |
| 504 | Ex23 | ESI+: 399 |
| 505 | Ex23 | ESI+: 399 |
| 506 | Ex23 | ESI+: 415 |
| 507 | Ex23 | ESI+: 413 |
| 508 | Ex23 | ESI+: 399 |
| 509 | Ex23 | ESI+: 397 |
| 510 | Ex23 | ESI+: 397 |

TABLE 117

| Ex | Syn | Dat |
|---|---|---|
| 511 | Ex23 | ESI+: 428 |
| 512 | Ex23 | ESI+: 414 |
| 513 | Ex23 | ESI+: 413 |
| 514 | Ex23 | ESI+: 399 |
| 515 | Ex23 | ESI+: 413 |
| 516 | Ex23 | ESI+: 399 |
| 517 | Ex23 | ESI+: 399 |
| 518 | Ex23 | ESI+: 449 |
| 519 | Ex23 | ESI+: 463 |
| 520 | Ex23 | ESI+: 379 |
| 521 | Ex23 | ESI+: 379 |
| 522 | Ex23 | ESI+: 379 |
| 523 | Ex23 | ESI+: 393 |
| 524 | Ex23 | ESI+: 393 |
| 525 | Ex23 | ESI+: 393 |
| 526 | Ex23 | ESI+: 407 |
| 527 | Ex23 | ESI+: 407 |
| 528 | Ex23 | ESI+: 378 |
| 529 | Ex23 | ESI+: 392 |
| 530 | Ex23 | ESI+: 392 |
| 531 | Ex23 | ESI+: 392 |
| 532 | Ex23 | ESI+: 396 |
| 533 | Ex23 | ESI+: 396 |
| 534 | Ex23 | ESI+: 392 |
| 535 | Ex23 | ESI+: 406 |
| 536 | Ex23 | ESI+: 406 |
| 537 | Ex23 | ESI+: 410 |
| 538 | Ex23 | ESI+: 454 |
| 539 | Ex23 | ESI+: 406 |
| 540 | Ex23 | ESI+: 408 |

TABLE 118

| Ex | Syn | Dat |
|---|---|---|
| 541 | Ex23 | ESI+: 408 |
| 542 | Ex23 | ESI+: 422 |
| 543 | Ex23 | ESI+: 422 |
| 544 | Ex23 | ESI+: 463 |
| 545 | Ex23 | ESI+: 408 |
| 546 | Ex23 | ESI+: 447 |
| 547 | Ex23 | ESI+: 447 |
| 548 | Ex23 | ESI+: 461 |
| 549 | Ex23 | ESI+: 465 |
| 550 | Ex23 | ESI+: 372 |
| 551 | Ex23 | ESI+: 386 |
| 552 | Ex23 | ESI+: 386 |
| 553 | Ex23 | ESI+: 386 |
| 554 | Ex23 | ESI+: 400 |

TABLE 118-continued

| Ex | Syn | Dat |
|---|---|---|
| 555 | Ex23 | ESI+: 433 |
| 556 | Ex23 | ESI+: 408 |
| 557 | Ex23 | ESI+: 413 |
| 558 | Ex23 | ESI+: 375 |
| 559 | Ex26 | ESI+: 422 |
| 560 | Ex26 | ESI+: 380 |
| 561 | Ex26 | ESI+: 382 |
| 562 | Ex26 | ESI+: 368 |
| 563 | Ex26 | ESI+: 410 |
| 564 | Ex26 | ESI+: 480, 482 |
| 565 | Ex26 | ESI+: 416 |
| 566 | Ex26 | ESI+: 436, 438 |
| 567 | Ex26 | ESI+: 427 |
| 568 | PEx5 | ESI+: 491 |
| 569 | Ex26 | ESI+: 438 |
| 570 | Ex26 | ESI+: 454, 456 |

TABLE 119

| Ex | Syn | Dat |
|---|---|---|
| 571 | Ex26 | ESI+: 434 |
| 572 | Ex26 | ESI+: 438 |
| 573 | Ex26 | ESI+: 454, 456 |
| 574 | Ex26 | ESI+: 456 |
| 575 | Ex26 | ESI+: 488 |
| 576 | Ex26 | ESI+: 456 |
| 577 | Ex26 | ESI+: 420 |
| 578 | Ex26 | ESI+: 438 |
| 579 | Ex26 | ESI+: 438 |
| 580 | Ex26 | ESI+: 420 |
| 581 | Ex26 | ESI+: 416 |
| 582 | Ex26 | ESI+: 403 |
| 583 | Ex26 | ESI+: 442, 444 |
| 584 | Ex26 | ESI+: 444, 446 |
| 585 | Ex26 | ESI+: 407 |
| 586 | Ex26 | ESI+: 443, 445 |
| 587 | Ex26 | ESI+: 423 |
| 588 | Ex24 | ESI+: 436 |
| 589 | Ex24 | ESI+: 376 |
| 590 | Ex1 | ESI+: 506 |
| 591 | Ex24 | ESI+: 438 |
| 592 | Ex24 | ESI+: 386 |
| 593 | Ex24 | ESI+: 402 |
| 594 | Ex24 | ESI+: 420 |
| 595 | Ex24 | ESI+: 402 |
| 596 | Ex24 | ESI+: 430 |
| 597 | Ex24 | ESI+: 500, 502 |
| 598 | Ex24 | ESI+: 428 |
| 599 | Ex24 | ESI+: 428 |
| 600 | Ex24 | ESI+: 400 |

TABLE 120

| Ex | Syn | Dat |
|---|---|---|
| 601 | Ex24 | ESI+: 386 |
| 602 | Ex24 | ESI+: 400 |
| 603 | Ex24 | ESI+: 402 |
| 604 | Ex24 | ESI+: 450 |
| 605 | Ex24 | ESI+: 514, 516 |
| 606 | Ex24 | ESI+: 480 |
| 607 | Ex24 | ESI+: 478 |
| 608 | Ex24 | ESI+: 464 |
| 609 | Ex24 | ESI+: 504 |
| 610 | Ex24 | ESI+: 481 |
| 611 | Ex24 | ESI+: 452 |
| 612 | Ex24 | ESI+: 504 |
| 613 | Ex24 | ESI+: 480 |
| 614 | Ex24 | ESI+: 514, 516 |
| 615 | Ex24 | ESI+: 450 |
| 616 | Ex24 | ESI+: 450 |
| 617 | Ex24 | ESI+: 464 |

TABLE 120-continued

| Ex | Syn | Dat |
| --- | --- | --- |
| 618 | Ex24 | ESI+: 514, 516 |
| 619 | Ex24 | ESI+: 478 |
| 620 | Ex24 | ESI+: 496 |
| 621 | Ex24 | ESI+: 494 |
| 622 | Ex24 | ESI+: 464 |
| 623 | Ex24 | ESI+: 472 |
| 624 | Ex24 | ESI+: 464 |
| 625 | Ex24 | ESI+: 430 |
| 626 | Ex24 | ESI+: 414 |
| 627 | Ex24 | ESI+: 400 |
| 628 | Ex24 | ESI+: 436 |
| 629 | Ex24 | ESI+: 374 |
| 630 | Ex24 | ESI+: 428 |

TABLE 121

| Ex | Syn | Dat |
| --- | --- | --- |
| 631 | Ex24 | ESI+: 414 |
| 632 | Ex24 | ESI+: 414 |
| 633 | Ex24 | ESI+: 422 |
| 634 | Ex24 | ESI+: 422 |
| 635 | Ex24 | ESI+: 436 |
| 636 | Ex24 | ESI+: 428 |
| 637 | Ex24 | ESI+: 436 |
| 638 | Ex24 | ESI+: 436 |
| 639 | Ex24 | ESI+: 505 |
| 640 | Ex23 | ESI+: 370 |
| 641 | PEx5 | ESI+: 492 |
| 642 | Ex25 | ESI+: 414 |
| 643 | Ex23 | ESI+: 368 |
| 644 | Ex23 | ESI+: 368 |
| 645 | Ex23 | ESI+: 412 |
| 646 | Ex23 | ESI+: 369 |
| 647 | Ex23 | ESI+: 382 |
| 648 | Ex23 | ESI+: 381 |
| 649 | Ex23 | ESI+: 399 |
| 650 | Ex23 | ESI+: 447 |
| 651 | Ex23 | ESI+: 413, 415 |
| 652 | Ex23 | ESI+: 410 |
| 653 | Ex23 | ESI+: 422 |
| 654 | Ex23 | ESI+: 404 |
| 655 | Ex23 | ESI+: 418 |
| 656 | Ex1 | ESI+: 450 |
| 657 | Ex1,16 | ESI+: 456 |
| 658 | Ex1,16 | ESI+: 406 |

TABLE 122

| Ex | Syn | Dat |
| --- | --- | --- |
| 659 | Ex1 | ESI+: 476 |
| 660 | Ex12 | ESI+: 454 |
| 661 | Ex661 | ESI+: 462 |
| 662 | PEx5 | ESI+: 448 |
| 663 | Ex663 | APCI/ESI+: 476 |
| 664 | PEx11, Ex1 | ESI+: 480 |
| 665 | Ex1 | ESI+: 462 |
| 666 | Ex1 | ESI+: 504 |
| 667 | Ex1 | ESI+: 480 |
| 668 | Ex1 | ESI+: 476 |
| 669 | Ex1 | ESI+: 476 |
| 670 | Ex1 | APCI/ESI+: 476 |
| 671 | Ex1 | ESI+: 510 |
| 672 | Ex1 | ESI+: 480 |
| 673 | Ex1 | ESI+: 506 |
| 674 | Ex1 | ESI+: 510 |
| 675 | Ex1 | ESI+: 518 |
| 676 | Ex1 | ESI+: 474 |
| 677 | Ex1 | ESI+: 492 |
| 678 | Ex1 | ESI+: 510 |
| 679 | Ex1 | ESI+: 510 |

TABLE 122-continued

| Ex | Syn | Dat |
| --- | --- | --- |
| 680 | Ex1 | ESI+: 540 |
| 681 | Ex1 | ESI+: 510 |
| 682 | Ex1 | ESI+: 540 |
| 683 | Ex1 | ESI+: 480 |
| 684 | Ex1 | ESI+: 480 |
| 685 | Ex1 | ESI+: 480 |
| 686 | Ex12 | ESI+: 448 |
| 687 | Ex12 | ESI+: 462 |
| 688 | Ex12 | ESI+: 484 |
| 689 | Ex12 | ESI+: 454 |
| 690 | Ex12 | ESI+: 484 |

TABLE 123

| Ex | Syn | Dat |
| --- | --- | --- |
| 691 | Ex661 | ESI+: 466 |
| 692 | Ex661 | ESI+: 462 |
| 693 | Ex661 | ESI+: 462<br>NMR (DMSO-$d_6$): 1.01-1.36 (5H, m), 1.62-1.77 (3H, m), 1.77-1.90 (3H, m), 2.24 (3H, s), 2.54 (3H, s), 2.99 (1H, dd, J = 8.7, 15.6 Hz), 3.19-3.36 (2H, m), 3.96 (2H, d, J = 6.2 Hz), 5.79 (1H, t, J = 8.5 Hz), 6.80 (1H, dd, J = 0.8, 7.8 Hz), 6.89 (1H, t, J = 7.3 Hz), 7.06-7.18 (3H, m), 8.41 (1H, d, J = 8.7 Hz), 8.55 (1H, dd, J = 0.8, 6.8 Hz), 12.48 (1H, s) |
| 694 | Ex661 | APCI/ESI+: 462 |
| 695 | Ex661 | APCI/ESI+: 462 |
| 696 | Ex661 | ESI+: 496 |
| 697 | Ex661 | EI: 466 |
| 698 | Ex661 | ESI+: 492<br>NMR (DMSO-$d_6$): 2.24 (3H, s), 2.51 (3H, s), 2.99 (1H, dd, J = 8.7, 15.6 Hz), 3.19-3.36 (2H, m), 5.32 (2H, s), 5.79 (1H, t, J = 8.5 Hz), 6.96 (1H, t, J = 7.2 Hz), 7.03 (1H, dd, J = 0.9, 7.8 Hz), 7.06-7.18 (3H, m), 7.19-7.27 (2H, m), 7.54-7.63 (1H, m), 8.43 (1H, d, J = 8.7 Hz), 8.61 (1H, dd, J = 0.9, 6.8 Hz), 12.48 (1H, s) |
| 699 | Ex661 | ESI+: 496<br>NMR (DMSO-$d_6$): 2.47 (3H, s), 3.06-3.18 (1H, m), 3.33-3.43 (2H, m), 5.31 (2H, s), 5.97 (1H, t, J = 7.7 Hz), 6.95 (1H, t, J = 7.2 Hz), 6.99-7.06 (2H, m), 7.12 (1H, d, J = 7.5 Hz), 7.19-7.27 (2H, m), 7.32 (1H, dt, Jd = 5.2, Jt = 7.7 Hz), 7.58 (1H, tt, J = 6.7, 8.5 Hz), 8.51-8.57 (2H, m), 12.56 (1H, s) |
| 700 | Ex661 | ESI+: 460 |
| 701 | Ex661 | ESI+: 478 |

TABLE 124

| Ex | Syn | Dat |
| --- | --- | --- |
| 702 | Ex661 | ESI+: 496<br>NMR (DMSO-$d_6$): 2.52 (3H, s), 3.10 (1H, dd, J = 8.9, 15.3 Hz), 3.22-3.38 (2H, m), 5.37 (2H, s), 5.79 (1H, t, J = 8.5 Hz), 6.97 (1H, t, J = 7.2 Hz), 7.03 (1H, dd, J = 0.9, 7.8 Hz), 7.22-7.33 (5H, m), 7.66 (1H, dq, Jd = 5.1, Jq = 9.6 Hz), 8.47 (1H, d, J = 8.8 Hz), 8.63 (1H, dd, J = 0.9, 6.8 Hz), 12.20-12.70 (1H, br) |
| 703 | Ex661 | ESI+: 466 |
| 704 | Ex661 | NMR (DMSO-$d_6$): 1.00-1.35 (5H, m), 1.62-1.77 (3H, m), 1.77-1.90 (3H, m), 2.50 (3H, s), 3.05-3.18 (1H, m), 3.32-3.43 (2H, m), 3.96 (2H, d, J = 6.2 Hz), 5.96 (1H, t, J = 7.6 Hz), 6.79 (1H, d, J = 7.6 Hz), 6.88 (1H, t, J = 7.3 Hz), 7.02 (1H, t, J = 9.0 Hz), 7.12 (1H, d, J = 7.5 Hz), 7.29-7.35 (1H, m), 8.46 (1H, d, J = 6.7 Hz), 8.52 (1H, d, J = 8.8 Hz), 12.55 (1H, s);<br>ESI+: 466 |

TABLE 124-continued

| Ex | Syn | Dat |
|---|---|---|
| 705 | Ex661 | ESI+: 466<br>NMR (DMSO-$d_6$): 1.00-1.34 (5H, m), 1.62-1.77 (3H, m), 1.77-1.90 (3H, m), 2.50 (3H, s), 3.05-3.18 (1H, m), 3.32-3.43 (2H, m), 3.96 (2H, d, J = 6.1 Hz), 5.97 (1H, t, J = 7.7 Hz), 6.79 (1H, d, J = 7.0 Hz), 6.88 (1H, t, J = 7.3 Hz), 7.02 (1H, t, J = 9.0 Hz), 7.12 (1H, d, J = 7.5 Hz), 7.29-7.35 (1H, m), 8.46 (1H, dd, J = 0.9, 6.8 Hz), 8.52 (1H, d, J = 8.9 Hz), 12.57 (1H, s) |
| 706 | Ex661 | ESI+: 466<br>NMR (DMSO-$d_6$): 1.01-1.36 (5H, m), 1.62-1.78 (3H, m), 1.78-1.91 (3H, m), 2.54 (3H, s), 3.10 (1H, dd, J = 9.1, 16.2 Hz), 3.23-3.42 (2H, m), 3.96 (2H, d, J = 6.1 Hz), 5.73 (1H, t, J = 8.4 Hz), 6.81 (1H, d, J = 7.4 Hz), 6.90 (1H, t, J = 7.3 Hz), 7.06 (1H, dt, Jd = 2.3, Jt = 8.8 Hz), 7.12 (1H, dd, J = 2.1, 9.1 Hz), 7.31 (1H, dd, J = 5.3, 8.1 Hz), 8.42 (1H, d, J = 8.6 Hz), 8.55 (1H, d, J = 6.8 Hz), 12.40-12.70 (1H, br) |
| 707 | Ex1 | ESI+: 462 |
| 708 | Ex1 | ESI+: 492 |
| 709 | Ex709 | APCI/ESI+: 482 |
| 710 | Ex710 | ESI+: 532 |
| 711 | Ex711 | ESI+: 448 |
| 712 | Ex712 | ESI+: 480 |
| 713 | Ex713 | ESI+: 392 |
| 714 | Ex714 | ESI+: 496 |
| 715 | Ex1 | ESI+: 512 |

TABLE 125

| Ex | Syn | Dat |
|---|---|---|
| 716 | Ex1 | NMR (CDCl$_3$): 1.00-1.12 (2H, m), 1.15-1.38 (3H, m), 1.66-1.81 (3H, m), 1.94-2.10 (3H, m), 2.85 (3H, s), 3.04 (2H, d, J = 5.0 Hz), 3.66 (3H, s), 3.95 (2H, d, J = 6.6 Hz), 5.68-5.74 (1H, m), 6.62 (1H, d, J = 7.7 Hz), 6.77 (1H, t, J = 7.1 Hz), 7.29 (1H, dd, J = 4.9 Hz, 8.0 Hz), 7.50 (1H, d, J = 8.0 Hz), 7.71 (1H, d, J = 8.0 Hz), 8.54 (1H, d, J = 4.8 Hz), 8.67 (1H, s), 9.00 (1H, d, J = 6.8 Hz) |
| 717 | Ex1 | ESI+: 478 |
| 718 | Ex1 | ESI+: 480 |
| 719 | Ex1 | ESI+: 454 |
| 720 | Ex1 | ESI+: 501 |
| 721 | Ex1 | ESI+: 409 |
| 722 | Ex1 | ESI+: 505 |
| 723 | Ex1 | ESI+: 498 |
| 724 | Ex1 | ESI+: 439 |
| 725 | Ex1 | ESI+: 450 |
| 726 | Ex1 | ESI+: 468 |
| 727 | Ex1 | ESI+: 505 |
| 728 | Ex1 | ESI+: 478 |
| 729 | Ex1 | ESI+: 508 |
| 730 | Ex1 | ESI+: 480 |
| 731 | Ex1 | ESI+: 506 |
| 732 | Ex1 | ESI+: 506 |
| 733 | Ex1 | ESI+: 508 |
| 734 | Ex1 | ESI+: 476 |
| 735 | Ex1 | ESI+: 466 |
| 736 | Ex1 | ESI+: 528 |
| 737 | Ex1 | ESI+: 478 |
| 738 | Ex1 | ESI+: 464 |
| 739 | Ex1 | ESI+: 472 |
| 740 | PEx10, 11, Ex1 | ESI+: 498 |
| 741 | Ex1 | ESI+: 464 |
| 742 | Ex1 | ESI+: 464 |

TABLE 126

| Ex | Syn | Dat |
|---|---|---|
| 743 | Ex1 | ESI+: 464 |
| 744 | Ex1 | ESI+: 464 |
| 745 | Ex1 | ESI+: 528 |
| 746 | Ex1 | ESI+: 414 |
| 747 | Ex1 | ESI+: 437 |
| 748 | Ex1 | ESI+: 476 |
| 749 | Ex1 | ESI+: 492 |
| 750 | Ex1 | ESI+: 522 |
| 751 | Ex1 | ESI+: 522 |
| 752 | Ex1 | ESI+: 464 |
| 753 | Ex1 | ESI+: 494 |
| 754 | Ex1 | ESI+: 462 |
| 755 | Ex1 | ESI+: 466 |
| 756 | Ex1 | ESI+: 466 |
| 757 | Ex1 | APCI/ESI+: 392 |
| 758 | Ex1 | ESI+: 466<br>NMR (DMSO-$d_6$): 2.55 (3H, s), 4.11 (1H, q, J = 7.2 Hz), 4.74 (1H, t, J = 6.4 Hz), 5.20 (1H, t, J = 8.4 Hz), 5.32 (2H, s), 5.58 (1H, d, J = 6.3 Hz), 5.76 (1H, d, J = 5.9 Hz), 6.96 (1H, t, J = 7.2 Hz), 7.03 (1H, dd, J = 0.9, 7.7 Hz), 7.18-7.35 (6H, m), 7.59 (1H, tt, J = 6.7, 8.4 Hz), 8.33 (1H, d, J = 8.8 Hz), 8.64 (1H, dd, J = 0.8, 6.8 Hz) |
| 759 | Ex1 | ESI+: 466<br>NMR (DMSO-$d_6$): 2.53 (3H, s), 4.18 (1H, q, J = 6.4 Hz), 4.82 (1H, t, J = 5.1 Hz), 5.06 (1H, d, J = 5.1 Hz), 5.10 (1H, d, J = 6.9 Hz), 5.32 (2H, s), 5.45 (1H, t, J = 7.9 Hz), 6.96 (1H, t, J = 7.2 Hz), 7.02 (1H, dd, J = 0.9, 7.8 Hz), 7.19-7.40 (6H, m), 7.59 (1H, tt, J = 6.7, 8.5 Hz), 8.26 (1H, d, J = 8.8 Hz), 8.64 (1H, dd, J = 0.8, 6.7 Hz) |
| 760 | Ex1 | ESI+: 468 |
| 761 | Ex1 | ESI+: 476 |
| 762 | Ex1 | ESI+: 496 |
| 763 | Ex1 | ESI+: 432 |

TABLE 127

| Ex | Syn | Dat |
|---|---|---|
| 764 | Ex1 | ESI+: 482 |
| 765 | Ex1 | APCI/ESI+: 509 |
| 766 | Ex1 | ESI+: 494<br>NMR (DMSO-$d_6$): 2.37 (4H, d, J = 5.3 Hz), 2.63 (3H, s), 4.04-4.12 (2H, m), 4.69 (2H, d, J = 4.5 Hz), 5.31 (2H, s), 6.87 (1H, t, J = 7.3 Hz), 6.98 (1H, dd, J = 0.7, 7.7 Hz), 7.17 (1H, t, J = 7.2 Hz), 7.23 (2H, t, J = 8.0 Hz), 7.30 (2H, t, J = 7.8 Hz), 7.37 (2H, dd, J = 1.2, 8.4 Hz), 7.58 (1H, tt, J = 6.7, 8.5 Hz), 8.21 (1H, s), 8.52 (1H, dd, J = 0.8, 6.9 Hz) |
| 767 | Ex1 | ESI+: 494<br>NMR (DMSO-$d_6$): 2.12 (2H, dd, J = 6.0, 14.2 Hz), 2.57 (3H, s), 2.64 (2H, dd, J = 6.2, 14.2 Hz), 4.10-4.18 (2H, m), 4.62 (2H, d, J = 4.3 Hz), 5.31 (2H, s), 6.89 (1H, t, J = 7.3 Hz), 6.98 (1H, d, J = 7.0 Hz), 7.17 (1H, t, J = 7.3 Hz), 7.23 (2H, t, J = 8.0 Hz), 7.30 (2H, t, J = 7.7 Hz), 7.46 (2H, dd, J = 1.1, 8.4 Hz), 7.59 (1H, tt, J = 6.7, 8.4 Hz), 8.19 (1H, s), 8.37 (1H, dd, J = 0.8, 6.9 Hz) |
| 768 | Ex1 | ESI+: 492 |
| 769 | Ex1 | ESI+: 462 |
| 770 | Ex1 | ESI+: 462 |
| 771 | Ex1 | ESI+: 432 |
| 772 | Ex1 | ESI+: 390<br>NMR (DMSO-$d_6$): 1.35 (6H, s), 2.49 (3H, s), 3.52 (2H, d, J = 5.7 Hz), 4.99 (1H, t, J = 5.7 Hz), 5.30 (2H, s), 6.91 (1H, t, J = 7.2 Hz), 6.99 (1H, dd, J = 0.9, 7.7 Hz), 7.14 (1H, s), 7.23 (2H, t, J = 8.0 Hz), 7.58 (1H, tt, J = 6.7, 8.5 Hz), 8.60 (1H, dd, J = 0.9, 6.9 Hz) |
| 773 | Ex1 | ESI+: 404 |
| 774 | Ex709 | ESI+: 451 |
| 775 | Ex1 | ESI+: 418 |

TABLE 127-continued

| Ex | Syn | Dat |
|---|---|---|
| 776 | Ex1 | ESI+: 376 |
| 777 | Ex1 | ESI+: 390 |
| 778 | Ex1 | ESI+: 404 |

TABLE 128

| Ex | Syn | Dat |
|---|---|---|
| 779 | Ex1 | ESI+: 402 |
| 780 | Ex1 | ESI+: 494 |
| 781 | Ex1 | APCI/ESI+: 478 |
| 782 | Ex1 | ESI+: 468 |
| 783 | Ex1 | ESI+: 468 |
| 784 | Ex1 | ESI+: 480 |
| 785 | Ex1 | ESI+: 480 |
| 786 | Ex1 | ESI+: 480 |
| 787 | Ex1 | ESI+: 480 |
| 788 | Ex1 | ESI+: 508 |
| 789 | Ex1 | ESI+: 452 |
| 790 | Ex1 | ESI+: 452 |
| 791 | Ex1 | ESI+: 480 |
| 792 | Ex1 | ESI+: 508 |
| 793 | Ex1 | ESI+: 424 |
| 794 | Ex1 | ESI+: 493 |
| 795 | Ex1 | ESI+: 493 |
| 796 | Ex1 | ESI+: 439 |
| 797 | Ex1 | ESI+: 466<br>NMR (DMSO-$d_6$): 2.55 (3H, s), 4.15-4.22 (1H, m), 4.82 (1H, brs), 5.04-5.12 (2H, m), 5.41 (2H, s), 5.45 (1H, t, J = 7.9 Hz), 6.92-7.01 (2H, m), 7.25-7.40 (5H, m), 7.42-7.54 (2H, m), 8.27 (1H, d, J = 8.8 Hz), 8.63 (1H, dd, J = 1.0, 6.6 Hz) |
| 798 | Ex1 | ESI+: 448<br>NMR (DMSO-$d_6$): 2.54 (3H, s), 4.15-4.22 (1H, m), 4.82 (1H, d, J = 5.1 Hz), 5.03-5.13 (2H, m), 5.34 (2H, s), 5.45 (1H, t, J = 7.9 Hz), 6.92-7.00 (2H, m), 7.25-7.40 (6H, m), 7.44-7.51 (1H, m), 7.63 (1H, dt, Jd = 1.7 Hz, Jt = 7.6 Hz), 8.26 (1H, d, J = 8.8 Hz), 8.62 (1H, dd, J = 1.1, 6.6 Hz) |
| 799 | Ex1,16 | ESI+: 383 |
| 800 | Ex1,16 | ESI+: 432 |
| 801 | Ex1,16 | ESI+: 450 |
| 802 | Ex1,16 | ESI+: 450 |
| 803 | Ex1,16 | ESI+: 468 |
| 804 | Ex1,16 | ESI+: 468 |
| 805 | Ex1,16 | ESI+: 438 |
| 806 | Ex1,16 | ESI+: 456 |
| 807 | Ex1,16 | ESI+: 474 |
| 808 | Ex1,16 | ESI+: 474 |
| 808 | Ex1,16 | ESI+: 474 |
| 809 | Ex1,16 | ESI+: 468 |
| 810 | Ex1.16 | ESI+: 464 |
| 811 | Ex1 | ESI+: 462 |
| 812 | Ex12 | ESI+: 456 |

TABLE 129

| Ex | Syn | Dat |
|---|---|---|
| 813 | Ex12 | ESI+: 472 |
| 814 | Ex12 | ESI+: 442 |
| 815 | Ex12 | ESI+: 472 |
| 816 | Ex12 | ESI+: 452 |
| 817 | Ex14 | ESI+: 464 |
| 818 | Ex16 | ESI+: 466 |
| 819 | Ex27,16 | ESI+: 441 |
| 820 | Ex31 | ESI+: 438 |
| 821 | Ex31, PEx5,Ex16 | ESI+: 506 |
| 822 | Ex5 | ESI+: 401 |
| 823 | Ex6 | ESI+: 549 |
| 824 | Ex1, PEx5 | ESI+: 448 |
| 825 | Ex661 | ESI+: 448 |

TABLE 129-continued

| Ex | Syn | Dat |
|---|---|---|
| 826 | Ex661 | ESI+: 448 |
| 827 | Ex709 | APCI/ESI+: 482 |
| 828 | Ex709 | ESI+: 450 |
| 829 | Ex709 | ESI+: 468<br>NMR (DMSO-$d_6$): 2.67 (3H, s), 3.98 (4H, d, J = 5.5 Hz), 5.05 (2H, t, J = 5.5 Hz), 5.41 (2H, s), 6.90 (1H, t, J = 7.3 Hz), 6.98 (1H, dd, J = 0.8, 7.7 Hz), 7.21 (1H, tt, J = 1.2, 7.3 Hz), 7.26-7.33 (3H, m), 7.40-7.54 (5H, m), 8.62 (1H, dd, J = 0.9, 6.9 Hz) |
| 830 | Ex709 | ESI+: 486 |
| 831 | Ex709 | APCI/ESI+: 482 |
| 832 | Ex709 | APCI/ESI+: 469 |
| 833 | Ex709 | ESI+: 494 |
| 834 | Ex709 | APCI/ESI+: 469<br>NMR (DMSO-$d_6$): 2.70 (3H, s), 3.99 (2H, dd, J = 6.2, 10.9 Hz), 4.21 (2H, dd, J = 5.4, 10.9 Hz), 4.94 (2H, t, J = 5.8 Hz), 5.32 (2H, s), 6.94 (1H, t, J = 7.3 Hz), 7.03 (1H, dd, J = 0.8, 7.8 Hz), 7.19-7.31 (3H, m), 7.54-7.63 (2H, m), 7.79 (1H, dt, Jd = 1.8 Hz, Jt = 7.8 Hz), 8.01 (1H, s), 8.53 (1H, ddd, J = 0.9, 1.8, 4.9 Hz), 8.76 (1H, dd, J = 0.9, 6.9 Hz) |

TABLE 130

| Ex | Syn | Dat |
|---|---|---|
| 835 | Ex713 | ESI+: 406 |
| 836 | Ex8 | APCI/ESI+: 522 |
| 837 | Ex8 | APCI/ESI+: 522 |
| 838 | Ex8 | APCI/ESI+: 522 |
| 839 | Ex8 | ESI+: 534 |
| 840 | Ex8 | APCI/ESI+: 509 |
| 841 | Ex8 | ESI+: 496 |
| 842 | Ex8 | ESI+: 484 |
| 843 | PEx12, Ex8 | ESI+: 490 |
| 844 | PEx12, Ex8 | ESI+: 508 |
| 845 | PEx12, Ex8 | ESI+: 526 |
| 846 | PEx165 | ESI+: 464 |
| 847 | PEx5 | ESI+: 437 |
| 848 | PEx5 | ESI+: 464 |
| 849 | PEx5 | ESI+: 466 |
| 850 | PEx5 | ESI+: 440 |
| 851 | PEx5 | ESI+: 484 |
| 852 | PEx5 | ESI+: 491 |
| 853 | PEx5 | ESI+: 436 |
| 854 | PEx5 | ESI+: 440 |
| 855 | PEx5 | ESI+: 464 |
| 856 | PEx5 | ESI+: 491 |
| 857 | PEx5 | ESI+: 494 |
| 858 | PEx5 | ESI+: 466 |
| 859 | PEx5 | ESI+: 492 |
| 860 | PEx5 | ESI+: 492 |
| 861 | PEx5 | ESI+: 480 |
| 862 | Ex1, PEx5 | ESI+: 448 |
| 863 | PEx5 | ESI+: 462 |
| 864 | PEx5 | ESI+: 452 |
| 865 | PEx5 | ESI+: 450 |
| 866 | PEx5 | ESI+: 458 |
| 867 | PEx5 | ESI+: 464 |
| 868 | PEx5 | ESI+: 450 |

TABLE 131

| Ex | Syn | Dat |
|---|---|---|
| 869 | PEx5 | ESI+: 450 |
| 870 | PEx5 | ESI+: 450 |
| 871 | PEx5 | ESI+: 450 |
| 872 | PEx5 | ESI+: 400 |
| 873 | PEx5 | ESI+: 462 |
| 874 | PEx5 | ESI+: 423 |

TABLE 131-continued

| Ex | Syn | Dat |
|---|---|---|
| 875 | PEx5 | ESI+: 478 |
| 876 | PEx5 | ESI+: 494 |
| 877 | PEx5 | ESI+: 480 |
| 878 | PEx5 | ESI+: 450 |
| 879 | PEx5 | ESI+: 448 |
| 880 | PEx5 | ESI+: 448 |
| 881 | PEx5 | ESI+: 480 |
| 882 | PEx5 | ESI+: 466 |
| 883 | PEx5 | ESI+: 450<br>NMR (DMSO-d$_6$): 1.00-1.33 (5H, m), 1.62-1.90 (6H, m), 1.72 (6H, s), 2.65 (3H, s), 3.95 (2H, d, J = 6.2 Hz), 6.76 (1H, dd, J = 0.9, 7.7 Hz), 6.81 (1H, t, J = 7.1 Hz), 7.45 (1H, t, J = 7.8 Hz), 7.70 (1H, dq, Jd = 7.9 Hz, Jq = 1.0 Hz), 7.78 (1H, dt, Jd = 7.8 Hz, Jt = 1.2 Hz), 8.05 (1H, t, J = 1.7 Hz), 8.17 (1H, s), 8.32 (1H, dd, J = 0.9, 6.7 Hz), 12.70-13.00 (1H, br) |
| 884 | PEx5 | ESI+: 494 |
| 885 | PEx5, Ex16 | ESI+: 494 |
| 886 | Ex709 | ESI+: 469 |
| 887 | Ex1 | ESI+: 491 |
| 888 | Ex1 | ESI+: 509 |
| 889 | Ex1 | ESI+: 392 |
| 890 | Ex1 | ESI+: 392 |
| 891 | Ex1 | ESI+: 362 |
| 892 | Ex709 | ESI+: 451 |

INDUSTRIAL APPLICABILITY

The compound of formula (I) has an sGC activation and can be used as an active ingredient of a pharmaceutical composition for treating or preventing sGC-related cardiovascular diseases, for example, hypertension, atherosclerosis, lumbar spinal canal stenosis, peripheral arterial diseases, as well as intermittent claudication and critical limb ischemia caused by the aforesaid peripheral arterial diseases, stable or unstable angina pectoris, heart failure, thrombosis, stroke, sexual dysfunction, pulmonary hypertension, or the like.

The invention claimed is:

1. A compound of formula (I)

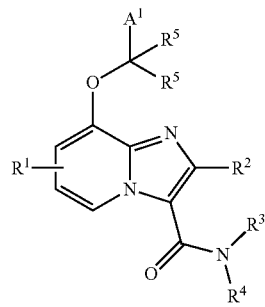

(I)

wherein:
A$^1$ is cyclohexyl, or phenyl optionally substituted with one or more F atoms,
R$^1$ is H,
R$^2$ is R$^0$,
R$^3$ is H,
R$^5$ is H,
R$^4$ is -Y-A$^2$ or A$^3$,
Y is C$_{1-10}$ alkylene optionally substituted with at least one group selected from Group G$^2$, Group G$^2$ is —CO$_2$H and —OH,
A$^2$ is H, cycloalkyl, pyridyl, or phenyl optionally substituted with a group selected from the group consisting of lower alkyl and —CO$_2$H,
A$^3$ is cycloalkyl selected from the group consisting of cyclopentyl, indanyl, dihydrocyclopentathienyl, dihydrocyclopentafuranyl, and dihydrocyclopentapyrrolyl, the above cycloalkyl is optionally substituted with at least one group selected from Group G$^1$, or piperidyl or pyrrolidyl each optionally substituted with at least one group selected from Group G$^1$,
Group G$^1$ is R$^0$, halogen, —CO$_2$H, —OH, —CO$_2$R$^0$, —CN, —NO$_2$, phenyl, and —SO$_2$—NH$_2$, and
each R$^0$ is independently lower alkyl,
or a salt thereof.

2. The compound according to claim 1, wherein A$^1$ is cyclohexyl, 2-fluorophenyl, 2,3-difluorophenyl, 2,6-difluorophenyl, or 2,3,6-trifluorophenyl, and R$^4$ is a group represented by any one of the following formulae (A), (B), (C), (D), (E), (F), and (G):

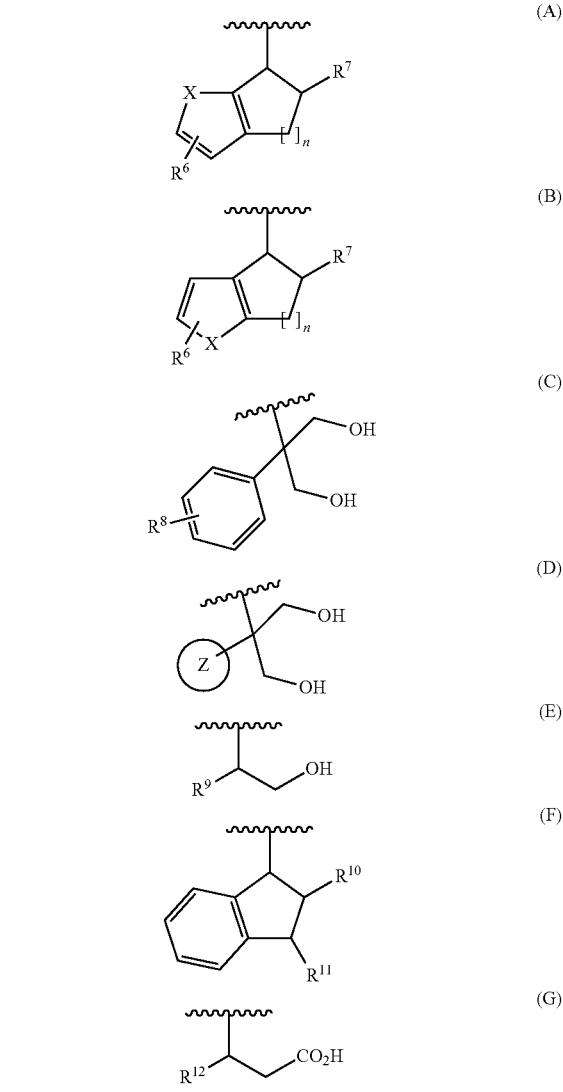

wherein
$R^6$ is H, halogen, or $R^0$,
$R^7$ is —$CO_2H$, —$CO_2R^0$, or —$NO_2$,
X is NH, $NR^0$, O, S, or —HC=CH—,
n is 1,
$R^8$ is H or lower alkyl,
Z is pyridyl,
$R^9$ is phenyl or lower alkyl,
$R^{10}$ is H or —OH,
$R^{11}$ is H or —OH, and
$R^{12}$ is lower alkyl, cycloalkyl, or phenyl,
or a salt thereof.

3. The compound according to claim 2, wherein
$A^1$ is 2,6-difluorophenyl,
$R^2$ is methyl,
$R^4$ is a group represented by the formula (A) or the formula (B),
X is —HC=CH—,
$R^6$ is F, and
$R^7$ is —$CO_2H$,
or a salt thereof.

4. The compound according to claim 2, wherein $R^2$ is methyl and $R^4$ is a group represented by the formula (C) or the formula (D), or a salt thereof.

5. The compound according to claim 2, wherein
$A^1$ is cyclohexyl or 2,6-difluorophenyl,
$R^2$ is methyl,
$R^4$ is a group represented by the formula (A) or the formula (B),
X is —HC=CH—,
$R^6$ is H, and
$R^7$ is —$CO_2H$,
or a salt thereof.

6. The compound according to claim 2, wherein $R^2$ is methyl and $R^4$ is a group represented by the formula (E), or a salt thereof.

7. The compound according to claim 2, wherein $R^2$ is methyl and $R^4$ is a group represented by the formula (F), or a salt thereof.

8. The compound according to claim 2, wherein $R^2$ is methyl and $R^4$ is a group represented by the formula (G), or a salt thereof.

9. The compound according to claim 2, which is selected from
the group consisting of:
(3 S)-3-({[8-(cyclohexylmethoxy)-2-methylimidazo[1,2-a]pyridin-3-yl]carbonyl}amino)-3-phenylpropanoic acid,
(1S,2R)-1-[({8-[(2,6-difluorobenzyl)oxy]-2-methylimidazo[1,2-a]pyridin-3-yl}carbonyl)amino]indane-2-carboxylic acid,
(1S,2R)-1-({[8-(cyclohexylmethoxy)-2-methylimidazo[1,2-a]pyridin-3-yl]carbonyl}amino)indane-2-carboxylic acid,
(1R,2S)-1-({[8-(cyclohexylmethoxy)-2-methylimidazo[1,2-a]pyridin-3-yl]carbonyl}amino)indane-2-carboxylic acid,
8-[((2,6-difluorobenzyl)oxy]-N-(1,3-dihydroxy-2-phenylpropan-2-yl)-2-methylimidazo[1,2-a]pyridine-3-carboxamide,
(1S,2R)-1-[({8-[(2,6-difluorobenzyl)oxy]-2-methylimidazo[1,2-a]pyridin-3-yl}carbonyl)amino]-7-fluoroindane-2-carboxylic acid,
(1S,2R)-1-[({8-[(2,6-difluorobenzyl)oxy]-2-methylimidazo[1,2-a]pyridin-3-yl}carbonyl)amino]-4-methylindane-2-carboxylic acid,
(1S,2R)-1-({[8-(cyclohexylmethoxy)-2-methylimidazo[1,2-a]pyridin-3-yl]carbonyl}amino)-5-fluoroindane-2-carboxylic acid,
(1S,2R)-1-({[8-(cyclohexylmethoxy)-2-methylimidazo[1,2-a]pyridin-3-yl]carbonyl}amino)-7-fluoroindane-2-carboxylic acid,
(1R,2S)-1-({[8-(cyclohexylmethoxy)-2-methylimidazo[1,2-a]pyridin-3-yl]carbonyl}amino)-7-fluoroindane-2-carboxylic acid,
(1S,2R)-1-({[8-(cyclohexylmethoxy)-2-methylimidazo[1,2-a]pyridin-3-yl]carbonyl}amino)-4-methylindane-2-carboxylic acid,
(1S,2R)-1-[({2-methyl-8-[(2,3,6-trifluorobenzyl)oxy]imidazo[1,2-a]pyridin-3-yl}carbonyl)amino]indane-2-carboxylic acid,
8-[((2,6-difluorobenzyl)oxy]-N-[(1R)-2-hydroxy-1-phenylethyl]-2-methylimidazo[1,2-a]pyridine-3-carboxamide,
8-[((2,6-difluorobenzyl)oxy-N-[(1R,2R)-2-hydroxy-2,3-dihydro-1H-inden-1-yl]-2-methylimidazo[1,2-a]pyridine-3-carboxamide,
8-[((2,3-difluorobenzyl)oxy]-N-(1,3-dihydroxy-2-phenylpropan-2-yl)-2-methylimidazo[1,2-a]pyridine-3-carboxamide,
8-[((2,6-difluorobenzyl)oxy]-N-[1,3-dihydroxy-2-(pyridin-2-yl)propan-2-yl]-2-methylimidazo[,2-a]pyridine-3-carboxamide,
8-((cyclohexylmethoxy)-N-[(1R)-2-hydroxy-1-phenylethyl]-2-methylimidazo[1,2-a]pyridine-3-carboxamide,
8-[((2,6-difluorobenzyl)oxy]-N-[(2R)-1-hydroxypropan-2-yl]-2-methylimidazo[1,2-a]pyridine-3-carboxamide,
8-[((2,6-difluorobenzyl)oxy]-N-[(2R)-1-hydroxy-3-methylbutan-2-yl]-2-methylimidazo[1,2-a]pyridine-3-carboxamide, and
N-(1,3-dihydroxy-2-phenylpropan-2-yl)-8-[(2-fluorobenzyl)oxy]-2-methylimidazo[1,2-a]pyridine-3-carboxamide,
or a salt thereof.

10. The compound according to claim 2, which is selected from
the group consisting of:
8-[((2,6-difluorobenzyl)oxy]-N-[(1R,2S,3 S)-2,3-dihydroxy-2,3-dihydro-1H-inden-1-yl]-2-methylimidazo[1,2-a]pyridine-3-carboxamide,
8-[((2,3-difluorobenzyl)oxy]-N-[(1R,2S,3 S)-2,3-dihydroxy-2,3-dihydro-1H-inden-1-yl]-2-methylimidazo[1,2-a]pyridine-3-carboxamide, and
N-[(1R,2S,3 S)-2,3-dihydroxy-2,3-dihydro-1H-inden-1-yl]-8-[(2-fluorobenzyl)oxy]-2-methylimidazo[1,2-a]pyridine-3-carboxamide,
or a salt thereof.

11. The compound according to claim 2, which is selected from
the group consisting of:
8-[((2,6-difluorobenzyl)oxy]-N-[(1R,2S,3R)-2,3-dihydroxy-2,3-dihydro-1H-inden-1-yl]-2-methylimidazo[1,2-a]pyridine-3-carboxamide,
8-[((2,3-difluorobenzyl)oxy]-N-[(1R,2S,3R)-2,3-dihydroxy-2,3-dihydro-1H-inden-1-yl]-2-methylimidazo[1,2-a]pyridine-3-carboxamide, and
N-[(1R,2S,3R)-2,3-dihydroxy-2,3-dihydro-1H-inden-1-yl]-8-[(2-fluorobenzyl)oxy]-2-methylimidazo[1,2-a]pyridine-3-carboxamide,
or a salt thereof.

12. The compound according to claim 1, which is selected from
the group consisting of:
8-[((2,6-difluorobenzyl)oxy]-N-[(1r,3R,4 S)-3,4-dihydroxy-1-phenylcyclopentyl]-2-methylimidazo[1,2-a]pyridine-3-carboxamide, and
8-[((2,6-difluorobenzyl)oxy]-N-[(1s,3R,4S)-3,4-dihydroxy-1-phenylcyclopentyl]-2-methylimidazo[1,2-a]pyridine-3-carboxamide,
or a salt thereof.

13. The compound according to claim 1, which is selected from
the group consisting of:
8-((cyclohexylmethoxy)-2-methyl-N-[(3 S)-1-methylpiperidin-3-yl]imidazo[1,2-a]pyridine-3-carboxamide,
(3R)-3-({[8-(cyclohexylmethoxy)-2-methylimidazo[1,2-a]pyridin-3-yl]carbonyl}amino)-5-methylhexanoic acid,
8-((cyclohexylmethoxy)-N-(1,3-dihydroxypropan-2-yl)-2-methylimidazo[1,2-a]pyridine-3-carboxamide,
8-((cyclohexylmethoxy)-2-methyl-N-[(3 S)-1-methylpyrrolidin-3-yl]imidazo[1,2-a]pyridine-3-carboxamide,
3-[((1 S)-1-({[8-(cyclohexylmethoxy)-2-methylimidazo[1,2-a]pyridin-3-yl]carbonyl}amino)ethyl]benzoic acid,
8-[((2,6-difluorobenzyl)oxy]-N-(1-hydroxy-2-methylpropan-2-yl)-2-methylimidazo [1,2-a]pyridine-3-carboxamide,
8-[((2,6-difluorobenzyl)oxy]-N-[(1R,2S)-2,3-dihydroxy-1-phenylpropyl]-2-methylimidazo[1,2-a]pyridine-3-carboxamide,
(3R)-4-cyclobutyl-3-({[8-(cyclohexylmethoxy)-2-methylimidazo1,2-a]pyridin-3-yl]carbonyl}amino)butanoic acid,
8-[((2,6-difluorobenzyl)oxy]-2-methyl-N-[(3 S)-1-sulfamoylpiperidin-3-yl]imidazo[1,2-a]pyridine-3-carboxamide, and
8-[((2,6-difluorobenzyl)oxy]-2-methyl-N-[(3 S)-piperidin-3-yl]imidazo[1,2-a]pyridine-3-carboxamide,
or a salt thereof.

14. A pharmaceutical composition comprising the compound or a salt thereof according to claim 1, and a pharmaceutically acceptable excipient.

15. A method for treating occlusive thrombotic vasculitis, peripheral arterial occlusive disease, intermittent claudication, critical limb ischemia, Raynaud's disease, Raynaud's syndrome, hypertension, or pulmonary hypertension, comprising administering to a subject an effective amount of the compound or a salt thereof according to claim 1.

* * * * *